United States Patent
Ting et al.

(10) Patent No.: US 10,556,954 B2
(45) Date of Patent: Feb. 11, 2020

(54) ANTI-PD-L1 NANOBODY, CODING SEQUENCE AND USE THEREOF

(71) Applicant: NANOMAB TECHNOLOGY LIMITED, Central, Hong Kong (CN)

(72) Inventors: Hong Hoi Ting, Shanghai (CN); Chung Lim Wong, Shanghai (CN)

(73) Assignee: NANOMAB TECHNOLOGY LIMITED, Hong Kong (CN)

( * ) Notice: Subject to any disclaimer, the term of this patent is extended or adjusted under 35 U.S.C. 154(b) by 0 days.

(21) Appl. No.: 16/085,899

(22) PCT Filed: Mar. 17, 2017

(86) PCT No.: PCT/CN2017/077122
§ 371 (c)(1),
(2) Date: Sep. 17, 2018

(87) PCT Pub. No.: WO2017/157334
PCT Pub. Date: Sep. 21, 2017

(65) Prior Publication Data
US 2019/0177416 A1    Jun. 13, 2019

(30) Foreign Application Priority Data

Mar. 18, 2016 (CN) .......................... 2016 1 0158493

(51) Int. Cl.
| | |
|---|---|
| *A61P 35/00* | (2006.01) |
| *C07K 16/28* | (2006.01) |
| *C07K 16/06* | (2006.01) |
| *C12N 15/62* | (2006.01) |
| *C12N 15/85* | (2006.01) |

(52) U.S. Cl.
CPC .......... *C07K 16/2827* (2013.01); *A61P 35/00* (2018.01); *C07K 16/065* (2013.01); *C12N 15/62* (2013.01); *C12N 15/85* (2013.01); *C07K 2317/569* (2013.01); *C12N 2015/8518* (2013.01)

(58) Field of Classification Search
None
See application file for complete search history.

(56) References Cited

U.S. PATENT DOCUMENTS 8,907,065 B2 * 12/2014 Hermans ............ C07K 16/2818
530/387.1

FOREIGN PATENT DOCUMENTS

| CN | 103421115 A | 12/2013 |
| CN | 103987405 A | 8/2014 |
| CN | 104736168 A | 6/2015 |

OTHER PUBLICATIONS

GenBank Accession No. KF179380.1, Comparison of *Camelus bactrianus* VHH sequences from conventional and heavy chain antibodies. Sep. 21, 2013.

* cited by examiner

*Primary Examiner* — Meera Natarajan
(74) *Attorney, Agent, or Firm* — McCarter & English, LLP; Marcie B. Clarke; Weiguo Zhou

(57) ABSTRACT

Provided in the present invention are a type of anti-human PD-L1 specific nanobodies and VHH chains thereof, coding sequences of the foregoing nanobodies or VHH chains thereof, corresponding expression vectors and host cells, and a method for producing antibodies.

12 Claims, 1 Drawing Sheet
Specification includes a Sequence Listing.

ANTI-PD-L1 NANOBODY, CODING SEQUENCE AND USE THEREOF

CROSS-REFERENCE TO RELATED APPLICATIONS

This application is a 35 U.S.C. § 371 national stage application of International Application No. PCT/CN2017/077122, filed on Mar. 17, 2017, which in turn claims the benefit of priority to Chinese Patent Application No. 201610158493.0, filed on Mar. 18, 2016. The entire contents of each of the aforementioned applications are incorporated herein by reference.

SEQUENCE LISTING

The instant application contains a Sequence Listing which has been submitted electronically in ASCII format and is hereby incorporated by reference in its entirety. Said ASCII copy, created on Feb. 20, 2019, is named P2018-1618_SEQLISTING.txt and is 266,333 bytes in size.

TECHNICAL FIELD

The invention relates to the field of biomedical or biopharmaceutical technology, and more particularly to PD-L1 single domain antibodies and its coding sequence and application.

BACKGROUND TECHNIQUE

Programmed death 1 ligand 1, also known as CD274, is a member of the B7 family and is a ligand for PD-1. PD-L1 is a type I transmembrane protein with a total of 290 amino acids, including an IgV-like region, an IgC-like region, a transmembrane hydrophobic region, and an intracellular region consisting of 30 amino acids.

Unlike other B7 family molecules, PD-L1 has a negative regulatory effect on immune responses. The study found that PD-L1 is mainly expressed in activated T cells, B cells, macrophages and dendritic cells. In addition to lymphocytes, PD-L1 is also expressed in other tissues endothelial cells such as thymus, heart, placenta, etc., as well as various non-lymphoids such as melanoma, liver cancer, gastric cancer, renal cell carcinoma, ovarian cancer, colon cancer, breast cancer, esophageal cancer, head and neck cancer, etc. PD-L1 is versatile in regulating autoreactive T, B cells and immune tolerance, and plays a role in peripheral T and B cell responses. The high expression of PD-L1 on tumor cells is associated with poor prognosis in cancer patients.

Programmed death-1 (PD-1), also known as CD279, is a member of the CD28 family. It has two tyrosine residues in the cytoplasmic region. One located near the N-terminus is in the immunoreceptor tyrosine-based inhibitory motif (ITIM) and another one near the C-terminus is located in the immunoreceptor tyrosine-based switch motif (ITSM). PD-1 is mainly expressed on the surface of activated T lymphocytes, B lymphocytes and macrophages. Under normal conditions, PD-1 can inhibit the function of T lymphocytes and promote the function of Treg, thereby inhibiting autoimmune responses and preventing autoimmune diseases. However, in the occurrence of tumors, PD-L1 expressed by tumor cells combined with PD-1 can promote tumor immune escape by inhibiting lymphocytes. The combination of PD-L1 and PD-1 can lead to a variety of biological changes, leading to immune regulation, such as inhibition of lymphocyte proliferation and activation, inhibition of CD4+ T cell differentiation into Th1 and Th17 cells, inhibition of inflammatory cytokine release, etc.

The successful application of monoclonal antibodies in the detection and bio-targeted treatment of cancer has caused a revolution in cancer treatment. However, the traditional monoclonal antibody (150 kD) molecular mass is too large. It is difficult for monoclonal antibody to penetrate the tissue, resulting in a low effective concentration of the tumor area, and the therapeutic effect is insufficient; the traditional antibody has high immunogenicity, and the modified antibody is difficult to reach the original affinity. In addition, the long-term development of fully humanized traditional antibodies, high production costs, insufficient stability and many other factors limit its application and popularity in the clinic.

Nanobodies are currently the smallest antibody molecules with a molecular weight of 1/10 of a normal antibody. In addition to the antigenic reactivity of monoclonal antibodies, nano-antibodies possess some unique functional properties, such as small molecular mass, strong stability, good solubility, easy expression, weak immunogenicity, strong penetrability, strong targeting, simple in humanization, low in preparation cost, etc. It almost completely overcomes the shortcomings of traditional antibody long-term development cycle, low stability and harsh storage conditions.

However, there is currently no satisfactory nanobody for PD-L1 in the field. Therefore, there is an urgent need in the field to develop new and specific nanobodies that are effective against PD-L1.

SUMMARY OF THE INVENTION

The object of the present invention is to provide a class of specific nanobodies that are effective against PD-L1.

In the first aspect of the present invention, it provides a VHH chain of an anti-PD-L1 nanobody, the amino acid sequence of which is shown in any one of SEQ ID NOs.: 1-150.

In another preferred embodiment, the PD-L1 is human PD-L1.

Furthermore, a VHH chain of an anti-PD-L1 nanobody is provided, the VHH comprises a frame region FR and a complementary determining region CDR, wherein the CDR comprises the corresponding CDR1, CDR2 and CDR3 of any one of SEQ ID NOs.: 1-150, as well as FR1, FR2, FR3 and FR4 separated by said CDR1-3.

Furthermore, a heavy chain variable region of an anti-human PD-L1 antibody is provided, the heavy chain variable region comprises three complementary determining regions CDR1, CDR2, and CDR3, and the three CDRs comprise the corresponding CDR1, CDR2 and CDR3 of any one of SEQ ID NO.: 1-150.

In another preferred embodiment, the three CDRs comprise CDR1, CDR2 and CDR3 as shown in Table 2.

In the second aspect of the present invention, an anti-PD-L1 nanobody is provided, which is an nanobody against PD-L1 epitope, and has a VHH chain as shown in the amino acid sequence of any one of SEQ ID NOs.: 1-150.

In another preferred embodiment, the anti-PD-L1 nanobody has a high affinity for PD-L1. In another preferred embodiment, the anti-PD-L1 nanobody has a very high specificity or selectivity for PD-L1 (relative to PD-L2) and has a selectivity ratio (such as a ratio of OD value)(PD-L1/PD-L2) as high as ≥20, preferably 20-40, or 21-35.

The third aspect of the present invention provides a polynucleotide, and the polynucleotide encodes a protein selected from the group consisting of the VHH chain of the anti-PD-L1 nanobody according to the first aspect, or the anti-PD-L1 nanobody according to the second aspect.

In another preferred embodiment, the polynucleotide comprises DNA or RNA.

In another preferred embodiment, the polynucleotide has a nucleotide sequence as shown in any one of SEQ ID NOs.: 151-300.

The fourth aspect of present invention provides an expression vector, the expression vector comprises the polynucleotide according to the third aspect.

The fifth aspect of the present invention provides a host cell, the host cell comprises the expression vector according to the fourth aspect, or the polynucleotide according to the third aspect is integrated within the genome of the host cell.

In another preferred embodiment, the host cell includes a prokaryocyte or an eukaryocyte.

In another preferred embodiment, the host cell is selected from the group consisting of *E. coli.* and yeast cell.

The sixth aspect of the present invention provides a method for producing an anti-PD-L1 nanobody comprising the steps of:

(a) culturing said host cell according to the fifth aspect under a condition suitable for producing a nanobody, thereby obtaining a culture containing said anti-PD-L1 nanobody; and (b) isolating or recovering said anti-PD-L1 nanobody from said culture.

In another preferred embodiment, the anti-PD-L1 nanobody has the amino acid sequence as shown in any one of SEQ ID NOs.: 1-150.

The seventh aspect of the present invention provides an immunoconjugate, and the immunoconjugate comprises:

(a) the VHH chain of the anti-PD-L1 nanobody according to the first aspect, or the anti-PD-L1 nanobody according to the second aspect; and (b) a conjugating part selected from the group consisting of a detectable marker, drug, toxin, cytokine, radionuclide, and enzyme.

In another preferred embodiment, the conjugating part is a drug or toxin.

In another preferred embodiment, the conjugating part is a detectable marker.

In another preferred embodiment, the conjugate is selected from the group consisting of fluorescent or luminescent markers, radiomarkers, MRI (magnetic resonance imaging) or CT (computed tomography) contrast agents, or enzymes, radionuclides, biotoxins, cytokines (eg, IL-2, etc.), antibodies, antibody Fc fragments, antibody scFv fragments, gold nanoparticles/nanorods, viral particles, liposomes, nanomagnetic particles, prodrug activating enzymes (eg, DT-diaphorase (DTD) or biphenyl hydrolase-like protein (BPHL), chemotherapeutic agents (eg, cisplatin) or any form of nanoparticles, etc. that can produce detectable products.

In another preferred embodiment, the immunoconjugate contains multivalent (such as bivalent) VHH chains of the anti-PD-L1 nanobody according to the first aspect of the present invention, or the anti-PD-L1 nanobody according to the second aspect of the present invention. Said multivalent refers that the amino acid sequence of the immunoconjugate contains several repeated VHH chains of the anti-PD-L1 nanobody according to the first aspect of the present invention, or the anti-PD-L1 nanobody according to the second aspect of the present invention.

The eighth aspect of the invention provides a use of the anti-PD-L1 nanobody according to the present invention for preparing (a) a reagent for detecting PD-L1 molecule; or (b) a medicament for treating cancers.

In another preferred embodiment, the detecting comprises detection conducted by flow cytometry or cell immunofluorescence.

The ninth aspect of the present invention provides a pharmaceutical composition comprising:

(i) the VHH according to the first aspect of the present invention, the anti-PD-L1 nanobody according to the second aspect of the present invention, or the immunoconjugate according to seventh aspect of the present invention; and (ii) a pharmaceutically acceptable carrier.

In another preferred embodiment, said pharmaceutical composition is in a form of injection.

In another preferred embodiment, said pharmaceutical composition is used for preparing a medicament for treating cancers, and said cancer is selected from the group consisting of gastric cancer, liver cancer, leukemia, renal tumor, lung cancer, small intestinal cancer, bone cancer, prostate cancer, colorectal cancer, breast cancer, colon cancer, prostate cancer, cervical cancer, lymphoma, adrenal tumor and bladder tumor.

The tenth aspect of the present invention provides one or more uses of the anti-PD-L1 nanobody according to the present invention:

(i) for detecting human PD-L1 molecule;

(ii) for flow cytometry assay;

(iii) for cell immunofluorescence detection;

(iv) for treating cancer;

(v) for diagnosing cancer.

In another preferred embodiment, the use is non-diagnostic and non-therapeutic.

The eleventh aspect of the present invention provides an antibody comprising: the heavy chain variable region VHH according to the first aspect of the present invention.

In another preferred embodiment, the antibody is an antibody specific for the PD-L1 protein. In another preferred embodiment, the antibody is a nanobody.

The twelfth aspect of the present invention provides a recombinant protein, and the recombinant protein has:

(i) the sequence of variable region of heavy chain VHH according to the first aspect of the present invention or the sequence of nanobody according to the second aspect of the present invention;

and (ii) an optional tag sequence assisting expression and/or purification.

In another preferred embodiment, the tag sequence includes 6His tag or HA tag.

In another preferred embodiment, the recombinant protein specifically binds to the PD-L1 protein. The thirteenth aspect of the present invention provides a use of the heavy chain variable region VHH according to the first aspect of the present disclosure, the nanobody according to the second aspect of the present invention, or the immunoconjugate according to seventh aspect of the present invention for preparing a medicament, agent, detecting plate or kit;

wherein, said agent, detecting plate or kit is used for detecting PD-L1 protein in the sample;

wherein, said medicament is used for treating or preventing cancers expressing PD-L1 (i.e. PD-L1 positive).

In another preferred embodiment, said cancer comprises gastric cancer, lymphoma, liver cancer, leukemia, renal tumor, lung cancer, small intestinal cancer, bone cancer, prostate cancer, colorectal cancer, breast cancer, colon cancer, prostate cancer, or adrenal tumors.

The fourteenth aspect of the present invention provides a method for detecting PD-L1 protein in a sample, and said method comprises the steps of:

(1) contacting the sample with the nanobody according to the second aspect of the present invention;

(2) detecting the antigen-antibody complex, wherein the detected complex indicated the presence of PD-L1 protein.

The fifteenth aspect of the present invention provides a method for treating a disease, comprising administering the nanobody or the immunoconjugate according to the present invention to a subject in need.

In another preferred embodiment, said subject includes mammals, such as human.

DRAWINGS DESCRIPTION

DETAILED DESCRIPTION

Figure 1:
FIG. 1 shows the insertion rate detection plot for the constructed library. The lanes are as follows: Lane M is the DNA molecular marker, and Lanes 1-24 are the PCR products for the detection of the insert, and the PCR product band is approximately 500 bp.

Upon extensive and intensive studies, the inventors have successfully obtained a class of anti-PD-L1 nanobodies after numerous screening. The experimental results show that the nanobodies are not only high specificity, and can efficiently bind to the PD-L1 molecules on cell lines (including the T cells or natural killer cells NK) expressing PD-L1 molecules significantly. It is possible to deliver functional molecules (toxins or small RNAs) by modifying this type of antibody to kill PD-L1 positive cells or perform other functional studies. Based on this discovery, the invention is completed.

In particular, the human PD-L1 protein as antigen was used to immunize a camel, thereby obtaining a gene library of nanobodies with high quality. The PD-L1 protein molecules were conjugated onto an ESLIA board and exhibited correct spatial structure of PD-L1 protein. The antigens in such configuration were used to screen the gene library of nanobodies by phage exhibition technology (phage exhibition of a gene library of camel heavy chain antibody) thereby obtaining genes of nanobodies with PD-L1 specificity. Then the genes were transferred into *E. coli* thereby obtaining the stains which can be effectively expressed in *E. coli* with high specificity.

As used herein, the terms "nanobodies of the invention", "anti-PD-L1 nanobodies of the invention", and "PD-L1 nanobodies of the present invention" are exchangeable and refer to nanobodies that specifically recognize and bind to PD-L1 (including human PD-L1). The more preferable nanobody is one comprising a VHH chain of amino acid sequence as set forth by any one of SEQ ID NO.:1-150.

As used herein, the term "antibody" or "immunoglobulin" is a heterotetrameric glycosaminoglycan protein of about 150,000 Dalton with the same structural features, consisting of two identical light (L) chains and two identical heavy (H) chains. Each light chain is linked to the heavy chain through a covalent disulfide bond, and the number of disulfide bonds between the heavy chains of different immunoglobulin isoforms is different. Each heavy and light chain also has intra-chain disulfide bonds which are regular spaced. Each heavy chain has a variable region (VH) at one end followed by a plurality of constant regions. Each light chain has a variable region (VL) at one end and a constant region at the other end; the constant region of the light chain is opposite to the first constant region of the heavy chain, and the variable region of the light chain is opposite to the variable region of the heavy chain. Special amino acid residues form an interface between the variable regions of the light and heavy chains.

As used herein, the terms "single domain antibody (VHH)" and "nanobodies" have the same meaning referring to a variable region of a heavy chain of an antibody, and construct a single domain antibody (VHH) consisting of only one heavy chain variable region. It is the smallest antigen-binding fragment with complete function. Generally, the antibodies with a natural deficiency of the light chain and the heavy chain constant region 1 (CH1) are first obtained, the variable regions of the heavy chain of the antibody are therefore cloned to construct a single domain antibody (VHH) consisting of only one heavy chain variable region.

As used herein, the term "variable" refers that certain portions of the variable region in the nanobodies vary in sequences, which forms the binding and specificity of various specific antibodies to their particular antigen. However, variability is not uniformly distributed throughout the nanobody variable region. It is concentrated in three segments called complementarity-determining regions (CDRs) or hypervariable regions in the variable regions of the light and heavy chain. The more conserved part of the variable region is called the framework region (FR). The variable regions of the natural heavy and light chains each contain four FR regions, which are substantially in a β-folded configuration, joined by three CDRs which form a linking loop, and in some cases can form a partially β-folded structure. The CDRs in each chain are closely adjacent to the others by the FR regions and form an antigen-binding site of the nanobody with the CDRs of the other chain (see Kabat et al., NIH Publ. No. 91-3242, Volume I, pages 647-669. (1991)). The constant regions are not directly involved in the binding of the nanobody to the antigen, but they exhibit different effects or functions, for example, involve in antibody-dependent cytotoxicity of the antibodies.

As known by those skilled in the art, immunoconjugates and fusion expression products include: conjugates formed by binding drugs, toxins, cytokines, radionuclides, enzymes, and other diagnostic or therapeutic molecules to the nanobodies or fragments thereof of the present invention. The invention also includes a cell surface marker or an antigen that binds to said anti-PD-L1 protein nanobody or the fragment thereof.

As used herein, the term "heavy chain variable region" and "$V_H$" can be used interchangeably. As used herein, the terms "variable region" and "complementary determining region (CDR)" can be used interchangeably.

In another preferred embodiment, the heavy chain variable region of said nanobody comprises 3 complementary determining regions: CDR1, CDR2, and CDR3.

In another preferred embodiment, the heavy chain of said nanobody comprises the above said heavy chain variable region and a heavy chain constant region.

According to the present invention, the terms "nanobody of the invention", "protein of the invention", and "polypeptide of the invention" are used interchangeably and all refer to a polypeptide, such as a protein or polypeptide having a heavy chain variable region, that specifically binds to PD-L1 protein. They may or may not contain a starting methionine.

The invention also provides other proteins or fusion expression products having the nanobodies of the invention. Specifically, the present invention includes any protein or protein conjugate and fusion expression product (i.e. immunoconjugate and fusion expression product) having a heavy chain containing a variable region, as long as the variable region are identical or at least 90% identical, preferably at least 95% identical to the heavy chain of the nanobody of the present invention.

In general, the antigen-binding properties of a nanobody can be described by three specific regions located in the variable region of the heavy chain, referred as variable regions (CDRs), and the segment is divided into four frame regions (FRs). The amino acid sequences of four FRs are relatively conservative and do not directly participate in binding reactions. These CDRs form a loop structure in which the β-sheets formed by the FRs therebetween are spatially close to each other, and the CDRs on the heavy chain and the CDRs on the corresponding light chain constitute the antigen-binding site of the nanobody. The amino acid sequences of the same type of nanobodies can be compared to determine which amino acids constitute the FR or CDR regions.

The variable regions of the heavy chains of the nanobodies of the invention become a particular interest because at least a part of them is involved in binding antigens. Thus, the present invention includes those molecules having a nanobody heavy chain variable region with a CDR, provided that their CDRs are 90% or more (preferably 95% or more, the most preferably 98% or more) identical to the CDRs identified herein.

The present invention includes not only intact nanobodies but also fragment(s) of immunologically active nanobody or fusion protein(s) formed from nanobodies with other sequences. Therefore, the present invention also includes fragments, derivatives and analogs of the nanobodies.

As used herein, the terms "fragment," "derivative," and "analog" refer to a polypeptide that substantially retains the same biological function or activity of a nanobody of the invention. Polypeptide fragments, derivatives or analogs of the invention may be (i) polypeptides having one or more conservative or non-conservative amino acid residues (preferably non-conservative amino acid residues) substituted. Such substituted amino acid residues may or may not be encoded by the genetic code; or (ii) a polypeptide having a substituent group in one or more amino acid residues; or (iii) a polypeptide formed by fusing a mature polypeptide and another compound (such as a compound that increases the half-life of the polypeptide, for example, polyethylene glycol); or (iv) a polypeptide formed by fusing an additional amino acid sequence to the polypeptide sequence (e.g., a leader or secretory sequence or a sequence used to purify this polypeptide or a proprotein sequence, or a fusion protein formed with a 6 His tag). According to the teachings herein, these fragments, derivatives, and analogs are within the scope of one of ordinary skill in the art.

The nanobody of the present invention refers to a polypeptide including the above CDR regions having PD-L1 protein binding activity. The term also encompasses variant forms of polypeptides comprising the above CDR regions that have the same function as the nanobodies of the invention. These variations include, but are not limited to, deletion insertions and/or substitutions of one or several (usually 1-50, preferably 1-30, more preferably 1-20, optimally 1-10) amino acids, and addition of one or several (generally less than 20, preferably less than 10, and more preferably less than 5) amino acids at C-terminus and/or N-terminus. For example, in the art, the substitution of amino acids with analogical or similar properties usually does not alter the function of the protein. For another example, addition of one or several amino acids at the C-terminus and/or N-terminus usually does not change the function of the protein. The term also includes active fragments and active derivatives of the nanobodies of the invention.

The variant forms of the polypeptide include: homologous sequences, conservative variants, allelic variants, natural mutants, induced mutants, proteins encoded by DNAs capable of hybridizing with DNA encoding the nanobody of the present invention under high or low stringent conditions, and polypeptides or proteins obtained using antiserum against the nanobodies of the invention.

The invention also provides other polypeptides, such as a fusion protein comprising nanobodies or fragments thereof. In addition to almost full-length polypeptides, the present invention also includes fragments of the nanobodies of the invention. Typically, the fragment has at least about 50 contiguous amino acids of the nanobody of the invention, preferably at least about 50 contiguous amino acids, more preferably at least about 80 contiguous amino acids, and most preferably at least about 100 contiguous amino acids.

In the present invention, "a conservative variant of a nanobody of the present invention" refers to the polypeptides in which there are up to 10, preferably up to 8, more preferably up to 5, and most preferably up to 3 amino acids substituted by amino acids having analogical or similar properties, compared to the amino acid sequence of the nanobody of the present invention. These conservative variant polypeptides are preferably produced according to the amino acid substitutions in Table 1.

TABLE 1

| Original residue | Representative substitution | Preferable substitution |
|---|---|---|
| Ala (A) | Val; Leu; Ile | Val |
| Arg (R) | Lys; Gln; Asn | Lys |
| Asn (N) | Gln; His; Lys; Arg | Gln |
| Asp (D) | Glu | Glu |
| Cys (C) | Ser | Ser |
| Gln (Q) | Asn | Asn |
| Glu (E) | Asp | Asp |
| Gly (G) | Pro; Ala | Ala |
| His (H) | Asn; Gln; Lys; Arg | Arg |
| Ile (I) | Leu; Val; Met; Ala; Phe | Leu |
| Leu (L) | Ile; Val; Met; Ala; Phe | Ile |
| Lys (K) | Arg; Gln; Asn | Arg |
| Met (M) | Leu; Phe; Ile | Leu |
| Phe (F) | Leu; Val; Ile; Ala; Tyr | Leu |
| Pro (P) | Ala | Ala |
| Ser (S) | Thr | Thr |
| Thr (T) | Ser | Ser |
| Trp (W) | Tyr; Phe | Tyr |
| Tyr (Y) | Trp; Phe; Thr; Ser | Phe |
| Val (V) | Ile; Leu; Met; Phe; Ala | Leu |

The present invention also provides a polynucleotide molecule encoding the above nanobody or fragment or fusion protein thereof. Polynucleotides of the invention may be in the form of DNA or RNA. DNA forms include cDNA, genomic DNA, or synthetic DNA. DNA can be single-stranded or double-stranded. DNA can be a coding strand or a non-coding strand.

Polynucleotides encoding the mature polypeptides of the invention include: coding sequences only encoding mature polypeptide; coding sequences for the mature polypeptide and various additional coding sequences; coding sequences (and optional additional coding sequences) and non-coding sequences for the mature polypeptide.

The term "polynucleotide encoding a polypeptide" may include a polynucleotide that encodes the polypeptide, and may also include a polynucleotide that includes additional coding and/or non-coding sequences.

The invention also relates to polynucleotides that hybridize to the sequences described above and that have at least 50%, preferably at least 70%, and more preferably at least 80% identity between the two sequences. The present invention specifically relates to polynucleotides that can be hybridized to the polynucleotides of the present invention under stringent conditions. In the present invention, "stringent conditions" refers to: (1) hybridization and elution at lower ionic strength and higher temperature, such as 0.2× SSC, 0.1% SDS, 60° C.; or (2) additional denaturants during hybridization, such as 50% (v/v) formamide, 0.1% fetal bovine serum/0.1% Ficoll, 42° C., etc.; or (3) hybridization occurs only under the identity between the two sequences at least over 90%, preferably over 95%. Also, polypeptides encoded by hybridizable polynucleotides have the same biological functions and activities as mature polypeptides.

The full-length nucleotide sequence of the nanobody of the present invention or a fragment thereof can generally be obtained by a PCR amplification method, a recombination method, or an artificial synthesis method. One possible method is to synthesize related sequences using synthetic methods, especially when the fragment length is short. In general, a long sequence of fragments can be obtained by first synthesizing a plurality of small fragments and then connecting them. In addition, the coding sequence of the heavy chain and the expression tag (eg, 6His) can be fused together to form a fusion protein.

Once the concerned sequences have been obtained, the concerned sequences can be obtained in large scale using recombinant methods. Usually, sequences can be obtained by cloning it into a vector, transferring it into cells, and then isolating the sequences from the proliferated host cells by conventional methods. Bio-molecules (nucleic acids, proteins, etc.) to which the present invention relates include bio-molecules that exist in isolated form.

At present, DNA sequences encoding the protein of the present invention (or a fragment thereof, or a derivative thereof) can be obtained completely by chemical synthesis. The DNA sequence then can be introduced into various existing DNA molecules (or e.g. vectors) and cells known in the art. In addition, mutations can also be introduced into the protein sequences of the invention by chemical synthesis.

The invention also relates to vectors comprising the above-mentioned suitable DNA sequences and suitable promoters or control sequences. These vectors can be used to transform an appropriate host cell so that it can express the protein.

The host cell can be a prokaryotic cell, such as a bacterial cell; or a lower eukaryotic cell, such as a yeast cell; or a higher eukaryotic cell, such as a mammalian cell. Representative examples are: *Escherichia coli, Streptomyces*, bacterial cells such as *Salmonella typhimurium*, fungal cells such as yeast, insect cells of *Drosophila* S2 or Sf9, animal cells of CHO, COST, 293 cells, and the like.

The transformation of the host cell with the recombinant DNA can be performed using conventional techniques well known to those skilled in the art. When the host is a prokaryotic organism such as *E. coli*, competent cells capable of absorbing DNA can be harvested after the exponential growth phase and treated with the $CaCl_2$ method. The procedures used are well known in the art. Another method is to use $MgCl_2$. If necessary, conversion can also be performed by electroporation. When the host is eukaryotic, the following DNA transfection methods can be used: calcium phosphate coprecipitation, conventional mechanical methods such as microinjection, electroporation, liposome packaging, and the like.

The obtained transformants can be cultured in a conventional manner to express the polypeptide encoded by the gene of the present invention. Depending on the host cells used, the medium used in the culture may be selected from various conventional media. The culture is performed under conditions suitable for the host cells growth. After the host cells are grown to an appropriate cell density, the selected promoter is induced by a suitable method (such as temperature shift or chemical induction) and the cells are incubated for a further period of time.

The recombinant polypeptide in the above method may be expressed intracellularly, or on the cell membrane, or secreted extracellularly. If necessary, the recombinant protein can be isolated and purified by various separation methods by utilizing its physical, chemical and other characteristics. These methods are well-known to those skilled in the art. Examples of these methods include, but are not limited to: conventional renaturation treatment, treatment with a protein precipitation agent (salting out method), centrifugation, osmotic disruption, super treatment, ultracentrifugation, molecular sieve chromatography (gel filtration), adsorption layer analysis, ion exchange chromatography, high performance liquid chromatography (HPLC), and various other liquid chromatography techniques and the combinations thereof.

The nanobodies of the invention may be used alone or in combination or conjugated with a detectable marker (for diagnostic purposes), a therapeutic agent, a PK (protein kinase) modification moiety, or a combination thereof.

Detectable markers for diagnostic purposes include, but are not limited to: fluorescent or luminescent markers, radioactive markers, MRI (magnetic resonance imaging) or CT (computed tomography) contrast agents, or enzymes capable of producing detectable products.

Therapeutic agents that can be binded or conjugated to the nanobodies of the present invention include, but are not limited to: 1. Radionuclides; 2. Biological poisons; 3. Cytokines such as IL-2, etc.; 4. Gold nanoparticles/nanorods; 5. Viruses Particles; 6. Liposome; 7. Nano magnetic particles; 8. Prodrug activating enzymes (for example, DT-diaphorase (DTD) or biphenyl hydrolase-like protein (BPHL)); 10. Chemotherapeutic agents (for example, cisplatin) or any form of nanoparticles, etc.

Pharmaceutical Composition

The invention also provides a composition. Preferably, said composition is a pharmaceutical composition comprising the above nanobody or active fragment or fusion protein thereof, and a pharmaceutically acceptable carrier. In general, these materials can be formulated in non-toxic, inert, and pharmaceutically acceptable aqueous carrier media wherein the pH is generally about 5-8, preferably about 6-8, although the pH can be varied with the nature of the formulation material and the condition to be treated. The formulated pharmaceutical compositions can be administered by conventional routes including, but not limited to, intratumoral, intraperitoneal, intravenous, or topical administration.

The pharmaceutical composition of the present invention can be directly used to bind PD-L1 protein molecules and thus can be used to treat tumors. In addition, other therapeutic agents can also be used at the same time.

The pharmaceutical composition of the present invention contains a safe and effective amount (for example, 0.001-99 wt %, preferably 0.01-90 wt %, and more preferably 0.1-80 wt %) of the above-mentioned nanobodies of the present invention (or their conjugates) and pharmaceutically acceptable carriers or excipients. Such carriers include, but are not limited to: saline, buffer, dextrose, water, glycerol, ethanol, and the combinations thereof. The drug formulation should be suitable for the mode of administration. The pharmaceutical composition of the present invention may be prepared in the form of an injection, for example, by a conventional method using physiological saline or an aqueous solution containing glucose and other adjuvant. Pharmaceutical compositions such as injections and solutions are preferably made under aseptic conditions. The amount of active ingredient administered is a therapeutically effective amount, for example, about 10 micrograms/kilogram body weight to about 50 milligrams/kilogram body weight per day. In addition, the polypeptides of the invention can also be used with other therapeutic agents.

When a pharmaceutical composition is used, a safe and effective amount of the immune-conjugate is administered to the mammal, wherein the safe and effective amount is usually at least about 10 micrograms/kilogram body weight, and in most cases, no more than about 50 mg/kilogram body weight, preferably the dose is about 10 micrograms/kilogram body weight to about 10 milligrams/kilogram body weight. Of course, factors such as the route of administration and the patient's health status should be considered to define the specific doses, all of which are within the skills of skilled physicians.

Nanobodies with Markers

In a preferred embodiment of the invention, the nanobodies carry detectable markers. More preferably, the marker is selected from the group consisting of isotopes, colloidal gold markers, colored markers, and fluorescent markers.

Colloidal gold markers can be performed using methods known to those skilled in the art. In a preferred embodiment of the invention, the anti-PD-L1 nanobodies are marked with colloidal gold to obtain colloidal gold-markered nanobodies.

The anti-PD-L1 nanobodies of the present invention have very good specificity and high potency.

Detection Method

The invention also relates to a method of detecting PD-L1 protein. The method steps are basically as follows: obtaining a sample of cells and/or tissue; dissolving the sample in a medium; and detecting the level of PD-L1 protein in the dissolved sample.

According to the detection method of the present invention, the sample used is not particularly limited, and a representative example is a sample containing cells which is present in a cell preservation solution.

Kits

The present invention also provides a kit containing a nanobody (or a fragment thereof) or a detection board of the present invention. In a preferred embodiment of the present invention, the kit further includes a container, an instruction, a buffer, and the like.

The present invention also provides a detection kit for detecting the level of PD-L1, and said kit comprises nanobodies that recognize PD-L1 protein, a lysis medium for dissolving a sample, a general reagent and a buffer needed for the detection, such as various buffer, detection markers, detection substrates, etc. The test kit can be an in vitro diagnostic device.

Application

As described above, the nanobodies of the present invention have extensive biological application value and clinical application value. Said applications involve various fields such as diagnosis and treatment of diseases related to PD-L1, basic medical research, and biological research. One preferred application is for clinical diagnosis and targeted treatment of PD-L1.

The main advantages of the present invention include:

(a) the nanobodies of the invention is highly specific to the human PD-L1 protein with correct spatial structure;

(b) the nanobodies of the invention have a strong affinity; and (c) the nanobodies of the invention are simple to produce.

The invention is further illustrated below in conjunction with specific embodiments. It is to be understood that the examples are merely illustrative of the invention and are not intended to limit the scope of the invention. The experimental methods in which the specific conditions are not indicated in the following examples are usually carried out according to the conditions described in the conventional conditions, for example, Sambrook et al., Molecular Cloning: Laboratory Manual (New York: Cold Spring Harbor Laboratory Press, 1989) manufacturing conditions or according to the conditions recommended by the manufacturer. Unless otherwise stated, percentages and parts are by weight and parts by weight.

Example 1: Construction of a PD-L1 Nanobody Library (1) 1 mg of PD-L1 antigen and Freund's adjuvant are mixed in equal volume, and a Xinjiang Bactrian camel is immunized once a week for 7 times to stimulate B cells to express antigen-specific nano-antibodies;
(2) After 7 immunizations, extract 100 mL of camel peripheral blood lymphocytes and extract total RNA;
(3) Synthesizing cDNA and amplifying VHH by nested PCR;
(4) 20 ug pMECS phage display vector (purchased from Biovector) and 10 ug VHH were digested with restriction endonucleases PstI and NotI, and two fragments were ligated to obtain a ligation product;
(5) The ligation product was transformed into a electrotransformed conventional competent cell TG1, and the PD-L1 nanobody library was constructed and the storage capacity was determined. The storage capacity was $1.5 \times 10^9$.

At the same time, 24 clones were randomly picked for colony PCR detection. The results are shown in FIG. 1. FIG. 1 shows the results of the insertion rate assay of the constructed single domain antibody library. The test results showed that the insertion rate of the library reached about 100%.

Example 2: Nanobody Screening Process for PD-L1

(1) 20 ug of PD-L1 antigen dissolved in 100 mM NaHCO$_3$ with pH 8.2 was coupled to a NUNC plate and placed at 4° C. overnight;
(2) Add 100 uL of 0.1% casein on the next day and block at room temperature for 2 h;
(3) After 2 h, add 100 uL of phage ($5 \times 10^{11}$ CFU immunized camelid nano-antibody phage display gene library) for 1 h at room temperature;
(4) Washing 5 times with 0.05% PBS+Tween-20 to wash away non-specific phage;
(5) Dissociate the phage specifically binding to PD-L1 with 100 mM TEA (triethylamine), and infect *E. coli* TG1 cells growing in log phase, incubate at 37° C. for 1 h, and produce and purify the phage for next round of screening. After the same screening process was repeated for 3-4 rounds and gradually enriched.

Example 3: Screening for Specific Single Positive Clones by Using Phage Enzyme-Linked Immunosorbent Assay (ELISA)

(1) From the cell culture dishes containing phage after 3-4 rounds of screening in Example 2, 1000 individual colonies were selected and inoculated into TB medium containing 100 μg/ml of ampicillin (1 liter of TB medium contains 2.3 g of potassium dihydrogen phosphate, 12.52 g of dipotassium hydrogen phosphate, 12 g of peptone, 24 g of yeast extract, 4 ml of glycerol), after growth to log phase, add a final concentration of 1 mmol of IPTG, culture at 28° C. overnight.

(2) The crude antibody was obtained by the infiltration method, and the antibody was transferred to an antigen-coated ELISA plate and placed at room temperature for 1 hour.

(3) Unbound antibody was washed away with PBST, and a mouse anti-HA tag antibody (anti-mouse anti-HA antibody, purchased from Beijing Kangwei Century Biotechnology Co., Ltd.) was added and placed at room temperature for 1 hour.

(4) Unbound antibody was washed away with PBST, and anti-mouse alkaline phosphatase conjugate (goat anti-mouse alkaline phosphatase-labeled antibody, purchased from Amytech Co., Ltd.) was added and placed at room temperature for 1 hour.

(5) Wash the unbound antibody with PBST, add alkaline phosphatase coloring solution, and read the absorbance at 405 nm on an ELISA apparatus.

(6) When the OD value of the sample well is more than 3 times the OD value of the control well (Ratio+/−→3), it is judged as a positive clone hole.

(7) The bacteria of the positive clone well were shaken in a LB liquid containing 100 μg per ml to extract a plasmid and perform sequencing.

Based on the sequence alignment software Vector NTI, the gene sequences of each clone were determined, and a total of 150 different antibodies were identified. The nucleotide sequence of the antibody VHH chain is shown in SEQ ID NO.: 1-150, respectively. Among them, VHH numbered n (n=a positive integer of 1-150), the amino acid sequence of which is SEQ ID NO.: n, and the corresponding coding sequence is SEQ ID NO.: 150+n.

TABLE 2

| Number | Amino acid sequences | Nucleotide sequences, | 3 CDR locations (based on amino acid sequences) | | |
|---|---|---|---|---|---|
| No. | SEQ ID NO.: | SEQ ID NO.: | CDR1 | CDR2 | CDR3 |
| 1 | 1 | 151 | 26-35 | 51-58 | 97-116 |
| 2 | 2 | 152 | 26-38 | 54-61 | 100-118 |
| 3 | 3 | 153 | 26-35 | 51-58 | 97-116 |
| 4 | 4 | 154 | 26-35 | 51-58 | 97-116 |
| 5 | 5 | 155 | 26-35 | 51-58 | 97-116 |
| 6 | 6 | 156 | 26-35 | 51-57 | 96-115 |
| 7 | 7 | 157 | 26-35 | 52-58 | 97-116 |
| 8 | 8 | 158 | 26-35 | 51-57 | 101-114 |
| 9 | 9 | 159 | 26-35 | 51-58 | 97-113 |
| 10 | 10 | 160 | 26-35 | 51-57 | 96-114 |
| 11 | 11 | 161 | 26-35 | 51-57 | 96-115 |
| 12 | 12 | 162 | 26-35 | 51-58 | 97-116 |
| ... | ... | ... | | | |
| n | n | 150 + n | | | |

The sequences of 150 strains of nanobodies are as follows, wherein the three CDR regions of the 1-12 strain of nanobodies are underlined, respectively.

SEQ ID NO. 1
QVQLQESGGGSVQTGGSLRLSCTAS TSIYSNNYMA WFSQSPGKGREGVAA VYMDDGRP YYADSVKGRFTISLDSAKNT
MYLQMNSLKPEDTAMYYC AAAPGPLSRNYWYTSANYDY WGQGTQVTVSS

SEQ ID NO. 2
QVQLQESGGGSVQAGGSLRLSCAVS RYSASNNVIKWMG WFRQAPGKEREGVAA LYTSGGNT YYADSVKGRFTISRDYS
ENTVSLQMNNLKPEDTGMYYC ATTVGTVLAGPLSARKYNY WGQGTQVTVSS

SEQ ID NO. 3
QVQLQESGGGSVQTGGSLRLSCAAS TSLYSYNYMA WFSQAPGKGREGVAA VYVGDGRP YYADSVKGRFTISLDSAKNA
VYLQMNSLKPEDTAMYYC AAAPGPLSHNYWYTSANYDY WGQGTQVTVSS

SEQ ID NO. 4
QVQLQESGGGSVQTGGSLRLSCAAS PSIYSANYMA WFSQAPGKGREGVAA VYIGDGRP YYADSVKGRFTISLDSAKNT
VYLQMNSLKPEDTAMYYC AAAPGPLGHNYWYTSANYDY WGQGTQVTVSS

SEQ ID NO. 5
QVQLQESGGGSVQTGGSLRLSCAAS TSIYSNNYMA WFSQAPGKGREGVAA VYIDDGRP YYADSVKGRFTISLDSAKNT
VYLQMNGLKPEDTAMYYC AAAPGPLSRNYWYTSANYDY WGQGTQVTVSS

SEQ ID NO. 6
QVQLQESGGGSVQAGETLRLSCTAS GDTFDASGVG WFRQVSGNECDLVSS INRDGTTY YAPSVAGRFTMSQNNAKNTV
YLQMNSLKPDDTAVYYC ATDPAVGIVVRSTCRGPFGY WGQGTQVTVSS

-continued

SEQ ID NO. 7
QVQLQESGGGSVQTGGSLRLSCACS<u>TSIYSTNYMA</u>WFSQAPGKGREGVAAV<u>YIGDGRP</u>YYADSVKGRFTISLDSAKNT
VYLQMNSLKPEDTAMYYC<u>AAAPGPLSRNYWYTSANYDY</u>WGQGTQVTVSS

SEQ ID NO. 8
QVQLQESGGDSVQAGGSLRLACKVPC<u>GFTSNTCAMA</u>WFRQAPGKEREFVSS<u>ISTGGTT</u>GYAESAKGRFTLSKDEAKDT
VYLQMNSLKPEDTAMYFCKSYAC<u>RTCIGRYCRTAPDA</u>WGQGTQVTVSS

SEQ ID NO. 9
QVQLQESGGGSVQAGGSLRLSCAAS<u>GYTYSNDGMG</u>WFRQIPGKEREGVAA<u>ISPTGRRT</u>EYADSVQGRFTISRDNAKNM
LSLQMNSLKPEDTGMYYC<u>AREGSGSFSLQNSAVRS</u>WGQGTQVTVSS

SEQ ID NO. 10
QVQLQESGGGSVQAGGSLRLSCTAP<u>GFTSKTCAMR</u>WYRQAPGKEREFVSA<u>ISTVGTTT</u>YADSVKGRFIISKDEAKDTV
YLQINSLKPEDTAMYSC<u>KTFACRHCIGQSCRTEPDY</u>WGQGTQVTVSS

SEQ ID NO. 11
QVQLQESGGGSVQAGETLRLSCTAS<u>GDTFDDSGVG</u>WFRQVSGNECDLVSS<u>INRDGTT</u>YYAPSVAGRFTISQNNAKNTV
YLQMNSLKPDDTAVYYC<u>ATVPAVGIVVRITCRGPFGY</u>WGQGTQVTVSS

SEQ ID NO. 12
QVQLQESGGGSVQAGGSLRLSCAAS<u>GYTRSSHCMV</u>WFRQAPGKEREGVAL<u>IYTGSGST</u>YYADSVKGRFTISQDNAKKT
LYLQMNSLKPEDTAMYYC<u>AAGTSSSSCPGLLGPPRYYN</u>WGQGTQVTVSS

SEQ ID NO. 13
QVQLQESGGGSVQTGGSLRLSCAASTSIYSNNYMAWFSQNPGKGREGVAAVYIGDGRPYYADSVKGRFTISLDSAKNT
VYLQMNSLKPEDTAMYYCAAAPGPLSRNYWYTSANYDYWGQGTQVTVSS

SEQ ID NO. 14
QVQLQESGGGSVQTGGSLRLSCAASTSIYSNNYMAWFSQAPGKGREGVAAVYIDDGRPYYADSVKGRFTISLDSAKNT
VYLQVNSLKPEDTAMYYCAAAPGPLSRNYWYTSANYDYWGQGTQVTVSS

SEQ ID NO. 15
QVQLQESGGGSVQTGGSLRLSCAASTSIYSNNYMAWFSQAPGKGREGVAAVYIDDGRTYYADSVKGRFTISLDSAKNT
VYLQMNSLKPEDTAMYYCAAAPGPLSYNYWYTSANYDYWGQGTQVTVSS

SEQ ID NO. 16
QVQLQESGGGSVQTGGSLRLSCAASPSIYSNNYMAWFSQAPGKGREGVAAVYIGDGRPYYADSVKGRFTISLDSAKNT
VYLQMNSLKPEDTAMYYCAAAPGPLSRNYWYTSANYDYWGQGTQVTVSS

SEQ ID NO. 17
QVQLQESGGGSVQTGGSLRLSCAASTSIYSLNYMAWFSQAPGKGREGVAAVYIDDGRPYYADHVKGRFTISLDTAKNT
VYLQMNSLKPEDTAMYYCAAAPGPLSRNYWYTSANYDYWGQGTQVTVSS

SEQ ID NO. 18
QVQLQESGGGSVQAGGSLRLSCAASGYTYSSDGMGWFRQTPGKEREGVAAISPTGRRTEYADSVKGRFTISRDNNKNM
LSLQMNSLKPEDTGMYYCAREGSWSFSLANSAVRSWGQGTQVTVSS

SEQ ID NO. 19
QVQLQESGGGSVQTGGSLRLSCAASTSIYSNNYMAWFSQAPGKGREGVAAVYIGDGRPYYADSVKGRFTISLDSAKNT
VYLQMNSLKPEDTAMYYCAAAPGPLSRNYWYTSANYDYWGQGTQVTVSS

SEQ ID NO. 20
QVQLQESGGGLVQPGGSLRLSCAASGFTGSIYAMSWVRQAPGKGLEWVSTISSSGGRRFYADSVKGRFTISRDNAKNT
LYLQLNSLKTEDTAMYYCARCSDIYCDNGASYRGQGTQVTVSS

SEQ ID NO. 21
QVQLQESGGGSVQTGGSLRLSCAASTSIYSLNYMAWFSQAPGKGREGVAAVYIGDGRPYYADSVKGRFTISLDSAKNT
VYLQMNSLKSEDTAMYYCAAAPGPLSRHYWYTSANYDYWGQGTQVTVSS

SEQ ID NO. 22
QVQLQESGGGSVQTGGSLRLSCAASTSIYSNNYMAWFSQAPRKGREGVAAVYIGDGRPYYADSVKGRFTISLDSAKNT
VYLQMNSLKPEDTAMYYCAAAPGPLSHNYWYTSANYDYWGQGTQVTVSS

```
                                                     SEQ ID NO. 23
QVQLQESGGGSVQTGGSLRLSCAASTSLYSYNYMAWFSQAPGKGREGVAAVYVGDGRPYYADSVKGRFTISLDSAKNT
VYLQMNSLKPEDTAMYYCAAAPGPLSHNYWYTSANYDYWGQGTQVTVSS

SEQ ID NO. 24
QVQLQESGGGSVQTGGSLRLSCTASTSIYSNNYMAWFSQSPGKGREGVAAVYMDDGRPYYADSVKGRFTISLDSAKNT
MYLQMNSLKPEDTAMYYCAAAPGPLSRNYWYTSANYDYWGQGTQVTVSS

SEQ ID NO. 25
QVQLQESGGGSVQTGGSLRLSCTASTSIYSNNYMAWFSQAPGKGREGVAAVYIGDGRPYYADSVKGRFTISLDSAKNT
VYLQMNSLKPEDTAMYYCAAAPGPLSHNYWYTSANYDYWGQGTQVTVSS

SEQ ID NO. 26
QVQLQESGGGSVQTGGSLRLSCAASTSIYNNNYMAWFSQAPGKEREGVAAVYIGDGRPYYADSVKGRFTISLDSAKNT
VYLQMNSLKPEDTAMYYCAAAPGPLSRNYWYTSANYDYWGQGTQVTVSS

SEQ ID NO. 27
QVQLQESGGGSVQTGGSLRLSCTASTSIYSNNYMAWFSQSPGKGREGVAAVYMDDGRPYYADSVKGRFTISLDSAKNT
MYLQMNSLKPEDTAMYYCAAAPGPLSRNYWYTSANYDYWGQGTQVTVSS

SEQ ID NO. 28
QVQLQESGGGSVQTGGSLRLSCAASTSIYSNNYMAWFRQAPGKGREGVAAVYIDDGRPYYADSVKGRFTISLDSAKNT
VYLQMNSLKPEDTAMYYCAAAPGPLSRHYWYTSANYDYWGPGTQVTVSS

SEQ ID NO. 29
QVQLQESGGGSVRTGGSLRLSCAASPSIYSNNYMAWFSQAPGKGREGVAAVYIDDGRPYYADSVKGRFTISLDSAKNT
VYLQMNSLKPEDTAMYYCAAAPGPLSRNYWYTSANYDYWGQGTQVTVSS

SEQ ID NO. 30
QVQLQESGGGSVQTGGSLRLSCTASTSIYSNNYMAWFSQAPGKGREGVAAVYIDDGRPYYADSVKGRFTISLDSAKNT
VYLQMNSLKPEDTAMYYCAAAPGPLSRNYWYTSANYDYWGQGTQVTVSS

SEQ ID NO. 31
QVQLQESGGGSVQTGGSLRLSCAASTSIYSNNYMAWFRQAPGKGREGVAGVYIGDGRPYYADSVKGRFTISLDSAKNT
VYLQMNSLKPEDTAMYYCAAAPGPLSHHYWYTSANYDYWGPGTQVTVSS

SEQ ID NO. 32
QVQLQESGGGSVQTGGSLRLSCAASTSIYSINYMAWFSQAPGKGREGVAAVYIGDGRPYYADSVKGRFTISLDSAKNT
VYLQMNSLKPEDTAMYYCAAAPGPLSQHYWYTSANYDYWGQGTQVTVSS

SEQ ID NO. 33
QVQLQESGGGSVQTGGSLRLSCACSTSIYSNNYMAWFSQAPGKGREGVAAVYIGDGRPYYADSVKGRFTISLDSAKNT
MYLQMNSLKPEDTAMYYCAAAPGPLSQHYWYTSANYDYWGQGTQVTVSS

SEQ ID NO. 34
QVQLQESGGGSVQAGGSLRLSCAASGYTRSLYCMGWFRQAPGREREGVAHVYTGDGSPYYADSVKGRFTISQDNGEST
LYLQMNNLKPEDTAMYYCAAGTSALSRPYGPISYGYWYWGQGTQVTVSS

SEQ ID NO. 35
QVQLQESGGGSVQTGGSLRLSCTASTSIYSNNYMAWFSQAPGKGREGVAAVYIDDGRPYYADSVKGRFTISLDSAKNT
VYLQMNSLKPEDTAMYYCAAAPGPLSRNYWYTSANYDYWGQGTQVTVSS

SEQ ID NO. 36
QVQLQESGGGSVQTGGSLRLSCAASTSLYSYNYMAWFSQAPGKGREGVAAVYVGDGRPYYAASVKGRFTISLDSAKNT
VYLQMNSLKPEDTAMYYCAAAPGPLSHNYWYTSANYDYWGQGTQVTVSS

SEQ ID NO. 37
QVQLQESGGGSVQTGGSLRLSCAASTSIYSINYMAWFRQAPGKGREGVAAVYIDDGRPYYADSVKGRFTISLDSAKNT
VYLQMTSLKSEDTAMYYCAAAPGPLSRSYWYTSANYDYWGQGTQVTVSS

SEQ ID NO. 38
QVQLQESGGGSVQTGGSLRLSCAASTSIYSNNYMAWFSQAPGKGREGVAAVYIGDGRPYYADSAKGRFTISLDSAKNT
VYLQMNSLKPEDTAMYYCAAAPGPLSRNYWYTSANYDYWGQGTQVTVSS
```

```
                                               SEQ ID NO. 39
QVQLQESGGGSVQTGGSLRLSCAASTSIYSNNYMAWFSQAPGKGREGVAALYIGDGRPYYADSVKGRFTIALDSAKNT
VYLQMNGLKPEDTAMYYCAAAPGPLKHNYWYTSANYDYWGQGTQVTVSS

SEQ ID NO. 40
QVQLQESGGGSVQTGGSLRLSCAASTSIYSNNYMAWFSQAPGKGREGVAALYIGDGRPYYADSVKGRFTIALDSAKNT
VYLQMNGLKPEDTAMYYCAAAPGPLKHNYWYTSANYDYWGQGTQVTVSS

SEQ ID NO. 41
QVQLQESGGGSVQTGGSLRLSCAASTSIYSNNYMAWFRQAPGKGREGVAAVYIGDGRPYYADSAKGRFTISLDSAKNT
VYLQMNSLKPEDTAMYYCAAAPGPLSRHYWYTSANYDYWGPGTQVTVSS

SEQ ID NO. 42
QVQLQESGGGSVQTGGSLTLSCAASTSIYSYNYMAWFRQAPGKGREGVAAVYIGDGRPYYADSVKGRFTISPDSAKNT
VYLQMNSLKPEDTAMYYCAAAPGPLSRHYWYTSANYDYWGPGTQVTVSS

SEQ ID NO. 43
QVQLQESGGGSVQTGGSLRLSCAASSSIASNNYMAWFSQAPGKGREGVAAVYIGDGRPYYADSVKGRFTISLDSAKNT
VYLQMNSLKPEDTAMYYCAAAPGPLSRNYWYTSANYDYWGQGTQVTVSS

SEQ ID NO. 44
QVQLQESGGGSVRTGGSLRLSCAASTSIYSLNYMAWFSQAPGKGREGVAAVYIDDGRPYYADHVKGRFTISLDTAKNT
VYLQMNSLKPEDTAMYYCAAAPGPLSRNYWYTSANYDYWGQGTQVTVSS

SEQ ID NO. 45
QVQLQESGGGLVQPGGSLRLSCAASGFTFSIKAMSWVRQAPGKGLEWVSTIDSGGGRRYYADSVKGRFTISRDNAKNT
LYLQLSSLKTEDTAMYFCARCSDIYCYNGASYRGQGTQVTVSS

SEQ ID NO. 46
QVQLQESGGGSVQTGGSLRLSCAASTSIDSNNYMAWFRQAPGKGREGVAAVYIDDGRPYYADSVKGRFTISLDSAKNT
VYLQMNSLKPEDTAMYYCAAAPGPLSRHYWYTSANYDYWGPGTQVTVSS

SEQ ID NO. 47
QVQLQESGGGSVQTGGSLRLSCTASTSIYNNNYMAWFSQSPGKGREGVAAVYMDDGRPYYADSVKGRFTISLDSAKNT
MYLQMNSLKPEDTAMYYCAAAPGPLSRNYWYTSANYDYWGQGTQVTVSS

SEQ ID NO. 48
QVQLQESGGGSVQTGGSLRLSCAASTSIYSNNYMAWFSQAPGKGREGVAAVYIDDGRTYYADSVKGRFTISLDSAKNT
VYLQMNSLKPEDTAMYYCAAAPGPLSHNYWYASANYDYWGQGTQVTVSS

SEQ ID NO. 49
QVQLQESGGGSVQTGGSLRLSCAASTSIYSINYMAWFSQAPGKGREGVAAVYIDDGRPYYADSVKGRFTISLDSAKNT
VYLQMNSLKPEDTAMYYCAAAPGPLSRNYWYTSANYDYWGQGTQVTVSS

SEQ ID NO. 50
QVQLQESGGGLVQPGGSLRLSCIASGFTFSIMAMSWVRQAPGKGLEWVSTINSDGGKTYYADSVKGRFTISRDNAKNT
LYLQLNSLRTEDMAMYYCRRCADIYCSGSGGWTGQGTQVTVSS

SEQ ID NO. 51
QVQLQESGGGSVQTGGSLRLSCTASTSIYSNSYMAWFSQAPGKGREGVAAVYIDDGRPYYADSVKGRFTISLDSAKNT
VYLQMNSLKPEDTAMYYCAAAPGPLSRHYWYTSANYDYWGQGTQVTVSS

SEQ ID NO. 52
QVQLQESGGGSVQTGGSLRLSCAASTSIYSNNYMAWFRQAPGKGREGVAAVYVDDGRPYYADSVKGRFTISRDSAKNT
VYLQMNSLKPEDTAMYYCAAAPGPLSRHYWYTSANYDYWGPGTQVTVSS

SEQ ID NO. 53
QVQLQESGGGSVQTGGSLRLSCAASTSIYSNNYMAWFSQAPGKGREGVAAVYIDDGRPYYADSVKGRFTISLDSAKNT
VYLQMNSLKPEDTAMYYCAAAPGPLSRNYWYTSANYDYWGQGTQVTVSS

SEQ ID NO. 54
QVQLQESGGGSVQTGGSLRLSCAPSTSIYDNNYMAWFSQAPGKGREGVAAIYIDDGRPYYADSVKGRFTISLDSAKNT
VYLQMNSLKPEDTAMYYCAAAPGPLSHNYWYTSANYDYWGQGTQVTVSS
```

```
                                                         SEQ ID NO. 55
QVQLQESGGGSVQTGGSLRLSCVASTSIFSNNYMAWFSQAPGKGREGVAAVYIGDGRPYYADSVKGRFTISLDSAKNT
VYLQMNSLKPEDTAMYYCAAAPGPLSHNYWYTSANYDYWGQGTQVTVSS

SEQ ID NO. 56
QVQLQESGGGSVQTGGSLRLSCAASPSIYSANYMAWFSQAPGKGREGVAAVYIGDGRPYYADSVKGRFTISLDSAKST
VYLQMNSLKPEDTAMYYCAAAPGPLSHNYWYTSANYDYWGQGTQVTVSS

SEQ ID NO. 57
QVQLQESGGGSVQTGGSLRLSCAASTSIYSINYMAWFSQAPGKGREGVAAVYIDDGRPYYADSVKGRFTISLDSAKNT
VYLQMNSLKSEDTAMYYCAAAPGPLSRNYWYTSANYDYWGQGTQVTVSS

SEQ ID NO. 58
QVQLQESGGGLVQPGGSLRLSCALSGFTSTIYAMSWVRQAPGKGLEWVSTINSDGGYRYYADSVKGRFTISRDNAKNT
LYLQLNSPKTEDTAMYYCARCSDIYCYNGPSYRGQGTQVTVSS

SEQ ID NO. 59
QVQLQESGGGSVQTGGSLRLSCACSTSIYSNNYMAWFSQAPGKGREGVAAVYIGDGRPYYTDSVKGRFTISLDSAKNT
LYLQMNSLKPEDTAMYYCAAAPGPLSHNYWYTSANYDYWGQGTQVTVSS

SEQ ID NO. 60
QVQLQESGGGSVQTGGSLRLSCAASTSIYSMNYMAWFSQAPGKGREGVAAVYIEDGRPYYADSVKGRFTISPDRAKNT
VYLQMNSLKPEDTAMYYCAAAPGPLSRNYWYTSANYDYWGQGTQVTVSS

SEQ ID NO. 61
QVQLQESGGGLVQPGGSLRLSCAASGFDFSSRAMSWVRQAPGKGLEWVSTINSGGGSRYYADSVKGRFTTSRDNAKNT
LALQLNSLKTEDTAMYYCARCSDIYCDNGAWYRGQGTQVTVSS

SEQ ID NO. 62
QVQLQESGGGSVQAGGSLRLSCAASTSIYSNNYMAWFRQTPGKGREGVAAVYIDDGRPYYADSVKGRFTISLDSAKNT
VYLQMNSLKPEDTAMYYCAAAPGPLSHDYWYTSANYDYWGPGTQVTVSS

SEQ ID NO. 63
QVQLQESGGGSVQTGGSLRLSCAASTSIYSNNYMAWFSQAPGKGREGVAAVYIDDGRPYYADSVKGRFTISLDSAKNT
VYLQMNRLKPEDTAMYYCAAAPGPLSHNYWYTSANYDYWGQGTQVTVSS

SEQ ID NO. 64
QVQLQESGGGSVQTGGSLRLSCAASTSIYSNNYMAWFSQAPGKGREGVAAVYIDDGRPYYADSVKGRFTISLDSAKNT
VYLQMNSLKPEDTAMYYCAATPGPLSQHYWYTSANYDYWGQGTQVTVSS

SEQ ID NO. 65
QVQLQESGGGLVQPGGSLRLSCAASGFTFSILAMSWVRQAPGKGLEWISTINNSGGTTFYADSVKGRFTISRDNAKNT
LYLQLNSLRTEDTAMYYCRRCTDIYCSLSGGWTGQGTQVTVSS

SEQ ID NO. 66
QVQLQESGGGSVQTGGSLRLSCAASTSIYNNNYMAWFSQAPGKGREGVAAVYVGDGRTYYADSVKGRFTISLDSAKNT
VYLQMNSLKPEDTAMYYCAAAPGPLSHNYWYTSANYDYWGQGTQVTVSS

SEQ ID NO. 67
QVQLQESGGGSVQTGGSLRLSCTASTSIYSNNYMAWFSQAPGKGREGVAAVYIDDGRPYYADSVKGRFTISLDSAKNT
VYLQMNSLKPEDTAMYYCAAAPGPLSRNYWYTSANYDYWGQGTQVTVSS

SEQ ID NO. 68
QVQLQESGGGSVQTGGSLRLSCTCSTSIYSNNYMAWFSQAPGKGREGVAAVYIGDGRPYYADSVKGRFTISLDSAKNT
VYLQMNSLKPEDTAMYYCAAAPGPLSHNYWYTSANYDYWGQGTQVTVSS

SEQ ID NO. 69
QVQLQESGGGSVQTGGSLRLSCAASTSIYSNNYMAWFSQAPGKGREGVAAVYIGDGRPYYADSVKGRFTISLDSAKNT
VYLQMNSLKPEDTAMYYCAAAPGPLSHNYWYTSANYDYWGQGTQVTVSS

SEQ ID NO. 70
QVQLQESGGGLVQPGGSLRLSCAASGFTFSIRAMSWVRQAPGKGLEWVSTINSGGDSRYYADSVKGRFTISRDNAKNT
MYLQLNSLKTEDTAMYYCVRCSDIYCYNGASYRGQGTQVTVSS
```

```
                                                       SEQ ID NO. 71
QVQLQESGGGLVQPGGSLRLSCAASGFTFSSYDMSWVRQAPGKGIEWVSVINSGGSNTDYADSVKGRFTISRDNAKNT
LYLQMNSLKTEDTAVYYCATAWMGYSDYLDGIARGQGTQVTVSS

SEQ ID NO. 72
QVQLQESGGGLVQPGGSLRLSCEASGLPFSIIAMSWVRQAPGKGLEWVSTINSDGGTTHYADSVKGRFTISRDNAKNT
LYLQLNSLRTEDTAMYYCRRCTDIYCSGSGGWTGQGTQVTVSS

SEQ ID NO. 73
QVQLQESGGGLVQPGGSLRLSCEASGLPFSIIAMSWVRQAPGKGLEWVSTINSDGGTTHYADSVKGRFTISRDNAKNT
LYLQLNSLRTEDTAMYYCRRCTDIYCSGFGGWTGQGTQVTVSS

SEQ ID NO. 74
QVQLQESGGGSVQAGGSLRLSCAASGFTGSIYAMSWVRQAPGKGLEWVSTISSSGGRRFYADSVKGRFTISRDNAKNT
LYLQLNSLKTEDTAMYYCARCSDIYCDNGASYRGQGTQVTVSS

SEQ ID NO. 75
QVQLQESGGGSVQTGGSLRLSCAASTSIYSNNYMAWFRQAPGKGREGVAAVYIGDGRPYYADSAKGRFTISLDSAKNT
VYLHMNSLKPEDTAMYYCAAAPGPLSRHYWYTSANYDYWGPGTQVTVSS

SEQ ID NO. 76
QVQLQESGGGSVQTGGSLRLSCAASTSIYSNNYMAWFRQVPGKGREGVAAVYIDDGRTYYADSVKGRFTISLDSAKNT
VYLQMNSLKPEDTAMYYCAAAPGPLSRHYWYTSANYDYWGPGTQVTVSS

SEQ ID NO. 77
QVQLQESGGGSVQTGGSLRLSCTASTSIYSNNYMAWFSQAPGKGREGVAAVYIDDGRPYYADSVKGRFTISLDSAKNT
VYLQMNSLKPEDTAMYYCAAAPGPLSRNYWYTSANYDYWGQGTQVTVSS

SEQ ID NO. 78
QVQLQESGGGSVQTGGSLRLSCAASTSLYSYNYMAWFSQAPGKGREGVAAVYVGDGRPYYADSVKGRFTISLDSAKNT
VYLQMNSLKPEDTAMYYCAAAPGPLSHNYWYTSANYDYWGQGTQVTVSS

SEQ ID NO. 79
QVQLQESGGGLVQPGGSLRLSCAASGLPFSIIAMSWVRQAPGKGIEWVSTINSGGGTTHYADSVKGRFTISRDNAKNT
LYLQLNSLRTEDTAVYYCRRCADIYCSGSGGWTGLGTQVTVSS

SEQ ID NO. 80
QVQLQESGGGSVQTGGSLRLSCVASTSIYSNNYMAWFSQAPGKGREGVAAVYIDDGRPYYADSVKGRFTISLDSAKNT
VYLQMNSLKPEDTAMYYCAAAPGPLSRSYWYTSANYDYWGQGTQVTVSS

SEQ ID NO. 81
QVQLQESGGGSVQTGGSLRLSCAASTSIYSNNYMAWFSQAPGKGREGVAAVYIDDGRTYYADSVKGRFTISLDSAKNT
VYLQMNSLKPEDTAMYYCAAAPGPLSRNYWYTSANYDYWGQGTQVTVSS

SEQ ID NO. 82
QVQLQESGGGSVQTGGSLRLSCTASTSIYSNNYMAWFSQAPGKGREGVAAVYIDDGRPYYADSVKGRFTISLDSAKNT
VYLQMNSLKPEDTAMYYCAAAPGPLSRNYWYTSANYDYWGQGTQVTVSS

SEQ ID NO. 83
QVQLQESGGGLVQTGGSLRLSCAASTSIYSNNYLAWFSQAPGKGREGVAAVYIGDGRPYYADSVKGRFPISLNSAQNK
VYLQMNSLKPEDTAMYYCAAAPGPLSRNYWYTSANYDYWGQGTQVTVSS

SEQ ID NO. 84
QVQLQESGGGSVQTGGSLRLSCAASTSIDSNNYMAWFRQAPGKGREGVAAVYIDDGRPYYADSVKGRFTISLDSAKNT
VYLQMNSLKPEDTAMYYCAAAPGPLSRHYWYTSANYDYWGPGTQVTVSS

SEQ ID NO. 85
QVQLQESGGGSVQTGGSLRLSCAASTSIYSNNYMAWFSQAPGKGREGVAAVYIADDRPYYADSVKGRFTISLDSAKNT
VYLQMNSLKPEDTAMYYCAAAPGPLSRNYWYTSANYDYWGQGTQVTVSS

SEQ ID NO. 86
QVQLQDSGGGSVQTGGSLRLSCAASTSIYSINYMAWFSQAPGKGREGVAAVYTGDGRPYYADSVKGRFTISLDSAKNT
VYLQMNSLKPEDTAMYYCAAAPGPLSRNYWYTSANYDYWGQGTQVTVSS
```

-continued

SEQ ID NO. 87
QVQLQESGGGSVQAGGSLRLSCAASGYTRSSYCMGWFRQAPGKERERVAYIYSGSGSTHYADSVKGRFTISQDNGKNT
LYLQMNNLKPEDTAMYYCAAGTSGTSCPTGAFMYEYWYWGQGTQVTVSS

SEQ ID NO. 88
QVQLQESGGGSVQAGGSLRLSCAASTSIYSNNYMAWFRQAPGKGREGVAAVYVGDGRPYYADSVKGRFTISLDSAKNT
VYLQMNSLKPEDTAMYYCAAAPGPLSHNYWYTSANYDYWGQGTQVTVSS

SEQ ID NO. 89
QVQLQESGGGSVQTGGSLRLSCAASTSIYSNNYMAWFSQAPGKGREGVAAVYIGDGRPYYADSVKGRFTISLDSARNT
VYLQMNSLKPEDTAMYYCAAAPGPLSRHYWYTSANYDYWGQGTQVTVSS

SEQ ID NO. 90
QVQLQESGGGSVQAGGSLRLSCAASTSIYSNNYMAWFSQAPGKGREGVAAVYIDDGRPYYADSVKGRFTISLDSAKNT
VYLQMNSLKPEDTAMYYCAAAPGPLSRNYWYTSANYDYWGQGTQVTVSS

SEQ ID NO. 91
QVQLQESGGDLVQPGGSLRLSCAASGLPFSIIAMSWVRQAPGKGLEWVSTINNDGGTTHYADSVKGRFTISRDNAKNT
LYLQLNSLRTEDTAMYYCRRCTDIYCSGSGGWTGQGTQVTVSS

SEQ ID NO. 92
QVQLQESGGGSVQTGGSLRLSCAASTSIYNNNYMAWFRQAPGKGREGVAAVYIDDGRPYYADSVKGRFTISLDSAKNT
VYLQMNSLKPEDTAMYYCAAAPGPLSRHYWYTSANYDYWGPGTQVTVSS

SEQ ID NO. 93
QVQLQESGGGSVQTGGSLRLSCAASTSIYSNNYMAWFRQAPGKGREGVAAVYIGDGRTYYADSAKGRFTISLDSAKNT
VYLHMNSLKPDDTAMYYCAAAPGPLTRHFWYTSANYDYWGPGTQVTVSS

SEQ ID NO. 94
QVQLQESGGGSVQTGGSLRLSCAASTSLYSYNYMAWFSQAPGKGRGGVAAVYVGDGRPYYADSVKGRFTISLDSAKNT
VYLQMNSLKPEDTAMYYCAAAPGPLSHNYWYTSANYDYWGQGTQVTVSS

SEQ ID NO. 95
QVQLQESGGGSVQAGGSLRLSCAASGYTVSNNYMGWFRQAPGKGREGVAAVYIGDGRPYYADSVKGRFTISLDSAKNT
VYLQMNSLKPEDTAMYYCAAAPGPLSQHYWYTSANYDYWGQGTQVTVSS

SEQ ID NO. 96
QVQLQESGGGLVQPGGSLRLSCAAFGFTFGSYWMKWVRQAPGKDLEWVPIIDNGGRSTWYADSVKGRFTISRDNAKNS
LYLQLNSLKIEDTAMYYCADRNGNRGQGTQVTVSS

SEQ ID NO. 97
QVQLQESGGGSVQTGGSLRHSCAASTSIYSNNYMAWFSQAPGKGREGVAAVYIDDGRPYYADSVKGRFTISLDSAKNT
VYLQMNSLKPEDTAMYYCAAAPGPLSHNYWYTSANYDYWGQGTQVTVSS

SEQ ID NO. 98
QVQLQESGGGSVQTGGSLRHSCAASTSIYSNNYMAWFSQAPGKGREGVAAVYIDDGRPYYADSVKGRFTISLDSAKNT
VYLQMNSLKPEDTAMYYCAAAPGPLSHNYWYTSANYDYWGQGTQVTVSS

SEQ ID NO. 99
QVQLQESGGGSVTTGGSLRLSCAASTSIYSNNYMAWFRQAPGKGREGVAAVYIGDGRPYYADSVKGRFTISLDSAKNT
VYLQMNSLKPEDTAMYYCAAAPGPLSRHYWYTSANYDYWGPGTQVTVSS

SEQ ID NO. 100
QVQLQESGGGLVQPGGSLRLSCAASGFTFSIMAMSWVRQAPGRGLEWVSTINSDGGKTYYADSVKGRFTASRDNAKNT
LYLQLNSLRTEDTAMYYCRRCADIYCSGSGGWTGQGTQVTVSS

SEQ ID NO. 101
QVQLQESGGGSVQTGGSLRLSCAVSGFTDTYFALGWFRQAPGKEREGVAAIDSDGSTSYADSVKGRFTISKDNAKNTV
YLQMNSLKPEDTAMYYCAAAPGPLSRNYWYTSANYDYWGQGTQVTVSS

SEQ ID NO. 102
QVQLQESGGGSVQTGGSLRLSCAASTSIYSNNYMAWFRQAPAKGREGVAAVYIGDGRPYYADSVKGRFTISLDSAKNT
VYLQMNSLKPEDTAIYYCAAAPGPLSRHYWYTSANYDYWGPGTQVTVSS

SEQ ID NO. 103
QVQLQESGGGSVQTGGSLRLSCAASTSIYNNNYMAWFSQAPGKGREGVAAVYIEDGRPYYADSVKGRFTISLDSAKNT
VYLQMNSLKPEDTAMYYCAAAPGPLSRNYWYTSANYDYWGQGTQVTVSS

SEQ ID NO. 104
QVQLQESGGGSVQTGGSLRLSCAASTSIYSNNYMAWFRQAPGKGREGVAAVYIDDGRTYYADSVKGRFAISLDSAKNT
VYLQMNSLKPEDTAMYYCAAAPGPLSRHYWYTSANYDYWGPGTQVTVSS

SEQ ID NO. 105
QVQLQESGGGLVQPGGSLRLSCAASGFTFSSLAMSWVRQAPGKGLEWVSTINSGGVYTYYADSVKGRFTISRDNAKNT
LYLQLNNLRTEDTAMYYCRRCTDIYCSGSGGWTGQGTQVTVSS

SEQ ID NO. 106
QVQLQESGGGLVQPGGSLRLSCAVSGFTFSIIAMSWVRQAPGKGLEWVSTINSDGGTTYYADSVKGRFTISRDNAKNT
LYLQLNSLRTEDTAMYYCRRCADIYCSGSGGWTGQGTQVTVSS

SEQ ID NO. 107
QVQLQESGGGLVQPGGSLRLSCEASGLPFSIIAMSWVRQAPGKGLEWVSTINSDGGTTHYADSVKGRFTISRDNAKNT
LYLQLNSLRSEDTAMYYCRRCTDIYCSGSGGSTKGQGTQVTVSS

SEQ ID NO. 108
QVQLQESGGGSVQTGGSLRLSCAASTSIYSNNYMAWFRQAPGKGREGVAAVYIGDGRPYYADSVKGRFTISLDSAKNT
VYLQMNSLKPEDTAMYYCAAAPGPLSRHYWYTTANYDYWGPGTQVTVSS

SEQ ID NO. 109
QVQLQESGGGSVQAGGSLRLSCAASGYTRSSYCMGWFRQAPGKERERVAHIYTGSGTTHYADSMKGRFTISQDNGKNT
LYLQMNNLKPEDTAMYYCAAGTSGTSCATGPFVYGYWYWGQGTQVTVSS

SEQ ID NO. 110
QVQLQESGGGSVQAGGSLRLSCAYTPRRLCMGMGWFRQGLGKEREGVATIDDAGSTTYADSVKARFTISQDNAKNTLY
LQMDSLKPEDSAMYYCAARAGVGWYQVSCPEESRTSAFVYWGQGTQVTVSS

SEQ ID NO. 111
QVQLQESGGGSVQTGGSLRLSCAASTSIYNNNYMAWFSQAPGKGREGVAAVYIEDGRPYYADSVKGRFTISLDSAKNT
VYLQMNSLKPEDTAMYYCAAAPGPLSRNYWYTSANYDYWGQGTQVTVSS

SEQ ID NO. 112
QVQLQESGGGLVQPGGSLRLSCAASGLTFSIVAMSWVRQAPGKGLEWVSTINSDGGSTYYADSVKGRFTISRDNAKNT
LYLQLNSLRTEDTAMYYCRRCTDIYCSGSGGWTGQGTQVTVSS

SEQ ID NO. 113
QVQLQESGGGSVQTGGSLRLSCAASTSIISFNYMAWFRRAPGKGREGVAAVYIDDGRPYYADSVKGRFTISLDSAKNT
VYLQMGSLRPEDTAMYYCAAAPGPLSRNYWHTPANYDYWGQGTQVTVSS

SEQ ID NO. 114
QVQLQESGGGSVQTGGSLRLSCAASGYAGRLYSMGWFRQVAGKEREGVSSIESDGSTFYTDSVKGRFTTTRDSAKNTL
YLQMNNLKPEDTAMYYCAAFCLRVGHGGRCTEYKYWGRGTQVTVSS

SEQ ID NO. 115
QVQLQESGGGSVQAGGSLRLSCAASGYTRSSYCMGWFRQAPGKERERVAHIYTGSGSTHYADSVKGRFTISQDNGKNT
LYLQMNNLKPEDTAMYYCAAGTSGTSCATGPFVYKYWYWGQGTQVTVSS

SEQ ID NO. 116
QLQESGGGLVQPGGSLRLSCAASGFAFSTYAMSWVRQAPGKGLEWVSGINGGGGNTYYADSVKGRFTISRDNAKNTLY
LQLNSLKTEDTAMYYCGQGAYWAYCNGGYCNPPGQGTQVTVSS

SEQ ID NO. 117
QVQLQESGGGSVQTGGSLRLSCAASTSIYSNNYMAWFSQAPGKGREGVAAVYIGDGRPYYADSVKGRFTISLDSAKDT
VYLQMNSLKPEDTAMYYCAAAPGPLSRNYWYTSANYDYWGQGTQVTVSS

SEQ ID NO. 118
QVQLQESGGGSVQTGGSLRLSCAASASIYSNNYMAWFSQAPGKGREGVAAVYIGDGRPYYDDSVKGLFTISLDSAKNT
VYLQMNSLKPEDTAMYYCAAAPGPLIRNYWYTSANYDYWGQGTQVTVSS

-continued

SEQ ID NO. 119
QVQLQESGGGSVQTGGSLRLSCAASTSLYSYNYMAWFSQAPGKGREGVAAVYVGDGRPYYADSVKGRFTISLDSAKNT
VYLQMNSLKPEDTAMYYCAAAPGPLSRNYWYTSANYDYWGQGTQVTVSS

SEQ ID NO. 120
QVQLQESGGGSVQAGGSLRLSCTAPGFTSNTCAMAWFRQAPGKEREFVSSMSTVGSTRFADSVKGRFTISKDEVKDTV
YLQMNSLKPEDTAMYFCKTYACRECTGRYCRTAPDAWGQGTQVTVSS

SEQ ID NO. 121
QVQLQESGGGSAQAGGSLRLSCTAPGFTSNTCAMAWYRQAPGKEREFVSSRSTVGTTGYADSVKGRFTISKDEAKDTV
YLQMNSLKPEDTAMYFCKTYACRNCIGRHCRTAPDAWGQGTQVTVSS

SEQ ID NO. 122
QVQLQESGGGSVQAGGSLRLSCTAPGFTSNTCAMAWFRQAPGKEREFVSSLSTVGTTGYADSVKGRFTISKDEAKDTV
YLLMNSLKPEDTAMYFCKTFACRDCSGRYCRTAPDAWGQGTQVTVSS

SEQ ID NO. 123
QVQLQESGGGSVQAGGSLRLSCTAPGFTSNTCAMAWYRQAPGKEREFVSSRSTVGTTGYADSVKGRFTISKDEAKDTV
YLQMNSLKPEDTAMYFCKTYACRNCIGRHCRTAPDAWGQGTQVTVSS

SEQ ID NO. 124
QVQLQESGGGSVQAGRSLRLSCAVSRYSASNNVIKWMGWFRQAPGKEREGVAALYTSGGNTYYADSVKGRFTISRDYS
ENTVSLQMNNLKPEDTGMYYCAATVGTVLAGPLSARKYNYWGQGTQVTVSS

SEQ ID NO. 125
QVQLQESGGGLVQPGGSLRLSCAASGFTFSNSDMAWFRQAPGKGLEWVSVIDSGGGYTYYADSVKGRFTISRDNAENT
LYLQLNSLKTEDTAMYYCAKTDLRYSRIYPYGKWGQGTQVTVSS

SEQ ID NO. 126
QVQLQESGGGSVQAGRSLRLPCAVSRYSASNNVIKWMGWFRQAPGKEREGVAALYTSGGNTYYADSVKGRFTISRDYS
ENTVSLQMNNLKPEDTGMYYCAATVGTVLAGPLSARKYNYWGQGTQVTVSS

SEQ ID NO. 127
QVQLQESGGGLVQAGGSLTLSCRGSGFTSNTCAMAWFRQAPGKEREFVSSMSTVGSTRFADSVKGRFTISKDEAKDTV
YLQMNSLKPEDTAMYFCKTYACRECTGRYCRTAPDAWGQGTQVTVSS

SEQ ID NO. 128
QVQLQESGGGSVQAGGSLRLSCTAPGFTSNTCAMAWFRQAPGKEREFVSSMSTGGTTGYGDSVKGRFTSSKDAAKDTV
YLQMNSLKPEDTAIYFCKTYACRDCIGRYCRTAPDAWGQGTQVTVSS

SEQ ID NO. 129
QVQLQESGGGSVQAGGSLRLSCTAPGFTSNTCAMAWYRQAPGKEREFVSSRSTVGTTGYADSVKGRFTLSKDEAKDTV
YLQMNSLKPEDTAMYFCKTYACRNCIGRHCRTAPDAWGQGTQVTVSS

SEQ ID NO. 130
QVQLQESGGGSVQAGETLRLSCTVSGDTFEASGVGWFRQVSGNECDLVSSINRDGTTYYTPSVAGRFTMSQNNAKNTV
YLQMNSLKPDDTAVYYCATDPAVGIVVRSTCRGPFGYWGQGTQVTVSS

SEQ ID NO. 131
QVQLQESGGGSVQAGGSLRLSCTVSGNTDSMNLMGWFRQAPGKEREGVASIYTGSRTITYPDSVKGRFTISQDNAKNT
VYLQMNSLKPEDTAMYYCAADYRARYGASLRTSAYTYWGQGTQVTVSS

SEQ ID NO. 132
QVQLQESGGGSVQAGGSLRLSCTAPGFTSNTCAMAWYRQAPGKEREFVSSRSTVGTTGYADSVKGRFTISKDEAKDTV
YLQMNSLKPEDTAKYFCKTYACRDCIGRYCRTAPDAWGQGTQVTVSS

SEQ ID NO. 133
QVQLQESGGGSVQAGGSLKLSCVVSGYTWCRYDMSWYRQAPGKEREFVSVIDDNGSTNYADSVKGRFTISKDNGNTVT
LQMTSLKPADTAMYYCQTGRYRSRLGYGRCPSGDYWGLGTQVTVSS

SEQ ID NO. 134
QVQLQESGGGSVQAGGSLRLSCAVSGYSISNYCMGWFRQPPGKEREGVANIDTWGVTSYTDSVKGRFTISKDNAKNTL
YLQMNSLKPEDTALYYCARRQFVNCGTLAPVNYVNWGQGTQVTVSS

-continued

SEQ ID NO. 135
QVQLQESGGGSVQAGGSLRLSCTASGFTFSTLAMSWVRQAPGKGLEWVSTISSTGGATYYADSVKGRFTISRDNAKNT
LYLQLNSLKPEDTAMYYCRRCTDIYCSNSARWTGQGTQVTVSS

SEQ ID NO. 136
QVQLQESGGGLVQPGGSLRLSCTASGFTFSTLAMSWVRQAPGKGLEWVSTISSTGGATYYADSVKGRFTISRDNAKNT
LYLQLNSLKPEDTAMYYCRRCTDIYCSNSARWTGQGTQVTVSS

SEQ ID NO. 137
QVQLQESGGGLVQPGGSLRLSCVASGFSFSSSGMSWVRQAPGKGLEWVSTISYNGGSTFYTDSVKGRFTISRDNAKNT
LYLQLNSLKTEDTAMYYCAKSGTPVLAPNSVRGQGTQVTVSS

SEQ ID NO. 138
QVQLQESGGGSVQAGGSLRLSCVSSGYAYNRYYMAWFSQAPGKGREGVAAVYIGDGRPYYADSVKGRFTISLDSAKNT
VYLQMNSLKPEDTAMYYCAAAPGPLSRNYWYTSANYDYWGQGTQVTVSS

SEQ ID NO. 139
QVQLQESGGGSVQAGGSLRLSCVASGYTNCRYDMSWYRQAPGKEREFVSSIDSEGVARHADSVKGRFGISQDNAKSTL
YLQMNSLKPEDTAVYYCKTDYITCRFGSWSDSTWGQGTQVTVSS

SEQ ID NO. 140
QVQLQESGGGSVQAGGSLRLSCVASGYTNCRYDMSWYRQAPGKEREFVSSIDSEGVARHADSVKGRFGISQDNAKSTL
YLQMNSLKPEDTAMYYCKMDYIRCRFGSWSESTWGQGTQVTVSS

SEQ ID NO. 141
QVQLQESGGGSVQAGGSLRLSCTAPGFTSNTCAMAWFRQAPGKEREFVSSMSTVGSTRFADSVKGRFTISKDEAKDTV
YLQMNSLKPEDTAMYFCKTYACRECTGRYCRTAPDAWGQGTQVTVSS

SEQ ID NO. 142
QVQLQESGGGSVQTGGSLRLSCAVSRYSASNNVIKWMGWFRQAPGKEREGVAALYTSGGNTYYADSVKGRFTISRDYS
ENTVSLQMNNLKPEDTGMYYCAATVGTVLAGPLSARKYNYWGQGTQVTVSS

SEQ ID NO. 143
QVQLQESGGGSVQAGGSLRLSCTAPGFTSNTCAMAWYRQAPGKEREFVSSISTVRTTAYADSVKGRFTISKDEAKATV
YLQMNSLKPEDTAMYFCKSYACRDCIGRYCRTAPDAWGQGTQVTVSS

SEQ ID NO. 144
QVQLQESGGGSVQAGQSLRLSCTASGYTDSRYCMGWFRQAPGKERERVTTIHTGTGITYYADSVKGRFSISQDNAQNT
MYLQMNSLEPEDTAMYYCATTDYVYSASASWCNGYGVFNNWGQGTQVTVSS

SEQ ID NO. 145
QVQLQESGGGSVQAGGSLRLSCTAPGFTSNTCAMAWYRQAPGKEREFVSSRSTVGTTGYADSVKGRFTISKDEAKDTV
YLQMNSLKPEDTAKYFCKTYACRDCIGRYCRTAPDAWGQGTQVTVSS

SEQ ID NO. 146
QVQLQESGGGSVQAGGSLRLSCAVSRYSASNNVIKWMGWFRQAPGKEREGVAALYTSGGNTYYADSVKGRFTISRDYS
ENTVSLQMNNLKPEDTGMYYCATTVGTVLAGPLSARKYNYWGQGTQVTVSS

SEQ ID NO. 147
QVQLQESGGGSVQAGGSLRLSCAASGYTSRPNFMVWFRQAPGKEREAVAGIYTVTGGTLYSDPVKGRFTISQDKAKNT
VYLQMNSLNPEDTAMYYCAVKWYGGSWSDAATFRTWGRGTQVTVSS

SEQ ID NO. 148
QVQLQESGGGSVQAGGSLRLSCAASGYSYNIDYMAWFRQAPGKEREGVAAIYTGSRRTYYSDSVKGRFAISQDNADNT
VYLQMNALKPEDTAMYFCAALVSRPGRSWDKNEYRYWGQGTQVTVSS

SEQ ID NO. 149
QVQLQESGGGLVQAGGSLRLSCTASGFTFDDYSMGWFRQAPGKEREGISCIDWSGGRTNYGDSVKGRFTISRDNAKNT
LYLQMNSLKPEDTAMYYCAANSAYSSCSLSTTHYKYWGQGTQVTVSS

SEQ ID NO. 150
QVQLQESGGGLVQPGGSLRLSCAASGFTFSAYGMSWVRQAPGKGFEWVSTINSGGGTTFYADSVKGRFTISRDNAKNT
LYLQLNSLRTEDTAMYYCRRCADIYCSLSGGWTGQGTQVTVSS

Combined with PE-LISA results, these VHH chains were classified into four categories according to the OD ratio (experimental group ($A_{405}$ nm)/control group ($A_{405}$ nm)), and the classification results are shown in Table 3.

TABLE 3

Affinity of nanobodies

| OD ratio (experimental group ($A_{405}$ nm)/control group ($A_{405}$ nm)) | Nanobody |
|---|---|
| >20 | SEQ ID NO.: 1-86 |
| 10-20 | SEQ ID NO.: 87-118 |
| 6-10 | SEQ ID NO.: 119-138 |
| 3-6 | SEQ ID NO.: 139-150 |

It is worth noting that for any of the VHHs of SEQ ID NO.: 1-86, the ratio of the corresponding OD values is as high as 20 or more, suggesting that it has a very high affinity for binding to PD-L1.

Even for any of the VHHs of SEQ ID NO.: 139-150, the corresponding OD value ratio is still more than 3 times, suggesting that it has a good affinity for binding to PD-L1.

Example 4: Nanobody Expression and Purification in Host Strain *E. coli*

(1) For Example 3, different clones obtained by sequencing analysis (150 nanobodies in Table 2) were electrotransformed into *E. coli* WK6 and coated on LA+glucose, a culture plate with ampicillin and glucose, and incubate at 37° C. overnight;
(2) Single colonies were selected and inoculated in 5 mL of LB medium containing ampicillin and cultured overnight at 37° C. on a shaker;
(3) Inoculate 1 mL of the overnight strain into 330 mL TB medium, incubate at 37° C. on a shaker. Until the OD value reaches 0.6-1, add IPTG, and incubate at 28° C. overnight on a shaker;
(4) centrifugation, collection of colonies;
(5) obtaining a crude extract of the antibody by an infiltration method;
(6) preparing a purified nanobody by nickel column ion affinity chromatography.

The purification results showed that the prepared nanoantibodies were all more than 95% purity.

Figure 2:
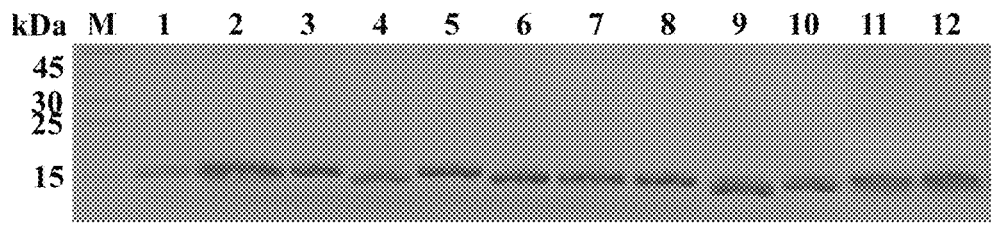
FIG. 2 is a purification map of 12 strains of anti-PD-L1 nanobodies. Lane M is a molecular weight standard, and lanes 1-12 correspond to nanobodies of SEQ ID NO.: 1-12 amino acid sequences, respectively.

Among them, the purification results of the 1-12th anti-PD-L1 nanobody (SEQ ID NO.: 1-12) are shown in FIG. 2. The figure was subjected to electrophoresis on SDS-PAGE of anti-PD-L1 nanobody after purification by nickel column resin gel affinity chromatography. The results showed that the anti-PD-L1 nanobody could achieve a purity of over 95% after the purification process.

Example 5: Enzyme-Linked Immunosorbent Assay (ELISA) was Used to Identify the Specificity of 12 Purified Nanobodies (1) Coated antigenic proteins PD-L1 and PD-L2: 0.5 μs per well (5 μg/mL, 100 μL), packaged $NaHCO_3$ (100 mM, pH8.2) was used as a blank control and overnight at 4° C.

(2) Wash the cells three times with PBST the next day, add 200 μL of 1% BSA to block at room temperature for 2 hours.
(3) Each purified nanobody was diluted to 10 μg/mL, and 100 μL of each of the purified nanobodies was incubated with the coated PD-L1, PD-L2 and the blank control group, and reacted at room temperature for 1 hour.
(4) Unbound antibody was washed away with PBST, and 100 μL of mouse anti-HA tag antibody (1:2000 dilution) was added and placed at room temperature for 1 hour.
(5) Unbound antibody was washed away with PBST, and anti-mouse alkaline phosphatase conjugate (1:2000 dilution) was added and placed at room temperature for 1 hour.
(6) Wash the unbound antibody with PBST, add alkaline phosphatase coloring solution, and read the absorbance at 405 nm on an ELISA apparatus. The specificity of the nanobody was judged based on the absorption value.

The test results are shown in Table 4.

TABLE 4

Specificity of nanobodies

| | | Coating antigen | | | |
|---|---|---|---|---|---|
| Nanobody incubation | | PD-L1 | PD-L2 | Blank control | OD ratio |
| ELISA absorbance ($A_{405\ nm}$) | SEQ ID NO.: 1 | 3.803 | 0.118 | 0.116 | 32.2 |
| | SEQ ID NO.: 2 | 3.626 | 0.114 | 0.118 | 31.8 |
| | SEQ ID NO.: 3 | 2.356 | 0.112 | 0.119 | 21.0 |
| | SEQ ID NO.: 4 | 3.512 | 0.137 | 0.124 | 25.6 |
| | SEQ ID NO.: 5 | 3.376 | 0.128 | 0.138 | 26.4 |
| | SEQ ID NO.: 6 | 3.437 | 0.115 | 0.129 | 29.9 |
| | SEQ ID NO.: 7 | 3.506 | 0.119 | 0.131 | 29.5 |
| | SEQ ID NO.: 8 | 3.371 | 0.133 | 0.110 | 25.3 |
| | SEQ ID NO.: 9 | 3.558 | 0.131 | 0.119 | 27.2 |
| | SEQ ID NO.: 10 | 3.342 | 0.117 | 0.126 | 28.6 |
| | SEQ ID NO.: 11 | 2.895 | 0.116 | 0.120 | 25.0 |
| | SEQ ID NO.: 12 | 2.987 | 0.125 | 0.117 | 23.9 |

The results in Table 4 show that the nanobodies of the invention have very high specificity, and their selectivity for PD-L1 is very high, and the ratio of OD values (PD-L1/PD-L2) is as high as 21-35.

In addition, the specificity of the PD-L1 nanobody was detected by flow cytometry. The PD-L1 full-length gene and the PD-L2 full-length gene were transiently transfected in a conventional 293F cell, and a nano-antibody (SEQ ID NO.: 1) of PD-L1 was selected for incubation for flow cytometry. Nanobody (SEQ ID NO.: 1) is 55% positive for PD-L1 transient cells, 0.1% for PD-L2 transient cells, and the difference is at least about 550 times, which further suggests the inventive nanobody has a very superior specificity for PD-L1.

All documents mentioned in the present application are hereby incorporated by reference in their entireties as if the disclosures in. In addition, it is to be understood that various modifications and changes may be made by those skilled in the field of the invention after reading the contents, in the form of the appended claims. These equivalent forms also apply for the scope defined by the appended claims.

The invention claimed is:

1. A VHH chain of an anti-PD-L1 nanobody, wherein the amino acid sequence of the VHH chain is shown in any one of SEQ ID NOs.: 18, 9, 63, 1, 12, 45, 70, 20, 74, and 50.

2. The VHH chain of the anti-PD-L1 nanobody according to claim 1, wherein the amino acid sequence of the VHH chain is shown in any one of SEQ ID NOs.: 18, 9, 63, and 1.

3. An immunoconjugate, wherein the immunoconjugate comprises:
(a) the VHH chain of the anti-PD-L1 nanobody according to claim 1; and
(b) a conjugating part selected from the group consisting of a detectable marker, drug, toxin, cytokine, radionuclide, and enzyme.

4. A pharmaceutical composition comprising:
(i) the VHH chain of the anti-PD-L1 nanobody according to claim 1, or an immunoconjugate comprising the VHH chain of the anti-PD-L1 antibody; and
(ii) a pharmaceutically acceptable carrier.

5. The VHH chain of the anti-PD-L1 nanobody according to claim 1, wherein the amino acid sequence of the VHH chain is shown in SEQ ID NOs.: 9 or 18.

6. The VHH chain of the anti-PD-L1 nanobody according to claim 1, wherein the amino acid sequence of the VHH chain is shown in any one of SEQ ID NOs.: 20, 45, 70, and 74.

7. The VHH chain of the anti-PD-L1 nanobody according to claim 1, which has a very high specificity or selectivity for PD-L1 (relative to PD-L2) and has a selectivity ratio (such as a ratio of OD value)(PD-L1/PD-L2) as high as ≥20.

8. A polynucleotide, wherein the polynucleotide encodes a protein selected from the group consisting of the VHH chains of the anti-PD-L1 nanobody according to claim 1.

9. The polynucleotide according to claim 8, wherein the polynucleotide has a nucleotide sequence as shown in any one of SEQ ID NOs.: 168, and 159.

10. The pharmaceutical composition according to claim 4, wherein the amino acid sequence of the VHH chain is shown in SEQ ID NOs.: 9 or 18.

11. The pharmaceutical composition according to claim 4, wherein the amino acid sequence of the VHH chain is shown in SEQ ID NO.: 18.

12. The VHH chain of the anti-PD-L1 nanobody according to claim 1, wherein the amino acid sequence of the VHH chain is shown in SEQ ID NO.: 18.

* * * * *

SEQUENCE LISTING

<160> NUMBER OF SEQ ID NOS: 300

<210> SEQ ID NO 1

```
<211> LENGTH: 127
<212> TYPE: PRT
<213> ORGANISM: Camelus bactrianus

<400> SEQUENCE: 1
```

Gln Val Gln Leu Gln Glu Ser Gly Gly Gly Ser Val Gln Thr Gly Gly
1               5                   10                  15

Ser Leu Arg Leu Ser Cys Thr Ala Ser Thr Ser Ile Tyr Ser Asn Asn
            20                  25                  30

Tyr Met Ala Trp Phe Ser Gln Ser Pro Gly Lys Gly Arg Glu Gly Val
        35                  40                  45

Ala Ala Val Tyr Met Asp Asp Gly Arg Pro Tyr Tyr Ala Asp Ser Val
    50                  55                  60

Lys Gly Arg Phe Thr Ile Ser Leu Asp Ser Ala Lys Asn Thr Met Tyr
65                  70                  75                  80

Leu Gln Met Asn Ser Leu Lys Pro Glu Asp Thr Ala Met Tyr Tyr Cys
                85                  90                  95

Ala Ala Ala Pro Gly Pro Leu Ser Arg Asn Tyr Trp Tyr Thr Ser Ala
            100                 105                 110

Asn Tyr Asp Tyr Trp Gly Gln Gly Thr Gln Val Thr Val Ser Ser
        115                 120                 125

```
<210> SEQ ID NO 2
<211> LENGTH: 129
<212> TYPE: PRT
<213> ORGANISM: Camelus bactrianus

<400> SEQUENCE: 2
```

Gln Val Gln Leu Gln Glu Ser Gly Gly Gly Ser Val Gln Ala Gly Gly
1               5                   10                  15

Ser Leu Arg Leu Ser Cys Ala Val Ser Arg Tyr Ser Ala Ser Asn Asn
            20                  25                  30

Val Ile Lys Trp Met Gly Trp Phe Arg Gln Ala Pro Gly Lys Glu Arg
        35                  40                  45

Glu Gly Val Ala Ala Leu Tyr Thr Ser Gly Gly Asn Thr Tyr Tyr Ala
    50                  55                  60

Asp Ser Val Lys Gly Arg Phe Thr Ile Ser Arg Asp Tyr Ser Glu Asn
65                  70                  75                  80

Thr Val Ser Leu Gln Met Asn Asn Leu Lys Pro Glu Asp Thr Gly Met
                85                  90                  95

Tyr Tyr Cys Ala Thr Thr Val Gly Thr Val Leu Ala Gly Pro Leu Ser
            100                 105                 110

Ala Arg Lys Tyr Asn Tyr Trp Gly Gln Gly Thr Gln Val Thr Val Ser
        115                 120                 125

Ser

```
<210> SEQ ID NO 3
<211> LENGTH: 127
<212> TYPE: PRT
<213> ORGANISM: Camelus bactrianus

<400> SEQUENCE: 3
```

Gln Val Gln Leu Gln Glu Ser Gly Gly Gly Ser Val Gln Thr Gly Gly
1               5                   10                  15

Ser Leu Arg Leu Ser Cys Ala Ala Ser Thr Ser Leu Tyr Ser Tyr Asn
            20                  25                  30

Tyr Met Ala Trp Phe Ser Gln Ala Pro Gly Lys Gly Arg Glu Gly Val

```
                35                  40                  45
Ala Ala Val Tyr Val Gly Asp Gly Arg Pro Tyr Tyr Ala Asp Ser Val
         50                  55                  60

Lys Gly Arg Phe Thr Ile Ser Leu Asp Ser Lys Asn Ala Val Tyr
 65                  70                  75                  80

Leu Gln Met Asn Ser Leu Lys Pro Glu Asp Thr Ala Met Tyr Tyr Cys
                 85                  90                  95

Ala Ala Ala Pro Gly Pro Leu Ser His Asn Tyr Trp Tyr Thr Ser Ala
                100                 105                 110

Asn Tyr Asp Tyr Trp Gly Gln Gly Thr Gln Val Thr Val Ser Ser
            115                 120                 125

<210> SEQ ID NO 4
<211> LENGTH: 127
<212> TYPE: PRT
<213> ORGANISM: Camelus bactrianus

<400> SEQUENCE: 4

Gln Val Gln Leu Gln Glu Ser Gly Gly Gly Ser Val Gln Thr Gly Gly
 1               5                  10                  15

Ser Leu Arg Leu Ser Cys Ala Ala Ser Pro Ser Ile Tyr Ser Ala Asn
             20                  25                  30

Tyr Met Ala Trp Phe Ser Gln Ala Pro Gly Lys Gly Arg Glu Gly Val
         35                  40                  45

Ala Ala Val Tyr Ile Gly Asp Gly Arg Pro Tyr Tyr Ala Asp Ser Val
         50                  55                  60

Lys Gly Arg Phe Thr Ile Ser Leu Asp Ser Ala Lys Asn Thr Val Tyr
 65                  70                  75                  80

Leu Gln Met Asn Ser Leu Lys Pro Glu Asp Thr Ala Met Tyr Tyr Cys
                 85                  90                  95

Ala Ala Ala Pro Gly Pro Leu Gly His Asn Tyr Trp Tyr Thr Ser Ala
                100                 105                 110

Asn Tyr Asp Tyr Trp Gly Gln Gly Thr Gln Val Thr Val Ser Ser
            115                 120                 125

<210> SEQ ID NO 5
<211> LENGTH: 127
<212> TYPE: PRT
<213> ORGANISM: Camelus bactrianus

<400> SEQUENCE: 5

Gln Val Gln Leu Gln Glu Ser Gly Gly Gly Ser Val Gln Thr Gly Gly
 1               5                  10                  15

Ser Leu Arg Leu Ser Cys Ala Ala Ser Thr Ser Ile Tyr Ser Asn Asn
             20                  25                  30

Tyr Met Ala Trp Phe Ser Gln Ala Pro Gly Lys Gly Arg Glu Gly Val
         35                  40                  45

Ala Ala Val Tyr Ile Asp Asp Gly Arg Pro Tyr Tyr Ala Asp Ser Val
         50                  55                  60

Lys Gly Arg Phe Thr Ile Ser Leu Asp Ser Ala Lys Asn Thr Val Tyr
 65                  70                  75                  80

Leu Gln Met Asn Gly Leu Lys Pro Glu Asp Thr Ala Met Tyr Tyr Cys
                 85                  90                  95

Ala Ala Ala Pro Gly Pro Leu Ser Arg Asn Tyr Trp Tyr Thr Ser Ala
                100                 105                 110

Asn Tyr Asp Tyr Trp Gly Gln Gly Thr Gln Val Thr Val Ser Ser
```

<210> SEQ ID NO 6
<211> LENGTH: 126
<212> TYPE: PRT
<213> ORGANISM: Camelus bactrianus

<400> SEQUENCE: 6

Gln Val Gln Leu Gln Glu Ser Gly Gly Gly Ser Val Gln Ala Gly Glu
1               5                   10                  15

Thr Leu Arg Leu Ser Cys Thr Ala Ser Gly Asp Thr Phe Asp Ala Ser
            20                  25                  30

Gly Val Gly Trp Phe Arg Gln Val Ser Gly Asn Glu Cys Asp Leu Val
        35                  40                  45

Ser Ser Ile Asn Arg Asp Gly Thr Thr Tyr Tyr Ala Pro Ser Val Ala
    50                  55                  60

Gly Arg Phe Thr Met Ser Gln Asn Asn Ala Lys Asn Thr Val Tyr Leu
65                  70                  75                  80

Gln Met Asn Ser Leu Lys Pro Asp Asp Thr Ala Val Tyr Tyr Cys Ala
                85                  90                  95

Thr Asp Pro Ala Val Gly Ile Val Val Arg Ser Thr Cys Arg Gly Pro
            100                 105                 110

Phe Gly Tyr Trp Gly Gln Gly Thr Gln Val Thr Val Ser Ser
        115                 120                 125

<210> SEQ ID NO 7
<211> LENGTH: 127
<212> TYPE: PRT
<213> ORGANISM: Camelus bactrianus

<400> SEQUENCE: 7

Gln Val Gln Leu Gln Glu Ser Gly Gly Gly Ser Val Gln Thr Gly Gly
1               5                   10                  15

Ser Leu Arg Leu Ser Cys Ala Cys Ser Thr Ser Ile Tyr Ser Thr Asn
            20                  25                  30

Tyr Met Ala Trp Phe Ser Gln Ala Pro Gly Lys Gly Arg Glu Gly Val
        35                  40                  45

Ala Ala Val Tyr Ile Gly Asp Gly Arg Pro Tyr Tyr Ala Asp Ser Val
    50                  55                  60

Lys Gly Arg Phe Thr Ile Ser Leu Asp Ser Ala Lys Asn Thr Val Tyr
65                  70                  75                  80

Leu Gln Met Asn Ser Leu Lys Pro Glu Asp Thr Ala Met Tyr Tyr Cys
                85                  90                  95

Ala Ala Ala Pro Gly Pro Leu Ser Arg Asn Tyr Trp Tyr Thr Ser Ala
            100                 105                 110

Asn Tyr Asp Tyr Trp Gly Gln Gly Thr Gln Val Thr Val Ser Ser
        115                 120                 125

<210> SEQ ID NO 8
<211> LENGTH: 125
<212> TYPE: PRT
<213> ORGANISM: Camelus bactrianus

<400> SEQUENCE: 8

Gln Val Gln Leu Gln Glu Ser Gly Gly Asp Ser Val Gln Ala Gly Gly
1               5                   10                  15

Ser Leu Arg Leu Ala Cys Lys Val Pro Gly Phe Thr Ser Asn Thr Cys
            20                  25                  30

```
Ala Met Ala Trp Phe Arg Gln Ala Pro Gly Lys Glu Arg Glu Phe Val
            35                  40                  45

Ser Ser Ile Ser Thr Gly Gly Thr Gly Tyr Ala Glu Ser Ala Lys
 50                  55                  60

Gly Arg Phe Thr Leu Ser Lys Asp Glu Ala Lys Asp Thr Val Tyr Leu
 65                  70                  75                  80

Gln Met Asn Ser Leu Lys Pro Glu Asp Thr Ala Met Tyr Phe Cys Lys
                 85                  90                  95

Ser Tyr Ala Cys Arg Thr Cys Ile Gly Arg Tyr Cys Arg Thr Ala Pro
                100                 105                 110

Asp Ala Trp Gly Gln Gly Thr Gln Val Thr Val Ser Ser
            115                 120                 125

<210> SEQ ID NO 9
<211> LENGTH: 124
<212> TYPE: PRT
<213> ORGANISM: Camelus bactrianus

<400> SEQUENCE: 9

Gln Val Gln Leu Gln Glu Ser Gly Gly Gly Ser Val Gln Ala Gly Gly
1               5                   10                  15

Ser Leu Arg Leu Ser Cys Ala Ala Ser Gly Tyr Thr Tyr Ser Asn Asp
                20                  25                  30

Gly Met Gly Trp Phe Arg Gln Ile Pro Gly Lys Glu Arg Glu Gly Val
            35                  40                  45

Ala Ala Ile Ser Pro Thr Gly Arg Arg Thr Glu Tyr Ala Asp Ser Val
 50                  55                  60

Gln Gly Arg Phe Thr Ile Ser Arg Asp Asn Ala Lys Asn Met Leu Ser
 65                  70                  75                  80

Leu Gln Met Asn Ser Leu Lys Pro Glu Asp Thr Gly Met Tyr Tyr Cys
                85                  90                  95

Ala Arg Glu Gly Ser Gly Ser Phe Ser Leu Gln Asn Ser Ala Val Arg
                100                 105                 110

Ser Trp Gly Gln Gly Thr Gln Val Thr Val Ser Ser
            115                 120

<210> SEQ ID NO 10
<211> LENGTH: 125
<212> TYPE: PRT
<213> ORGANISM: Camelus bactrianus

<400> SEQUENCE: 10

Gln Val Gln Leu Gln Glu Ser Gly Gly Gly Ser Val Gln Ala Gly Gly
1               5                   10                  15

Ser Leu Arg Leu Ser Cys Thr Ala Pro Gly Phe Thr Ser Lys Thr Cys
                20                  25                  30

Ala Met Arg Trp Tyr Arg Gln Ala Pro Gly Lys Glu Arg Glu Phe Val
            35                  40                  45

Ser Ala Ile Ser Thr Val Gly Thr Thr Thr Tyr Ala Asp Ser Val Lys
 50                  55                  60

Gly Arg Phe Ile Ile Ser Lys Asp Glu Ala Lys Asp Thr Val Tyr Leu
 65                  70                  75                  80

Gln Ile Asn Ser Leu Lys Pro Glu Asp Thr Ala Met Tyr Ser Cys Lys
                85                  90                  95

Thr Phe Ala Cys Arg His Cys Ile Gly Gln Ser Cys Arg Thr Glu Pro
                100                 105                 110
```

-continued

Asp Tyr Trp Gly Gln Gly Thr Gln Val Thr Val Ser Ser
        115                 120                 125

<210> SEQ ID NO 11
<211> LENGTH: 126
<212> TYPE: PRT
<213> ORGANISM: Camelus bactrianus

<400> SEQUENCE: 11

Gln Val Gln Leu Gln Glu Ser Gly Gly Gly Ser Val Gln Ala Gly Glu
1               5                   10                  15

Thr Leu Arg Leu Ser Cys Thr Ala Ser Gly Asp Thr Phe Asp Asp Ser
            20                  25                  30

Gly Val Gly Trp Phe Arg Gln Val Ser Gly Asn Glu Cys Asp Leu Val
        35                  40                  45

Ser Ser Ile Asn Arg Asp Gly Thr Thr Tyr Tyr Ala Pro Ser Val Ala
    50                  55                  60

Gly Arg Phe Thr Ile Ser Gln Asn Asn Ala Lys Asn Thr Val Tyr Leu
65                  70                  75                  80

Gln Met Asn Ser Leu Lys Pro Asp Asp Thr Ala Val Tyr Tyr Cys Ala
                85                  90                  95

Thr Val Pro Ala Val Gly Ile Val Val Arg Ile Thr Cys Arg Gly Pro
            100                 105                 110

Phe Gly Tyr Trp Gly Gln Gly Thr Gln Val Thr Val Ser Ser
        115                 120                 125

<210> SEQ ID NO 12
<211> LENGTH: 127
<212> TYPE: PRT
<213> ORGANISM: Camelus bactrianus

<400> SEQUENCE: 12

Gln Val Gln Leu Gln Glu Ser Gly Gly Gly Ser Val Gln Ala Gly Gly
1               5                   10                  15

Ser Leu Arg Leu Ser Cys Ala Ala Ser Gly Tyr Thr Arg Ser Ser His
            20                  25                  30

Cys Met Val Trp Phe Arg Gln Ala Pro Gly Lys Glu Arg Glu Gly Val
        35                  40                  45

Ala Leu Ile Tyr Thr Gly Ser Gly Ser Thr Tyr Tyr Ala Asp Ser Val
    50                  55                  60

Lys Gly Arg Phe Thr Ile Ser Gln Asp Asn Ala Lys Lys Thr Leu Tyr
65                  70                  75                  80

Leu Gln Met Asn Ser Leu Lys Pro Glu Asp Thr Ala Met Tyr Tyr Cys
                85                  90                  95

Ala Ala Gly Thr Ser Ser Ser Cys Pro Gly Leu Leu Gly Pro Pro
            100                 105                 110

Arg Tyr Tyr Asn Trp Gly Gln Gly Thr Gln Val Thr Val Ser Ser
        115                 120                 125

<210> SEQ ID NO 13
<211> LENGTH: 127
<212> TYPE: PRT
<213> ORGANISM: Camelus bactrianus

<400> SEQUENCE: 13

Gln Val Gln Leu Gln Glu Ser Gly Gly Gly Ser Val Gln Thr Gly Gly
1               5                   10                  15

Ser Leu Arg Leu Ser Cys Ala Ala Ser Thr Ser Ile Tyr Ser Asn Asn
            20                  25                  30

Tyr Met Ala Trp Phe Ser Gln Asn Pro Gly Lys Gly Arg Glu Gly Val
        35                  40                  45

Ala Ala Val Tyr Ile Gly Asp Gly Arg Pro Tyr Tyr Ala Asp Ser Val
    50                  55                  60

Lys Gly Arg Phe Thr Ile Ser Leu Asp Ser Ala Lys Asn Thr Val Tyr
65                  70                  75                  80

Leu Gln Met Asn Ser Leu Lys Pro Glu Asp Thr Ala Met Tyr Tyr Cys
                85                  90                  95

Ala Ala Ala Pro Gly Pro Leu Ser Arg Asn Tyr Trp Tyr Thr Ser Ala
            100                 105                 110

Asn Tyr Asp Tyr Trp Gly Gln Gly Thr Gln Val Thr Val Ser Ser
        115                 120                 125

<210> SEQ ID NO 14
<211> LENGTH: 127
<212> TYPE: PRT
<213> ORGANISM: Camelus bactrianus

<400> SEQUENCE: 14

Gln Val Gln Leu Gln Glu Ser Gly Gly Gly Ser Val Gln Thr Gly Gly
1               5                   10                  15

Ser Leu Arg Leu Ser Cys Ala Ala Ser Thr Ser Ile Tyr Ser Asn Asn
            20                  25                  30

Tyr Met Ala Trp Phe Ser Gln Ala Pro Gly Lys Gly Arg Glu Gly Val
        35                  40                  45

Ala Ala Val Tyr Ile Asp Asp Gly Arg Pro Tyr Tyr Ala Asp Ser Val
    50                  55                  60

Lys Gly Arg Phe Thr Ile Ser Leu Asp Ser Ala Lys Asn Thr Val Tyr
65                  70                  75                  80

Leu Gln Val Asn Ser Leu Lys Pro Glu Asp Thr Ala Met Tyr Tyr Cys
                85                  90                  95

Ala Ala Ala Pro Gly Pro Leu Ser Arg Asn Tyr Trp Tyr Thr Ser Ala
            100                 105                 110

Asn Tyr Asp Tyr Trp Gly Gln Gly Thr Gln Val Thr Val Ser Ser
        115                 120                 125

<210> SEQ ID NO 15
<211> LENGTH: 127
<212> TYPE: PRT
<213> ORGANISM: Camelus bactrianus

<400> SEQUENCE: 15

Gln Val Gln Leu Gln Glu Ser Gly Gly Gly Ser Val Gln Thr Gly Gly
1               5                   10                  15

Ser Leu Arg Leu Ser Cys Ala Ala Ser Thr Ser Ile Tyr Ser Asn Asn
            20                  25                  30

Tyr Met Ala Trp Phe Ser Gln Ala Pro Gly Lys Gly Arg Glu Gly Val
        35                  40                  45

Ala Ala Val Tyr Ile Asp Asp Gly Arg Thr Tyr Tyr Ala Asp Ser Val
    50                  55                  60

Lys Gly Arg Phe Thr Ile Ser Leu Asp Ser Ala Lys Asn Thr Val Tyr
65                  70                  75                  80

Leu Gln Met Asn Ser Leu Lys Pro Glu Asp Thr Ala Met Tyr Tyr Cys
                85                  90                  95

```
Ala Ala Ala Pro Gly Pro Leu Ser Tyr Asn Tyr Trp Tyr Thr Ser Ala
            100                 105                 110

Asn Tyr Asp Tyr Trp Gly Gln Gly Thr Gln Val Thr Val Ser Ser
        115                 120                 125

<210> SEQ ID NO 16
<211> LENGTH: 127
<212> TYPE: PRT
<213> ORGANISM: Camelus bactrianus

<400> SEQUENCE: 16

Gln Val Gln Leu Gln Glu Ser Gly Gly Gly Ser Val Gln Thr Gly Gly
1               5                   10                  15

Ser Leu Arg Leu Ser Cys Ala Ala Ser Pro Ser Ile Tyr Ser Asn Asn
            20                  25                  30

Tyr Met Ala Trp Phe Ser Gln Ala Pro Gly Lys Gly Arg Glu Gly Val
        35                  40                  45

Ala Ala Val Tyr Ile Gly Asp Gly Arg Pro Tyr Tyr Ala Asp Ser Val
    50                  55                  60

Lys Gly Arg Phe Thr Ile Ser Leu Asp Ser Ala Lys Asn Thr Val Tyr
65                  70                  75                  80

Leu Gln Met Asn Ser Leu Lys Pro Glu Asp Thr Ala Met Tyr Tyr Cys
                85                  90                  95

Ala Ala Ala Pro Gly Pro Leu Ser Arg Asn Tyr Trp Tyr Thr Ser Ala
            100                 105                 110

Asn Tyr Asp Tyr Trp Gly Gln Gly Thr Gln Val Thr Val Ser Ser
        115                 120                 125

<210> SEQ ID NO 17
<211> LENGTH: 127
<212> TYPE: PRT
<213> ORGANISM: Camelus bactrianus

<400> SEQUENCE: 17

Gln Val Gln Leu Gln Glu Ser Gly Gly Gly Ser Val Gln Thr Gly Gly
1               5                   10                  15

Ser Leu Arg Leu Ser Cys Ala Ala Ser Thr Ser Ile Tyr Ser Leu Asn
            20                  25                  30

Tyr Met Ala Trp Phe Ser Gln Ala Pro Gly Lys Gly Arg Glu Gly Val
        35                  40                  45

Ala Ala Val Tyr Ile Asp Asp Gly Arg Pro Tyr Tyr Ala Asp His Val
    50                  55                  60

Lys Gly Arg Phe Thr Ile Ser Leu Asp Thr Ala Lys Asn Thr Val Tyr
65                  70                  75                  80

Leu Gln Met Asn Ser Leu Lys Pro Glu Asp Thr Ala Met Tyr Tyr Cys
                85                  90                  95

Ala Ala Ala Pro Gly Pro Leu Ser Arg Asn Tyr Trp Tyr Thr Ser Ala
            100                 105                 110

Asn Tyr Asp Tyr Trp Gly Gln Gly Thr Gln Val Thr Val Ser Ser
        115                 120                 125

<210> SEQ ID NO 18
<211> LENGTH: 124
<212> TYPE: PRT
<213> ORGANISM: Camelus bactrianus

<400> SEQUENCE: 18

Gln Val Gln Leu Gln Glu Ser Gly Gly Gly Ser Val Gln Ala Gly Gly
```

```
1               5                   10                  15
Ser Leu Arg Leu Ser Cys Ala Ala Ser Gly Tyr Thr Tyr Ser Ser Asp
            20                  25                  30

Gly Met Gly Trp Phe Arg Gln Thr Pro Gly Lys Glu Arg Glu Gly Val
            35                  40                  45

Ala Ala Ile Ser Pro Thr Gly Arg Arg Thr Glu Tyr Ala Asp Ser Val
            50                  55                  60

Lys Gly Arg Phe Thr Ile Ser Arg Asp Asn Lys Asn Met Leu Ser
65                  70                  75                  80

Leu Gln Met Asn Ser Leu Lys Pro Glu Asp Thr Gly Met Tyr Tyr Cys
                85                  90                  95

Ala Arg Glu Gly Ser Trp Ser Phe Ser Leu Ala Asn Ser Ala Val Arg
                100                 105                 110

Ser Trp Gly Gln Gly Thr Gln Val Thr Val Ser Ser
                115                 120
```

<210> SEQ ID NO 19
<211> LENGTH: 127
<212> TYPE: PRT
<213> ORGANISM: Camelus bactrianus

<400> SEQUENCE: 19

```
Gln Val Gln Leu Gln Glu Ser Gly Gly Gly Ser Val Gln Thr Gly Gly
1               5                   10                  15

Ser Leu Arg Leu Ser Cys Ala Ala Ser Thr Ser Ile Tyr Ser Asn Asn
            20                  25                  30

Tyr Met Ala Trp Phe Ser Gln Ala Pro Gly Lys Gly Arg Glu Gly Val
            35                  40                  45

Ala Ala Val Tyr Ile Gly Asp Gly Arg Pro Tyr Tyr Ala Asp Ser Val
            50                  55                  60

Lys Gly Arg Phe Thr Ile Ser Leu Asp Ser Ala Lys Asn Thr Val Tyr
65                  70                  75                  80

Leu Gln Met Asn Ser Leu Lys Pro Glu Asp Thr Ala Met Tyr Tyr Cys
                85                  90                  95

Ala Ala Ala Pro Gly Pro Leu Ser Arg Asn Tyr Trp Tyr Thr Ser Ala
                100                 105                 110

Asn Tyr Asp Tyr Trp Gly Gln Gly Thr Gln Val Thr Val Ser Ser
            115                 120                 125
```

<210> SEQ ID NO 20
<211> LENGTH: 121
<212> TYPE: PRT
<213> ORGANISM: Camelus bactrianus

<400> SEQUENCE: 20

```
Gln Val Gln Leu Gln Glu Ser Gly Gly Gly Leu Val Gln Pro Gly Gly
1               5                   10                  15

Ser Leu Arg Leu Ser Cys Ala Ala Ser Gly Phe Thr Gly Ser Ile Tyr
            20                  25                  30

Ala Met Ser Trp Val Arg Gln Ala Pro Gly Lys Gly Leu Glu Trp Val
            35                  40                  45

Ser Thr Ile Ser Ser Ser Gly Gly Arg Arg Phe Tyr Ala Asp Ser Val
            50                  55                  60

Lys Gly Arg Phe Thr Ile Ser Arg Asp Asn Ala Lys Asn Thr Leu Tyr
65                  70                  75                  80

Leu Gln Leu Asn Ser Leu Lys Thr Glu Asp Thr Ala Met Tyr Tyr Cys
```

```
                        85                  90                  95
Ala Arg Cys Ser Asp Ile Tyr Cys Asp Asn Gly Ala Ser Tyr Arg Gly
                100                 105                 110

Gln Gly Thr Gln Val Thr Val Ser Ser
        115                 120

<210> SEQ ID NO 21
<211> LENGTH: 127
<212> TYPE: PRT
<213> ORGANISM: Camelus bactrianus

<400> SEQUENCE: 21

Gln Val Gln Leu Gln Glu Ser Gly Gly Gly Ser Val Gln Thr Gly Gly
1               5                   10                  15

Ser Leu Arg Leu Ser Cys Ala Ala Ser Thr Ser Ile Tyr Ser Leu Asn
            20                  25                  30

Tyr Met Ala Trp Phe Ser Gln Ala Pro Gly Lys Gly Arg Glu Gly Val
        35                  40                  45

Ala Ala Val Tyr Ile Gly Asp Gly Arg Pro Tyr Tyr Ala Asp Ser Val
    50                  55                  60

Lys Gly Arg Phe Thr Ile Ser Leu Asp Ser Ala Lys Asn Thr Val Tyr
65                  70                  75                  80

Leu Gln Met Asn Ser Leu Lys Ser Glu Asp Thr Ala Met Tyr Tyr Cys
                85                  90                  95

Ala Ala Ala Pro Gly Pro Leu Ser Arg His Tyr Trp Tyr Thr Ser Ala
                100                 105                 110

Asn Tyr Asp Tyr Trp Gly Gln Gly Thr Gln Val Thr Val Ser Ser
            115                 120                 125

<210> SEQ ID NO 22
<211> LENGTH: 127
<212> TYPE: PRT
<213> ORGANISM: Camelus bactrianus

<400> SEQUENCE: 22

Gln Val Gln Leu Gln Glu Ser Gly Gly Gly Ser Val Gln Thr Gly Gly
1               5                   10                  15

Ser Leu Arg Leu Ser Cys Ala Ala Ser Thr Ser Ile Tyr Ser Asn Asn
            20                  25                  30

Tyr Met Ala Trp Phe Ser Gln Ala Pro Arg Lys Gly Arg Glu Gly Val
        35                  40                  45

Ala Ala Val Tyr Ile Gly Asp Gly Arg Pro Tyr Tyr Ala Asp Ser Val
    50                  55                  60

Lys Gly Arg Phe Thr Ile Ser Leu Asp Ser Ala Lys Asn Thr Val Tyr
65                  70                  75                  80

Leu Gln Met Asn Ser Leu Lys Pro Glu Asp Thr Ala Met Tyr Tyr Cys
                85                  90                  95

Ala Ala Ala Pro Gly Pro Leu His Asn Tyr Trp Tyr Thr Ser Ala
                100                 105                 110

Asn Tyr Asp Tyr Trp Gly Gln Gly Thr Gln Val Thr Val Ser Ser
            115                 120                 125

<210> SEQ ID NO 23
<211> LENGTH: 127
<212> TYPE: PRT
<213> ORGANISM: Camelus bactrianus

<400> SEQUENCE: 23
```

Gln Val Gln Leu Gln Glu Ser Gly Gly Gly Ser Val Gln Thr Gly Gly
1               5                   10                  15

Ser Leu Arg Leu Ser Cys Ala Ala Ser Thr Ser Leu Tyr Ser Tyr Asn
            20                  25                  30

Tyr Met Ala Trp Phe Ser Gln Ala Pro Gly Lys Gly Arg Glu Gly Val
        35                  40                  45

Ala Ala Val Tyr Val Gly Asp Gly Arg Pro Tyr Tyr Ala Asp Ser Val
    50                  55                  60

Lys Gly Arg Phe Thr Ile Ser Leu Asp Ser Ala Lys Asn Thr Val Tyr
65                  70                  75                  80

Leu Gln Met Asn Ser Leu Lys Pro Glu Asp Thr Ala Met Tyr Tyr Cys
                85                  90                  95

Ala Ala Ala Pro Gly Pro Leu Ser His Asn Tyr Trp Tyr Thr Ser Ala
            100                 105                 110

Asn Tyr Asp Tyr Trp Gly Gln Gly Thr Gln Val Thr Val Ser Ser
            115                 120                 125

<210> SEQ ID NO 24
<211> LENGTH: 127
<212> TYPE: PRT
<213> ORGANISM: Camelus bactrianus

<400> SEQUENCE: 24

Gln Val Gln Leu Gln Glu Ser Gly Gly Gly Ser Val Gln Thr Gly Gly
1               5                   10                  15

Ser Leu Arg Leu Ser Cys Thr Ala Ser Thr Ser Ile Tyr Ser Asn Asn
            20                  25                  30

Tyr Met Ala Trp Phe Ser Gln Ser Pro Gly Lys Gly Arg Glu Gly Val
        35                  40                  45

Ala Ala Val Tyr Met Asp Asp Gly Arg Pro Tyr Tyr Ala Asp Ser Val
    50                  55                  60

Lys Gly Arg Phe Thr Ile Ser Leu Asp Ser Ala Lys Asn Thr Met Tyr
65                  70                  75                  80

Leu Gln Met Asn Ser Leu Lys Pro Glu Asp Thr Ala Met Tyr Tyr Cys
                85                  90                  95

Ala Ala Ala Pro Gly Pro Leu Ser Arg Asn Tyr Trp Tyr Thr Ser Ala
            100                 105                 110

Asn Tyr Asp Tyr Trp Gly Gln Gly Thr Gln Val Thr Val Ser Ser
            115                 120                 125

<210> SEQ ID NO 25
<211> LENGTH: 127
<212> TYPE: PRT
<213> ORGANISM: Camelus bactrianus

<400> SEQUENCE: 25

Gln Val Gln Leu Gln Glu Ser Gly Gly Gly Ser Val Gln Thr Gly Gly
1               5                   10                  15

Ser Leu Arg Leu Ser Cys Thr Ala Ser Thr Ser Ile Tyr Ser Asn Asn
            20                  25                  30

Tyr Met Ala Trp Phe Ser Gln Ala Pro Gly Lys Gly Arg Glu Gly Val
        35                  40                  45

Ala Ala Val Tyr Ile Gly Asp Gly Arg Pro Tyr Tyr Ala Asp Ser Val
    50                  55                  60

Lys Gly Arg Phe Thr Ile Ser Leu Asp Ser Ala Lys Asn Thr Val Tyr
65                  70                  75                  80

-continued

Leu Gln Met Asn Ser Leu Lys Pro Glu Asp Thr Ala Met Tyr Tyr Cys
                85                  90                  95

Ala Ala Ala Pro Gly Pro Leu Ser His Asn Tyr Trp Tyr Thr Ser Ala
            100                 105                 110

Asn Tyr Asp Tyr Trp Gly Gln Gly Thr Gln Val Thr Val Ser Ser
        115                 120                 125

<210> SEQ ID NO 26
<211> LENGTH: 127
<212> TYPE: PRT
<213> ORGANISM: Camelus bactrianus

<400> SEQUENCE: 26

Gln Val Gln Leu Gln Glu Ser Gly Gly Gly Ser Val Gln Thr Gly Gly
1               5                   10                  15

Ser Leu Arg Leu Ser Cys Ala Ala Ser Thr Ser Ile Tyr Asn Asn Asn
            20                  25                  30

Tyr Met Ala Trp Phe Ser Gln Ala Pro Gly Lys Glu Arg Glu Gly Val
        35                  40                  45

Ala Ala Val Tyr Ile Gly Asp Gly Arg Pro Tyr Tyr Ala Asp Ser Val
    50                  55                  60

Lys Gly Arg Phe Thr Ile Ser Leu Asp Ser Ala Lys Asn Thr Val Tyr
65                  70                  75                  80

Leu Gln Met Asn Ser Leu Lys Pro Glu Asp Thr Ala Met Tyr Tyr Cys
                85                  90                  95

Ala Ala Ala Pro Gly Pro Leu Ser Arg Asn Tyr Trp Tyr Thr Ser Ala
            100                 105                 110

Asn Tyr Asp Tyr Trp Gly Gln Gly Thr Gln Val Thr Val Ser Ser
        115                 120                 125

<210> SEQ ID NO 27
<211> LENGTH: 127
<212> TYPE: PRT
<213> ORGANISM: Camelus bactrianus

<400> SEQUENCE: 27

Gln Val Gln Leu Gln Glu Ser Gly Gly Gly Ser Val Gln Thr Gly Gly
1               5                   10                  15

Ser Leu Arg Leu Ser Cys Thr Ala Ser Thr Ser Ile Tyr Ser Asn Asn
            20                  25                  30

Tyr Met Ala Trp Phe Ser Gln Ser Pro Gly Lys Gly Arg Glu Gly Val
        35                  40                  45

Ala Ala Val Tyr Met Asp Asp Gly Arg Pro Tyr Tyr Ala Asp Ser Val
    50                  55                  60

Lys Gly Arg Phe Thr Ile Ser Leu Asp Ser Ala Lys Asn Thr Met Tyr
65                  70                  75                  80

Leu Gln Met Asn Ser Leu Lys Pro Glu Asp Thr Ala Met Tyr Tyr Cys
                85                  90                  95

Ala Ala Ala Pro Gly Pro Leu Ser Arg Asn Tyr Trp Tyr Thr Ser Ala
            100                 105                 110

Asn Tyr Asp Tyr Trp Gly Gln Gly Thr Gln Val Thr Val Ser Ser
        115                 120                 125

<210> SEQ ID NO 28
<211> LENGTH: 127
<212> TYPE: PRT
<213> ORGANISM: Camelus bactrianus

<400> SEQUENCE: 28

Gln Val Gln Leu Gln Glu Ser Gly Gly Gly Ser Val Gln Thr Gly Gly
1               5                   10                  15

Ser Leu Arg Leu Ser Cys Ala Ala Ser Thr Ser Ile Tyr Ser Asn Asn
            20                  25                  30

Tyr Met Ala Trp Phe Arg Gln Ala Pro Gly Lys Gly Arg Glu Gly Val
        35                  40                  45

Ala Ala Val Tyr Ile Asp Asp Gly Arg Pro Tyr Tyr Ala Asp Ser Val
    50                  55                  60

Lys Gly Arg Phe Thr Ile Ser Leu Asp Ser Ala Lys Asn Thr Val Tyr
65                  70                  75                  80

Leu Gln Met Asn Ser Leu Lys Pro Glu Asp Thr Ala Met Tyr Tyr Cys
                85                  90                  95

Ala Ala Ala Pro Gly Pro Leu Ser Arg His Tyr Trp Tyr Thr Ser Ala
            100                 105                 110

Asn Tyr Asp Tyr Trp Gly Pro Gly Thr Gln Val Thr Val Ser Ser
        115                 120                 125

<210> SEQ ID NO 29
<211> LENGTH: 127
<212> TYPE: PRT
<213> ORGANISM: Camelus bactrianus

<400> SEQUENCE: 29

Gln Val Gln Leu Gln Glu Ser Gly Gly Gly Ser Val Arg Thr Gly Gly
1               5                   10                  15

Ser Leu Arg Leu Ser Cys Ala Ala Ser Pro Ser Ile Tyr Ser Asn Asn
            20                  25                  30

Tyr Met Ala Trp Phe Ser Gln Ala Pro Gly Lys Gly Arg Glu Gly Val
        35                  40                  45

Ala Ala Val Tyr Ile Asp Asp Gly Arg Pro Tyr Tyr Ala Asp Ser Val
    50                  55                  60

Lys Gly Arg Phe Thr Ile Ser Leu Asp Ser Ala Lys Asn Thr Val Tyr
65                  70                  75                  80

Leu Gln Met Asn Ser Leu Lys Pro Glu Asp Thr Ala Met Tyr Tyr Cys
                85                  90                  95

Ala Ala Ala Pro Gly Pro Leu Ser Arg Asn Tyr Trp Tyr Thr Ser Ala
            100                 105                 110

Asn Tyr Asp Tyr Trp Gly Gln Gly Thr Gln Val Thr Val Ser Ser
        115                 120                 125

<210> SEQ ID NO 30
<211> LENGTH: 127
<212> TYPE: PRT
<213> ORGANISM: Camelus bactrianus

<400> SEQUENCE: 30

Gln Val Gln Leu Gln Glu Ser Gly Gly Gly Ser Val Gln Thr Gly Gly
1               5                   10                  15

Ser Leu Arg Leu Ser Cys Thr Ala Ser Thr Ser Ile Tyr Ser Asn Asn
            20                  25                  30

Tyr Met Ala Trp Phe Ser Gln Ala Pro Gly Lys Gly Arg Glu Gly Val
        35                  40                  45

Ala Ala Val Tyr Ile Asp Asp Gly Arg Pro Tyr Tyr Ala Asp Ser Val
    50                  55                  60

```
Lys Gly Arg Phe Thr Ile Ser Leu Asp Ser Ala Lys Asn Thr Val Tyr
 65                  70                  75                  80

Leu Gln Met Asn Ser Leu Lys Pro Glu Asp Thr Ala Met Tyr Tyr Cys
                 85                  90                  95

Ala Ala Ala Pro Gly Pro Leu Ser Arg Asn Tyr Trp Tyr Thr Ser Ala
            100                 105                 110

Asn Tyr Asp Tyr Trp Gly Gln Gly Thr Gln Val Thr Val Ser Ser
            115                 120                 125
```

<210> SEQ ID NO 31
<211> LENGTH: 127
<212> TYPE: PRT
<213> ORGANISM: Camelus bactrianus

<400> SEQUENCE: 31

```
Gln Val Gln Leu Gln Glu Ser Gly Gly Gly Ser Val Gln Thr Gly Gly
 1               5                  10                  15

Ser Leu Arg Leu Ser Cys Ala Ala Ser Thr Ser Ile Tyr Ser Asn Asn
             20                  25                  30

Tyr Met Ala Trp Phe Arg Gln Ala Pro Gly Lys Gly Arg Glu Gly Val
         35                  40                  45

Ala Gly Val Tyr Ile Gly Asp Gly Arg Pro Tyr Tyr Ala Asp Ser Val
     50                  55                  60

Lys Gly Arg Phe Thr Ile Ser Leu Asp Ser Ala Lys Asn Thr Val Tyr
 65                  70                  75                  80

Leu Gln Met Asn Ser Leu Lys Pro Glu Asp Thr Ala Met Tyr Tyr Cys
                 85                  90                  95

Ala Ala Ala Pro Gly Pro Leu Ser His His Tyr Trp Tyr Thr Ser Ala
            100                 105                 110

Asn Tyr Asp Tyr Trp Gly Pro Gly Thr Gln Val Thr Val Ser Ser
            115                 120                 125
```

<210> SEQ ID NO 32
<211> LENGTH: 127
<212> TYPE: PRT
<213> ORGANISM: Camelus bactrianus

<400> SEQUENCE: 32

```
Gln Val Gln Leu Gln Glu Ser Gly Gly Gly Ser Val Gln Thr Gly Gly
 1               5                  10                  15

Ser Leu Arg Leu Ser Cys Ala Ala Ser Thr Ser Ile Tyr Ser Ile Asn
             20                  25                  30

Tyr Met Ala Trp Phe Ser Gln Ala Pro Gly Lys Gly Arg Glu Gly Val
         35                  40                  45

Ala Ala Val Tyr Ile Gly Asp Gly Arg Pro Tyr Tyr Ala Asp Ser Val
     50                  55                  60

Lys Gly Arg Phe Thr Ile Ser Leu Asp Ser Ala Lys Asn Thr Val Tyr
 65                  70                  75                  80

Leu Gln Met Asn Ser Leu Lys Pro Glu Asp Thr Ala Met Tyr Tyr Cys
                 85                  90                  95

Ala Ala Ala Pro Gly Pro Leu Ser Gln His Tyr Trp Tyr Thr Ser Ala
            100                 105                 110

Asn Tyr Asp Tyr Trp Gly Gln Gly Thr Gln Val Thr Val Ser Ser
            115                 120                 125
```

<210> SEQ ID NO 33
<211> LENGTH: 127

```
<212> TYPE: PRT
<213> ORGANISM: Camelus bactrianus

<400> SEQUENCE: 33

Gln Val Gln Leu Gln Glu Ser Gly Gly Gly Ser Val Gln Thr Gly Gly
1               5                   10                  15

Ser Leu Arg Leu Ser Cys Ala Cys Ser Thr Ser Ile Tyr Ser Asn Asn
            20                  25                  30

Tyr Met Ala Trp Phe Ser Gln Ala Pro Gly Lys Gly Arg Glu Gly Val
        35                  40                  45

Ala Ala Val Tyr Ile Gly Asp Gly Arg Pro Tyr Tyr Ala Asp Ser Val
    50                  55                  60

Lys Gly Arg Phe Thr Ile Ser Leu Asp Ser Ala Lys Asn Thr Met Tyr
65                  70                  75                  80

Leu Gln Met Asn Ser Leu Lys Pro Glu Asp Thr Ala Met Tyr Tyr Cys
                85                  90                  95

Ala Ala Ala Pro Gly Pro Leu Ser Gln His Tyr Trp Tyr Thr Ser Ala
            100                 105                 110

Asn Tyr Asp Tyr Trp Gly Gln Gly Thr Gln Val Thr Val Ser Ser
        115                 120                 125

<210> SEQ ID NO 34
<211> LENGTH: 127
<212> TYPE: PRT
<213> ORGANISM: Camelus bactrianus

<400> SEQUENCE: 34

Gln Val Gln Leu Gln Glu Ser Gly Gly Gly Ser Val Gln Ala Gly Gly
1               5                   10                  15

Ser Leu Arg Leu Ser Cys Ala Ala Ser Gly Tyr Thr Arg Ser Leu Tyr
            20                  25                  30

Cys Met Gly Trp Phe Arg Gln Ala Pro Gly Arg Glu Arg Glu Gly Val
        35                  40                  45

Ala His Val Tyr Thr Gly Asp Gly Ser Pro Tyr Tyr Ala Asp Ser Val
    50                  55                  60

Lys Gly Arg Phe Thr Ile Ser Gln Asp Asn Gly Glu Ser Thr Leu Tyr
65                  70                  75                  80

Leu Gln Met Asn Asn Leu Lys Pro Glu Asp Thr Ala Met Tyr Tyr Cys
                85                  90                  95

Ala Ala Gly Thr Ser Ala Leu Ser Arg Pro Tyr Gly Pro Ile Ser Tyr
            100                 105                 110

Gly Tyr Trp Tyr Trp Gly Gln Gly Thr Gln Val Thr Val Ser Ser
        115                 120                 125

<210> SEQ ID NO 35
<211> LENGTH: 127
<212> TYPE: PRT
<213> ORGANISM: Camelus bactrianus

<400> SEQUENCE: 35

Gln Val Gln Leu Gln Glu Ser Gly Gly Gly Ser Val Gln Thr Gly Gly
1               5                   10                  15

Ser Leu Arg Leu Ser Cys Thr Ala Ser Thr Ser Ile Tyr Ser Asn Asn
            20                  25                  30

Tyr Met Ala Trp Phe Ser Gln Ala Pro Gly Lys Gly Arg Glu Gly Val
        35                  40                  45

Ala Ala Val Tyr Ile Asp Asp Gly Arg Pro Tyr Tyr Ala Asp Ser Val
```

```
                 50                  55                  60
Lys Gly Arg Phe Thr Ile Ser Leu Asp Ser Ala Lys Asn Thr Val Tyr
 65                  70                  75                  80

Leu Gln Met Asn Ser Leu Lys Pro Glu Asp Thr Ala Met Tyr Tyr Cys
                     85                  90                  95

Ala Ala Ala Pro Gly Pro Leu Ser Arg Asn Tyr Trp Tyr Thr Ser Ala
                100                 105                 110

Asn Tyr Asp Tyr Trp Gly Gln Gly Thr Gln Val Thr Val Ser Ser
            115                 120                 125
```

<210> SEQ ID NO 36
<211> LENGTH: 127
<212> TYPE: PRT
<213> ORGANISM: Camelus bactrianus

<400> SEQUENCE: 36

```
Gln Val Gln Leu Gln Glu Ser Gly Gly Gly Ser Val Gln Thr Gly Gly
 1               5                   10                  15

Ser Leu Arg Leu Ser Cys Ala Ala Ser Thr Ser Leu Tyr Ser Tyr Asn
                20                  25                  30

Tyr Met Ala Trp Phe Ser Gln Ala Pro Gly Lys Gly Arg Glu Gly Val
             35                  40                  45

Ala Ala Val Tyr Val Gly Asp Gly Arg Pro Tyr Tyr Ala Ala Ser Val
         50                  55                  60

Lys Gly Arg Phe Thr Ile Ser Leu Asp Ser Ala Lys Asn Thr Val Tyr
 65                  70                  75                  80

Leu Gln Met Asn Ser Leu Lys Pro Glu Asp Thr Ala Met Tyr Tyr Cys
                     85                  90                  95

Ala Ala Ala Pro Gly Pro Leu Ser His Asn Tyr Trp Tyr Thr Ser Ala
                100                 105                 110

Asn Tyr Asp Tyr Trp Gly Gln Gly Thr Gln Val Thr Val Ser Ser
            115                 120                 125
```

<210> SEQ ID NO 37
<211> LENGTH: 127
<212> TYPE: PRT
<213> ORGANISM: Camelus bactrianus

<400> SEQUENCE: 37

```
Gln Val Gln Leu Gln Glu Ser Gly Gly Gly Ser Val Gln Thr Gly Gly
 1               5                   10                  15

Ser Leu Arg Leu Ser Cys Ala Ala Ser Thr Ser Ile Tyr Ser Ile Asn
                20                  25                  30

Tyr Met Ala Trp Phe Arg Gln Ala Pro Gly Lys Gly Arg Glu Gly Val
             35                  40                  45

Ala Ala Val Tyr Ile Asp Asp Gly Arg Pro Tyr Tyr Ala Asp Ser Val
         50                  55                  60

Lys Gly Arg Phe Thr Ile Ser Leu Asp Ser Ala Lys Asn Thr Val Tyr
 65                  70                  75                  80

Leu Gln Met Thr Ser Leu Lys Ser Glu Asp Thr Ala Met Tyr Tyr Cys
                     85                  90                  95

Ala Ala Ala Pro Gly Pro Leu Ser Arg Ser Tyr Trp Tyr Thr Ser Ala
                100                 105                 110

Asn Tyr Asp Tyr Trp Gly Gln Gly Thr Gln Val Thr Val Ser Ser
            115                 120                 125
```

<210> SEQ ID NO 38
<211> LENGTH: 127
<212> TYPE: PRT
<213> ORGANISM: Camelus bactrianus

<400> SEQUENCE: 38

Gln Val Gln Leu Gln Glu Ser Gly Gly Gly Ser Val Gln Thr Gly Gly
1               5                   10                  15

Ser Leu Arg Leu Ser Cys Ala Ala Ser Thr Ser Ile Tyr Ser Asn Asn
            20                  25                  30

Tyr Met Ala Trp Phe Ser Gln Ala Pro Gly Lys Gly Arg Glu Gly Val
        35                  40                  45

Ala Ala Val Tyr Ile Gly Asp Gly Arg Pro Tyr Tyr Ala Asp Ser Ala
    50                  55                  60

Lys Gly Arg Phe Thr Ile Ser Leu Asp Ser Ala Lys Asn Thr Val Tyr
65                  70                  75                  80

Leu Gln Met Asn Ser Leu Lys Pro Glu Asp Thr Ala Met Tyr Tyr Cys
                85                  90                  95

Ala Ala Ala Pro Gly Pro Leu Ser Arg Asn Tyr Trp Tyr Thr Ser Ala
            100                 105                 110

Asn Tyr Asp Tyr Trp Gly Gln Gly Thr Gln Val Thr Val Ser Ser
        115                 120                 125

<210> SEQ ID NO 39
<211> LENGTH: 127
<212> TYPE: PRT
<213> ORGANISM: Camelus bactrianus

<400> SEQUENCE: 39

Gln Val Gln Leu Gln Glu Ser Gly Gly Gly Ser Val Gln Thr Gly Gly
1               5                   10                  15

Ser Leu Arg Leu Ser Cys Ala Ala Ser Thr Ser Ile Tyr Ser Asn Asn
            20                  25                  30

Tyr Met Ala Trp Phe Ser Gln Ala Pro Gly Lys Gly Arg Glu Gly Val
        35                  40                  45

Ala Ala Leu Tyr Ile Gly Asp Gly Arg Pro Tyr Tyr Ala Asp Ser Val
    50                  55                  60

Lys Gly Arg Phe Thr Ile Ala Leu Asp Ser Ala Lys Asn Thr Val Tyr
65                  70                  75                  80

Leu Gln Met Asn Gly Leu Lys Pro Glu Asp Thr Ala Met Tyr Tyr Cys
                85                  90                  95

Ala Ala Ala Pro Gly Pro Leu Lys His Asn Tyr Trp Tyr Thr Ser Ala
            100                 105                 110

Asn Tyr Asp Tyr Trp Gly Gln Gly Thr Gln Val Thr Val Ser Ser
        115                 120                 125

<210> SEQ ID NO 40
<211> LENGTH: 127
<212> TYPE: PRT
<213> ORGANISM: Camelus bactrianus

<400> SEQUENCE: 40

Gln Val Gln Leu Gln Glu Ser Gly Gly Gly Ser Val Gln Thr Gly Gly
1               5                   10                  15

Ser Leu Arg Leu Ser Cys Ala Ala Ser Thr Ser Ile Tyr Ser Asn Asn
            20                  25                  30

Tyr Met Ala Trp Phe Ser Gln Ala Pro Gly Lys Gly Arg Glu Gly Val
        35                  40                  45

Ala Ala Leu Tyr Ile Gly Asp Gly Arg Pro Tyr Tyr Ala Asp Ser Val
            50                  55                  60

Lys Gly Arg Phe Thr Ile Ala Leu Asp Ser Ala Lys Asn Thr Val Tyr
 65                  70                  75                  80

Leu Gln Met Asn Gly Leu Lys Pro Glu Asp Thr Ala Met Tyr Tyr Cys
                85                  90                  95

Ala Ala Ala Pro Gly Pro Leu Lys His Asn Tyr Trp Tyr Thr Ser Ala
               100                 105                 110

Asn Tyr Asp Tyr Trp Gly Gln Gly Thr Gln Val Thr Val Ser Ser
               115                 120                 125

<210> SEQ ID NO 41
<211> LENGTH: 127
<212> TYPE: PRT
<213> ORGANISM: Camelus bactrianus

<400> SEQUENCE: 41

Gln Val Gln Leu Gln Glu Ser Gly Gly Gly Ser Val Gln Thr Gly Gly
  1               5                  10                  15

Ser Leu Arg Leu Ser Cys Ala Ala Ser Thr Ser Ile Tyr Ser Asn Asn
                 20                  25                  30

Tyr Met Ala Trp Phe Arg Gln Ala Pro Gly Lys Gly Arg Glu Gly Val
                35                  40                  45

Ala Ala Val Tyr Ile Gly Asp Gly Arg Pro Tyr Tyr Ala Asp Ser Ala
            50                  55                  60

Lys Gly Arg Phe Thr Ile Ser Leu Asp Ser Ala Lys Asn Thr Val Tyr
 65                  70                  75                  80

Leu Gln Met Asn Ser Leu Lys Pro Glu Asp Thr Ala Met Tyr Tyr Cys
                85                  90                  95

Ala Ala Ala Pro Gly Pro Leu Ser Arg His Tyr Trp Tyr Thr Ser Ala
               100                 105                 110

Asn Tyr Asp Tyr Trp Gly Pro Gly Thr Gln Val Thr Val Ser Ser
               115                 120                 125

<210> SEQ ID NO 42
<211> LENGTH: 127
<212> TYPE: PRT
<213> ORGANISM: Camelus bactrianus

<400> SEQUENCE: 42

Gln Val Gln Leu Gln Glu Ser Gly Gly Gly Ser Val Gln Thr Gly Gly
  1               5                  10                  15

Ser Leu Thr Leu Ser Cys Ala Ala Ser Thr Ser Ile Tyr Ser Tyr Asn
                 20                  25                  30

Tyr Met Ala Trp Phe Arg Gln Ala Pro Gly Lys Gly Arg Glu Gly Val
                35                  40                  45

Ala Ala Val Tyr Ile Gly Asp Gly Arg Pro Tyr Tyr Ala Asp Ser Val
            50                  55                  60

Lys Gly Arg Phe Thr Ile Ser Pro Asp Ser Ala Lys Asn Thr Val Tyr
 65                  70                  75                  80

Leu Gln Met Asn Ser Leu Lys Pro Glu Asp Thr Ala Met Tyr Tyr Cys
                85                  90                  95

Ala Ala Ala Pro Gly Pro Leu Ser Arg His Tyr Trp Tyr Thr Ser Ala
               100                 105                 110

Asn Tyr Asp Tyr Trp Gly Pro Gly Thr Gln Val Thr Val Ser Ser
               115                 120                 125

```
<210> SEQ ID NO 43
<211> LENGTH: 127
<212> TYPE: PRT
<213> ORGANISM: Camelus bactrianus

<400> SEQUENCE: 43
```

| Gln | Val | Gln | Leu | Gln | Glu | Ser | Gly | Gly | Gly | Ser | Val | Gln | Thr | Gly | Gly |
|---|---|---|---|---|---|---|---|---|---|---|---|---|---|---|---|
| 1 | | | | 5 | | | | | 10 | | | | | 15 | |

| Ser | Leu | Arg | Leu | Ser | Cys | Ala | Ala | Ser | Ser | Ile | Ala | Ser | Asn | Asn |
|---|---|---|---|---|---|---|---|---|---|---|---|---|---|---|
| | | | 20 | | | | | 25 | | | | | 30 | |

| Tyr | Met | Ala | Trp | Phe | Ser | Gln | Ala | Pro | Gly | Lys | Gly | Arg | Glu | Gly | Val |
|---|---|---|---|---|---|---|---|---|---|---|---|---|---|---|---|
| | | | 35 | | | | | 40 | | | | | 45 | | |

| Ala | Ala | Val | Tyr | Ile | Gly | Asp | Gly | Arg | Pro | Tyr | Tyr | Ala | Asp | Ser | Val |
|---|---|---|---|---|---|---|---|---|---|---|---|---|---|---|---|
| | 50 | | | | | 55 | | | | | 60 | | | | |

| Lys | Gly | Arg | Phe | Thr | Ile | Ser | Leu | Asp | Ser | Ala | Lys | Asn | Thr | Val | Tyr |
|---|---|---|---|---|---|---|---|---|---|---|---|---|---|---|---|
| 65 | | | | | 70 | | | | | 75 | | | | | 80 |

| Leu | Gln | Met | Asn | Ser | Leu | Lys | Pro | Glu | Asp | Thr | Ala | Met | Tyr | Tyr | Cys |
|---|---|---|---|---|---|---|---|---|---|---|---|---|---|---|---|
| | | | | 85 | | | | | 90 | | | | | 95 | |

| Ala | Ala | Ala | Pro | Gly | Pro | Leu | Ser | Arg | Asn | Tyr | Trp | Tyr | Thr | Ser | Ala |
|---|---|---|---|---|---|---|---|---|---|---|---|---|---|---|---|
| | | | 100 | | | | | 105 | | | | | 110 | | |

| Asn | Tyr | Asp | Tyr | Trp | Gly | Gln | Gly | Thr | Gln | Val | Thr | Val | Ser | Ser |
|---|---|---|---|---|---|---|---|---|---|---|---|---|---|---|
| | | 115 | | | | | 120 | | | | | 125 | | |

```
<210> SEQ ID NO 44
<211> LENGTH: 127
<212> TYPE: PRT
<213> ORGANISM: Camelus bactrianus

<400> SEQUENCE: 44
```

| Gln | Val | Gln | Leu | Gln | Glu | Ser | Gly | Gly | Gly | Ser | Val | Arg | Thr | Gly | Gly |
|---|---|---|---|---|---|---|---|---|---|---|---|---|---|---|---|
| 1 | | | | 5 | | | | | 10 | | | | | 15 | |

| Ser | Leu | Arg | Leu | Ser | Cys | Ala | Ala | Ser | Thr | Ser | Ile | Tyr | Ser | Leu | Asn |
|---|---|---|---|---|---|---|---|---|---|---|---|---|---|---|---|
| | | | 20 | | | | | 25 | | | | | 30 | | |

| Tyr | Met | Ala | Trp | Phe | Ser | Gln | Ala | Pro | Gly | Lys | Gly | Arg | Glu | Gly | Val |
|---|---|---|---|---|---|---|---|---|---|---|---|---|---|---|---|
| | | | 35 | | | | | 40 | | | | | 45 | | |

| Ala | Ala | Val | Tyr | Ile | Asp | Asp | Gly | Arg | Pro | Tyr | Tyr | Ala | Asp | His | Val |
|---|---|---|---|---|---|---|---|---|---|---|---|---|---|---|---|
| | 50 | | | | | 55 | | | | | 60 | | | | |

| Lys | Gly | Arg | Phe | Thr | Ile | Ser | Leu | Asp | Thr | Ala | Lys | Asn | Thr | Val | Tyr |
|---|---|---|---|---|---|---|---|---|---|---|---|---|---|---|---|
| 65 | | | | | 70 | | | | | 75 | | | | | 80 |

| Leu | Gln | Met | Asn | Ser | Leu | Lys | Pro | Glu | Asp | Thr | Ala | Met | Tyr | Tyr | Cys |
|---|---|---|---|---|---|---|---|---|---|---|---|---|---|---|---|
| | | | | 85 | | | | | 90 | | | | | 95 | |

| Ala | Ala | Ala | Pro | Gly | Pro | Leu | Ser | Arg | Asn | Tyr | Trp | Tyr | Thr | Ser | Ala |
|---|---|---|---|---|---|---|---|---|---|---|---|---|---|---|---|
| | | | 100 | | | | | 105 | | | | | 110 | | |

| Asn | Tyr | Asp | Tyr | Trp | Gly | Gln | Gly | Thr | Gln | Val | Thr | Val | Ser | Ser |
|---|---|---|---|---|---|---|---|---|---|---|---|---|---|---|
| | | 115 | | | | | 120 | | | | | 125 | | |

```
<210> SEQ ID NO 45
<211> LENGTH: 121
<212> TYPE: PRT
<213> ORGANISM: Camelus bactrianus

<400> SEQUENCE: 45
```

| Gln | Val | Gln | Leu | Gln | Glu | Ser | Gly | Gly | Gly | Leu | Val | Gln | Pro | Gly | Gly |
|---|---|---|---|---|---|---|---|---|---|---|---|---|---|---|---|
| 1 | | | | 5 | | | | | 10 | | | | | 15 | |

| Ser | Leu | Arg | Leu | Ser | Cys | Ala | Ala | Ser | Gly | Phe | Thr | Phe | Ser | Ile | Lys |
|---|---|---|---|---|---|---|---|---|---|---|---|---|---|---|---|
| | | | 20 | | | | | 25 | | | | | 30 | | |

Ala Met Ser Trp Val Arg Gln Ala Pro Gly Lys Gly Leu Glu Trp Val
            35                  40                  45

Ser Thr Ile Asp Ser Gly Gly Arg Arg Tyr Tyr Ala Asp Ser Val
 50                  55                  60

Lys Gly Arg Phe Thr Ile Ser Arg Asp Asn Ala Lys Asn Thr Leu Tyr
 65                  70                  75                  80

Leu Gln Leu Ser Ser Leu Lys Thr Glu Asp Thr Ala Met Tyr Phe Cys
                 85                  90                  95

Ala Arg Cys Ser Asp Ile Tyr Cys Tyr Asn Gly Ala Ser Tyr Arg Gly
            100                 105                 110

Gln Gly Thr Gln Val Thr Val Ser Ser
            115                 120

<210> SEQ ID NO 46
<211> LENGTH: 127
<212> TYPE: PRT
<213> ORGANISM: Camelus bactrianus

<400> SEQUENCE: 46

Gln Val Gln Leu Gln Glu Ser Gly Gly Gly Ser Val Gln Thr Gly Gly
 1               5                   10                  15

Ser Leu Arg Leu Ser Cys Ala Ala Ser Thr Ser Ile Asp Ser Asn Asn
            20                  25                  30

Tyr Met Ala Trp Phe Arg Gln Ala Pro Gly Lys Gly Arg Glu Gly Val
            35                  40                  45

Ala Ala Val Tyr Ile Asp Asp Gly Arg Pro Tyr Tyr Ala Asp Ser Val
 50                  55                  60

Lys Gly Arg Phe Thr Ile Ser Leu Asp Ser Ala Lys Asn Thr Val Tyr
 65                  70                  75                  80

Leu Gln Met Asn Ser Leu Lys Pro Glu Asp Thr Ala Met Tyr Tyr Cys
                 85                  90                  95

Ala Ala Ala Pro Gly Pro Leu Ser Arg His Tyr Trp Tyr Thr Ser Ala
            100                 105                 110

Asn Tyr Asp Tyr Trp Gly Pro Gly Thr Gln Val Thr Val Ser Ser
            115                 120                 125

<210> SEQ ID NO 47
<211> LENGTH: 127
<212> TYPE: PRT
<213> ORGANISM: Camelus bactrianus

<400> SEQUENCE: 47

Gln Val Gln Leu Gln Glu Ser Gly Gly Gly Ser Val Gln Thr Gly Gly
 1               5                   10                  15

Ser Leu Arg Leu Ser Cys Thr Ala Ser Thr Ser Ile Tyr Asn Asn Asn
            20                  25                  30

Tyr Met Ala Trp Phe Ser Gln Ser Pro Gly Lys Gly Arg Glu Gly Val
            35                  40                  45

Ala Ala Val Tyr Met Asp Asp Gly Arg Pro Tyr Tyr Ala Asp Ser Val
 50                  55                  60

Lys Gly Arg Phe Thr Ile Ser Leu Asp Ser Ala Lys Asn Thr Met Tyr
 65                  70                  75                  80

Leu Gln Met Asn Ser Leu Lys Pro Glu Asp Thr Ala Met Tyr Tyr Cys
                 85                  90                  95

Ala Ala Ala Pro Gly Pro Leu Ser Arg Asn Tyr Trp Tyr Thr Ser Ala
            100                 105                 110

```
Asn Tyr Asp Tyr Trp Gly Gln Gly Thr Gln Val Thr Val Ser Ser
            115                 120                 125
```

<210> SEQ ID NO 48
<211> LENGTH: 127
<212> TYPE: PRT
<213> ORGANISM: Camelus bactrianus

<400> SEQUENCE: 48

```
Gln Val Gln Leu Gln Glu Ser Gly Gly Gly Ser Val Gln Thr Gly Gly
1               5                   10                  15

Ser Leu Arg Leu Ser Cys Ala Ala Ser Thr Ser Ile Tyr Ser Asn Asn
            20                  25                  30

Tyr Met Ala Trp Phe Ser Gln Ala Pro Gly Lys Gly Arg Glu Gly Val
            35                  40                  45

Ala Ala Val Tyr Ile Asp Gly Arg Thr Tyr Tyr Ala Asp Ser Val
    50                  55                  60

Lys Gly Arg Phe Thr Ile Ser Leu Asp Ser Ala Lys Asn Thr Val Tyr
65                  70                  75                  80

Leu Gln Met Asn Ser Leu Lys Pro Glu Asp Thr Ala Met Tyr Tyr Cys
                85                  90                  95

Ala Ala Ala Pro Gly Pro Leu Ser His Asn Tyr Trp Tyr Ala Ser Ala
            100                 105                 110

Asn Tyr Asp Tyr Trp Gly Gln Gly Thr Gln Val Thr Val Ser Ser
            115                 120                 125
```

<210> SEQ ID NO 49
<211> LENGTH: 127
<212> TYPE: PRT
<213> ORGANISM: Camelus bactrianus

<400> SEQUENCE: 49

```
Gln Val Gln Leu Gln Glu Ser Gly Gly Gly Ser Val Gln Thr Gly Gly
1               5                   10                  15

Ser Leu Arg Leu Ser Cys Ala Ala Ser Thr Ser Ile Tyr Ser Ile Asn
            20                  25                  30

Tyr Met Ala Trp Phe Ser Gln Ala Pro Gly Lys Gly Arg Glu Gly Val
            35                  40                  45

Ala Ala Val Tyr Ile Asp Asp Gly Arg Pro Tyr Tyr Ala Asp Ser Val
    50                  55                  60

Lys Gly Arg Phe Thr Ile Ser Leu Asp Ser Ala Lys Asn Thr Val Tyr
65                  70                  75                  80

Leu Gln Met Asn Ser Leu Lys Pro Glu Asp Thr Ala Met Tyr Tyr Cys
                85                  90                  95

Ala Ala Ala Pro Gly Pro Leu Ser Arg Asn Tyr Trp Tyr Thr Ser Ala
            100                 105                 110

Asn Tyr Asp Tyr Trp Gly Gln Gly Thr Gln Val Thr Val Ser Ser
            115                 120                 125
```

<210> SEQ ID NO 50
<211> LENGTH: 121
<212> TYPE: PRT
<213> ORGANISM: Camelus bactrianus

<400> SEQUENCE: 50

```
Gln Val Gln Leu Gln Glu Ser Gly Gly Gly Leu Val Gln Pro Gly Gly
1               5                   10                  15

Ser Leu Arg Leu Ser Cys Ile Ala Ser Gly Phe Thr Phe Ser Ile Met
```

```
                     20                  25                  30
Ala Met Ser Trp Val Arg Gln Ala Pro Gly Lys Gly Leu Glu Trp Val
                 35                  40                  45

Ser Thr Ile Asn Ser Asp Gly Gly Lys Thr Tyr Tyr Ala Asp Ser Val
         50                   55                  60

Lys Gly Arg Phe Thr Ile Ser Arg Asp Asn Ala Lys Asn Thr Leu Tyr
 65                  70                  75                  80

Leu Gln Leu Asn Ser Leu Arg Thr Glu Asp Met Ala Met Tyr Tyr Cys
                 85                  90                  95

Arg Arg Cys Ala Asp Ile Tyr Cys Ser Gly Ser Gly Gly Trp Thr Gly
             100                 105                 110

Gln Gly Thr Gln Val Thr Val Ser Ser
             115                 120
```

<210> SEQ ID NO 51
<211> LENGTH: 127
<212> TYPE: PRT
<213> ORGANISM: Camelus bactrianus

<400> SEQUENCE: 51

```
Gln Val Gln Leu Gln Glu Ser Gly Gly Gly Ser Val Gln Thr Gly Gly
 1               5                  10                  15

Ser Leu Arg Leu Ser Cys Thr Ala Ser Thr Ser Ile Tyr Ser Asn Ser
                 20                  25                  30

Tyr Met Ala Trp Phe Ser Gln Ala Pro Gly Lys Gly Arg Glu Gly Val
                 35                  40                  45

Ala Ala Val Tyr Ile Asp Asp Gly Arg Pro Tyr Tyr Ala Asp Ser Val
             50                  55                  60

Lys Gly Arg Phe Thr Ile Ser Leu Asp Ser Ala Lys Asn Thr Val Tyr
 65                  70                  75                  80

Leu Gln Met Asn Ser Leu Lys Pro Glu Asp Thr Ala Met Tyr Tyr Cys
                 85                  90                  95

Ala Ala Ala Pro Gly Pro Leu Ser Arg His Tyr Trp Tyr Thr Ser Ala
             100                 105                 110

Asn Tyr Asp Tyr Trp Gly Gln Gly Thr Gln Val Thr Val Ser Ser
             115                 120                 125
```

<210> SEQ ID NO 52
<211> LENGTH: 127
<212> TYPE: PRT
<213> ORGANISM: Camelus bactrianus

<400> SEQUENCE: 52

```
Gln Val Gln Leu Gln Glu Ser Gly Gly Gly Ser Val Gln Thr Gly Gly
 1               5                  10                  15

Ser Leu Arg Leu Ser Cys Ala Ala Ser Thr Ser Ile Tyr Ser Asn Asn
                 20                  25                  30

Tyr Met Ala Trp Phe Arg Gln Ala Pro Gly Lys Gly Arg Glu Gly Val
                 35                  40                  45

Ala Ala Val Tyr Val Asp Asp Gly Arg Pro Tyr Tyr Ala Asp Ser Val
             50                  55                  60

Lys Gly Arg Phe Thr Ile Ser Arg Asp Ser Ala Lys Asn Thr Val Tyr
 65                  70                  75                  80

Leu Gln Met Asn Ser Leu Lys Pro Glu Asp Thr Ala Met Tyr Tyr Cys
                 85                  90                  95

Ala Ala Ala Pro Gly Pro Leu Ser Arg His Tyr Trp Tyr Thr Ser Ala
```

Asn Tyr Asp Tyr Trp Gly Pro Gly Thr Gln Val Thr Val Ser Ser
            115                 120                 125

<210> SEQ ID NO 53
<211> LENGTH: 127
<212> TYPE: PRT
<213> ORGANISM: Camelus bactrianus

<400> SEQUENCE: 53

Gln Val Gln Leu Gln Glu Ser Gly Gly Gly Ser Val Gln Thr Gly Gly
1               5                   10                  15

Ser Leu Arg Leu Ser Cys Ala Ala Ser Thr Ser Ile Tyr Ser Asn Asn
            20                  25                  30

Tyr Met Ala Trp Phe Ser Gln Ala Pro Gly Lys Gly Arg Glu Gly Val
        35                  40                  45

Ala Ala Val Tyr Ile Asp Asp Gly Arg Pro Tyr Tyr Ala Asp Ser Val
    50                  55                  60

Lys Gly Arg Phe Thr Ile Ser Leu Asp Ser Ala Lys Asn Thr Val Tyr
65                  70                  75                  80

Leu Gln Met Asn Ser Leu Lys Pro Glu Asp Thr Ala Met Tyr Tyr Cys
                85                  90                  95

Ala Ala Ala Pro Gly Pro Leu Ser Arg Asn Tyr Trp Tyr Thr Ser Ala
            100                 105                 110

Asn Tyr Asp Tyr Trp Gly Gln Gly Thr Gln Val Thr Val Ser Ser
            115                 120                 125

<210> SEQ ID NO 54
<211> LENGTH: 127
<212> TYPE: PRT
<213> ORGANISM: Camelus bactrianus

<400> SEQUENCE: 54

Gln Val Gln Leu Gln Glu Ser Gly Gly Gly Ser Val Gln Thr Gly Gly
1               5                   10                  15

Ser Leu Arg Leu Ser Cys Ala Pro Ser Thr Ser Ile Tyr Asp Asn Asn
            20                  25                  30

Tyr Met Ala Trp Phe Ser Gln Ala Pro Gly Lys Gly Arg Glu Gly Val
        35                  40                  45

Ala Ala Ile Tyr Ile Asp Asp Gly Arg Pro Tyr Tyr Ala Asp Ser Val
    50                  55                  60

Lys Gly Arg Phe Thr Ile Ser Leu Asp Ser Ala Lys Asn Thr Val Tyr
65                  70                  75                  80

Leu Gln Met Asn Ser Leu Lys Pro Glu Asp Thr Ala Met Tyr Tyr Cys
                85                  90                  95

Ala Ala Ala Pro Gly Pro Leu Ser His Asn Tyr Trp Tyr Thr Ser Ala
            100                 105                 110

Asn Tyr Asp Tyr Trp Gly Gln Gly Thr Gln Val Thr Val Ser Ser
            115                 120                 125

<210> SEQ ID NO 55
<211> LENGTH: 127
<212> TYPE: PRT
<213> ORGANISM: Camelus bactrianus

<400> SEQUENCE: 55

Gln Val Gln Leu Gln Glu Ser Gly Gly Gly Ser Val Gln Thr Gly Gly
1               5                   10                  15

-continued

Ser Leu Arg Leu Ser Cys Val Ala Ser Thr Ser Ile Phe Ser Asn Asn
            20                  25                  30

Tyr Met Ala Trp Phe Ser Gln Ala Pro Gly Lys Gly Arg Glu Gly Val
        35                  40                  45

Ala Ala Val Tyr Ile Gly Asp Gly Arg Pro Tyr Tyr Ala Asp Ser Val
 50                  55                  60

Lys Gly Arg Phe Thr Ile Ser Leu Asp Ser Ala Lys Asn Thr Val Tyr
65                  70                  75                  80

Leu Gln Met Asn Ser Leu Lys Pro Glu Asp Thr Ala Met Tyr Tyr Cys
                85                  90                  95

Ala Ala Ala Pro Gly Pro Leu Ser His Asn Tyr Trp Tyr Thr Ser Ala
            100                 105                 110

Asn Tyr Asp Tyr Trp Gly Gln Gly Thr Gln Val Thr Val Ser Ser
        115                 120                 125

<210> SEQ ID NO 56
<211> LENGTH: 127
<212> TYPE: PRT
<213> ORGANISM: Camelus bactrianus

<400> SEQUENCE: 56

Gln Val Gln Leu Gln Glu Ser Gly Gly Gly Ser Val Gln Thr Gly Gly
1               5                   10                  15

Ser Leu Arg Leu Ser Cys Ala Ala Ser Pro Ser Ile Tyr Ser Ala Asn
            20                  25                  30

Tyr Met Ala Trp Phe Ser Gln Ala Pro Gly Lys Gly Arg Glu Gly Val
        35                  40                  45

Ala Ala Val Tyr Ile Gly Asp Gly Arg Pro Tyr Tyr Ala Asp Ser Val
 50                  55                  60

Lys Gly Arg Phe Thr Ile Ser Leu Asp Ser Ala Lys Ser Thr Val Tyr
65                  70                  75                  80

Leu Gln Met Asn Ser Leu Lys Pro Glu Asp Thr Ala Met Tyr Tyr Cys
                85                  90                  95

Ala Ala Ala Pro Gly Pro Leu Ser His Asn Tyr Trp Tyr Thr Ser Ala
            100                 105                 110

Asn Tyr Asp Tyr Trp Gly Gln Gly Thr Gln Val Thr Val Ser Ser
        115                 120                 125

<210> SEQ ID NO 57
<211> LENGTH: 127
<212> TYPE: PRT
<213> ORGANISM: Camelus bactrianus

<400> SEQUENCE: 57

Gln Val Gln Leu Gln Glu Ser Gly Gly Gly Ser Val Gln Thr Gly Gly
1               5                   10                  15

Ser Leu Arg Leu Ser Cys Ala Ala Ser Thr Ser Ile Tyr Ser Ile Asn
            20                  25                  30

Tyr Met Ala Trp Phe Ser Gln Ala Pro Gly Lys Gly Arg Glu Gly Val
        35                  40                  45

Ala Ala Val Tyr Ile Asp Asp Gly Arg Pro Tyr Tyr Ala Asp Ser Val
 50                  55                  60

Lys Gly Arg Phe Thr Ile Ser Leu Asp Ser Ala Lys Asn Thr Val Tyr
65                  70                  75                  80

Leu Gln Met Asn Ser Leu Lys Ser Glu Asp Thr Ala Met Tyr Tyr Cys
                85                  90                  95

-continued

Ala Ala Ala Pro Gly Pro Leu Ser Arg Asn Tyr Trp Tyr Thr Ser Ala
            100                 105                 110

Asn Tyr Asp Tyr Trp Gly Gln Gly Thr Gln Val Thr Val Ser Ser
        115                 120                 125

<210> SEQ ID NO 58
<211> LENGTH: 121
<212> TYPE: PRT
<213> ORGANISM: Camelus bactrianus

<400> SEQUENCE: 58

Gln Val Gln Leu Gln Glu Ser Gly Gly Gly Leu Val Gln Pro Gly Gly
1               5                   10                  15

Ser Leu Arg Leu Ser Cys Ala Leu Ser Gly Phe Thr Ser Thr Ile Tyr
            20                  25                  30

Ala Met Ser Trp Val Arg Gln Ala Pro Gly Lys Gly Leu Glu Trp Val
        35                  40                  45

Ser Thr Ile Asn Ser Asp Gly Gly Tyr Arg Tyr Tyr Ala Asp Ser Val
    50                  55                  60

Lys Gly Arg Phe Thr Ile Ser Arg Asp Asn Ala Lys Asn Thr Leu Tyr
65                  70                  75                  80

Leu Gln Leu Asn Ser Pro Lys Thr Glu Asp Thr Ala Met Tyr Tyr Cys
                85                  90                  95

Ala Arg Cys Ser Asp Ile Tyr Cys Tyr Asn Gly Pro Ser Tyr Arg Gly
            100                 105                 110

Gln Gly Thr Gln Val Thr Val Ser Ser
        115                 120

<210> SEQ ID NO 59
<211> LENGTH: 127
<212> TYPE: PRT
<213> ORGANISM: Camelus bactrianus

<400> SEQUENCE: 59

Gln Val Gln Leu Gln Glu Ser Gly Gly Gly Ser Val Gln Thr Gly Gly
1               5                   10                  15

Ser Leu Arg Leu Ser Cys Ala Cys Ser Thr Ser Ile Tyr Ser Asn Asn
            20                  25                  30

Tyr Met Ala Trp Phe Ser Gln Ala Pro Gly Lys Gly Arg Glu Gly Val
        35                  40                  45

Ala Ala Val Tyr Ile Gly Asp Gly Arg Pro Tyr Tyr Thr Asp Ser Val
    50                  55                  60

Lys Gly Arg Phe Thr Ile Ser Leu Asp Ser Ala Lys Asn Thr Leu Tyr
65                  70                  75                  80

Leu Gln Met Asn Ser Leu Lys Pro Glu Asp Thr Ala Met Tyr Tyr Cys
                85                  90                  95

Ala Ala Ala Pro Gly Pro Leu Ser His Asn Tyr Trp Tyr Thr Ser Ala
            100                 105                 110

Asn Tyr Asp Tyr Trp Gly Gln Gly Thr Gln Val Thr Val Ser Ser
        115                 120                 125

<210> SEQ ID NO 60
<211> LENGTH: 127
<212> TYPE: PRT
<213> ORGANISM: Camelus bactrianus

<400> SEQUENCE: 60

```
Gln Val Gln Leu Gln Glu Ser Gly Gly Gly Ser Val Gln Thr Gly Gly
1               5                   10                  15

Ser Leu Arg Leu Ser Cys Ala Ala Ser Thr Ser Ile Tyr Ser Met Asn
            20                  25                  30

Tyr Met Ala Trp Phe Ser Gln Ala Pro Gly Lys Gly Arg Glu Gly Val
        35                  40                  45

Ala Ala Val Tyr Ile Glu Asp Gly Arg Pro Tyr Tyr Ala Asp Ser Val
    50                  55                  60

Lys Gly Arg Phe Thr Ile Ser Pro Asp Arg Ala Lys Asn Thr Val Tyr
65                  70                  75                  80

Leu Gln Met Asn Ser Leu Lys Pro Glu Asp Thr Ala Met Tyr Tyr Cys
                85                  90                  95

Ala Ala Ala Pro Gly Pro Leu Ser Arg Asn Tyr Trp Tyr Thr Ser Ala
            100                 105                 110

Asn Tyr Asp Tyr Trp Gly Gln Gly Thr Gln Val Thr Val Ser Ser
            115                 120                 125
```

<210> SEQ ID NO 61
<211> LENGTH: 121
<212> TYPE: PRT
<213> ORGANISM: Camelus bactrianus

<400> SEQUENCE: 61

```
Gln Val Gln Leu Gln Glu Ser Gly Gly Gly Leu Val Gln Pro Gly Gly
1               5                   10                  15

Ser Leu Arg Leu Ser Cys Ala Ala Ser Gly Phe Asp Phe Ser Ser Arg
            20                  25                  30

Ala Met Ser Trp Val Arg Gln Ala Pro Gly Lys Gly Leu Glu Trp Val
        35                  40                  45

Ser Thr Ile Asn Ser Gly Gly Ser Arg Tyr Tyr Ala Asp Ser Val
    50                  55                  60

Lys Gly Arg Phe Thr Thr Ser Arg Asp Asn Ala Lys Asn Thr Leu Ala
65                  70                  75                  80

Leu Gln Leu Asn Ser Leu Lys Thr Glu Asp Thr Ala Met Tyr Tyr Cys
                85                  90                  95

Ala Arg Cys Ser Asp Ile Tyr Cys Asp Asn Gly Ala Trp Tyr Arg Gly
            100                 105                 110

Gln Gly Thr Gln Val Thr Val Ser Ser
            115                 120
```

<210> SEQ ID NO 62
<211> LENGTH: 127
<212> TYPE: PRT
<213> ORGANISM: Camelus bactrianus

<400> SEQUENCE: 62

```
Gln Val Gln Leu Gln Glu Ser Gly Gly Gly Ser Val Gln Ala Gly Gly
1               5                   10                  15

Ser Leu Arg Leu Ser Cys Ala Ala Ser Thr Ser Ile Tyr Ser Asn Asn
            20                  25                  30

Tyr Met Ala Trp Phe Arg Gln Thr Pro Gly Lys Gly Arg Glu Gly Val
        35                  40                  45

Ala Ala Val Tyr Ile Asp Asp Gly Arg Pro Tyr Tyr Ala Asp Ser Val
    50                  55                  60

Lys Gly Arg Phe Thr Ile Ser Leu Asp Ser Ala Lys Asn Thr Val Tyr
65                  70                  75                  80
```

```
Leu Gln Met Asn Ser Leu Lys Pro Glu Asp Thr Ala Met Tyr Tyr Cys
                85                  90                  95

Ala Ala Ala Pro Gly Pro Leu Ser His Asp Tyr Trp Tyr Thr Ser Ala
            100                 105                 110

Asn Tyr Asp Tyr Trp Gly Pro Gly Thr Gln Val Thr Val Ser Ser
        115                 120                 125
```

<210> SEQ ID NO 63
<211> LENGTH: 127
<212> TYPE: PRT
<213> ORGANISM: Camelus bactrianus

<400> SEQUENCE: 63

```
Gln Val Gln Leu Gln Glu Ser Gly Gly Gly Ser Val Gln Thr Gly Gly
1               5                   10                  15

Ser Leu Arg Leu Ser Cys Ala Ala Ser Thr Ser Ile Tyr Ser Asn Asn
            20                  25                  30

Tyr Met Ala Trp Phe Ser Gln Ala Pro Gly Lys Gly Arg Glu Gly Val
        35                  40                  45

Ala Ala Val Tyr Ile Asp Asp Gly Arg Pro Tyr Tyr Ala Asp Ser Val
    50                  55                  60

Lys Gly Arg Phe Thr Ile Ser Leu Asp Ser Ala Lys Asn Thr Val Tyr
65                  70                  75                  80

Leu Gln Met Asn Arg Leu Lys Pro Glu Asp Thr Ala Met Tyr Tyr Cys
                85                  90                  95

Ala Ala Ala Pro Gly Pro Leu Ser His Asn Tyr Trp Tyr Thr Ser Ala
            100                 105                 110

Asn Tyr Asp Tyr Trp Gly Gln Gly Thr Gln Val Thr Val Ser Ser
        115                 120                 125
```

<210> SEQ ID NO 64
<211> LENGTH: 127
<212> TYPE: PRT
<213> ORGANISM: Camelus bactrianus

<400> SEQUENCE: 64

```
Gln Val Gln Leu Gln Glu Ser Gly Gly Gly Ser Val Gln Thr Gly Gly
1               5                   10                  15

Ser Leu Arg Leu Ser Cys Ala Ala Ser Thr Ser Ile Tyr Ser Asn Asn
            20                  25                  30

Tyr Met Ala Trp Phe Ser Gln Ala Pro Gly Lys Gly Arg Glu Gly Val
        35                  40                  45

Ala Ala Val Tyr Ile Asp Asp Gly Arg Pro Tyr Tyr Ala Asp Ser Val
    50                  55                  60

Lys Gly Arg Phe Thr Ile Ser Leu Asp Ser Ala Lys Asn Thr Val Tyr
65                  70                  75                  80

Leu Gln Met Asn Ser Leu Lys Pro Glu Asp Thr Ala Met Tyr Tyr Cys
                85                  90                  95

Ala Ala Thr Pro Gly Pro Leu Ser Gln His Tyr Trp Tyr Thr Ser Ala
            100                 105                 110

Asn Tyr Asp Tyr Trp Gly Gln Gly Thr Gln Val Thr Val Ser Ser
        115                 120                 125
```

<210> SEQ ID NO 65
<211> LENGTH: 121
<212> TYPE: PRT
<213> ORGANISM: Camelus bactrianus

<400> SEQUENCE: 65

Gln Val Gln Leu Gln Glu Ser Gly Gly Gly Leu Val Gln Pro Gly Gly
1               5                   10                  15
Ser Leu Arg Leu Ser Cys Ala Ala Ser Gly Phe Thr Phe Ser Ile Leu
            20                  25                  30
Ala Met Ser Trp Val Arg Gln Ala Pro Gly Lys Gly Leu Glu Trp Ile
        35                  40                  45
Ser Thr Ile Asn Asn Ser Gly Gly Thr Thr Phe Tyr Ala Asp Ser Val
    50                  55                  60
Lys Gly Arg Phe Thr Ile Ser Arg Asp Asn Ala Lys Asn Thr Leu Tyr
65                  70                  75                  80
Leu Gln Leu Asn Ser Leu Arg Thr Glu Asp Thr Ala Met Tyr Tyr Cys
                85                  90                  95
Arg Arg Cys Thr Asp Ile Tyr Cys Ser Leu Ser Gly Gly Trp Thr Gly
            100                 105                 110
Gln Gly Thr Gln Val Thr Val Ser Ser
        115                 120

<210> SEQ ID NO 66
<211> LENGTH: 127
<212> TYPE: PRT
<213> ORGANISM: Camelus bactrianus

<400> SEQUENCE: 66

Gln Val Gln Leu Gln Glu Ser Gly Gly Gly Ser Val Gln Thr Gly Gly
1               5                   10                  15
Ser Leu Arg Leu Ser Cys Ala Ala Ser Thr Ser Ile Tyr Asn Asn Asn
            20                  25                  30
Tyr Met Ala Trp Phe Ser Gln Ala Pro Gly Lys Gly Arg Glu Gly Val
        35                  40                  45
Ala Ala Val Tyr Val Gly Asp Gly Arg Thr Tyr Tyr Ala Asp Ser Val
    50                  55                  60
Lys Gly Arg Phe Thr Ile Ser Leu Asp Ser Ala Lys Asn Thr Val Tyr
65                  70                  75                  80
Leu Gln Met Asn Ser Leu Lys Pro Glu Asp Thr Ala Met Tyr Tyr Cys
                85                  90                  95
Ala Ala Ala Pro Gly Pro Leu Ser His Asn Tyr Trp Tyr Thr Ser Ala
            100                 105                 110
Asn Tyr Asp Tyr Trp Gly Gln Gly Thr Gln Val Thr Val Ser Ser
        115                 120                 125

<210> SEQ ID NO 67
<211> LENGTH: 127
<212> TYPE: PRT
<213> ORGANISM: Camelus bactrianus

<400> SEQUENCE: 67

Gln Val Gln Leu Gln Glu Ser Gly Gly Gly Ser Val Gln Thr Gly Gly
1               5                   10                  15
Ser Leu Arg Leu Ser Cys Thr Ala Ser Thr Ser Ile Tyr Ser Asn Asn
            20                  25                  30
Tyr Met Ala Trp Phe Ser Gln Ala Pro Gly Lys Gly Arg Glu Gly Val
        35                  40                  45
Ala Ala Val Tyr Ile Asp Asp Gly Arg Pro Tyr Tyr Ala Asp Ser Val
    50                  55                  60
Lys Gly Arg Phe Thr Ile Ser Leu Asp Ser Ala Lys Asn Thr Val Tyr

```
                65                  70                  75                  80
Leu Gln Met Asn Ser Leu Lys Pro Glu Asp Thr Ala Met Tyr Tyr Cys
                    85                  90                  95

Ala Ala Ala Pro Gly Pro Leu Ser Arg Asn Tyr Trp Tyr Thr Ser Ala
                100                 105                 110

Asn Tyr Asp Tyr Trp Gly Gln Gly Thr Gln Val Thr Val Ser Ser
            115                 120                 125

<210> SEQ ID NO 68
<211> LENGTH: 127
<212> TYPE: PRT
<213> ORGANISM: Camelus bactrianus

<400> SEQUENCE: 68

Gln Val Gln Leu Gln Glu Ser Gly Gly Gly Ser Val Gln Thr Gly Gly
1               5                   10                  15

Ser Leu Arg Leu Ser Cys Thr Cys Ser Thr Ser Ile Tyr Ser Asn Asn
                20                  25                  30

Tyr Met Ala Trp Phe Ser Gln Ala Pro Gly Lys Gly Arg Glu Gly Val
            35                  40                  45

Ala Ala Val Tyr Ile Gly Asp Gly Arg Pro Tyr Tyr Ala Asp Ser Val
        50                  55                  60

Lys Gly Arg Phe Thr Ile Ser Leu Asp Ser Ala Lys Asn Thr Val Tyr
65                  70                  75                  80

Leu Gln Met Asn Ser Leu Lys Pro Glu Asp Thr Ala Met Tyr Tyr Cys
                85                  90                  95

Ala Ala Ala Pro Gly Pro Leu Ser His Asn Tyr Trp Tyr Thr Ser Ala
                100                 105                 110

Asn Tyr Asp Tyr Trp Gly Gln Gly Thr Gln Val Thr Val Ser Ser
            115                 120                 125

<210> SEQ ID NO 69
<211> LENGTH: 127
<212> TYPE: PRT
<213> ORGANISM: Camelus bactrianus

<400> SEQUENCE: 69

Gln Val Gln Leu Gln Glu Ser Gly Gly Gly Ser Val Gln Thr Gly Gly
1               5                   10                  15

Ser Leu Arg Leu Ser Cys Ala Ala Ser Thr Ser Ile Tyr Ser Asn Asn
                20                  25                  30

Tyr Met Ala Trp Phe Ser Gln Ala Pro Gly Lys Gly Arg Glu Gly Val
            35                  40                  45

Ala Ala Val Tyr Ile Gly Asp Gly Arg Pro Tyr Tyr Ala Asp Ser Val
        50                  55                  60

Lys Gly Arg Phe Thr Ile Ser Leu Asp Ser Ala Lys Asn Thr Val Tyr
65                  70                  75                  80

Leu Gln Met Asn Ser Leu Lys Pro Glu Asp Thr Ala Met Tyr Tyr Cys
                85                  90                  95

Ala Ala Ala Pro Gly Pro Leu Ser His Asn Tyr Trp Tyr Thr Ser Ala
                100                 105                 110

Asn Tyr Asp Tyr Trp Gly Gln Gly Thr Gln Val Thr Val Ser Ser
            115                 120                 125

<210> SEQ ID NO 70
<211> LENGTH: 121
<212> TYPE: PRT
```

```
<213> ORGANISM: Camelus bactrianus

<400> SEQUENCE: 70

Gln Val Gln Leu Gln Glu Ser Gly Gly Gly Leu Val Gln Pro Gly Gly
1               5                   10                  15

Ser Leu Arg Leu Ser Cys Ala Ala Ser Gly Phe Thr Phe Ser Ile Arg
            20                  25                  30

Ala Met Ser Trp Val Arg Gln Ala Pro Gly Lys Gly Leu Glu Trp Val
        35                  40                  45

Ser Thr Ile Asn Ser Gly Gly Asp Ser Arg Tyr Tyr Ala Asp Ser Val
    50                  55                  60

Lys Gly Arg Phe Thr Ile Ser Arg Asp Asn Ala Lys Asn Thr Met Tyr
65                  70                  75                  80

Leu Gln Leu Asn Ser Leu Lys Thr Glu Asp Thr Ala Met Tyr Tyr Cys
                85                  90                  95

Val Arg Cys Ser Asp Ile Tyr Cys Tyr Asn Gly Ala Ser Tyr Arg Gly
            100                 105                 110

Gln Gly Thr Gln Val Thr Val Ser Ser
        115                 120

<210> SEQ ID NO 71
<211> LENGTH: 122
<212> TYPE: PRT
<213> ORGANISM: Camelus bactrianus

<400> SEQUENCE: 71

Gln Val Gln Leu Gln Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Asp Met Ser Trp Val Arg Gln Ala Pro Gly Lys Gly Ile Glu Trp Val
        35                  40                  45

Ser Val Ile Asn Ser Gly Gly Ser Asn Thr Asp Tyr Ala Asp Ser Val
    50                  55                  60

Lys Gly Arg Phe Thr Ile Ser Arg Asp Asn Ala Lys Asn Thr Leu Tyr
65                  70                  75                  80

Leu Gln Met Asn Ser Leu Lys Thr Glu Asp Thr Ala Val Tyr Tyr Cys
                85                  90                  95

Ala Thr Ala Trp Met Gly Tyr Ser Asp Tyr Leu Asp Gly Ile Ala Arg
            100                 105                 110

Gly Gln Gly Thr Gln Val Thr Val Ser Ser
        115                 120

<210> SEQ ID NO 72
<211> LENGTH: 121
<212> TYPE: PRT
<213> ORGANISM: Camelus bactrianus

<400> SEQUENCE: 72

Gln Val Gln Leu Gln Glu Ser Gly Gly Gly Leu Val Gln Pro Gly Gly
1               5                   10                  15

Ser Leu Arg Leu Ser Cys Glu Ala Ser Gly Leu Pro Phe Ser Ile Ile
            20                  25                  30

Ala Met Ser Trp Val Arg Gln Ala Pro Gly Lys Gly Leu Glu Trp Val
        35                  40                  45

Ser Thr Ile Asn Ser Asp Gly Gly Thr Thr His Tyr Ala Asp Ser Val
    50                  55                  60
```

```
Lys Gly Arg Phe Thr Ile Ser Arg Asp Asn Ala Lys Asn Thr Leu Tyr
 65                  70                  75                  80

Leu Gln Leu Asn Ser Leu Arg Thr Glu Asp Thr Ala Met Tyr Tyr Cys
                 85                  90                  95

Arg Arg Cys Thr Asp Ile Tyr Cys Ser Gly Ser Gly Trp Thr Gly
                100                 105                 110

Gln Gly Thr Gln Val Thr Val Ser Ser
            115                 120

<210> SEQ ID NO 73
<211> LENGTH: 121
<212> TYPE: PRT
<213> ORGANISM: Camelus bactrianus

<400> SEQUENCE: 73

Gln Val Gln Leu Gln Glu Ser Gly Gly Gly Leu Val Gln Pro Gly Gly
  1               5                  10                  15

Ser Leu Arg Leu Ser Cys Glu Ala Ser Gly Leu Pro Phe Ser Ile Ile
                 20                  25                  30

Ala Met Ser Trp Val Arg Gln Ala Pro Gly Lys Gly Leu Glu Trp Val
             35                  40                  45

Ser Thr Ile Asn Ser Asp Gly Thr Thr His Tyr Ala Asp Ser Val
 50                  55                  60

Lys Gly Arg Phe Thr Ile Ser Arg Asp Asn Ala Lys Asn Thr Leu Tyr
 65                  70                  75                  80

Leu Gln Leu Asn Ser Leu Arg Thr Glu Asp Thr Ala Met Tyr Tyr Cys
                 85                  90                  95

Arg Arg Cys Thr Asp Ile Tyr Cys Ser Gly Phe Gly Gly Trp Thr Gly
                100                 105                 110

Gln Gly Thr Gln Val Thr Val Ser Ser
            115                 120

<210> SEQ ID NO 74
<211> LENGTH: 121
<212> TYPE: PRT
<213> ORGANISM: Camelus bactrianus

<400> SEQUENCE: 74

Gln Val Gln Leu Gln Glu Ser Gly Gly Gly Ser Val Gln Ala Gly Gly
  1               5                  10                  15

Ser Leu Arg Leu Ser Cys Ala Ala Ser Gly Phe Thr Gly Ser Ile Tyr
                 20                  25                  30

Ala Met Ser Trp Val Arg Gln Ala Pro Gly Lys Gly Leu Glu Trp Val
             35                  40                  45

Ser Thr Ile Ser Ser Ser Gly Gly Arg Arg Phe Tyr Ala Asp Ser Val
 50                  55                  60

Lys Gly Arg Phe Thr Ile Ser Arg Asp Asn Ala Lys Asn Thr Leu Tyr
 65                  70                  75                  80

Leu Gln Leu Asn Ser Leu Lys Thr Glu Asp Thr Ala Met Tyr Tyr Cys
                 85                  90                  95

Ala Arg Cys Ser Asp Ile Tyr Cys Asp Asn Gly Ala Ser Tyr Arg Gly
                100                 105                 110

Gln Gly Thr Gln Val Thr Val Ser Ser
            115                 120

<210> SEQ ID NO 75
```

<211> LENGTH: 127
<212> TYPE: PRT
<213> ORGANISM: Camelus bactrianus

<400> SEQUENCE: 75

Gln Val Gln Leu Gln Glu Ser Gly Gly Gly Ser Val Gln Thr Gly Gly
1               5                   10                  15

Ser Leu Arg Leu Ser Cys Ala Ala Ser Thr Ser Ile Tyr Ser Asn Asn
            20                  25                  30

Tyr Met Ala Trp Phe Arg Gln Ala Pro Gly Lys Gly Arg Glu Gly Val
        35                  40                  45

Ala Ala Val Tyr Ile Gly Asp Gly Arg Pro Tyr Tyr Ala Asp Ser Ala
    50                  55                  60

Lys Gly Arg Phe Thr Ile Ser Leu Asp Ser Ala Lys Asn Thr Val Tyr
65                  70                  75                  80

Leu His Met Asn Ser Leu Lys Pro Glu Asp Thr Ala Met Tyr Tyr Cys
                85                  90                  95

Ala Ala Ala Pro Gly Pro Leu Ser Arg His Tyr Trp Tyr Thr Ser Ala
            100                 105                 110

Asn Tyr Asp Tyr Trp Gly Pro Gly Thr Gln Val Thr Val Ser Ser
        115                 120                 125

<210> SEQ ID NO 76
<211> LENGTH: 127
<212> TYPE: PRT
<213> ORGANISM: Camelus bactrianus

<400> SEQUENCE: 76

Gln Val Gln Leu Gln Glu Ser Gly Gly Gly Ser Val Gln Thr Gly Gly
1               5                   10                  15

Ser Leu Arg Leu Ser Cys Ala Ala Ser Thr Ser Ile Tyr Ser Asn Asn
            20                  25                  30

Tyr Met Ala Trp Phe Arg Gln Val Pro Gly Lys Gly Arg Glu Gly Val
        35                  40                  45

Ala Ala Val Tyr Ile Asp Asp Gly Arg Thr Tyr Tyr Ala Asp Ser Val
    50                  55                  60

Lys Gly Arg Phe Thr Ile Ser Leu Asp Ser Ala Lys Asn Thr Val Tyr
65                  70                  75                  80

Leu Gln Met Asn Ser Leu Lys Pro Glu Asp Thr Ala Met Tyr Tyr Cys
                85                  90                  95

Ala Ala Ala Pro Gly Pro Leu Ser Arg His Tyr Trp Tyr Thr Ser Ala
            100                 105                 110

Asn Tyr Asp Tyr Trp Gly Pro Gly Thr Gln Val Thr Val Ser Ser
        115                 120                 125

<210> SEQ ID NO 77
<211> LENGTH: 127
<212> TYPE: PRT
<213> ORGANISM: Camelus bactrianus

<400> SEQUENCE: 77

Gln Val Gln Leu Gln Glu Ser Gly Gly Gly Ser Val Gln Thr Gly Gly
1               5                   10                  15

Ser Leu Arg Leu Ser Cys Thr Ala Ser Thr Ser Ile Tyr Ser Asn Asn
            20                  25                  30

Tyr Met Ala Trp Phe Ser Gln Ala Pro Gly Lys Gly Arg Glu Gly Val
        35                  40                  45

```
Ala Ala Val Tyr Ile Asp Asp Gly Arg Pro Tyr Tyr Ala Asp Ser Val
 50                  55                  60

Lys Gly Arg Phe Thr Ile Ser Leu Asp Ser Ala Lys Asn Thr Val Tyr
 65                  70                  75                  80

Leu Gln Met Asn Ser Leu Lys Pro Glu Asp Thr Ala Met Tyr Tyr Cys
                 85                  90                  95

Ala Ala Ala Pro Gly Pro Leu Ser Arg Asn Tyr Trp Tyr Thr Ser Ala
                100                 105                 110

Asn Tyr Asp Tyr Trp Gly Gln Gly Thr Gln Val Thr Val Ser Ser
            115                 120                 125
```

<210> SEQ ID NO 78
<211> LENGTH: 127
<212> TYPE: PRT
<213> ORGANISM: Camelus bactrianus

<400> SEQUENCE: 78

```
Gln Val Gln Leu Gln Glu Ser Gly Gly Gly Ser Val Gln Thr Gly Gly
 1               5                  10                  15

Ser Leu Arg Leu Ser Cys Ala Ala Ser Thr Ser Leu Tyr Ser Tyr Asn
            20                  25                  30

Tyr Met Ala Trp Phe Ser Gln Ala Pro Gly Lys Gly Arg Glu Gly Val
         35                  40                  45

Ala Ala Val Tyr Val Gly Asp Gly Arg Pro Tyr Tyr Ala Asp Ser Val
 50                  55                  60

Lys Gly Arg Phe Thr Ile Ser Leu Asp Ser Ala Lys Asn Thr Val Tyr
 65                  70                  75                  80

Leu Gln Met Asn Ser Leu Lys Pro Glu Asp Thr Ala Met Tyr Tyr Cys
                 85                  90                  95

Ala Ala Ala Pro Gly Pro Leu Ser His Asn Tyr Trp Tyr Thr Ser Ala
                100                 105                 110

Asn Tyr Asp Tyr Trp Gly Gln Gly Thr Gln Val Thr Val Ser Ser
            115                 120                 125
```

<210> SEQ ID NO 79
<211> LENGTH: 121
<212> TYPE: PRT
<213> ORGANISM: Camelus bactrianus

<400> SEQUENCE: 79

```
Gln Val Gln Leu Gln Glu Ser Gly Gly Gly Leu Val Gln Pro Gly Gly
 1               5                  10                  15

Ser Leu Arg Leu Ser Cys Ala Ala Ser Gly Leu Pro Phe Ser Ile Ile
            20                  25                  30

Ala Met Ser Trp Val Arg Gln Ala Pro Gly Lys Gly Ile Glu Trp Val
         35                  40                  45

Ser Thr Ile Asn Ser Gly Gly Gly Thr Thr His Tyr Ala Asp Ser Val
 50                  55                  60

Lys Gly Arg Phe Thr Ile Ser Arg Asp Asn Ala Lys Asn Thr Leu Tyr
 65                  70                  75                  80

Leu Gln Leu Asn Ser Leu Arg Thr Glu Asp Thr Ala Val Tyr Tyr Cys
                 85                  90                  95

Arg Arg Cys Ala Asp Ile Tyr Cys Ser Gly Ser Gly Gly Trp Thr Gly
                100                 105                 110

Leu Gly Thr Gln Val Thr Val Ser Ser
            115                 120
```

<210> SEQ ID NO 80
<211> LENGTH: 127
<212> TYPE: PRT
<213> ORGANISM: Camelus bactrianus

<400> SEQUENCE: 80

Gln Val Gln Leu Gln Glu Ser Gly Gly Gly Ser Val Gln Thr Gly Gly
1               5                   10                  15

Ser Leu Arg Leu Ser Cys Val Ala Ser Thr Ser Ile Tyr Ser Asn Asn
            20                  25                  30

Tyr Met Ala Trp Phe Ser Gln Ala Pro Gly Lys Gly Arg Glu Gly Val
        35                  40                  45

Ala Ala Val Tyr Ile Asp Asp Gly Arg Pro Tyr Tyr Ala Asp Ser Val
    50                  55                  60

Lys Gly Arg Phe Thr Ile Ser Leu Asp Ser Ala Lys Asn Thr Val Tyr
65                  70                  75                  80

Leu Gln Met Asn Ser Leu Lys Pro Glu Asp Thr Ala Met Tyr Tyr Cys
                85                  90                  95

Ala Ala Ala Pro Gly Pro Leu Ser Arg Ser Tyr Trp Tyr Thr Ser Ala
            100                 105                 110

Asn Tyr Asp Tyr Trp Gly Gln Gly Thr Gln Val Thr Val Ser Ser
        115                 120                 125

<210> SEQ ID NO 81
<211> LENGTH: 127
<212> TYPE: PRT
<213> ORGANISM: Camelus bactrianus

<400> SEQUENCE: 81

Gln Val Gln Leu Gln Glu Ser Gly Gly Gly Ser Val Gln Thr Gly Gly
1               5                   10                  15

Ser Leu Arg Leu Ser Cys Ala Ala Ser Thr Ser Ile Tyr Ser Asn Asn
            20                  25                  30

Tyr Met Ala Trp Phe Ser Gln Ala Pro Gly Lys Gly Arg Glu Gly Val
        35                  40                  45

Ala Ala Val Tyr Ile Asp Asp Gly Arg Thr Tyr Tyr Ala Asp Ser Val
    50                  55                  60

Lys Gly Arg Phe Thr Ile Ser Leu Asp Ser Ala Lys Asn Thr Val Tyr
65                  70                  75                  80

Leu Gln Met Asn Ser Leu Lys Pro Glu Asp Thr Ala Met Tyr Tyr Cys
                85                  90                  95

Ala Ala Ala Pro Gly Pro Leu Ser Arg Asn Tyr Trp Tyr Thr Ser Ala
            100                 105                 110

Asn Tyr Asp Tyr Trp Gly Gln Gly Thr Gln Val Thr Val Ser Ser
        115                 120                 125

<210> SEQ ID NO 82
<211> LENGTH: 127
<212> TYPE: PRT
<213> ORGANISM: Camelus bactrianus

<400> SEQUENCE: 82

Gln Val Gln Leu Gln Glu Ser Gly Gly Gly Ser Val Gln Thr Gly Gly
1               5                   10                  15

Ser Leu Arg Leu Ser Cys Thr Ala Ser Thr Ser Ile Tyr Ser Asn Asn
            20                  25                  30

Tyr Met Ala Trp Phe Ser Gln Ala Pro Gly Lys Gly Arg Glu Gly Val

-continued

```
                35                  40                  45
Ala Ala Val Tyr Ile Asp Asp Gly Arg Pro Tyr Tyr Ala Asp Ser Val
            50                  55                  60
Lys Gly Arg Phe Thr Ile Ser Leu Asp Ser Ala Lys Asn Thr Val Tyr
 65                  70                  75                  80
Leu Gln Met Asn Ser Leu Lys Pro Glu Asp Thr Ala Met Tyr Tyr Cys
                85                  90                  95
Ala Ala Ala Pro Gly Pro Leu Ser Arg Asn Tyr Trp Tyr Thr Ser Ala
            100                 105                 110
Asn Tyr Asp Tyr Trp Gly Gln Gly Thr Gln Val Thr Val Ser Ser
        115                 120                 125

<210> SEQ ID NO 83
<211> LENGTH: 127
<212> TYPE: PRT
<213> ORGANISM: Camelus bactrianus

<400> SEQUENCE: 83

Gln Val Gln Leu Gln Glu Ser Gly Gly Gly Leu Val Gln Thr Gly Gly
 1               5                  10                  15
Ser Leu Arg Leu Ser Cys Ala Ala Ser Thr Ser Ile Tyr Ser Asn Asn
            20                  25                  30
Tyr Leu Ala Trp Phe Ser Gln Ala Pro Gly Lys Gly Arg Glu Gly Val
                35                  40                  45
Ala Ala Val Tyr Ile Gly Asp Gly Arg Pro Tyr Tyr Ala Asp Ser Val
            50                  55                  60
Lys Gly Arg Phe Pro Ile Ser Leu Asn Ser Ala Gln Asn Lys Val Tyr
 65                  70                  75                  80
Leu Gln Met Asn Ser Leu Lys Pro Glu Asp Thr Ala Met Tyr Tyr Cys
                85                  90                  95
Ala Ala Ala Pro Gly Pro Leu Ser Arg Asn Tyr Trp Tyr Thr Ser Ala
            100                 105                 110
Asn Tyr Asp Tyr Trp Gly Gln Gly Thr Gln Val Thr Val Ser Ser
        115                 120                 125

<210> SEQ ID NO 84
<211> LENGTH: 127
<212> TYPE: PRT
<213> ORGANISM: Camelus bactrianus

<400> SEQUENCE: 84

Gln Val Gln Leu Gln Glu Ser Gly Gly Gly Ser Val Gln Thr Gly Gly
 1               5                  10                  15
Ser Leu Arg Leu Ser Cys Ala Ala Ser Thr Ser Ile Asp Ser Asn Asn
            20                  25                  30
Tyr Met Ala Trp Phe Arg Gln Ala Pro Gly Lys Gly Arg Glu Gly Val
                35                  40                  45
Ala Ala Val Tyr Ile Asp Asp Gly Arg Pro Tyr Tyr Ala Asp Ser Val
            50                  55                  60
Lys Gly Arg Phe Thr Ile Ser Leu Asp Ser Ala Lys Asn Thr Val Tyr
 65                  70                  75                  80
Leu Gln Met Asn Ser Leu Lys Pro Glu Asp Thr Ala Met Tyr Tyr Cys
                85                  90                  95
Ala Ala Ala Pro Gly Pro Leu Ser Arg His Tyr Trp Tyr Thr Ser Ala
            100                 105                 110
Asn Tyr Asp Tyr Trp Gly Pro Gly Thr Gln Val Thr Val Ser Ser
```

-continued

<210> SEQ ID NO 85
<211> LENGTH: 127
<212> TYPE: PRT
<213> ORGANISM: Camelus bactrianus

<400> SEQUENCE: 85

Gln Val Gln Leu Gln Glu Ser Gly Gly Gly Ser Val Gln Thr Gly Gly
1               5                   10                  15

Ser Leu Arg Leu Ser Cys Ala Ala Ser Thr Ser Ile Tyr Ser Asn Asn
            20                  25                  30

Tyr Met Ala Trp Phe Ser Gln Ala Pro Gly Lys Gly Arg Glu Gly Val
        35                  40                  45

Ala Ala Val Tyr Ile Ala Asp Asp Arg Pro Tyr Tyr Ala Asp Ser Val
    50                  55                  60

Lys Gly Arg Phe Thr Ile Ser Leu Asp Ser Ala Lys Asn Thr Val Tyr
65                  70                  75                  80

Leu Gln Met Asn Ser Leu Lys Pro Glu Asp Thr Ala Met Tyr Tyr Cys
                85                  90                  95

Ala Ala Ala Pro Gly Pro Leu Ser Arg Asn Tyr Trp Tyr Thr Ser Ala
            100                 105                 110

Asn Tyr Asp Tyr Trp Gly Gln Gly Thr Gln Val Thr Val Ser Ser
        115                 120                 125

<210> SEQ ID NO 86
<211> LENGTH: 127
<212> TYPE: PRT
<213> ORGANISM: Camelus bactrianus

<400> SEQUENCE: 86

Gln Val Gln Leu Gln Asp Ser Gly Gly Gly Ser Val Gln Thr Gly Gly
1               5                   10                  15

Ser Leu Arg Leu Ser Cys Ala Ala Ser Thr Ser Ile Tyr Ser Ile Asn
            20                  25                  30

Tyr Met Ala Trp Phe Ser Gln Ala Pro Gly Lys Gly Arg Glu Gly Val
        35                  40                  45

Ala Ala Val Tyr Thr Gly Asp Gly Arg Pro Tyr Tyr Ala Asp Ser Val
    50                  55                  60

Lys Gly Arg Phe Thr Ile Ser Leu Asp Ser Ala Lys Asn Thr Val Tyr
65                  70                  75                  80

Leu Gln Met Asn Ser Leu Lys Pro Glu Asp Thr Ala Met Tyr Tyr Cys
                85                  90                  95

Ala Ala Ala Pro Gly Pro Leu Ser Arg Asn Tyr Trp Tyr Thr Ser Ala
            100                 105                 110

Asn Tyr Asp Tyr Trp Gly Gln Gly Thr Gln Val Thr Val Ser Ser
        115                 120                 125

<210> SEQ ID NO 87
<211> LENGTH: 127
<212> TYPE: PRT
<213> ORGANISM: Camelus bactrianus

<400> SEQUENCE: 87

Gln Val Gln Leu Gln Glu Ser Gly Gly Gly Ser Val Gln Ala Gly Gly
1               5                   10                  15

Ser Leu Arg Leu Ser Cys Ala Ala Ser Gly Tyr Thr Arg Ser Ser Tyr
            20                  25                  30

Cys Met Gly Trp Phe Arg Gln Ala Pro Gly Lys Glu Arg Glu Arg Val
            35                  40                  45

Ala Tyr Ile Tyr Ser Gly Ser Gly Ser Thr His Tyr Ala Asp Ser Val
        50                  55                  60

Lys Gly Arg Phe Thr Ile Ser Gln Asp Asn Gly Lys Asn Thr Leu Tyr
65                  70                  75                  80

Leu Gln Met Asn Asn Leu Lys Pro Glu Asp Thr Ala Met Tyr Tyr Cys
                85                  90                  95

Ala Ala Gly Thr Ser Gly Thr Ser Cys Pro Thr Gly Ala Phe Met Tyr
            100                 105                 110

Glu Tyr Trp Tyr Trp Gly Gln Gly Thr Gln Val Thr Val Ser Ser
        115                 120                 125

<210> SEQ ID NO 88
<211> LENGTH: 127
<212> TYPE: PRT
<213> ORGANISM: Camelus bactrianus

<400> SEQUENCE: 88

Gln Val Gln Leu Gln Glu Ser Gly Gly Gly Ser Val Gln Ala Gly Gly
1               5                   10                  15

Ser Leu Arg Leu Ser Cys Ala Ala Ser Thr Ser Ile Tyr Ser Asn Asn
            20                  25                  30

Tyr Met Ala Trp Phe Arg Gln Ala Pro Gly Lys Gly Arg Glu Gly Val
            35                  40                  45

Ala Ala Val Tyr Val Gly Asp Gly Arg Pro Tyr Tyr Ala Asp Ser Val
        50                  55                  60

Lys Gly Arg Phe Thr Ile Ser Leu Asp Ser Ala Lys Asn Thr Val Tyr
65                  70                  75                  80

Leu Gln Met Asn Ser Leu Lys Pro Glu Asp Thr Ala Met Tyr Tyr Cys
                85                  90                  95

Ala Ala Ala Pro Gly Pro Leu Ser His Asn Tyr Trp Tyr Thr Ser Ala
            100                 105                 110

Asn Tyr Asp Tyr Trp Gly Gln Gly Thr Gln Val Thr Val Ser Ser
        115                 120                 125

<210> SEQ ID NO 89
<211> LENGTH: 127
<212> TYPE: PRT
<213> ORGANISM: Camelus bactrianus

<400> SEQUENCE: 89

Gln Val Gln Leu Gln Glu Ser Gly Gly Gly Ser Val Gln Thr Gly Gly
1               5                   10                  15

Ser Leu Arg Leu Ser Cys Ala Ala Ser Thr Ser Ile Tyr Ser Asn Asn
            20                  25                  30

Tyr Met Ala Trp Phe Ser Gln Ala Pro Gly Lys Gly Arg Glu Gly Val
            35                  40                  45

Ala Ala Val Tyr Ile Gly Asp Gly Arg Pro Tyr Tyr Ala Asp Ser Val
        50                  55                  60

Lys Gly Arg Phe Thr Ile Ser Leu Asp Ser Ala Arg Asn Thr Val Tyr
65                  70                  75                  80

Leu Gln Met Asn Ser Leu Lys Pro Glu Asp Thr Ala Met Tyr Tyr Cys
                85                  90                  95

Ala Ala Ala Pro Gly Pro Leu Ser Arg His Tyr Trp Tyr Thr Ser Ala
            100                 105                 110

-continued

Asn Tyr Asp Tyr Trp Gly Gln Gly Thr Gln Val Thr Val Ser Ser
            115                 120                 125

<210> SEQ ID NO 90
<211> LENGTH: 127
<212> TYPE: PRT
<213> ORGANISM: Camelus bactrianus

<400> SEQUENCE: 90

Gln Val Gln Leu Gln Glu Ser Gly Gly Gly Ser Val Gln Ala Gly Gly
1               5                   10                  15

Ser Leu Arg Leu Ser Cys Ala Ala Ser Thr Ser Ile Tyr Ser Asn Asn
            20                  25                  30

Tyr Met Ala Trp Phe Ser Gln Ala Pro Gly Lys Gly Arg Glu Gly Val
        35                  40                  45

Ala Ala Val Tyr Ile Asp Asp Gly Arg Pro Tyr Tyr Ala Asp Ser Val
    50                  55                  60

Lys Gly Arg Phe Thr Ile Ser Leu Asp Ser Ala Lys Asn Thr Val Tyr
65                  70                  75                  80

Leu Gln Met Asn Ser Leu Lys Pro Glu Asp Thr Ala Met Tyr Tyr Cys
                85                  90                  95

Ala Ala Ala Pro Gly Pro Leu Ser Arg Asn Tyr Trp Tyr Thr Ser Ala
            100                 105                 110

Asn Tyr Asp Tyr Trp Gly Gln Gly Thr Gln Val Thr Val Ser Ser
            115                 120                 125

<210> SEQ ID NO 91
<211> LENGTH: 121
<212> TYPE: PRT
<213> ORGANISM: Camelus bactrianus

<400> SEQUENCE: 91

Gln Val Gln Leu Gln Glu Ser Gly Gly Asp Leu Val Gln Pro Gly Gly
1               5                   10                  15

Ser Leu Arg Leu Ser Cys Ala Ala Ser Gly Leu Pro Phe Ser Ile Ile
            20                  25                  30

Ala Met Ser Trp Val Arg Gln Ala Pro Gly Lys Gly Leu Glu Trp Val
        35                  40                  45

Ser Thr Ile Asn Asn Asp Gly Gly Thr Thr His Tyr Ala Asp Ser Val
    50                  55                  60

Lys Gly Arg Phe Thr Ile Ser Arg Asp Asn Ala Lys Asn Thr Leu Tyr
65                  70                  75                  80

Leu Gln Leu Asn Ser Leu Arg Thr Glu Asp Thr Ala Met Tyr Tyr Cys
                85                  90                  95

Arg Arg Cys Thr Asp Ile Tyr Cys Ser Gly Ser Gly Trp Thr Gly
            100                 105                 110

Gln Gly Thr Gln Val Thr Val Ser Ser
            115                 120

<210> SEQ ID NO 92
<211> LENGTH: 127
<212> TYPE: PRT
<213> ORGANISM: Camelus bactrianus

<400> SEQUENCE: 92

Gln Val Gln Leu Gln Glu Ser Gly Gly Gly Ser Val Gln Thr Gly Gly
1               5                   10                  15

Ser Leu Arg Leu Ser Cys Ala Ala Ser Thr Ser Ile Tyr Asn Asn Asn
            20                  25                  30

Tyr Met Ala Trp Phe Arg Gln Ala Pro Gly Lys Gly Arg Glu Gly Val
            35                  40                  45

Ala Ala Val Tyr Ile Asp Asp Gly Arg Pro Tyr Tyr Ala Asp Ser Val
        50                  55                  60

Lys Gly Arg Phe Thr Ile Ser Leu Asp Ser Ala Lys Asn Thr Val Tyr
65                  70                  75                  80

Leu Gln Met Asn Ser Leu Lys Pro Glu Asp Thr Ala Met Tyr Tyr Cys
                85                  90                  95

Ala Ala Ala Pro Gly Pro Leu Ser Arg His Tyr Trp Tyr Thr Ser Ala
            100                 105                 110

Asn Tyr Asp Tyr Trp Gly Pro Gly Thr Gln Val Thr Val Ser Ser
            115                 120                 125

<210> SEQ ID NO 93
<211> LENGTH: 127
<212> TYPE: PRT
<213> ORGANISM: Camelus bactrianus

<400> SEQUENCE: 93

Gln Val Gln Leu Gln Glu Ser Gly Gly Gly Ser Val Gln Thr Gly Gly
1               5                   10                  15

Ser Leu Arg Leu Ser Cys Ala Ala Ser Thr Ser Ile Tyr Ser Asn Asn
            20                  25                  30

Tyr Met Ala Trp Phe Arg Gln Ala Pro Gly Lys Gly Arg Glu Gly Val
            35                  40                  45

Ala Ala Val Tyr Ile Gly Asp Gly Arg Thr Tyr Tyr Ala Asp Ser Ala
        50                  55                  60

Lys Gly Arg Phe Thr Ile Ser Leu Asp Ser Ala Lys Asn Thr Val Tyr
65                  70                  75                  80

Leu His Met Asn Ser Leu Lys Pro Asp Asp Thr Ala Met Tyr Tyr Cys
                85                  90                  95

Ala Ala Ala Pro Gly Pro Leu Thr Arg His Phe Trp Tyr Thr Ser Ala
            100                 105                 110

Asn Tyr Asp Tyr Trp Gly Pro Gly Thr Gln Val Thr Val Ser Ser
            115                 120                 125

<210> SEQ ID NO 94
<211> LENGTH: 127
<212> TYPE: PRT
<213> ORGANISM: Camelus bactrianus

<400> SEQUENCE: 94

Gln Val Gln Leu Gln Glu Ser Gly Gly Gly Ser Val Gln Thr Gly Gly
1               5                   10                  15

Ser Leu Arg Leu Ser Cys Ala Ala Ser Thr Ser Leu Tyr Ser Tyr Asn
            20                  25                  30

Tyr Met Ala Trp Phe Ser Gln Ala Pro Gly Lys Gly Arg Gly Gly Val
            35                  40                  45

Ala Ala Val Tyr Val Gly Asp Gly Arg Pro Tyr Tyr Ala Asp Ser Val
        50                  55                  60

Lys Gly Arg Phe Thr Ile Ser Leu Asp Ser Ala Lys Asn Thr Val Tyr
65                  70                  75                  80

Leu Gln Met Asn Ser Leu Lys Pro Glu Asp Thr Ala Met Tyr Tyr Cys
                85                  90                  95

Ala Ala Ala Pro Gly Pro Leu Ser His Asn Tyr Trp Tyr Thr Ser Ala
            100                 105                 110

Asn Tyr Asp Tyr Trp Gly Gln Gly Thr Gln Val Thr Val Ser Ser
        115                 120                 125

<210> SEQ ID NO 95
<211> LENGTH: 127
<212> TYPE: PRT
<213> ORGANISM: Camelus bactrianus

<400> SEQUENCE: 95

Gln Val Gln Leu Gln Glu Ser Gly Gly Gly Ser Val Gln Ala Gly Gly
1               5                   10                  15

Ser Leu Arg Leu Ser Cys Ala Ala Ser Gly Tyr Thr Val Ser Asn Asn
            20                  25                  30

Tyr Met Gly Trp Phe Arg Gln Ala Pro Gly Lys Gly Arg Glu Gly Val
        35                  40                  45

Ala Ala Val Tyr Ile Gly Asp Gly Arg Pro Tyr Tyr Ala Asp Ser Val
    50                  55                  60

Lys Gly Arg Phe Thr Ile Ser Leu Asp Ser Ala Lys Asn Thr Val Tyr
65                  70                  75                  80

Leu Gln Met Asn Ser Leu Lys Pro Glu Asp Thr Ala Met Tyr Tyr Cys
                85                  90                  95

Ala Ala Ala Pro Gly Pro Leu Ser Gln His Tyr Trp Tyr Thr Ser Ala
            100                 105                 110

Asn Tyr Asp Tyr Trp Gly Gln Gly Thr Gln Val Thr Val Ser Ser
        115                 120                 125

<210> SEQ ID NO 96
<211> LENGTH: 113
<212> TYPE: PRT
<213> ORGANISM: Camelus bactrianus

<400> SEQUENCE: 96

Gln Val Gln Leu Gln Glu Ser Gly Gly Gly Leu Val Gln Pro Gly Gly
1               5                   10                  15

Ser Leu Arg Leu Ser Cys Ala Ala Phe Gly Phe Thr Phe Gly Ser Tyr
            20                  25                  30

Trp Met Lys Trp Val Arg Gln Ala Pro Gly Lys Asp Leu Glu Trp Val
        35                  40                  45

Pro Ile Ile Asp Asn Gly Gly Arg Ser Thr Trp Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Leu Asn Ser Leu Lys Ile Glu Asp Thr Ala Met Tyr Tyr Cys
                85                  90                  95

Ala Asp Arg Asn Gly Asn Arg Gly Gln Gly Thr Gln Val Thr Val Ser
            100                 105                 110

Ser

<210> SEQ ID NO 97
<211> LENGTH: 127
<212> TYPE: PRT
<213> ORGANISM: Camelus bactrianus

<400> SEQUENCE: 97

Gln Val Gln Leu Gln Glu Ser Gly Gly Gly Ser Val Gln Thr Gly Gly
1               5                   10                  15

Ser Leu Arg His Ser Cys Ala Ala Ser Thr Ser Ile Tyr Ser Asn Asn
            20                  25                  30

Tyr Met Ala Trp Phe Ser Gln Ala Pro Gly Lys Gly Arg Glu Gly Val
            35                  40                  45

Ala Ala Val Tyr Ile Asp Asp Gly Arg Pro Tyr Tyr Ala Asp Ser Val
 50                  55                  60

Lys Gly Arg Phe Thr Ile Ser Leu Asp Ser Ala Lys Asn Thr Val Tyr
 65                  70                  75                  80

Leu Gln Met Asn Ser Leu Lys Pro Glu Asp Thr Ala Met Tyr Tyr Cys
                85                  90                  95

Ala Ala Ala Pro Gly Pro Leu Ser His Asn Tyr Trp Tyr Thr Ser Ala
            100                 105                 110

Asn Tyr Asp Tyr Trp Gly Gln Gly Thr Gln Val Thr Val Ser Ser
            115                 120                 125

<210> SEQ ID NO 98
<211> LENGTH: 127
<212> TYPE: PRT
<213> ORGANISM: Camelus bactrianus

<400> SEQUENCE: 98

Gln Val Gln Leu Gln Glu Ser Gly Gly Gly Ser Val Gln Thr Gly Gly
 1               5                  10                  15

Ser Leu Arg His Ser Cys Ala Ala Ser Thr Ser Ile Tyr Ser Asn Asn
            20                  25                  30

Tyr Met Ala Trp Phe Ser Gln Ala Pro Gly Lys Gly Arg Glu Gly Val
            35                  40                  45

Ala Ala Val Tyr Ile Asp Asp Gly Arg Pro Tyr Tyr Ala Asp Ser Val
 50                  55                  60

Lys Gly Arg Phe Thr Ile Ser Leu Asp Ser Ala Lys Asn Thr Val Tyr
 65                  70                  75                  80

Leu Gln Met Asn Ser Leu Lys Pro Glu Asp Thr Ala Met Tyr Tyr Cys
                85                  90                  95

Ala Ala Ala Pro Gly Pro Leu Ser His Asn Tyr Trp Tyr Thr Ser Ala
            100                 105                 110

Asn Tyr Asp Tyr Trp Gly Gln Gly Thr Gln Val Thr Val Ser Ser
            115                 120                 125

<210> SEQ ID NO 99
<211> LENGTH: 127
<212> TYPE: PRT
<213> ORGANISM: Camelus bactrianus

<400> SEQUENCE: 99

Gln Val Gln Leu Gln Glu Ser Gly Gly Gly Ser Val Thr Thr Gly Gly
 1               5                  10                  15

Ser Leu Arg Leu Ser Cys Ala Ala Ser Thr Ser Ile Tyr Ser Asn Asn
            20                  25                  30

Tyr Met Ala Trp Phe Arg Gln Ala Pro Gly Lys Gly Arg Glu Gly Val
            35                  40                  45

Ala Ala Val Tyr Ile Gly Asp Gly Arg Pro Tyr Tyr Ala Asp Ser Val
 50                  55                  60

Lys Gly Arg Phe Thr Ile Ser Leu Asp Ser Ala Lys Asn Thr Val Tyr
 65                  70                  75                  80

Leu Gln Met Asn Ser Leu Lys Pro Glu Asp Thr Ala Met Tyr Tyr Cys
                85                  90                  95

Ala Ala Ala Pro Gly Pro Leu Ser Arg His Tyr Trp Tyr Thr Ser Ala
            100                 105                 110

Asn Tyr Asp Tyr Trp Gly Pro Gly Thr Gln Val Thr Val Ser Ser
            115                 120                 125

<210> SEQ ID NO 100
<211> LENGTH: 121
<212> TYPE: PRT
<213> ORGANISM: Camelus bactrianus

<400> SEQUENCE: 100

Gln Val Gln Leu Gln Glu Ser Gly Gly Gly Leu Val Gln Pro Gly Gly
1               5                   10                  15

Ser Leu Arg Leu Ser Cys Ala Ala Ser Gly Phe Thr Phe Ser Ile Met
            20                  25                  30

Ala Met Ser Trp Val Arg Gln Ala Pro Gly Arg Gly Leu Glu Trp Val
        35                  40                  45

Ser Thr Ile Asn Ser Asp Gly Gly Lys Thr Tyr Tyr Ala Asp Ser Val
    50                  55                  60

Lys Gly Arg Phe Thr Ala Ser Arg Asp Asn Ala Lys Asn Thr Leu Tyr
65                  70                  75                  80

Leu Gln Leu Asn Ser Leu Arg Thr Glu Asp Thr Ala Met Tyr Tyr Cys
                85                  90                  95

Arg Arg Cys Ala Asp Ile Tyr Cys Ser Gly Ser Gly Trp Thr Gly
            100                 105                 110

Gln Gly Thr Gln Val Thr Val Ser Ser
        115                 120

<210> SEQ ID NO 101
<211> LENGTH: 126
<212> TYPE: PRT
<213> ORGANISM: Camelus bactrianus

<400> SEQUENCE: 101

Gln Val Gln Leu Gln Glu Ser Gly Gly Gly Ser Val Gln Thr Gly Gly
1               5                   10                  15

Ser Leu Arg Leu Ser Cys Ala Val Ser Gly Phe Thr Asp Thr Tyr Phe
            20                  25                  30

Ala Leu Gly Trp Phe Arg Gln Ala Pro Gly Lys Glu Arg Glu Gly Val
        35                  40                  45

Ala Ala Ile Asp Ser Asp Gly Ser Thr Ser Tyr Ala Asp Ser Val Lys
    50                  55                  60

Gly Arg Phe Thr Ile Ser Lys Asp Asn Ala Lys Asn Thr Val Tyr Leu
65                  70                  75                  80

Gln Met Asn Ser Leu Lys Pro Glu Asp Thr Ala Met Tyr Tyr Cys Ala
                85                  90                  95

Ala Ala Pro Gly Pro Leu Ser Arg Asn Tyr Trp Tyr Thr Ser Ala Asn
            100                 105                 110

Tyr Asp Tyr Trp Gly Gln Gly Thr Gln Val Thr Val Ser Ser
        115                 120                 125

<210> SEQ ID NO 102
<211> LENGTH: 127
<212> TYPE: PRT
<213> ORGANISM: Camelus bactrianus

<400> SEQUENCE: 102

Gln Val Gln Leu Gln Glu Ser Gly Gly Gly Ser Val Gln Thr Gly Gly
1               5                   10                  15

Ser Leu Arg Leu Ser Cys Ala Ala Ser Thr Ser Ile Tyr Ser Asn Asn
            20                  25                  30

Tyr Met Ala Trp Phe Arg Gln Ala Pro Ala Lys Gly Arg Glu Gly Val
        35                  40                  45

Ala Ala Val Tyr Ile Gly Asp Gly Arg Pro Tyr Tyr Ala Asp Ser Val
    50                  55                  60

Lys Gly Arg Phe Thr Ile Ser Leu Asp Ser Ala Lys Asn Thr Val Tyr
65                  70                  75                  80

Leu Gln Met Asn Ser Leu Lys Pro Glu Asp Thr Ala Ile Tyr Tyr Cys
                85                  90                  95

Ala Ala Ala Pro Gly Pro Leu Ser Arg His Tyr Trp Tyr Thr Ser Ala
            100                 105                 110

Asn Tyr Asp Tyr Trp Gly Pro Gly Thr Gln Val Thr Val Ser Ser
            115                 120                 125

<210> SEQ ID NO 103
<211> LENGTH: 127
<212> TYPE: PRT
<213> ORGANISM: Camelus bactrianus

<400> SEQUENCE: 103

Gln Val Gln Leu Gln Glu Ser Gly Gly Gly Ser Val Gln Thr Gly Gly
1               5                   10                  15

Ser Leu Arg Leu Ser Cys Ala Ala Ser Thr Ser Ile Tyr Asn Asn Asn
            20                  25                  30

Tyr Met Ala Trp Phe Ser Gln Ala Pro Gly Lys Gly Arg Glu Gly Val
        35                  40                  45

Ala Ala Val Tyr Ile Glu Asp Gly Arg Pro Tyr Tyr Ala Asp Ser Val
    50                  55                  60

Lys Gly Arg Phe Thr Ile Ser Leu Asp Ser Ala Lys Asn Thr Val Tyr
65                  70                  75                  80

Leu Gln Met Asn Ser Leu Lys Pro Glu Asp Thr Ala Met Tyr Tyr Cys
                85                  90                  95

Ala Ala Ala Pro Gly Pro Leu Ser Arg Asn Tyr Trp Tyr Thr Ser Ala
            100                 105                 110

Asn Tyr Asp Tyr Trp Gly Gln Gly Thr Gln Val Thr Val Ser Ser
            115                 120                 125

<210> SEQ ID NO 104
<211> LENGTH: 127
<212> TYPE: PRT
<213> ORGANISM: Camelus bactrianus

<400> SEQUENCE: 104

Gln Val Gln Leu Gln Glu Ser Gly Gly Gly Ser Val Gln Thr Gly Gly
1               5                   10                  15

Ser Leu Arg Leu Ser Cys Ala Ala Ser Thr Ser Ile Tyr Ser Asn Asn
            20                  25                  30

Tyr Met Ala Trp Phe Arg Gln Ala Pro Gly Lys Gly Arg Glu Gly Val
        35                  40                  45

Ala Ala Val Tyr Ile Asp Asp Gly Arg Thr Tyr Tyr Ala Asp Ser Val
    50                  55                  60

Lys Gly Arg Phe Ala Ile Ser Leu Asp Ser Ala Lys Asn Thr Val Tyr
65                  70                  75                  80

Leu Gln Met Asn Ser Leu Lys Pro Glu Asp Thr Ala Met Tyr Tyr Cys
                    85                  90                  95

Ala Ala Ala Pro Gly Pro Leu Ser Arg His Tyr Trp Tyr Thr Ser Ala
            100                 105                 110

Asn Tyr Asp Tyr Trp Gly Pro Gly Thr Gln Val Thr Val Ser Ser
        115                 120                 125

<210> SEQ ID NO 105
<211> LENGTH: 121
<212> TYPE: PRT
<213> ORGANISM: Camelus bactrianus

<400> SEQUENCE: 105

Gln Val Gln Leu Gln Glu Ser Gly Gly Gly Leu Val Gln Pro Gly Gly
1               5                   10                  15

Ser Leu Arg Leu Ser Cys Ala Ala Ser Gly Phe Thr Phe Ser Ser Leu
            20                  25                  30

Ala Met Ser Trp Val Arg Gln Ala Pro Gly Lys Gly Leu Glu Trp Val
            35                  40                  45

Ser Thr Ile Asn Ser Gly Gly Val Tyr Thr Tyr Tyr Ala Asp Ser Val
        50                  55                  60

Lys Gly Arg Phe Thr Ile Ser Arg Asp Asn Ala Lys Asn Thr Leu Tyr
65                  70                  75                  80

Leu Gln Leu Asn Asn Leu Arg Thr Glu Asp Thr Ala Met Tyr Tyr Cys
                    85                  90                  95

Arg Arg Cys Thr Asp Ile Tyr Cys Ser Gly Ser Gly Gly Trp Thr Gly
            100                 105                 110

Gln Gly Thr Gln Val Thr Val Ser Ser
        115                 120

<210> SEQ ID NO 106
<211> LENGTH: 121
<212> TYPE: PRT
<213> ORGANISM: Camelus bactrianus

<400> SEQUENCE: 106

Gln Val Gln Leu Gln Glu Ser Gly Gly Gly Leu Val Gln Pro Gly Gly
1               5                   10                  15

Ser Leu Arg Leu Ser Cys Ala Val Ser Gly Phe Thr Phe Ser Ile Ile
            20                  25                  30

Ala Met Ser Trp Val Arg Gln Ala Pro Gly Lys Gly Leu Glu Trp Val
            35                  40                  45

Ser Thr Ile Asn Ser Asp Gly Gly Thr Thr Tyr Tyr Ala Asp Ser Val
        50                  55                  60

Lys Gly Arg Phe Thr Ile Ser Arg Asp Asn Ala Lys Asn Thr Leu Tyr
65                  70                  75                  80

Leu Gln Leu Asn Ser Leu Arg Thr Glu Asp Thr Ala Met Tyr Tyr Cys
                    85                  90                  95

Arg Arg Cys Ala Asp Ile Tyr Cys Ser Gly Ser Gly Gly Trp Thr Gly
            100                 105                 110

Gln Gly Thr Gln Val Thr Val Ser Ser
        115                 120

<210> SEQ ID NO 107
<211> LENGTH: 122
<212> TYPE: PRT
<213> ORGANISM: Camelus bactrianus -continued

<400> SEQUENCE: 107

Gln Val Gln Leu Gln Glu Ser Gly Gly Gly Leu Val Gln Pro Gly Gly
1               5                   10                  15

Ser Leu Arg Leu Ser Cys Glu Ala Ser Gly Leu Pro Phe Ser Ile Ile
            20                  25                  30

Ala Met Ser Trp Val Arg Gln Ala Pro Gly Lys Gly Leu Glu Trp Val
        35                  40                  45

Ser Thr Ile Asn Ser Asp Gly Gly Thr Thr His Tyr Ala Asp Ser Val
    50                  55                  60

Lys Gly Arg Phe Thr Ile Ser Arg Asp Asn Ala Lys Asn Thr Leu Tyr
65                  70                  75                  80

Leu Gln Leu Asn Ser Leu Arg Ser Glu Asp Thr Ala Met Tyr Tyr Cys
                85                  90                  95

Arg Arg Cys Thr Asp Ile Tyr Cys Ser Gly Ser Gly Ser Thr Lys
            100                 105                 110

Gly Gln Gly Thr Gln Val Thr Val Ser Ser
        115                 120

<210> SEQ ID NO 108
<211> LENGTH: 127
<212> TYPE: PRT
<213> ORGANISM: Camelus bactrianus

<400> SEQUENCE: 108

Gln Val Gln Leu Gln Glu Ser Gly Gly Gly Ser Val Gln Thr Gly Gly
1               5                   10                  15

Ser Leu Arg Leu Ser Cys Ala Ala Ser Thr Ser Ile Tyr Ser Asn Asn
            20                  25                  30

Tyr Met Ala Trp Phe Arg Gln Ala Pro Gly Lys Gly Arg Glu Gly Val
        35                  40                  45

Ala Ala Val Tyr Ile Gly Asp Gly Arg Pro Tyr Tyr Ala Asp Ser Val
    50                  55                  60

Lys Gly Arg Phe Thr Ile Ser Leu Asp Ser Ala Lys Asn Thr Val Tyr
65                  70                  75                  80

Leu Gln Met Asn Ser Leu Lys Pro Glu Asp Thr Ala Met Tyr Tyr Cys
                85                  90                  95

Ala Ala Ala Pro Gly Pro Leu Ser Arg His Tyr Trp Tyr Thr Thr Ala
            100                 105                 110

Asn Tyr Asp Tyr Trp Gly Pro Gly Thr Gln Val Thr Val Ser Ser
        115                 120                 125

<210> SEQ ID NO 109
<211> LENGTH: 127
<212> TYPE: PRT
<213> ORGANISM: Camelus bactrianus

<400> SEQUENCE: 109

Gln Val Gln Leu Gln Glu Ser Gly Gly Gly Ser Val Gln Ala Gly Gly
1               5                   10                  15

Ser Leu Arg Leu Ser Cys Ala Ala Ser Gly Tyr Thr Arg Ser Ser Tyr
            20                  25                  30

Cys Met Gly Trp Phe Arg Gln Ala Pro Gly Lys Glu Arg Glu Arg Val
        35                  40                  45

Ala His Ile Tyr Thr Gly Ser Gly Thr Thr His Tyr Ala Asp Ser Met
    50                  55                  60

Lys Gly Arg Phe Thr Ile Ser Gln Asp Asn Gly Lys Asn Thr Leu Tyr

```
                 65                  70                  75                  80

Leu Gln Met Asn Asn Leu Lys Pro Glu Asp Thr Ala Met Tyr Tyr Cys
                 85                  90                  95

Ala Ala Gly Thr Ser Gly Thr Ser Cys Ala Thr Gly Pro Phe Val Tyr
            100                 105                 110

Gly Tyr Trp Tyr Trp Gly Gln Gly Thr Gln Val Thr Val Ser Ser
            115                 120                 125

<210> SEQ ID NO 110
<211> LENGTH: 129
<212> TYPE: PRT
<213> ORGANISM: Camelus bactrianus

<400> SEQUENCE: 110

Gln Val Gln Leu Gln Glu Ser Gly Gly Gly Ser Val Gln Ala Gly Gly
1               5                   10                  15

Ser Leu Arg Leu Ser Cys Ala Tyr Thr Pro Arg Arg Leu Cys Met Gly
            20                  25                  30

Met Gly Trp Phe Arg Gln Gly Leu Gly Lys Glu Arg Glu Gly Val Ala
        35                  40                  45

Thr Ile Asp Asp Ala Gly Ser Thr Thr Tyr Ala Asp Ser Val Lys Ala
    50                  55                  60

Arg Phe Thr Ile Ser Gln Asp Asn Ala Lys Asn Thr Leu Tyr Leu Gln
65                  70                  75                  80

Met Asp Ser Leu Lys Pro Glu Asp Ser Ala Met Tyr Tyr Cys Ala Ala
                85                  90                  95

Arg Ala Gly Val Gly Trp Tyr Gln Val Ser Cys Pro Glu Glu Ser Arg
            100                 105                 110

Thr Ser Ala Phe Val Tyr Trp Gly Gln Gly Thr Gln Val Thr Val Ser
            115                 120                 125

Ser

<210> SEQ ID NO 111
<211> LENGTH: 127
<212> TYPE: PRT
<213> ORGANISM: Camelus bactrianus

<400> SEQUENCE: 111

Gln Val Gln Leu Gln Glu Ser Gly Gly Gly Ser Val Gln Thr Gly Gly
1               5                   10                  15

Ser Leu Arg Leu Ser Cys Ala Ala Ser Thr Ser Ile Tyr Asn Asn Asn
            20                  25                  30

Tyr Met Ala Trp Phe Ser Gln Ala Pro Gly Lys Gly Arg Glu Gly Val
        35                  40                  45

Ala Ala Val Tyr Ile Glu Asp Gly Arg Pro Tyr Tyr Ala Asp Ser Val
    50                  55                  60

Lys Gly Arg Phe Thr Ile Ser Leu Asp Ser Ala Lys Asn Thr Val Tyr
65                  70                  75                  80

Leu Gln Met Asn Ser Leu Lys Pro Glu Asp Thr Ala Met Tyr Tyr Cys
                85                  90                  95

Ala Ala Ala Pro Gly Pro Leu Ser Arg Asn Tyr Trp Tyr Thr Ser Ala
            100                 105                 110

Asn Tyr Asp Tyr Trp Gly Gln Gly Thr Gln Val Thr Val Ser Ser
            115                 120                 125

<210> SEQ ID NO 112
```

```
<211> LENGTH: 121
<212> TYPE: PRT
<213> ORGANISM: Camelus bactrianus

<400> SEQUENCE: 112

Gln Val Gln Leu Gln Glu Ser Gly Gly Gly Leu Val Gln Pro Gly Gly
1               5                   10                  15

Ser Leu Arg Leu Ser Cys Ala Ala Ser Gly Leu Thr Phe Ser Ile Val
            20                  25                  30

Ala Met Ser Trp Val Arg Gln Ala Pro Gly Lys Gly Leu Glu Trp Val
        35                  40                  45

Ser Thr Ile Asn Ser Asp Gly Gly Ser Thr Tyr Tyr Ala Asp Ser Val
    50                  55                  60

Lys Gly Arg Phe Thr Ile Ser Arg Asp Asn Ala Lys Asn Thr Leu Tyr
65                  70                  75                  80

Leu Gln Leu Asn Ser Leu Arg Thr Glu Asp Thr Ala Met Tyr Tyr Cys
                85                  90                  95

Arg Arg Cys Thr Asp Ile Tyr Cys Ser Gly Ser Gly Trp Thr Gly
            100                 105                 110

Gln Gly Thr Gln Val Thr Val Ser Ser
        115                 120

<210> SEQ ID NO 113
<211> LENGTH: 127
<212> TYPE: PRT
<213> ORGANISM: Camelus bactrianus

<400> SEQUENCE: 113

Gln Val Gln Leu Gln Glu Ser Gly Gly Gly Ser Val Gln Thr Gly Gly
1               5                   10                  15

Ser Leu Arg Leu Ser Cys Ala Ala Ser Thr Ser Ile Ile Ser Phe Asn
            20                  25                  30

Tyr Met Ala Trp Phe Arg Arg Ala Pro Gly Lys Gly Arg Glu Gly Val
        35                  40                  45

Ala Ala Val Tyr Ile Asp Asp Gly Arg Pro Tyr Tyr Ala Asp Ser Val
    50                  55                  60

Lys Gly Arg Phe Thr Ile Ser Leu Asp Ser Ala Lys Asn Thr Val Tyr
65                  70                  75                  80

Leu Gln Met Gly Ser Leu Arg Pro Glu Asp Thr Ala Met Tyr Tyr Cys
                85                  90                  95

Ala Ala Ala Pro Gly Pro Leu Ser Arg Asn Tyr Trp His Thr Pro Ala
            100                 105                 110

Asn Tyr Asp Tyr Trp Gly Gln Gly Thr Gln Val Thr Val Ser Ser
        115                 120                 125

<210> SEQ ID NO 114
<211> LENGTH: 124
<212> TYPE: PRT
<213> ORGANISM: Camelus bactrianus

<400> SEQUENCE: 114

Gln Val Gln Leu Gln Glu Ser Gly Gly Gly Ser Val Gln Thr Gly Gly
1               5                   10                  15

Ser Leu Arg Leu Ser Cys Ala Ala Ser Gly Tyr Ala Gly Arg Leu Tyr
            20                  25                  30

Ser Met Gly Trp Phe Arg Gln Val Ala Gly Lys Glu Arg Glu Gly Val
        35                  40                  45
```

Ser Ser Ile Glu Ser Asp Gly Ser Thr Phe Tyr Thr Asp Ser Val Lys
        50                  55                  60

Gly Arg Phe Thr Thr Thr Arg Asp Ser Ala Lys Asn Thr Leu Tyr Leu
65                  70                  75                  80

Gln Met Asn Asn Leu Lys Pro Glu Asp Thr Ala Met Tyr Tyr Cys Ala
                85                  90                  95

Ala Phe Cys Leu Arg Val Gly His Gly Gly Arg Cys Thr Glu Tyr Lys
            100                 105                 110

Tyr Trp Gly Arg Gly Thr Gln Val Thr Val Ser Ser
            115                 120

<210> SEQ ID NO 115
<211> LENGTH: 127
<212> TYPE: PRT
<213> ORGANISM: Camelus bactrianus

<400> SEQUENCE: 115

Gln Val Gln Leu Gln Glu Ser Gly Gly Gly Ser Val Gln Ala Gly Gly
1               5                   10                  15

Ser Leu Arg Leu Ser Cys Ala Ala Ser Gly Tyr Thr Arg Ser Ser Tyr
            20                  25                  30

Cys Met Gly Trp Phe Arg Gln Ala Pro Gly Lys Glu Arg Glu Arg Val
        35                  40                  45

Ala His Ile Tyr Thr Gly Ser Gly Ser Thr His Tyr Ala Asp Ser Val
    50                  55                  60

Lys Gly Arg Phe Thr Ile Ser Gln Asp Asn Gly Lys Asn Thr Leu Tyr
65                  70                  75                  80

Leu Gln Met Asn Asn Leu Lys Pro Glu Asp Thr Ala Met Tyr Tyr Cys
                85                  90                  95

Ala Ala Gly Thr Ser Gly Thr Ser Cys Ala Thr Gly Pro Phe Val Tyr
            100                 105                 110

Lys Tyr Trp Tyr Trp Gly Gln Gly Thr Gln Val Thr Val Ser Ser
            115                 120                 125

<210> SEQ ID NO 116
<211> LENGTH: 121
<212> TYPE: PRT
<213> ORGANISM: Camelus bactrianus

<400> SEQUENCE: 116

Gln Leu Gln Glu Ser Gly Gly Gly Leu Val Gln Pro Gly Gly Ser Leu
1               5                   10                  15

Arg Leu Ser Cys Ala Ala Ser Gly Phe Ala Phe Ser Thr Tyr Ala Met
            20                  25                  30

Ser Trp Val Arg Gln Ala Pro Gly Lys Gly Leu Glu Trp Val Ser Gly
        35                  40                  45

Ile Asn Gly Gly Gly Gly Asn Thr Tyr Tyr Ala Asp Ser Val Lys Gly
    50                  55                  60

Arg Phe Thr Ile Ser Arg Asp Asn Ala Lys Asn Thr Leu Tyr Leu Gln
65                  70                  75                  80

Leu Asn Ser Leu Lys Thr Glu Asp Thr Ala Met Tyr Tyr Cys Gly Gln
                85                  90                  95

Gly Ala Tyr Trp Ala Tyr Cys Asn Gly Tyr Cys Asn Pro Pro Gly
            100                 105                 110

Gln Gly Thr Gln Val Thr Val Ser Ser
            115                 120

<210> SEQ ID NO 117
<211> LENGTH: 127
<212> TYPE: PRT
<213> ORGANISM: Camelus bactrianus

<400> SEQUENCE: 117

Gln Val Gln Leu Gln Glu Ser Gly Gly Gly Ser Val Gln Thr Gly Gly
1               5                   10                  15

Ser Leu Arg Leu Ser Cys Ala Ala Ser Thr Ser Ile Tyr Ser Asn Asn
            20                  25                  30

Tyr Met Ala Trp Phe Ser Gln Ala Pro Gly Lys Gly Arg Glu Gly Val
        35                  40                  45

Ala Ala Val Tyr Ile Gly Asp Gly Arg Pro Tyr Tyr Ala Asp Ser Val
    50                  55                  60

Lys Gly Arg Phe Thr Ile Ser Leu Asp Ser Ala Lys Asp Thr Val Tyr
65                  70                  75                  80

Leu Gln Met Asn Ser Leu Lys Pro Glu Asp Thr Ala Met Tyr Tyr Cys
                85                  90                  95

Ala Ala Ala Pro Gly Pro Leu Ser Arg Asn Tyr Trp Tyr Thr Ser Ala
            100                 105                 110

Asn Tyr Asp Tyr Trp Gly Gln Gly Thr Gln Val Thr Val Ser Ser
        115                 120                 125

<210> SEQ ID NO 118
<211> LENGTH: 127
<212> TYPE: PRT
<213> ORGANISM: Camelus bactrianus

<400> SEQUENCE: 118

Gln Val Gln Leu Gln Glu Ser Gly Gly Gly Ser Val Gln Thr Gly Gly
1               5                   10                  15

Ser Leu Arg Leu Ser Cys Ala Ala Ser Ala Ser Ile Tyr Ser Asn Asn
            20                  25                  30

Tyr Met Ala Trp Phe Ser Gln Ala Pro Gly Lys Gly Arg Glu Gly Val
        35                  40                  45

Ala Ala Val Tyr Ile Gly Asp Gly Arg Pro Tyr Tyr Asp Asp Ser Val
    50                  55                  60

Lys Gly Leu Phe Thr Ile Ser Leu Asp Ser Ala Lys Asn Thr Val Tyr
65                  70                  75                  80

Leu Gln Met Asn Ser Leu Lys Pro Glu Asp Thr Ala Met Tyr Tyr Cys
                85                  90                  95

Ala Ala Ala Pro Gly Pro Leu Ile Arg Asn Tyr Trp Tyr Thr Ser Ala
            100                 105                 110

Asn Tyr Asp Tyr Trp Gly Gln Gly Thr Gln Val Thr Val Ser Ser
        115                 120                 125

<210> SEQ ID NO 119
<211> LENGTH: 127
<212> TYPE: PRT
<213> ORGANISM: Camelus bactrianus

<400> SEQUENCE: 119

Gln Val Gln Leu Gln Glu Ser Gly Gly Gly Ser Val Gln Thr Gly Gly
1               5                   10                  15

Ser Leu Arg Leu Ser Cys Ala Ala Ser Thr Ser Leu Tyr Ser Tyr Asn
            20                  25                  30

Tyr Met Ala Trp Phe Ser Gln Ala Pro Gly Lys Gly Arg Glu Gly Val

```
                35                  40                  45
Ala Ala Val Tyr Val Gly Asp Gly Arg Pro Tyr Tyr Ala Asp Ser Val
        50                  55                  60
Lys Gly Arg Phe Thr Ile Ser Leu Asp Ser Lys Asn Thr Val Tyr
 65                  70                  75                  80
Leu Gln Met Asn Ser Leu Lys Pro Glu Asp Thr Ala Met Tyr Tyr Cys
                85                  90                  95
Ala Ala Ala Pro Gly Pro Leu Ser Arg Asn Tyr Trp Tyr Thr Ser Ala
            100                 105                 110
Asn Tyr Asp Tyr Trp Gly Gln Gly Thr Gln Val Thr Val Ser Ser
            115                 120                 125

<210> SEQ ID NO 120
<211> LENGTH: 125
<212> TYPE: PRT
<213> ORGANISM: Camelus bactrianus

<400> SEQUENCE: 120

Gln Val Gln Leu Gln Glu Ser Gly Gly Gly Ser Val Gln Ala Gly Gly
 1               5                  10                  15
Ser Leu Arg Leu Ser Cys Thr Ala Pro Gly Phe Thr Ser Asn Thr Cys
            20                  25                  30
Ala Met Ala Trp Phe Arg Gln Ala Pro Gly Lys Glu Arg Glu Phe Val
            35                  40                  45
Ser Ser Met Ser Thr Val Gly Ser Thr Arg Phe Ala Asp Ser Val Lys
        50                  55                  60
Gly Arg Phe Thr Ile Ser Lys Asp Glu Val Lys Asp Thr Val Tyr Leu
 65                  70                  75                  80
Gln Met Asn Ser Leu Lys Pro Glu Asp Thr Ala Met Tyr Phe Cys Lys
                85                  90                  95
Thr Tyr Ala Cys Arg Glu Cys Thr Gly Arg Tyr Cys Arg Thr Ala Pro
            100                 105                 110
Asp Ala Trp Gly Gln Gly Thr Gln Val Thr Val Ser Ser
            115                 120                 125

<210> SEQ ID NO 121
<211> LENGTH: 125
<212> TYPE: PRT
<213> ORGANISM: Camelus bactrianus

<400> SEQUENCE: 121

Gln Val Gln Leu Gln Glu Ser Gly Gly Gly Ser Ala Gln Ala Gly Gly
 1               5                  10                  15
Ser Leu Arg Leu Ser Cys Thr Ala Pro Gly Phe Thr Ser Asn Thr Cys
            20                  25                  30
Ala Met Ala Trp Tyr Arg Gln Ala Pro Gly Lys Glu Arg Glu Phe Val
            35                  40                  45
Ser Ser Arg Ser Thr Val Gly Thr Thr Gly Tyr Ala Asp Ser Val Lys
        50                  55                  60
Gly Arg Phe Thr Ile Ser Lys Asp Glu Ala Lys Asp Thr Val Tyr Leu
 65                  70                  75                  80
Gln Met Asn Ser Leu Lys Pro Glu Asp Thr Ala Met Tyr Phe Cys Lys
                85                  90                  95
Thr Tyr Ala Cys Arg Asn Cys Ile Gly Arg His Cys Arg Thr Ala Pro
            100                 105                 110
Asp Ala Trp Gly Gln Gly Thr Gln Val Thr Val Ser Ser
```

<210> SEQ ID NO 122
<211> LENGTH: 125
<212> TYPE: PRT
<213> ORGANISM: Camelus bactrianus

<400> SEQUENCE: 122

Gln Val Gln Leu Gln Glu Ser Gly Gly Gly Ser Val Gln Ala Gly Gly
1               5                   10                  15

Ser Leu Arg Leu Ser Cys Thr Ala Pro Gly Phe Thr Ser Asn Thr Cys
            20                  25                  30

Ala Met Ala Trp Phe Arg Gln Ala Pro Gly Lys Glu Arg Glu Phe Val
        35                  40                  45

Ser Ser Leu Ser Thr Val Gly Thr Thr Gly Tyr Ala Asp Ser Val Lys
    50                  55                  60

Gly Arg Phe Thr Ile Ser Lys Asp Glu Ala Lys Asp Thr Val Tyr Leu
65                  70                  75                  80

Leu Met Asn Ser Leu Lys Pro Glu Asp Thr Ala Met Tyr Phe Cys Lys
                85                  90                  95

Thr Phe Ala Cys Arg Asp Cys Ser Gly Arg Tyr Cys Arg Thr Ala Pro
            100                 105                 110

Asp Ala Trp Gly Gln Gly Thr Gln Val Thr Val Ser Ser
        115                 120                 125

<210> SEQ ID NO 123
<211> LENGTH: 125
<212> TYPE: PRT
<213> ORGANISM: Camelus bactrianus

<400> SEQUENCE: 123

Gln Val Gln Leu Gln Glu Ser Gly Gly Gly Ser Val Gln Ala Gly Gly
1               5                   10                  15

Ser Leu Arg Leu Ser Cys Thr Ala Pro Gly Phe Thr Ser Asn Thr Cys
            20                  25                  30

Ala Met Ala Trp Tyr Arg Gln Ala Pro Gly Lys Glu Arg Glu Phe Val
        35                  40                  45

Ser Ser Arg Ser Thr Val Gly Thr Thr Gly Tyr Ala Asp Ser Val Lys
    50                  55                  60

Gly Arg Phe Thr Ile Ser Lys Asp Glu Ala Lys Asp Thr Val Tyr Leu
65                  70                  75                  80

Gln Met Asn Ser Leu Lys Pro Glu Asp Thr Ala Met Tyr Phe Cys Lys
                85                  90                  95

Thr Tyr Ala Cys Arg Asn Cys Ile Gly Arg His Cys Arg Thr Ala Pro
            100                 105                 110

Asp Ala Trp Gly Gln Gly Thr Gln Val Thr Val Ser Ser
        115                 120                 125

<210> SEQ ID NO 124
<211> LENGTH: 129
<212> TYPE: PRT
<213> ORGANISM: Camelus bactrianus

<400> SEQUENCE: 124

Gln Val Gln Leu Gln Glu Ser Gly Gly Gly Ser Val Gln Ala Gly Arg
1               5                   10                  15

Ser Leu Arg Leu Ser Cys Ala Val Ser Arg Tyr Ser Ala Ser Asn Asn
            20                  25                  30

```
Val Ile Lys Trp Met Gly Trp Phe Arg Gln Ala Pro Gly Lys Glu Arg
            35                  40                  45

Glu Gly Val Ala Ala Leu Tyr Thr Ser Gly Gly Asn Thr Tyr Tyr Ala
 50                      55                  60

Asp Ser Val Lys Gly Arg Phe Thr Ile Ser Arg Asp Tyr Ser Glu Asn
 65                  70                  75                  80

Thr Val Ser Leu Gln Met Asn Asn Leu Lys Pro Glu Asp Thr Gly Met
                 85                  90                  95

Tyr Tyr Cys Ala Ala Thr Val Gly Thr Val Leu Ala Gly Pro Leu Ser
            100                 105                 110

Ala Arg Lys Tyr Asn Tyr Trp Gly Gln Gly Thr Gln Val Thr Val Ser
            115                 120                 125

Ser

<210> SEQ ID NO 125
<211> LENGTH: 122
<212> TYPE: PRT
<213> ORGANISM: Camelus bactrianus

<400> SEQUENCE: 125

Gln Val Gln Leu Gln Glu Ser Gly Gly Gly Leu Val Gln Pro Gly Gly
 1               5                  10                  15

Ser Leu Arg Leu Ser Cys Ala Ala Ser Gly Phe Thr Phe Ser Asn Ser
            20                  25                  30

Asp Met Ala Trp Phe Arg Gln Ala Pro Gly Lys Gly Leu Glu Trp Val
            35                  40                  45

Ser Val Ile Asp Ser Gly Gly Gly Tyr Thr Tyr Tyr Ala Asp Ser Val
 50                      55                  60

Lys Gly Arg Phe Thr Ile Ser Arg Asp Asn Ala Glu Asn Thr Leu Tyr
 65                  70                  75                  80

Leu Gln Leu Asn Ser Leu Lys Thr Glu Asp Thr Ala Met Tyr Tyr Cys
                 85                  90                  95

Ala Lys Thr Asp Leu Arg Tyr Ser Arg Ile Tyr Pro Tyr Gly Lys Trp
            100                 105                 110

Gly Gln Gly Thr Gln Val Thr Val Ser Ser
            115                 120

<210> SEQ ID NO 126
<211> LENGTH: 129
<212> TYPE: PRT
<213> ORGANISM: Camelus bactrianus

<400> SEQUENCE: 126

Gln Val Gln Leu Gln Glu Ser Gly Gly Gly Ser Val Gln Ala Gly Arg
 1               5                  10                  15

Ser Leu Arg Leu Pro Cys Ala Val Ser Arg Tyr Ser Ala Ser Asn Asn
            20                  25                  30

Val Ile Lys Trp Met Gly Trp Phe Arg Gln Ala Pro Gly Lys Glu Arg
            35                  40                  45

Glu Gly Val Ala Ala Leu Tyr Thr Ser Gly Gly Asn Thr Tyr Tyr Ala
 50                      55                  60

Asp Ser Val Lys Gly Arg Phe Thr Ile Ser Arg Asp Tyr Ser Glu Asn
 65                  70                  75                  80

Thr Val Ser Leu Gln Met Asn Asn Leu Lys Pro Glu Asp Thr Gly Met
                 85                  90                  95
```

Tyr Tyr Cys Ala Ala Thr Val Gly Thr Val Leu Ala Gly Pro Leu Ser
            100                 105                 110

Ala Arg Lys Tyr Asn Tyr Trp Gly Gln Gly Thr Gln Val Thr Val Ser
        115                 120                 125

Ser

<210> SEQ ID NO 127
<211> LENGTH: 125
<212> TYPE: PRT
<213> ORGANISM: Camelus bactrianus

<400> SEQUENCE: 127

Gln Val Gln Leu Gln Glu Ser Gly Gly Gly Leu Val Gln Ala Gly Gly
1               5                   10                  15

Ser Leu Thr Leu Ser Cys Arg Gly Ser Gly Phe Thr Ser Asn Thr Cys
            20                  25                  30

Ala Met Ala Trp Phe Arg Gln Ala Pro Gly Lys Glu Arg Glu Phe Val
        35                  40                  45

Ser Ser Met Ser Thr Val Gly Ser Thr Arg Phe Ala Asp Ser Val Lys
    50                  55                  60

Gly Arg Phe Thr Ile Ser Lys Asp Glu Ala Lys Asp Thr Val Tyr Leu
65                  70                  75                  80

Gln Met Asn Ser Leu Lys Pro Glu Asp Thr Ala Met Tyr Phe Cys Lys
            85                  90                  95

Thr Tyr Ala Cys Arg Glu Cys Thr Gly Arg Tyr Cys Arg Thr Ala Pro
        100                 105                 110

Asp Ala Trp Gly Gln Gly Thr Gln Val Thr Val Ser Ser
    115                 120                 125

<210> SEQ ID NO 128
<211> LENGTH: 125
<212> TYPE: PRT
<213> ORGANISM: Camelus bactrianus

<400> SEQUENCE: 128

Gln Val Gln Leu Gln Glu Ser Gly Gly Gly Ser Val Gln Ala Gly Gly
1               5                   10                  15

Ser Leu Arg Leu Ser Cys Thr Ala Pro Gly Phe Thr Ser Asn Thr Cys
            20                  25                  30

Ala Met Ala Trp Phe Arg Gln Ala Pro Gly Lys Glu Arg Glu Phe Val
        35                  40                  45

Ser Ser Met Ser Thr Gly Gly Thr Thr Gly Tyr Gly Asp Ser Val Lys
    50                  55                  60

Gly Arg Phe Thr Ser Ser Lys Asp Ala Ala Lys Asp Thr Val Tyr Leu
65                  70                  75                  80

Gln Met Asn Ser Leu Lys Pro Glu Asp Thr Ala Ile Tyr Phe Cys Lys
            85                  90                  95

Thr Tyr Ala Cys Arg Asp Cys Ile Gly Arg Tyr Cys Arg Thr Ala Pro
        100                 105                 110

Asp Ala Trp Gly Gln Gly Thr Gln Val Thr Val Ser Ser
    115                 120                 125

<210> SEQ ID NO 129
<211> LENGTH: 125
<212> TYPE: PRT
<213> ORGANISM: Camelus bactrianus

<400> SEQUENCE: 129

Gln Val Gln Leu Gln Glu Ser Gly Gly Gly Ser Val Gln Ala Gly Gly
1               5                   10                  15

Ser Leu Arg Leu Ser Cys Thr Ala Pro Gly Phe Thr Ser Asn Thr Cys
            20                  25                  30

Ala Met Ala Trp Tyr Arg Gln Ala Pro Gly Lys Glu Arg Glu Phe Val
        35                  40                  45

Ser Ser Arg Ser Thr Val Gly Thr Thr Gly Tyr Ala Asp Ser Val Lys
50                  55                  60

Gly Arg Phe Thr Leu Ser Lys Asp Glu Ala Lys Asp Thr Val Tyr Leu
65                  70                  75                  80

Gln Met Asn Ser Leu Lys Pro Glu Asp Thr Ala Met Tyr Phe Cys Lys
            85                  90                  95

Thr Tyr Ala Cys Arg Asn Cys Ile Gly Arg His Cys Arg Thr Ala Pro
        100                 105                 110

Asp Ala Trp Gly Gln Gly Thr Gln Val Thr Val Ser Ser
            115                 120                 125

<210> SEQ ID NO 130
<211> LENGTH: 126
<212> TYPE: PRT
<213> ORGANISM: Camelus bactrianus

<400> SEQUENCE: 130

Gln Val Gln Leu Gln Glu Ser Gly Gly Gly Ser Val Gln Ala Gly Glu
1               5                   10                  15

Thr Leu Arg Leu Ser Cys Thr Val Ser Gly Asp Thr Phe Glu Ala Ser
            20                  25                  30

Gly Val Gly Trp Phe Arg Gln Val Ser Gly Asn Glu Cys Asp Leu Val
        35                  40                  45

Ser Ser Ile Asn Arg Asp Gly Thr Thr Tyr Tyr Thr Pro Ser Val Ala
50                  55                  60

Gly Arg Phe Thr Met Ser Gln Asn Asn Ala Lys Asn Thr Val Tyr Leu
65                  70                  75                  80

Gln Met Asn Ser Leu Lys Pro Asp Asp Thr Ala Val Tyr Tyr Cys Ala
            85                  90                  95

Thr Asp Pro Ala Val Gly Ile Val Val Arg Ser Thr Cys Arg Gly Pro
        100                 105                 110

Phe Gly Tyr Trp Gly Gln Gly Thr Gln Val Thr Val Ser Ser
            115                 120                 125

<210> SEQ ID NO 131
<211> LENGTH: 126
<212> TYPE: PRT
<213> ORGANISM: Camelus bactrianus

<400> SEQUENCE: 131

Gln Val Gln Leu Gln Glu Ser Gly Gly Gly Ser Val Gln Ala Gly Gly
1               5                   10                  15

Ser Leu Arg Leu Ser Cys Thr Val Ser Gly Asn Thr Asp Ser Met Asn
            20                  25                  30

Leu Met Gly Trp Phe Arg Gln Ala Pro Gly Lys Glu Arg Glu Gly Val
        35                  40                  45

Ala Ser Ile Tyr Thr Gly Ser Arg Thr Ile Tyr Tyr Pro Asp Ser Val
50                  55                  60

Lys Gly Arg Phe Thr Ile Ser Gln Asp Asn Ala Lys Asn Thr Val Tyr
65                  70                  75                  80

```
Leu Gln Met Asn Ser Leu Lys Pro Glu Asp Thr Ala Met Tyr Tyr Cys
                85                  90                  95

Ala Ala Asp Tyr Arg Ala Arg Tyr Gly Ala Ser Leu Arg Thr Ser Ala
            100                 105                 110

Tyr Thr Tyr Trp Gly Gln Gly Thr Gln Val Thr Val Ser Ser
        115                 120                 125

<210> SEQ ID NO 132
<211> LENGTH: 125
<212> TYPE: PRT
<213> ORGANISM: Camelus bactrianus

<400> SEQUENCE: 132

Gln Val Gln Leu Gln Glu Ser Gly Gly Ser Val Gln Ala Gly Gly
1               5                   10                  15

Ser Leu Arg Leu Ser Cys Thr Ala Pro Gly Phe Thr Ser Asn Thr Cys
            20                  25                  30

Ala Met Ala Trp Tyr Arg Gln Ala Pro Gly Lys Glu Arg Glu Phe Val
            35                  40                  45

Ser Ser Arg Ser Thr Val Gly Thr Thr Gly Tyr Ala Asp Ser Val Lys
50                  55                  60

Gly Arg Phe Thr Ile Ser Lys Asp Glu Ala Lys Asp Thr Val Tyr Leu
65                  70                  75                  80

Gln Met Asn Ser Leu Lys Pro Glu Asp Thr Ala Lys Tyr Phe Cys Lys
                85                  90                  95

Thr Tyr Ala Cys Arg Asp Cys Ile Gly Arg Tyr Cys Arg Thr Ala Pro
            100                 105                 110

Asp Ala Trp Gly Gln Gly Thr Gln Val Thr Val Ser Ser
            115                 120                 125

<210> SEQ ID NO 133
<211> LENGTH: 124
<212> TYPE: PRT
<213> ORGANISM: Camelus bactrianus

<400> SEQUENCE: 133

Gln Val Gln Leu Gln Glu Ser Gly Gly Ser Val Gln Ala Gly Gly
1               5                   10                  15

Ser Leu Lys Leu Ser Cys Val Val Ser Gly Tyr Thr Trp Cys Arg Tyr
            20                  25                  30

Asp Met Ser Trp Tyr Arg Gln Ala Pro Gly Lys Glu Arg Glu Phe Val
            35                  40                  45

Ser Val Ile Asp Asp Asn Gly Ser Thr Asn Tyr Ala Asp Ser Val Lys
50                  55                  60

Gly Arg Phe Thr Ile Ser Lys Asp Asn Gly Asn Thr Val Thr Leu Gln
65                  70                  75                  80

Met Thr Ser Leu Lys Pro Ala Asp Thr Ala Met Tyr Tyr Cys Gln Thr
                85                  90                  95

Gly Arg Tyr Arg Ser Arg Leu Gly Tyr Gly Arg Cys Pro Ser Gly Asp
            100                 105                 110

Tyr Trp Gly Leu Gly Thr Gln Val Thr Val Ser Ser
            115                 120

<210> SEQ ID NO 134
<211> LENGTH: 124
<212> TYPE: PRT
<213> ORGANISM: Camelus bactrianus
```

<400> SEQUENCE: 134

Gln Val Gln Leu Gln Glu Ser Gly Gly Gly Ser Val Gln Ala Gly Gly
1               5                   10                  15

Ser Leu Arg Leu Ser Cys Ala Val Ser Gly Tyr Ser Ile Ser Asn Tyr
            20                  25                  30

Cys Met Gly Trp Phe Arg Gln Pro Pro Gly Lys Glu Arg Glu Gly Val
        35                  40                  45

Ala Asn Ile Asp Thr Trp Gly Val Thr Ser Tyr Thr Asp Ser Val Lys
    50                  55                  60

Gly Arg Phe Thr Ile Ser Lys Asp Asn Ala Lys Asn Thr Leu Tyr Leu
65                  70                  75                  80

Gln Met Asn Ser Leu Lys Pro Glu Asp Thr Ala Leu Tyr Tyr Cys Ala
                85                  90                  95

Arg Arg Gln Phe Val Asn Cys Gly Thr Leu Ala Pro Val Asn Tyr Val
            100                 105                 110

Asn Trp Gly Gln Gly Thr Gln Val Thr Val Ser Ser
        115                 120

<210> SEQ ID NO 135
<211> LENGTH: 121
<212> TYPE: PRT
<213> ORGANISM: Camelus bactrianus

<400> SEQUENCE: 135

Gln Val Gln Leu Gln Glu Ser Gly Gly Gly Ser Val Gln Ala Gly Gly
1               5                   10                  15

Ser Leu Arg Leu Ser Cys Thr Ala Ser Gly Phe Thr Phe Ser Thr Leu
            20                  25                  30

Ala Met Ser Trp Val Arg Gln Ala Pro Gly Lys Gly Leu Glu Trp Val
        35                  40                  45

Ser Thr Ile Ser Ser Thr Gly Gly Ala Thr Tyr Tyr Ala Asp Ser Val
    50                  55                  60

Lys Gly Arg Phe Thr Ile Ser Arg Asp Asn Ala Lys Asn Thr Leu Tyr
65                  70                  75                  80

Leu Gln Leu Asn Ser Leu Lys Pro Glu Asp Thr Ala Met Tyr Tyr Cys
                85                  90                  95

Arg Arg Cys Thr Asp Ile Tyr Cys Ser Asn Ser Ala Arg Trp Thr Gly
            100                 105                 110

Gln Gly Thr Gln Val Thr Val Ser Ser
        115                 120

<210> SEQ ID NO 136
<211> LENGTH: 121
<212> TYPE: PRT
<213> ORGANISM: Camelus bactrianus

<400> SEQUENCE: 136

Gln Val Gln Leu Gln Glu Ser Gly Gly Gly Leu Val Gln Pro Gly Gly
1               5                   10                  15

Ser Leu Arg Leu Ser Cys Thr Ala Ser Gly Phe Thr Phe Ser Thr Leu
            20                  25                  30

Ala Met Ser Trp Val Arg Gln Ala Pro Gly Lys Gly Leu Glu Trp Val
        35                  40                  45

Ser Thr Ile Ser Ser Thr Gly Gly Ala Thr Tyr Tyr Ala Asp Ser Val
    50                  55                  60

```
Lys Gly Arg Phe Thr Ile Ser Arg Asp Asn Ala Lys Asn Thr Leu Tyr
 65                  70                  75                  80

Leu Gln Leu Asn Ser Leu Lys Pro Glu Asp Thr Ala Met Tyr Tyr Cys
                 85                  90                  95

Arg Arg Cys Thr Asp Ile Tyr Cys Ser Asn Ser Ala Arg Trp Thr Gly
            100                 105                 110

Gln Gly Thr Gln Val Thr Val Ser Ser
            115                 120
```

<210> SEQ ID NO 137
<211> LENGTH: 120
<212> TYPE: PRT
<213> ORGANISM: Camelus bactrianus

<400> SEQUENCE: 137

```
Gln Val Gln Leu Gln Glu Ser Gly Gly Gly Leu Val Gln Pro Gly Gly
 1               5                  10                  15

Ser Leu Arg Leu Ser Cys Val Ala Ser Gly Phe Ser Phe Ser Ser Ser
                 20                  25                  30

Gly Met Ser Trp Val Arg Gln Ala Pro Gly Lys Gly Leu Glu Trp Val
             35                  40                  45

Ser Thr Ile Ser Tyr Asn Gly Gly Ser Thr Phe Tyr Thr Asp Ser Val
 50                  55                  60

Lys Gly Arg Phe Thr Ile Ser Arg Asp Asn Ala Lys Asn Thr Leu Tyr
 65                  70                  75                  80

Leu Gln Leu Asn Ser Leu Lys Thr Glu Asp Thr Ala Met Tyr Tyr Cys
                 85                  90                  95

Ala Lys Ser Gly Thr Pro Val Leu Ala Pro Asn Ser Val Arg Gly Gln
            100                 105                 110

Gly Thr Gln Val Thr Val Ser Ser
            115                 120
```

<210> SEQ ID NO 138
<211> LENGTH: 127
<212> TYPE: PRT
<213> ORGANISM: Camelus bactrianus

<400> SEQUENCE: 138

```
Gln Val Gln Leu Gln Glu Ser Gly Gly Gly Ser Val Gln Ala Gly Gly
 1               5                  10                  15

Ser Leu Arg Leu Ser Cys Val Ser Ser Gly Tyr Ala Tyr Asn Arg Tyr
                 20                  25                  30

Tyr Met Ala Trp Phe Ser Gln Ala Pro Gly Lys Gly Arg Glu Gly Val
             35                  40                  45

Ala Ala Val Tyr Ile Gly Asp Gly Arg Pro Tyr Tyr Ala Asp Ser Val
 50                  55                  60

Lys Gly Arg Phe Thr Ile Ser Leu Asp Ser Ala Lys Asn Thr Val Tyr
 65                  70                  75                  80

Leu Gln Met Asn Ser Leu Lys Pro Glu Asp Thr Ala Met Tyr Tyr Cys
                 85                  90                  95

Ala Ala Ala Pro Gly Pro Leu Ser Arg Asn Tyr Trp Tyr Thr Ser Ala
            100                 105                 110

Asn Tyr Asp Tyr Trp Gly Gln Gly Thr Gln Val Thr Val Ser Ser
            115                 120                 125
```

<210> SEQ ID NO 139
<211> LENGTH: 122

<212> TYPE: PRT
<213> ORGANISM: Camelus bactrianus

<400> SEQUENCE: 139

Gln Val Gln Leu Gln Glu Ser Gly Gly Gly Ser Val Gln Ala Gly Gly
1               5                   10                  15

Ser Leu Arg Leu Ser Cys Val Ala Ser Gly Tyr Thr Asn Cys Arg Tyr
            20                  25                  30

Asp Met Ser Trp Tyr Arg Gln Ala Pro Gly Lys Glu Arg Glu Phe Val
        35                  40                  45

Ser Ser Ile Asp Ser Glu Gly Val Ala Arg His Ala Asp Ser Val Lys
50                  55                  60

Gly Arg Phe Gly Ile Ser Gln Asp Asn Ala Lys Ser Thr Leu Tyr Leu
65                  70                  75                  80

Gln Met Asn Ser Leu Lys Pro Glu Asp Thr Ala Val Tyr Tyr Cys Lys
                85                  90                  95

Thr Asp Tyr Ile Thr Cys Arg Phe Gly Ser Trp Ser Asp Ser Thr Trp
            100                 105                 110

Gly Gln Gly Thr Gln Val Thr Val Ser Ser
        115                 120

<210> SEQ ID NO 140
<211> LENGTH: 122
<212> TYPE: PRT
<213> ORGANISM: Camelus bactrianus

<400> SEQUENCE: 140

Gln Val Gln Leu Gln Glu Ser Gly Gly Gly Ser Val Gln Ala Gly Gly
1               5                   10                  15

Ser Leu Arg Leu Ser Cys Val Ala Ser Gly Tyr Thr Asn Cys Arg Tyr
            20                  25                  30

Asp Met Ser Trp Tyr Arg Gln Ala Pro Gly Lys Glu Arg Glu Phe Val
        35                  40                  45

Ser Ser Ile Asp Ser Glu Gly Val Ala Arg His Ala Asp Ser Val Lys
50                  55                  60

Gly Arg Phe Gly Ile Ser Gln Asp Asn Ala Lys Ser Thr Leu Tyr Leu
65                  70                  75                  80

Gln Met Asn Ser Leu Lys Pro Glu Asp Thr Ala Met Tyr Tyr Cys Lys
                85                  90                  95

Met Asp Tyr Ile Arg Cys Arg Phe Gly Ser Trp Ser Glu Ser Thr Trp
            100                 105                 110

Gly Gln Gly Thr Gln Val Thr Val Ser Ser
        115                 120

<210> SEQ ID NO 141
<211> LENGTH: 125
<212> TYPE: PRT
<213> ORGANISM: Camelus bactrianus

<400> SEQUENCE: 141

Gln Val Gln Leu Gln Glu Ser Gly Gly Gly Ser Val Gln Ala Gly Gly
1               5                   10                  15

Ser Leu Arg Leu Ser Cys Thr Ala Pro Gly Phe Thr Ser Asn Thr Cys
            20                  25                  30

Ala Met Ala Trp Phe Arg Gln Ala Pro Gly Lys Glu Arg Glu Phe Val
        35                  40                  45

Ser Ser Met Ser Thr Val Gly Ser Thr Arg Phe Ala Asp Ser Val Lys

```
            50                  55                  60
Gly Arg Phe Thr Ile Ser Lys Asp Glu Ala Lys Asp Thr Val Tyr Leu
 65                  70                  75                  80

Gln Met Asn Ser Leu Lys Pro Glu Asp Thr Ala Met Tyr Phe Cys Lys
                 85                  90                  95

Thr Tyr Ala Cys Arg Glu Cys Thr Gly Arg Tyr Cys Arg Thr Ala Pro
            100                 105                 110

Asp Ala Trp Gly Gln Gly Thr Gln Val Thr Val Ser Ser
            115                 120                 125

<210> SEQ ID NO 142
<211> LENGTH: 129
<212> TYPE: PRT
<213> ORGANISM: Camelus bactrianus

<400> SEQUENCE: 142

Gln Val Gln Leu Gln Glu Ser Gly Gly Gly Ser Val Gln Thr Gly Gly
 1               5                  10                  15

Ser Leu Arg Leu Ser Cys Ala Val Ser Arg Tyr Ser Ala Ser Asn Asn
                20                  25                  30

Val Ile Lys Trp Met Gly Trp Phe Arg Gln Ala Pro Gly Lys Glu Arg
            35                  40                  45

Glu Gly Val Ala Ala Leu Tyr Thr Ser Gly Gly Asn Thr Tyr Tyr Ala
 50                  55                  60

Asp Ser Val Lys Gly Arg Phe Thr Ile Ser Arg Asp Tyr Ser Glu Asn
 65                  70                  75                  80

Thr Val Ser Leu Gln Met Asn Asn Leu Lys Pro Glu Asp Thr Gly Met
                85                  90                  95

Tyr Tyr Cys Ala Ala Thr Val Gly Thr Val Leu Ala Gly Pro Leu Ser
            100                 105                 110

Ala Arg Lys Tyr Asn Tyr Trp Gly Gln Gly Thr Gln Val Thr Val Ser
            115                 120                 125

Ser

<210> SEQ ID NO 143
<211> LENGTH: 125
<212> TYPE: PRT
<213> ORGANISM: Camelus bactrianus

<400> SEQUENCE: 143

Gln Val Gln Leu Gln Glu Ser Gly Gly Gly Ser Val Gln Ala Gly Gly
 1               5                  10                  15

Ser Leu Arg Leu Ser Cys Thr Ala Pro Gly Phe Thr Ser Asn Thr Cys
                20                  25                  30

Ala Met Ala Trp Tyr Arg Gln Ala Pro Gly Lys Glu Arg Glu Phe Val
            35                  40                  45

Ser Ser Ile Ser Thr Val Arg Thr Thr Ala Tyr Ala Asp Ser Val Lys
 50                  55                  60

Gly Arg Phe Thr Ile Ser Lys Asp Glu Ala Lys Ala Thr Val Tyr Leu
 65                  70                  75                  80

Gln Met Asn Ser Leu Lys Pro Glu Asp Thr Ala Met Tyr Phe Cys Lys
                85                  90                  95

Ser Tyr Ala Cys Arg Asp Cys Ile Gly Arg Tyr Cys Arg Thr Ala Pro
            100                 105                 110

Asp Ala Trp Gly Gln Gly Thr Gln Val Thr Val Ser Ser
            115                 120                 125
```

<210> SEQ ID NO 144
<211> LENGTH: 129
<212> TYPE: PRT
<213> ORGANISM: Camelus bactrianus

<400> SEQUENCE: 144

Gln Val Gln Leu Gln Glu Ser Gly Gly Gly Ser Val Gln Ala Gly Gln
1               5                   10                  15

Ser Leu Arg Leu Ser Cys Thr Ala Ser Gly Tyr Thr Asp Ser Arg Tyr
            20                  25                  30

Cys Met Gly Trp Phe Arg Gln Ala Pro Gly Lys Glu Arg Glu Arg Val
        35                  40                  45

Thr Thr Ile His Thr Gly Thr Gly Ile Thr Tyr Ala Asp Ser Val
    50                  55                  60

Lys Gly Arg Phe Ser Ile Ser Gln Asp Asn Ala Gln Asn Thr Met Tyr
65                  70                  75                  80

Leu Gln Met Asn Ser Leu Glu Pro Glu Asp Thr Ala Met Tyr Tyr Cys
                85                  90                  95

Ala Thr Thr Asp Tyr Val Tyr Ser Ala Ser Ala Ser Trp Cys Asn Gly
            100                 105                 110

Tyr Gly Val Phe Asn Asn Trp Gly Gln Gly Thr Gln Val Thr Val Ser
        115                 120                 125

Ser

<210> SEQ ID NO 145
<211> LENGTH: 125
<212> TYPE: PRT
<213> ORGANISM: Camelus bactrianus

<400> SEQUENCE: 145

Gln Val Gln Leu Gln Glu Ser Gly Gly Gly Ser Val Gln Ala Gly Gly
1               5                   10                  15

Ser Leu Arg Leu Ser Cys Thr Ala Pro Gly Phe Thr Ser Asn Thr Cys
            20                  25                  30

Ala Met Ala Trp Tyr Arg Gln Ala Pro Gly Lys Glu Arg Glu Phe Val
        35                  40                  45

Ser Ser Arg Ser Thr Val Gly Thr Thr Gly Tyr Ala Asp Ser Val Lys
    50                  55                  60

Gly Arg Phe Thr Ile Ser Lys Asp Glu Ala Lys Asp Thr Val Tyr Leu
65                  70                  75                  80

Gln Met Asn Ser Leu Lys Pro Glu Asp Thr Ala Lys Tyr Phe Cys Lys
                85                  90                  95

Thr Tyr Ala Cys Arg Asp Cys Ile Gly Arg Tyr Cys Arg Thr Ala Pro
            100                 105                 110

Asp Ala Trp Gly Gln Gly Thr Gln Val Thr Val Ser Ser
        115                 120                 125

<210> SEQ ID NO 146
<211> LENGTH: 129
<212> TYPE: PRT
<213> ORGANISM: Camelus bactrianus

<400> SEQUENCE: 146

Gln Val Gln Leu Gln Glu Ser Gly Gly Gly Ser Val Gln Ala Gly Gly
1               5                   10                  15

Ser Leu Arg Leu Ser Cys Ala Val Ser Arg Tyr Ser Ala Ser Asn Asn

```
            20                  25                  30
Val Ile Lys Trp Met Gly Trp Phe Arg Gln Ala Pro Gly Lys Glu Arg
            35                  40                  45

Glu Gly Val Ala Ala Leu Tyr Thr Ser Gly Gly Asn Thr Tyr Tyr Ala
        50                  55                  60

Asp Ser Val Lys Gly Arg Phe Thr Ile Ser Arg Asp Tyr Ser Glu Asn
65                  70                  75                  80

Thr Val Ser Leu Gln Met Asn Asn Leu Lys Pro Glu Asp Thr Gly Met
                85                  90                  95

Tyr Tyr Cys Ala Thr Val Gly Thr Val Leu Ala Gly Pro Leu Ser
            100                 105                 110

Ala Arg Lys Tyr Asn Tyr Trp Gly Gln Gly Thr Gln Val Thr Val Ser
            115                 120                 125

Ser

<210> SEQ ID NO 147
<211> LENGTH: 124
<212> TYPE: PRT
<213> ORGANISM: Camelus bactrianus

<400> SEQUENCE: 147

Gln Val Gln Leu Gln Glu Ser Gly Gly Gly Ser Val Gln Ala Gly Gly
1               5                   10                  15

Ser Leu Arg Leu Ser Cys Ala Ala Ser Gly Tyr Thr Ser Arg Pro Asn
            20                  25                  30

Phe Met Val Trp Phe Arg Gln Ala Pro Gly Lys Glu Arg Glu Ala Val
            35                  40                  45

Ala Gly Ile Tyr Thr Val Thr Gly Gly Thr Leu Tyr Ser Asp Pro Val
        50                  55                  60

Lys Gly Arg Phe Thr Ile Ser Gln Asp Lys Ala Lys Asn Thr Val Tyr
65                  70                  75                  80

Leu Gln Met Asn Ser Leu Asn Pro Glu Asp Thr Ala Met Tyr Tyr Cys
                85                  90                  95

Ala Val Lys Trp Tyr Gly Gly Ser Trp Ser Asp Ala Ala Thr Phe Arg
            100                 105                 110

Thr Trp Gly Arg Gly Thr Gln Val Thr Val Ser Ser
            115                 120

<210> SEQ ID NO 148
<211> LENGTH: 125
<212> TYPE: PRT
<213> ORGANISM: Camelus bactrianus

<400> SEQUENCE: 148

Gln Val Gln Leu Gln Glu Ser Gly Gly Gly Ser Val Gln Ala Gly Gly
1               5                   10                  15

Ser Leu Arg Leu Ser Cys Ala Ala Ser Gly Tyr Ser Tyr Asn Ile Asp
            20                  25                  30

Tyr Met Ala Trp Phe Arg Gln Ala Pro Gly Lys Glu Arg Glu Gly Val
            35                  40                  45

Ala Ala Ile Tyr Thr Gly Ser Arg Arg Thr Tyr Tyr Ser Asp Ser Val
        50                  55                  60

Lys Gly Arg Phe Ala Ile Ser Gln Asp Asn Ala Asp Asn Thr Val Tyr
65                  70                  75                  80

Leu Gln Met Asn Ala Leu Lys Pro Glu Asp Thr Ala Met Tyr Phe Cys
                85                  90                  95
```

```
Ala Ala Leu Val Ser Arg Pro Gly Arg Ser Trp Asp Lys Asn Glu Tyr
            100                 105                 110

Arg Tyr Trp Gly Gln Gly Thr Gln Val Thr Val Ser Ser
            115                 120                 125

<210> SEQ ID NO 149
<211> LENGTH: 125
<212> TYPE: PRT
<213> ORGANISM: Camelus bactrianus

<400> SEQUENCE: 149

Gln Val Gln Leu Gln Glu Ser Gly Gly Gly Leu Val Gln Ala Gly Gly
1               5                   10                  15

Ser Leu Arg Leu Ser Cys Thr Ala Ser Gly Phe Thr Phe Asp Asp Tyr
            20                  25                  30

Ser Met Gly Trp Phe Arg Gln Ala Pro Gly Lys Glu Arg Glu Gly Ile
        35                  40                  45

Ser Cys Ile Asp Trp Ser Gly Arg Thr Asn Tyr Gly Asp Ser Val
    50                  55                  60

Lys Gly Arg Phe Thr Ile Ser Arg Asp Asn Ala Lys Asn Thr Leu Tyr
65                  70                  75                  80

Leu Gln Met Asn Ser Leu Lys Pro Glu Asp Thr Ala Met Tyr Tyr Cys
                85                  90                  95

Ala Ala Asn Ser Ala Tyr Ser Ser Cys Ser Leu Ser Thr Thr His Tyr
            100                 105                 110

Lys Tyr Trp Gly Gln Gly Thr Gln Val Thr Val Ser Ser
            115                 120                 125

<210> SEQ ID NO 150
<211> LENGTH: 121
<212> TYPE: PRT
<213> ORGANISM: Camelus bactrianus

<400> SEQUENCE: 150

Gln Val Gln Leu Gln Glu Ser Gly Gly Gly Leu Val Gln Pro Gly Gly
1               5                   10                  15

Ser Leu Arg Leu Ser Cys Ala Ala Ser Gly Phe Thr Phe Ser Ala Tyr
            20                  25                  30

Gly Met Ser Trp Val Arg Gln Ala Pro Gly Lys Gly Phe Glu Trp Val
        35                  40                  45

Ser Thr Ile Asn Ser Gly Gly Gly Thr Thr Phe Tyr Ala Asp Ser Val
    50                  55                  60

Lys Gly Arg Phe Thr Ile Ser Arg Asp Asn Ala Lys Asn Thr Leu Tyr
65                  70                  75                  80

Leu Gln Leu Asn Ser Leu Arg Thr Glu Asp Thr Ala Met Tyr Tyr Cys
                85                  90                  95

Arg Arg Cys Ala Asp Ile Tyr Cys Ser Leu Ser Gly Gly Trp Thr Gly
            100                 105                 110

Gln Gly Thr Gln Val Thr Val Ser Ser
            115                 120

<210> SEQ ID NO 151
<211> LENGTH: 381
<212> TYPE: DNA
<213> ORGANISM: Camelus bactrianus

<400> SEQUENCE: 151
```

```
caggtgcagc tgcaggagtc tggaggaggc tcggtgcaga ccggagggtc tctgagactc        60
tcctgtacag cctctacatc aatatacagt aacaactaca tggcctggtt cagccagtct       120
ccaggaaagg ggcgcgaggg ggtcgcagct gtttatatgg atgatggtcg cccatactat       180
gccgattccg tgaagggccg attcaccatc tccctagaca cgccaagaa cacgatgtat        240 ttgcaaatga acagcctgaa acctgaggac actgccatgt actactgtgc ggcagctcca       300
ggccccttaa gtcgtaacta ctggtacacg tccgccaact atgactactg gggccagggg      360
acccaggtca ccgtctcctc a                                                 381

<210> SEQ ID NO 152
<211> LENGTH: 378
<212> TYPE: DNA
<213> ORGANISM: Camelus bactrianus

<400> SEQUENCE: 152
caggtgcagc tgcaggagtc tggaggaggg tcggtgcagg ctggagagac tctgagactc        60
tcctgtacag cctctggaga cactttgat gactctggcg tgggctggtt ccgccaggtt       120
tcagggaatg agtgcgactt ggtctcaagt attaatcgtg atggtaacac atactataca      180
ccctccgtgg cgggccgatt taccatctcc caaaacaacg ccaagaacac ggtatatctg       240
caaatgaaca gcctgaaacc tgacgacaca gccgtgtatt actgtgcgac agaccccgcc      300
gtggggattg tagtgaggac tacctgtaga ggcccctttg gttactgggg ccaggggacc      360
caggtcaccg tctcctca                                                    378

<210> SEQ ID NO 153
<211> LENGTH: 381
<212> TYPE: DNA
<213> ORGANISM: Camelus bactrianus

<400> SEQUENCE: 153
caggtgcagc tgcaggagtc tgggggaggc tcggtgcaga ccggagggtc tctgagactc        60
tcctgtgcag cctctacatc actatacagt tacaactaca tggcctggtt cagccaggct      120
ccaggaaagg ggcgcgaggg ggtcgcagct gtttatgttg gtgatggtcg cccatactat      180
gccgactccg tgaagggccg attcaccatc tccctagaca cgccaagaa cgcggtgtat        240 ctgcaaatga acagcctgaa acctgaggac actgccatgt actactgtgc ggcagctcca      300
ggccccttaa gtcataatta ctggtacacg tccgccaact atgactactg gggccagggg      360
acccaggtca ccgtctcctc a                                                 381

<210> SEQ ID NO 154
<211> LENGTH: 381
<212> TYPE: DNA
<213> ORGANISM: Camelus bactrianus

<400> SEQUENCE: 154
caggtgcagc tgcaggagtc tggaggaggc tcggtgcaga ccggagggtc tctgagactc        60
tcctgtgcag cctctccatc aatatacagt gccaactaca tggcctggtt cagccaggct      120
ccaggaaagg ggcgcgaggg ggtcgcagct gtttatattg gtgatggtcg cccatactat      180
gccgactccg tgaagggccg attcaccatc tccctagaca cgccaagaa cacggtgtat        240 ctgcaaatga acagcctgaa acctgaggac actgccatgt actactgtgc ggcagctcca      300
ggccccttag gtcataatta ctggtacacg tccgccaact atgactactg gggccagggg      360
acccaggtca ccgtctcctc a                                                 381
```

<210> SEQ ID NO 155
<211> LENGTH: 381
<212> TYPE: DNA
<213> ORGANISM: Camelus bactrianus

<400> SEQUENCE: 155

```
caggtgcagc tgcaggagtc tgggggaggc tcggtgcaga ccggagggtc tctgagactc      60
tcctgtgcag cctctacatc aatatacagt aacaactaca tggcctggtt cagccaggct     120
ccaggaaagg ggcgcgaggg ggtcgcagct gtttacattg atgatggtcg cccatactat     180
gccgactccg tgaagggccg attcaccatc tccctagaca cgccaagaa cacggtgtat      240 ctgcaaatga acggcctgaa acctgaggac actgccatgt actactgtgc ggcagctcca     300
ggccccttaa gtcgtaatta ctggtacacg tccgccaact atgactactg gggccagggg    360
acccaggtca ccgtctcctc a                                               381
```

<210> SEQ ID NO 156
<211> LENGTH: 378
<212> TYPE: DNA
<213> ORGANISM: Camelus bactrianus

<400> SEQUENCE: 156

```
caggtgcagc tgcaggagtc tgggggaggg tcggtgcagg ctggagagac tctgagactc      60
tcctgtacag cctctggaga cactttttgat gcctctggcg tgggctggtt ccgccaggtt    120
tcagggaatg aatgcgactt ggtctcaagt attaatcgtg atggtaccac atactatgca    180
ccctccgtgg cgggccgatt tacgatgtcc caaaacaacg ccaagaacac ggtatatctg    240
caaatgaaca gcctgaaacc tgacgacaca gccgtgtatt actgtgcgac agaccccgcc    300
gtggggattg tagtgaggag cacctgtaga ggccccttg gttactgggg ccaggggacc    360
caggtcaccg tctcctca                                                   378
```

<210> SEQ ID NO 157
<211> LENGTH: 381
<212> TYPE: DNA
<213> ORGANISM: Camelus bactrianus

<400> SEQUENCE: 157

```
caggtgcagc tgcaggagtc tgggggaggc tcggtgcaga ccggagggtc tctgagactc      60
tcctgtgcat gctctacatc aatatacagt accaactaca tggcctggtt cagccaggct     120
ccaggaaagg ggcgcgaggg ggtcgcagct gtttatattg gtgatggtcg cccatactat     180
gccgactccg tgaagggccg attcaccatc tccctagaca cgccaagaa cacggtgtat      240 ctgcaaatga acagcctgaa acctgaggac actgccatgt actactgtgc ggcagctcca     300
ggccccttaa gtcgtaatta ctggtacacg tccgccaact atgactactg gggccagggg    360
acccaggtca ccgtctcctc a                                               381
```

<210> SEQ ID NO 158
<211> LENGTH: 375
<212> TYPE: DNA
<213> ORGANISM: Camelus bactrianus

<400> SEQUENCE: 158

```
caggtgcagc tgcaggagtc tgggggagac tcagtgcagg ctgggggtc tctgagactc       60 gcctgcaaag tccctggatt cacctccaac acctgcgcca tggcgtggtt ccgccaggct    120
```

| | |
|---|---|
| ccagggaaag agcgcgagtt cgtctcatct atcagcactg gcggtaccac ggggtatgca | 180 |
| gaatccgcga agggccgatt caccctctcc aaagacgaag ccaaggacac ggtctatctg | 240 |
| caaatgaaca gcctgaaacc ggaggacacg gccatgtatt tttgtaagag ctatgcgtgt | 300 |
| agaacttgta ttggtcggta ttgtcgtaca gctccggatg catggggcca ggggacacag | 360 |
| gtcaccgtct cctca | 375 |

<210> SEQ ID NO 159
<211> LENGTH: 372
<212> TYPE: DNA
<213> ORGANISM: Camelus bactrianus

<400> SEQUENCE: 159

| | |
|---|---|
| caggtgcagc tgcaggagtc tggaggaggc tcggtgcagg ctggagggtc tctgagactc | 60 |
| tcctgtgcag cctctggata tacttacagt aacgacggta tgggctggtt ccgccagatt | 120 |
| ccagggaagg agcgcgaggg ggtcgcagct attagtccta ctggtaggcg cacagagtat | 180 |
| gccgactccg tgcagggccg attcaccatc tcccgcgaca acgccaagaa catgttatct | 240 |
| ctgcaaatga acagcctgaa acctgaggac actgggatgt actactgtgc acgcgagggg | 300 |
| tcggggtcct tttccctgca aaatagcgcg gtgagatcgt ggggccaggg gacccaggtc | 360 |
| accgtctcct ca | 372 |

<210> SEQ ID NO 160
<211> LENGTH: 375
<212> TYPE: DNA
<213> ORGANISM: Camelus bactrianus

<400> SEQUENCE: 160

| | |
|---|---|
| caggtgcagc tgcaggagtc tgggggaggc tcagtgcagg ctgggggtc tctgagactc | 60 |
| tcctgcacag cccctggatt cacctccaag acctgcgcca tgcgctggta ccgccaggct | 120 |
| ccagggaaag agcgcgagtt cgtctcagca atcagcactg tcggtaccac aacgtatgca | 180 |
| gactccgtga agggccgatt cattatctcc aaagacgaag ccaaggacac ggtctatctt | 240 |
| caaataaaca gcctgaaacc tgaggacact gccatgtatt cttgtaagac ctttgcgtgt | 300 |
| agacattgta ttggtcaatc ttgtcgtaca gaaccggatt attggggcca ggggacacag | 360 |
| gtcaccgtct cctca | 375 |

<210> SEQ ID NO 161
<211> LENGTH: 378
<212> TYPE: DNA
<213> ORGANISM: Camelus bactrianus

<400> SEQUENCE: 161

| | |
|---|---|
| caggtgcagc tgcaggagtc tgggggaggg tcggtgcagg ctggagagac tctgagactc | 60 |
| tcctgtacag cctctggaga cacttttgat gactctggcg tgggctggtt ccgccaggtt | 120 |
| tcagggaatg aatgcgactt ggtctcaagt attaatcgtg atggtaccac atactatgca | 180 |
| ccctccgtgg cgggccgatt taccatctcc caaaacaacg ccagaacac ggtatatctg | 240 |
| caaatgaaca gcctgaaacc tgacgacaca gccgtgtatt actgtgcgac agtccccgcc | 300 |
| gtggggattg tagtgaggat tacctgtaga ggccccttg gttactgggg ccaggggacc | 360 |
| caggtcaccg tctcctca | 378 |

<210> SEQ ID NO 162
<211> LENGTH: 381

```
<212> TYPE: DNA
<213> ORGANISM: Camelus bactrianus

<400> SEQUENCE: 162
caggtgcagc tgcaggagtc tgggggaggc tcggtgcagg ctggagggtc cctgagactc      60
tcctgtgcag cctctggata cacccgcagt agtcactgca tggtctggtt ccgtcaggct     120
ccagggaagg agcgcgaggg ggtcgctctt atttatactg gtagtggttc aacatactat     180
gccgactccg tgaagggccg attcaccatc tcccaagaca acgccaagaa gacgctgtat     240
ctgcaaatga acagcctgaa acctgaggac actgccatgt attactgtgc ggcaggaacg     300
agttcatcat cctgccccgg cctcttgggc cctccgaggt attacaactg gggccagggg     360
acccaggtca ccgtctcctc a                                               381

<210> SEQ ID NO 163
<211> LENGTH: 381
<212> TYPE: DNA
<213> ORGANISM: Camelus bactrianus

<400> SEQUENCE: 163
caggtgcagc tgcaggagtc tgggggaggc tcggtgcaga ccggagggtc tctgagactc      60
tcctgtgcag cctctacatc aatatacagt aacaactaca tggcctggtt cagccagaat     120
ccaggaaagg ggcgcgaggg ggtcgcagct gtttatattg gtgatggtcg cccatactat     180
gccgactccg tgaagggccg attcaccatc tccctagaca gcgccaagaa cacggtgtat     240
ctgcaaatga acagcctgaa acctgaggac actgccatgt actactgtgc ggcagctcca     300
ggcccttaa gtcgaaatta ctggtacacg tccgccaact atgactactg gggccagggg     360
acccaggtca ccgtctcctc a                                               381

<210> SEQ ID NO 164
<211> LENGTH: 381
<212> TYPE: DNA
<213> ORGANISM: Camelus bactrianus

<400> SEQUENCE: 164
caggtgcagc tgcaggagtc tgggggaggc tcggtgcaga ccggagggtc tctgagactc      60
tcctgtgcag cctctacatc aatatacagt aacaactaca tggcctggtt cagccaggct     120
ccaggaaagg ggcgcgaggg ggtcgcagct gtttatattg atgatggtcg cccatactat     180
gccgactccg tgaagggccg attcaccatc tccctagaca gcgccaagaa cacggtgtat     240
ctgcaagtga acagcctgaa acctgaggac actgccatgt actactgtgc ggcagctcca     300
ggcccttaa gtcgtaatta ctggtacacg tccgccaact atgactactg gggccagggg     360
acccaggtca ccgtctcctc a                                               381

<210> SEQ ID NO 165
<211> LENGTH: 381
<212> TYPE: DNA
<213> ORGANISM: Camelus bactrianus

<400> SEQUENCE: 165
caggtgcagc tgcaggagtc tgggggaggc tcggtgcaga ccggagggtc tctgagactc      60
tcctgtgcag cctctacatc aatatacagt aacaactaca tggcctggtt cagccaggct     120
ccaggaaagg ggcgcgaggg ggtcgcagct gtttatattg atgatggtcg cacatactat     180
gccgactccg tgaagggccg attcaccatc tccctagaca gcgccaagaa cacggtgtat     240
```

```
ctgcaaatga acagcctgaa acctgaggac actgccatgt actactgtgc ggcagctcca    300
ggccccttaa gttataatta ctggtacacg tccgccaact atgactactg gggccagggg    360
acccaggtca ccgtctcctc a                                              381
```

<210> SEQ ID NO 166
<211> LENGTH: 381
<212> TYPE: DNA
<213> ORGANISM: Camelus bactrianus

<400> SEQUENCE: 166

```
caggtgcagc tgcaggagtc tgggggaggc tcggtgcaga ccggagggtc tctgagactc     60
tcctgtgcag cctcgccatc aatatacagt aacaactaca tggcctggtt cagccaggct    120
ccaggaaagg ggcgcgaggg ggtcgcagct gtttatattg gtgatggtcg cccatactat    180
gccgactccg tgaagggccg attcaccatc tccctagaca gcgccaagaa cacggtgtat    240
ctgcaaatga acagcctgaa acctgaggac actgccatgt actactgtgc ggcagctcca    300
ggccccttaa gtcgtaatta ctggtacacg tccgccaact atgactactg gggccagggg    360
acccaggtca ccgtctcctc a                                              381
```

<210> SEQ ID NO 167
<211> LENGTH: 381
<212> TYPE: DNA
<213> ORGANISM: Camelus bactrianus

<400> SEQUENCE: 167

```
caggtgcagc tgcaggagtc tggaggaggc tcggtgcaga ccggagggtc tctgagactc     60
tcctgtgcag cctctacatc aatatacagt ctcaactaca tggcctggtt cagccaggct    120
ccaggaaagg ggcgcgaggg ggtcgcagct gtttatattg atgatggtcg cccatactat    180
gccgatcacg tgaagggccg attcaccatc tccctagaca ccgccaagaa cacggtgtat    240
ttgcaaatga acagcctgaa acctgaggac actgccatgt actactgtgc ggcagctcca    300
ggccccttaa gtcgtaacta ctggtacacg tccgccaact atgactactg gggccagggg    360
acccaggtca ccgtctcctc a                                              381
```

<210> SEQ ID NO 168
<211> LENGTH: 372
<212> TYPE: DNA
<213> ORGANISM: Camelus bactrianus

<400> SEQUENCE: 168

```
caggtgcagc tgcaggagtc tgggggaggc tcggtgcagg ctggagggtc tctgagactc     60
tcctgtgcag cctctggata tacttacagt agcgacggta tgggctggtt ccgccagact    120
ccagggaagg agcgcgaggg ggtcgcagct attagtccta ccggtaggcg cacagagtat    180
gccgactccg tgaagggccg attcaccatc tcccgcgaca caacaagaa catgttatct     240 ctgcaaatga acagcctgaa acctgaggac actgggatgt actactgtgc acgcgagggg    300
tcgtggtcct tttccctggc aaatagcgcg gtgagatcgt ggggccaggg gacccaggtc    360
accgtctcct ca                                                        372
```

<210> SEQ ID NO 169
<211> LENGTH: 381
<212> TYPE: DNA
<213> ORGANISM: Camelus bactrianus

<400> SEQUENCE: 169

| | |
|---|---|
| caggtgcagc tgcaggagtc tggaggaggc tcggtgcaga ccggagggtc tctgagactc | 60 |
| tcctgtgcag cctctacatc aatatacagt aacaactaca tggcctggtt cagccaggct | 120 |
| ccaggaaagg ggcgcgaggg ggtcgcagct gtttatattg gtgatggtcg cccatactat | 180 |
| gccgactccg tgaagggccg attcaccatc tccctagaca gcgccaagaa cacggtgtat | 240 |
| ctgcaaatga acagcctgaa acctgaggac actgccatgt actactgtgc ggcagctcca | 300 |
| ggccccttaa gtcgtaatta ctggtacacg tccgccaact atgactactg gggccagggg | 360 |
| acccaggtca ccgtctcctc a | 381 |

<210> SEQ ID NO 170
<211> LENGTH: 363
<212> TYPE: DNA
<213> ORGANISM: Camelus bactrianus

<400> SEQUENCE: 170

| | |
|---|---|
| caggtgcagc tgcaggagtc tgggggaggc ttggtgcagc ctggggggtc tctgagactc | 60 |
| tcctgtgcag cctctggatt caccggcagt atttatgcca tgagctgggt ccgccaggct | 120 |
| ccagggaagg gactcgagtg gtctcaact attagtagta gtggtggtag gcgattctat | 180 |
| gcagactccg tgaagggccg attcaccatc tccagagaca acgccaagaa cacgctgtat | 240 |
| ctgcaattga acagcttaa aactgaggac acgccatgt attactgtgc aagatgtagt | 300 |
| gatatttact gcgacaacgg agcgtcgtat aggggccagg ggacccaggt caccgtctcc | 360 |
| tca | 363 |

<210> SEQ ID NO 171
<211> LENGTH: 381
<212> TYPE: DNA
<213> ORGANISM: Camelus bactrianus

<400> SEQUENCE: 171

| | |
|---|---|
| caggtgcagc tgcaggagtc tggaggaggc tcggtgcaga ccggagggtc tctgagactc | 60 |
| tcctgtgcag cctctacatc aatatacagt ctcaactaca tggcctggtt cagccaggct | 120 |
| ccaggaaagg ggcgcgaggg ggtcgctgct gtttatattg gtgatggtcg cccatactat | 180 |
| gccgactccg tgaagggccg attcaccatc tccctagaca gcgccaagaa cacggtgtat | 240 |
| ctgcaaatga acagcctgaa atctgaggac actgccatgt actactgtgc ggcagctcca | 300 |
| ggccccttaa gtcgtcatta ctggtacacg tccgccaact atgactactg gggccagggg | 360 |
| acccaggtca ccgtctcctc a | 381 |

<210> SEQ ID NO 172
<211> LENGTH: 381
<212> TYPE: DNA
<213> ORGANISM: Camelus bactrianus

<400> SEQUENCE: 172

| | |
|---|---|
| caggtgcagc tgcaggagtc tgggggaggc tcggtgcaga ccggagggtc tctgagactc | 60 |
| tcctgtgcag cctctacatc aatctacagt aacaactaca tggcctggtt cagccaggct | 120 |
| ccaagaaagg ggcgcgaggg ggtcgcagct gtttatattg gtgatggtcg cccatactat | 180 |
| gccgactccg tgaagggccg attcaccatc tccctagaca gcgccaagaa cacggtgtat | 240 |
| ctgcaaatga acagcctgaa acctgaggac actgccatgt actactgtgc ggcagctcca | 300 |
| ggccccttaa gtcataatta ctggtacacg tccgccaact atgactactg gggccagggg | 360 |

```
acccaggtca ccgtctcctc a                                            381

<210> SEQ ID NO 173
<211> LENGTH: 381
<212> TYPE: DNA
<213> ORGANISM: Camelus bactrianus

<400> SEQUENCE: 173
caggtgcagc tgcaggagtc tgggggaggc tcggtgcaga ccggagggtc tctgagactc    60
tcctgtgcag cctctacatc actatacagt tacaactaca tggcctggtt cagccaggct   120
ccaggaaagg ggcgcgaggg ggtcgcagct gtttatgttg gtgatggtcg cccatactat   180
gccgactccg tgaagggccg attcaccatc tccctagaca gcgccaagaa cacggtgtat   240
ctgcaaatga acagcctgaa acctgaggac actgccatgt actactgtgc ggcagctcca   300
ggccccttaa gtcataatta ctggtacacg tccgccaact atgactactg gggccagggg   360
acccaggtca ccgtctcctc a                                            381

<210> SEQ ID NO 174
<211> LENGTH: 381
<212> TYPE: DNA
<213> ORGANISM: Camelus bactrianus

<400> SEQUENCE: 174
caggtgcagc tgcaggagtc tgggggaggc tcggtgcaga ccggagggtc tctgagactc    60
tcctgtacag cctctacatc aatatacagt aacaactaca tggcctggtt cagccagtct   120
ccaggaaagg ggcgcgaggg ggtcgcagct gtttatatgg atgatggtcg cccatactat   180
gccgattccg tgaagggccg attcaccatc tccctagaca gcgccaagaa cacgatgtat   240
ctgcaaatga acagcctgaa acctgaggac actgccatgt actactgtgc ggcagctcca   300
ggccccttaa gtcgtaacta ctggtacacg tccgccaact atgactactg gggccagggg   360
acccaggtca ccgtctcctc a                                            381

<210> SEQ ID NO 175
<211> LENGTH: 381
<212> TYPE: DNA
<213> ORGANISM: Camelus bactrianus

<400> SEQUENCE: 175
caggtgcagc tgcaggagtc tggaggaggc tcggtgcaga ccggagggtc tctgagactc    60
tcctgtacag cctctacatc aatatacagt aacaactaca tggcctggtt cagccaggct   120
ccaggaaagg ggcgcgaggg ggtcgcagct gtttatattg gtgatggtcg accatactat   180
gccgactccg tgaagggccg attcaccatc tccctagaca gcgccaagaa cacggtgtat   240
ctgcaaatga acagcctgaa acctgaggac actgccatgt actactgtgc ggcagctcca   300
ggccccttaa gtcataatta ctggtacacg tctgccaact atgactactg gggccagggg   360
acccaggtca ccgtctcctc a                                            381

<210> SEQ ID NO 176
<211> LENGTH: 381
<212> TYPE: DNA
<213> ORGANISM: Camelus bactrianus

<400> SEQUENCE: 176
caggtgcagc tgcaggagtc tgggggaggc tcggtgcaga ccggagggtc tctgagactc    60
tcctgtgcag cctctacatc aatatacaat aacaactaca tggcctggtt cagccaggct   120
```

```
ccaggaaagg agcgcgaggg ggtcgcagct gtttatattg gtgatggtcg cccatactat      180
gccgactccg tgaagggccg attcaccatc tccctagaca gcgccaagaa cacggtgtat      240
ctgcaaatga acagcctgaa acctgaggac actgccatgt actactgtgc ggcagctcca      300
ggccccttaa gtcgtaatta ctggtacacg tccgccaact atgactactg gggccagggg      360
acccaggtca ccgtctcctc a                                                381
```

<210> SEQ ID NO 177
<211> LENGTH: 381
<212> TYPE: DNA
<213> ORGANISM: Camelus bactrianus

<400> SEQUENCE: 177

```
caggtgcagc tgcaggagtc tgggggaggc tcggtgcaga ccggagggtc tctgagactc       60
tcctgtacag cctctacatc aatatacagt aacaactaca tggcctggtt cagccagtct      120
ccaggaaagg ggcgcgaggg ggtcgcagct gtttatatgg atgatggtcg cccatactat      180
gccgattccg tgaagggccg attcaccatc tccctagaca gcgccaagaa cacgatgtat      240
ttgcaaatga acagcctgaa acctgaggac actgccatgt actactgtgc ggcagctcca      300
ggccccttaa gtcgtaacta ctggtacacg tccgccaact atgactactg gggccagggg      360
acccaggtca ccgtctcctc a                                                381
```

<210> SEQ ID NO 178
<211> LENGTH: 381
<212> TYPE: DNA
<213> ORGANISM: Camelus bactrianus

<400> SEQUENCE: 178

```
caggtgcagc tgcaggagtc tgggggaggc tcggtgcaga ccggagggtc tctgagactc       60
tcctgtgcag cctctacatc aatatacagt aacaactaca tggcctggtt ccgccaggct      120
ccaggaaagg ggcgcgaggg ggtcgcagct gtttatattg atgatggtcg cccatactat      180
gccgactccg tgaagggccg attcaccatc tccctagaca gcgccaagaa cacggtgtat      240
ctgcaaatga acagcctgaa acctgaggac actgccatgt actactgtgc ggcagctcca      300
ggccccttaa gtcgtcatta ctggtacacg tccgccaact atgactactg gggcccgggg      360
acccaggtca ccgtctcctc a                                                381
```

<210> SEQ ID NO 179
<211> LENGTH: 381
<212> TYPE: DNA
<213> ORGANISM: Camelus bactrianus

<400> SEQUENCE: 179

```
caggtgcagc tgcaggagtc tggaggaggc tcggtgcgga ccggagggtc tctgagactc       60
tcctgtgcag cctcgccatc aatatacagt aacaactaca tggcctggtt cagccaggct      120
ccaggaaagg ggcgcgaggg ggtcgcagct gtttatattg atgatggtcg cccatactat      180
gccgactccg tgaagggccg gttcaccatc tccctagaca gcgccaagaa cacggtgtat      240
ctgcaaatga acagcctgaa accgaggac actgccatgt actactgtgc ggcagctcca       300
ggccccttaa gtcgtaacta ctggtacacg tccgccaact atgactactg gggccagggg      360
acccaggtca ccgtctcctc a                                                381
```

<210> SEQ ID NO 180

```
<211> LENGTH: 381
<212> TYPE: DNA
<213> ORGANISM: Camelus bactrianus

<400> SEQUENCE: 180
caggtgcagc tgcaggagtc tgggggaggc tcggtgcaga ccggagggtc tctgagactc        60
tcctgtacag cctctacatc aatatacagt aacaactaca tggcctggtt cagccaggct       120
ccaggaaagg ggcgcgaggg ggtcgcagct gtttatattg acgatggtcg cccatactat       180
gccgactccg tgaagggccg attcaccatc tccctagaca gcgccaagaa cacggtgtat       240
ctgcaaatga acagcctgaa acctgaggac actgccatgt actactgtgc ggcagctcca       300
ggccccttaa gtcgtaatta ctggtacacg tccgccaact atgactactg gggccagggg       360
acccaggtca ccgtctcctc a                                                 381

<210> SEQ ID NO 181
<211> LENGTH: 381
<212> TYPE: DNA
<213> ORGANISM: Camelus bactrianus

<400> SEQUENCE: 181
caggtgcagc tgcaggagtc tgaggaggc tcggtgcaga ccggagggtc tctgagactc         60
tcctgtgcag cctctacatc aatatacagt aacaactaca tggcctggtt ccgccaggct       120
ccaggaaagg ggcgcgaggg ggtcgccggt gtttatattg gtgatggtcg cccatactat       180
gccgactccg tgaagggccg attcaccatc tccctagaca gcgccaagaa cacggtgtat       240
ctgcaaatga acagcctgaa gcctgaggac actgccatgt actactgtgc ggcagctcca       300
ggccccttaa gtcatcatta ctggtacacg tccgccaact atgactactg gggcccgggg       360
acccaggtca ccgtctcctc a                                                 381

<210> SEQ ID NO 182
<211> LENGTH: 381
<212> TYPE: DNA
<213> ORGANISM: Camelus bactrianus

<400> SEQUENCE: 182
caggtgcagc tgcaggagtc tgggggaggc tcggtgcaga ccggagggtc tctgagactc        60
tcctgtgcag cctctacatc aatatacagt atcaactaca tggcctggtt cagccaggct       120
ccaggaaagg ggcgcgaggg ggtcgcagct gtttatattg gtgatggtcg cccatactat       180
gccgactccg tgaagggccg attcaccatc tccctagaca gcgccaagaa cacggtgtat       240
ctgcaaatga acagcctgaa acctgaggac actgccatgt actactgtgc ggcagcacca       300
ggccccttaa gtcagcatta ctggtacacg tccgccaact atgactactg gggccagggg       360
acccaggtca ccgtctcctc a                                                 381

<210> SEQ ID NO 183
<211> LENGTH: 381
<212> TYPE: DNA
<213> ORGANISM: Camelus bactrianus

<400> SEQUENCE: 183
caggtgcagc tgcaggagtc tgggggaggc tcggtgcaga ccggagggtc tctgagactc        60
tcctgtgcat gctctacatc aatatacagt aacaactaca tggcctggtt cagccaggct       120
ccaggaaagg ggcgcgaggg ggtcgcagct gtttatattg gtgatggtcg cccatactat       180
gccgactccg tgaagggccg attcaccatc tccctagaca gcgccaagaa cacgatgtat       240
```

| | |
|---|---|
| ctgcaaatga acagcctgaa acctgaggac actgccatgt actactgtgc ggcagcacca | 300 |
| ggcccttaa gtcagcatta ctggtacacg tccgccaact atgactactg gggccagggg | 360 |
| acccaggtca ccgtctcctc a | 381 |

<210> SEQ ID NO 184
<211> LENGTH: 381
<212> TYPE: DNA
<213> ORGANISM: Camelus bactrianus

<400> SEQUENCE: 184

| | |
|---|---|
| caggtgcagc tgcaggagtc tgggggaggc tcggtgcagg ctggagggtc tctgagactc | 60 |
| tcctgtgcag cctctggata cacccgcagt ctgtactgca tgggctggtt ccgccaggct | 120 |
| ccagggaggg agcgcgaggg ggtcgcacat gtttatactg gtgatggaag cccatactat | 180 |
| gccgactccg tgaagggccg attcaccatc tcccaagaca acggcgagag cacgctgtat | 240 |
| ctgcaaatga acaatctgaa acctgaggac actgccatgt actactgtgc ggcaggtaca | 300 |
| agtgccttat ctcgccccta cggtcccatc tcgtatggct actggtactg gggccagggg | 360 |
| acccaggtca ccgtctcctc a | 381 |

<210> SEQ ID NO 185
<211> LENGTH: 381
<212> TYPE: DNA
<213> ORGANISM: Camelus bactrianus

<400> SEQUENCE: 185

| | |
|---|---|
| caggtgcagc tgcaggagtc tgggggaggc tcggtgcaga ccggagggtc tctgagactc | 60 |
| tcctgtacag cctctacatc aatatacagt aacaactaca tggcctggtt cagccaggct | 120 |
| ccaggaaagg ggcgcgaggg ggtcgcagct gtttatattg acgatggtcg cccatactat | 180 |
| gccgactccg tgaagggccg attcaccatc tccctagaca cgccaagaa cacggtgtat | 240 |
| ctgcaaatga acagcctgaa acctgaggac actgccatgt actactgtgc ggcagctcca | 300 |
| ggcccttaa gtcgtaatta ctggtacacg tccgccaact atgactactg gggccagggg | 360 |
| acccaggtca ccgtctcctc a | 381 |

<210> SEQ ID NO 186
<211> LENGTH: 381
<212> TYPE: DNA
<213> ORGANISM: Camelus bactrianus

<400> SEQUENCE: 186

| | |
|---|---|
| caggtgcagc tgcaggagtc tgggggaggc tcggtgcaga ccggagggtc tctgagactc | 60 |
| tcctgtgcag cctctacatc actatacagt acaactaca tggcctggtt cagccaggct | 120 |
| ccaggaaagg ggcgcgaggg ggtcgcagct gtttatgttg gtgatggtcg cccatactat | 180 |
| gccgcctccg tgaagggccg attcaccatc tccctagaca cgccaagaa cacggtgtat | 240 |
| ctgcaaatga acagcctgaa acctgaggac actgccatgt actactgtgc ggcagctcca | 300 |
| ggcccttaa gtcataatta ctggtacacg tccgccaact atgactactg gggccagggg | 360 |
| acccaggtca ccgtctcctc a | 381 |

<210> SEQ ID NO 187
<211> LENGTH: 387
<212> TYPE: DNA
<213> ORGANISM: Camelus bactrianus

<400> SEQUENCE: 187

```
atggcccagg tgcagctgca ggagtctggg ggaggctcgg tgcagaccgg agggtctctg      60
agactctcct gtgcagcctc tacatcaata tacagtatca actacatggc ctggttcagg     120
caggctccag gaaaggggcg cgaggggtc gcagctgttt atattgatga tggtcgccca      180
tactatgccg actccgtgaa gggccgattc accatctccc tagacagcgc caagaacacg     240
gtgtatctgc aaatgaccag cctgaaatct gaggacactg ccatgtacta ctgtgcggca     300
gctccaggcc ccttaagtcg tagttactgg tacacgtccg ccaactatga ctactggggc     360
caggggaccc aggtcaccgt ctcctca                                         387
```

<210> SEQ ID NO 188
<211> LENGTH: 381
<212> TYPE: DNA
<213> ORGANISM: Camelus bactrianus

<400> SEQUENCE: 188

```
caggtgcagc tgcaggagtc tgggggaggc tcggtgcaga ccggagggtc tctgagactc      60
tcctgtgcag cctctacatc aatatacagt aacaactaca tggcctggtt cagccaggct     120
ccaggaaagg ggcgcgaggg ggtcgcagct gtttatattg gtgatggtcg cccatactat     180
gccgactccg cgaagggccg attcaccatc tccctagaca cgccaagaa cacggtgtat      240
ctgcaaatga cagcctgaa acctgaggac actgccatgt actactgtgc ggcagctcca      300
ggccccttaa gtcgtaatta ctggtacacg tccgccaact atgactactg ggccagggg      360
acccaggtca ccgtctcctc a                                               381
```

<210> SEQ ID NO 189
<211> LENGTH: 381
<212> TYPE: DNA
<213> ORGANISM: Camelus bactrianus

<400> SEQUENCE: 189

```
caggtgcagc tgcaggagtc tgggggaggc tcggtgcaga ccggagggtc tctgagactc      60
tcctgtgcag cctctacatc aatatacagt aacaactaca tggcctggtt cagccaggct     120
ccaggaaagg ggcgcgaggg ggtcgcagcg ctttatattg gtgatggtcg cccatactat     180
gccgactccg tgaagggccg attcaccatc gccctagaca cgccaagaa cacggtgtat      240
ctgcaaatga acggcctgaa acctgaggac actgccatgt actactgtgc ggcagctcca      300
ggccccttaa acataatta ctggtacacg tccgccaact atgactactg ggccagggg      360
acccaggtca ccgtctcctc a                                               381
```

<210> SEQ ID NO 190
<211> LENGTH: 381
<212> TYPE: DNA
<213> ORGANISM: Camelus bactrianus

<400> SEQUENCE: 190

```
caggtgcagc tgcaggagtc tgggggaggc tcggtgcaga ccggagggtc tctgagactc      60
tcctgtgcag cctctacatc aatatacagt aacaactaca tggcctggtt cagccaggct     120
ccaggaaagg ggcgcgaggg ggtcgcagcg ctttatattg gtgatggtcg cccatactat     180
gccgactccg tgaagggccg attcaccatc gccctagaca cgccaagaa cacggtgtat      240
ctgcaaatga acggcctgaa acctgaggac actgccatgt actactgtgc ggcagctcca      300
ggccccttaa acataatta ctggtacacg tccgccaact atgactactg ggccagggg      360
```

```
acccaggtca ccgtctcctc a                                               381

<210> SEQ ID NO 191
<211> LENGTH: 381
<212> TYPE: DNA
<213> ORGANISM: Camelus bactrianus

<400> SEQUENCE: 191
caggtgcagc tgcaggagtc tgggggaggc tcggtgcaga ccggagggtc tctgagactc    60
tcctgtgcag cctctacatc aatatacagt aacaactaca tggcctggtt ccgccaggct   120
ccaggaaagg ggcgcgaggg ggtcgcagct gtttatattg gtgatggtcg cccgtactat   180
gccgactccg cgaagggccg attcaccatc tccctagaca cgccaagaa cacggtgtat    240 ctgcaaatga acagcctgaa acctgaggac actgccatgt actactgtgc ggcagctcca   300
ggccccttaa gtcgtcatta ctggtacacg tccgccaact atgattactg gggcccgggg   360
acccaggtca ccgtctcctc a                                              381

<210> SEQ ID NO 192
<211> LENGTH: 391
<212> TYPE: DNA
<213> ORGANISM: Camelus bactrianus

<400> SEQUENCE: 192
ggccatggcc caggtgcagc tgcaggagtc tggaggaggc tcggtgcaga ccggagggtc    60
tctgacgctc tcctgtgcag cctctacatc aatatacagt tacaactaca tggcctggtt   120
ccgccaggct ccaggaaagg ggcgcgaggg ggtcgcagct gtttatattg gtgacggtcg   180
cccatactat gccgactccg tgaagggccg attcaccatc tccccggaca cgccaagaa   240 cacggtgtat ctgcaaatga acagcctgaa acctgaggac actgccatgt actactgtgc   300
ggcagctcca ggccccttaa gtcgtcatta ctggtacacg tccgccaact atgactactg   360
gggcccgggg acccaggtca ccgtctcctc a                                   391

<210> SEQ ID NO 193
<211> LENGTH: 381
<212> TYPE: DNA
<213> ORGANISM: Camelus bactrianus

<400> SEQUENCE: 193
caggtgcagc tgcaggagtc tgggggaggc tcggtgcaga ccggagggtc tctgagactc    60
tcctgtgcag cctcttcatc aatagccagt aacaactaca tggcctggtt cagccaggct   120
ccaggaaagg ggcgcgaggg ggtcgcagct gtttatattg gtgatggtcg cccatactat   180
gccgactccg tgaagggccg attcaccatc tccctagaca cgccaagaa cacggtgtat    240 ctgcaaatga acagcctgaa acctgaggac actgccatgt actactgtgc ggcagctcca   300
ggccccttaa gtcgtaatta ctggtacacg tccgccaact atgactactg gggccagggg   360
acccaggtca ccgtctcctc a                                              381

<210> SEQ ID NO 194
<211> LENGTH: 381
<212> TYPE: DNA
<213> ORGANISM: Camelus bactrianus

<400> SEQUENCE: 194
caggtgcagc tgcaggagtc tgggggaggc tcggtgcgga ccggagggtc tctgagactc    60
```

| | |
|---|---|
| tcctgtgcag cctctacatc aatatacagt ctcaactaca tggcctggtt cagccaggct | 120 |
| ccaggaaagg ggcgcgaggg ggtcgcagct gtttatattg atgatggtcg cccatactat | 180 |
| gccgatcacg tgaagggccg attcaccatc tccctagaca ccgccaagaa cacggtgtat | 240 |
| ttgcaaatga acagcctgaa acctgaggac actgccatgt actactgtgc ggcagctcca | 300 |
| ggccccttaa gtcgtaacta ctggtacacg tccgccaact atgactactg gggccagggg | 360 |
| acccaggtca ccgtctcctc a | 381 |

<210> SEQ ID NO 195
<211> LENGTH: 363
<212> TYPE: DNA
<213> ORGANISM: Camelus bactrianus

<400> SEQUENCE: 195

| | |
|---|---|
| caggtgcagc tgcaggagtc tgggggaggc ttggtgcagc ctggggggtc tctgagactc | 60 |
| tcctgtgcag cctctggatt caccttcagt attaaagcca tgagctgggt ccgccaggct | 120 |
| ccagggaagg gactcgagtg ggtctcaact attgatagtg gtggtgggcg ccgatactat | 180 |
| gcagactccg tgaagggccg attcaccatc tccagagaca cgccaagaa cacgctgtat | 240 |
| ctgcaattga gcagcctgaa aactgaggac acggccatgt attttgtgc aagatgtagt | 300 |
| gatatttact gctacaacgg agcgtcgtat aggggccagg gaacccaggt caccgtctcc | 360 |
| tca | 363 |

<210> SEQ ID NO 196
<211> LENGTH: 381
<212> TYPE: DNA
<213> ORGANISM: Camelus bactrianus

<400> SEQUENCE: 196

| | |
|---|---|
| caggtgcagc tgcaggagtc tgggggaggc tcggtgcaga ccggagggtc tctgagactc | 60 |
| tcctgtgcag cctctacatc aatcgacagt aacaactaca tggcctggtt ccgccaggct | 120 |
| ccaggaaagg ggcgcgaggg ggtcgcagct gtttatattg atgatggtcg cccatactat | 180 |
| gccgactccg tgaagggccg attcaccatc tccctagaca cgccaagaa cacggtgtat | 240 |
| ctgcaaatga acagcctgaa acctgaggac actgccatgt actactgtgc ggcagctcca | 300 |
| ggccccttaa gtcgtcatta ctggtacacg tccgccaact atgactactg gggcccgggg | 360 |
| acccaggtca ccgtctcctc a | 381 |

<210> SEQ ID NO 197
<211> LENGTH: 381
<212> TYPE: DNA
<213> ORGANISM: Camelus bactrianus

<400> SEQUENCE: 197

| | |
|---|---|
| caggtgcagc tgcaggagtc tggaggaggc tcggtgcaga ccggagggtc tctgagactc | 60 |
| tcctgtacag cctctacatc aatatacaat aacaactaca tggcctggtt cagccagtct | 120 |
| ccaggaaagg ggcgcgaggg ggtcgcagct gtttatatgg atgatggtcg cccatactat | 180 |
| gccgattccg tgaagggccg attcaccatc tccctagaca cgccaagaa cacgatgtat | 240 |
| ttgcaaatga acagcctgaa acctgaggac actgccatgt actactgtgc ggcagctcca | 300 |
| ggccccttaa gtcgtaacta ctggtacacg tccgccaact atgactactg gggccagggg | 360 |
| acccaggtca ccgtctcctc a | 381 |

<210> SEQ ID NO 198
<211> LENGTH: 381
<212> TYPE: DNA
<213> ORGANISM: Camelus bactrianus

<400> SEQUENCE: 198
caggtgcagc tgcaggagtc tgggggaggc tcggtgcaga ccggagggtc tctgagactc        60
tcctgtgcag cctctacatc aatatacagt aacaactaca tggcctggtt cagccaggct       120
ccaggaaagg ggcgcgaagg ggtcgcgagct gtttatattg atgatggtcg cacatactat      180
gccgactccg tgaagggccg attcaccatc tccctagaca gcgccaagaa cacggtgtat       240
ctacaaatga acagcctgaa acctgaggac actgccatgt actactgtgc ggcagctcca       300
ggccccttaa gtcataatta ctggtacgcg tccgccaact atgactactg gggccagggg      360
acccaggtca ccgtctcctc a                                                 381

<210> SEQ ID NO 199
<211> LENGTH: 381
<212> TYPE: DNA
<213> ORGANISM: Camelus bactrianus

<400> SEQUENCE: 199
caggtgcagc tgcaggagtc tgggggaggc tcggtgcaga ccggagggtc tctgagactc        60
tcctgtgcag cctctacatc aatatacagt atcaactaca tggcctggtt cagccaggct       120
ccaggaaagg ggcgcgaggg ggtcgcagct gtttatattg atgatggtcg cccatactat       180
gccgactccg tgaagggccg attcaccatc tccctagaca gcgccaagaa cacggtgtat       240
ctgcaaatga acagcctgaa acctgaggac actgccatgt actactgtgc ggcagctcca       300
ggccccttaa gtcgtaatta ctggtacacg tccgccaact atgactactg gggccagggg      360
acccaggtca ccgtctcctc a                                                 381

<210> SEQ ID NO 200
<211> LENGTH: 363
<212> TYPE: DNA
<213> ORGANISM: Camelus bactrianus

<400> SEQUENCE: 200
caggtgcagc tgcaggagtc tgggggaggc ttggtgcagc ctgggggtc tctgagactc         60 tcctgtatag cctctggatt caccttcagt atcatggcca tgagctgggt ccgccaggct       120
ccagggaagg gactcgagtg ggtctcaact attaatagtg atggtggcaa aacatactat       180
gcagactccg tgaagggccg cttcaccatc tccagagaca cgccaagaa cacgctgtat        240 ctgcaattga atagcctgag aactgaggat atggccatgt attactgccg acggtgcgcg       300
gatatttact gttcaggttc cggcggatgg acgggccagg ggacccaggt caccgtctcc       360
tca                                                                      363

<210> SEQ ID NO 201
<211> LENGTH: 381
<212> TYPE: DNA
<213> ORGANISM: Camelus bactrianus

<400> SEQUENCE: 201
caggtgcagc tgcaggagtc tgggggaggc tcggtgcaga ccggagggtc tctgagactc        60
tcctgtacag cctctacatc aatatacagt aacagctaca tggcctggtt cagccaggct       120
ccaggaaagg ggcgcgaggg ggtcgcagct gtttatattg atgatggtcg cccatactat       180

```
gccgactccg tgaagggccg tttcaccatc tccctagaca gcgccaagaa cacggtgtat      240
ctgcaaatga acagcctgaa acctgaggac actgccatgt actactgtgc ggcagctcca      300
ggccccttaa gtcgtcatta ctggtacacg tccgccaact atgactactg gggccagggg      360
acccaggtca ccgtctcctc a                                                381

<210> SEQ ID NO 202
<211> LENGTH: 381
<212> TYPE: DNA
<213> ORGANISM: Camelus bactrianus

<400> SEQUENCE: 202
caggtgcagc tgcaggagtc tggaggaggc tcggtgcaga ctggagggtc tctgagactc       60
tcctgtgcag cctctacatc aatatacagt aacaactaca tggcctggtt ccgccaggct      120
ccaggaaagg ggcgcgaggg ggtcgcagct gtttatgttg atgatggtcg cccatactat      180
gccgactccg tgaagggccg attcaccatc tcccgcgaca cgccaagaa cacggtgtat       240 ctgcaaatga acagcctgaa acctgaggac actgccatgt actactgtgc ggcagctcca      300
ggccccttaa gtcgtcatta ctggtacacg tccgccaact atgactactg gggcccgggg      360
acccaggtca ccgtctcctc a                                                381

<210> SEQ ID NO 203
<211> LENGTH: 381
<212> TYPE: DNA
<213> ORGANISM: Camelus bactrianus

<400> SEQUENCE: 203
caggtgcagc tgcaggagtc tgggggaggc tcggtgcaga ccggagggtc tctgagactc       60
tcctgtgcag cctctacatc aatatacagt aacaactaca tggcctggtt cagccaggct      120
ccaggaaagg ggcgcgaggg ggtcgcagct gtttatattg atgatggtcg cccatactat      180
gccgactccg tgaagggccg attcaccatc tccctagaca gcgccaagaa cacggtgtat      240
ctgcaaatga acagcctgaa acctgaggac actgccatgt actactgtgc ggcagctcca      300
ggccccttaa gtcgtaatta ctggtacacg tccgccaact atgactactg gggccagggg      360
acccaggtca ccgtctcctc a                                                381

<210> SEQ ID NO 204
<211> LENGTH: 381
<212> TYPE: DNA
<213> ORGANISM: Camelus bactrianus

<400> SEQUENCE: 204
caggtgcagc tgcaggagtc tgggggaggc tcggtgcaga ccggagggtc tctgagactc       60
tcctgtgcac cctctacatc aatatacgat aacaactaca tggcctggtt cagccaggct      120
ccaggaaagg ggcgcgaggg ggtcgcagcg atttatattg atgatggtcg cccatactat      180
gccgactccg tgaagggccg attcaccatc tccctagaca gcgccaagaa cacggtgtat      240
ctgcaaatga acagcctgaa acctgaggac actgccatgt actactgtgc ggcagctcca      300
ggccccttaa gtcataatta ctggtacacg tccgccaact atgactactg gggccagggg      360
acccaggtca ccgtctcctc a                                                381

<210> SEQ ID NO 205
<211> LENGTH: 381
<212> TYPE: DNA
<213> ORGANISM: Camelus bactrianus
```

<400> SEQUENCE: 205

| | | | | |
|---|---|---|---|---|
| caggtgcagc | tgcaggagtc | tggaggaggc | tcggtgcaga | ccggagggtc tctgagactc | 60 |
| tcctgtgtag | cctctacatc | gatattcagt | aacaactaca | tggcctggtt cagccaggct | 120 |
| ccaggaaagg | ggcgcgaggg | ggtcgcagct | gtttatattg | gtgatggtcg cccatactat | 180 |
| gccgactccg | tgaagggccg | attcaccatc | tccctagaca | gcgccaagaa cacggtgtat | 240 |
| ctgcaaatga | acagcctgaa | acctgaggac | actgccatgt | actactgtgc ggcagctcca | 300 |
| ggccccttaa | gtcacaatta | ttggtacacg | tccgccaact | atgactactg gggccagggg | 360 |
| acccaggtca | ccgtctcctc | a | | | 381 |

<210> SEQ ID NO 206
<211> LENGTH: 381
<212> TYPE: DNA
<213> ORGANISM: Camelus bactrianus

<400> SEQUENCE: 206

| | | | | |
|---|---|---|---|---|
| caggtgcagc | tgcaggagtc | tgggggaggc | tcggtgcaga | ccggagggtc tctgagactc | 60 |
| tcctgtgcag | cctctccatc | aatatacagt | gccaactaca | tggcctggtt cagccaggct | 120 |
| ccaggaaagg | ggcgcgaggg | ggtcgcagct | gtttatattg | gtgatggtcg cccatactat | 180 |
| gccgactccg | tgaagggccg | attcaccatc | tccctagaca | gcgccaagag cacggtgtat | 240 |
| ctgcaaatga | acagcctgaa | acctgaggac | actgccatgt | actactgtgc ggcagctcca | 300 |
| ggccccttaa | gtcataatta | ctggtacacg | tccgccaact | atgactactg gggccagggg | 360 |
| acccaggtca | ccgtctcctc | a | | | 381 |

<210> SEQ ID NO 207
<211> LENGTH: 381
<212> TYPE: DNA
<213> ORGANISM: Camelus bactrianus

<400> SEQUENCE: 207

| | | | | |
|---|---|---|---|---|
| caggtgcagc | tgcaggagtc | tggaggaggc | tcggtgcaga | ccggagggtc tctgagactc | 60 |
| tcctgtgcag | cctctacatc | aatatacagt | atcaactaca | tggcctggtt cagccaggct | 120 |
| ccaggaaagg | ggcgcgaggg | ggtcgcagct | gtttatattg | atgatggtcg cccatactat | 180 |
| gccgactccg | tgaagggccg | attcaccatc | tccctagaca | gcgccaagaa cacggtgtat | 240 |
| ctgcaaatga | acagcctgaa | atctgaggac | actgccatgt | actactgtgc ggcagctcca | 300 |
| ggccccttaa | gtcgtaatta | ctggtacacg | tccgccaact | atgactactg gggccagggg | 360 |
| acccaggtca | ccgtctcctc | a | | | 381 |

<210> SEQ ID NO 208
<211> LENGTH: 363
<212> TYPE: DNA
<213> ORGANISM: Camelus bactrianus

<400> SEQUENCE: 208

| | | | | |
|---|---|---|---|---|
| caggtgcagc | tgcaggagtc | tggaggaggc | ttggtgcagc | ctgggggtc tctgagactc | 60 |
| tcctgtgcac | tatctggatt | cacctctact | atatatgcca | tgagctgggt ccgccaggct | 120 |
| ccagggaagg | gactcgagtg | ggtctcaact | attaatagtg | atggtggcta ccgatactat | 180 |
| gcagactccg | tgaagggccg | attcaccatc | tccagagaca | atgccaagaa cacgctgtat | 240 |
| ctgcaattga | acagcccgaa | aactgaggac | acggccatgt | attactgtgc aagatgtagt | 300 |

```
gatatttact gttacaacgg accgtcgtat aggggccagg ggacccaggt caccgtctcc    360
tca                                                                  363

<210> SEQ ID NO 209
<211> LENGTH: 381
<212> TYPE: DNA
<213> ORGANISM: Camelus bactrianus

<400> SEQUENCE: 209
caggtgcagc tgcaggagtc tgggggaggc tcggtgcaga ccggagggtc tctgagactc     60
tcctgtgcat gctctacatc aatatacagt aacaactaca tggcctggtt cagccaggct   120
ccaggaaagg ggcgcgaggg ggtcgcagct gtttatattg gtgatggtcg cccttactat   180
accgactccg tgaagggccg attcaccatc tccctagaca cgccaagaa cacactgtat    240 ctgcaaatga acagcctgaa acctgaggac actgccatgt actactgtgc ggcagctcca   300
ggccccttaa gtcataatta ctggtacacg tccgccaact atgactactg gggccagggg   360
acccaggtca ccgtctcctc a                                             381

<210> SEQ ID NO 210
<211> LENGTH: 381
<212> TYPE: DNA
<213> ORGANISM: Camelus bactrianus

<400> SEQUENCE: 210
caggtgcagc tgcaggagtc tgggggaggc tcggtgcaga ccggagggtc tctgagactc     60
tcctgtgcag cctctacatc aatatacagt atgaactaca tggcctggtt cagccaggct   120
ccaggaaagg ggcgcgaggg ggtcgcagct gtttatattg aagatggtcg cccatactat   180
gccgactccg tgaagggccg attcaccatc tccccagaca gggccaagaa cacggtgtat   240
ctgcaaatga acagcctgaa acctgaggac actgccatgt actactgtgc ggcagctcca   300
ggccccttaa gtcgtaatta ctggtacacg tccgccaact atgactactg gggccagggg   360
acccaggtca ccgtctcctc a                                             381

<210> SEQ ID NO 211
<211> LENGTH: 363
<212> TYPE: DNA
<213> ORGANISM: Camelus bactrianus

<400> SEQUENCE: 211
caggtgcagc tgcaggagtc tggaggaggc ttggtgcagc ctgggggggtc tctgagactc    60 tcctgtgcag cctctggatt cgacttcagt agcagagcca tgagctgggt ccgccaggct   120
ccagggaagg gactcgagtg ggtctcaact attaatagtg gtggtggtag ccgatactat   180
gcagactccg tgaagggccg attcaccacc tccagagaca cgccaagaa cacgctggct    240 ctgcaattga acagcctgaa aactgaggac acggccatgt attactgtgc aagatgtagt   300
gatatttact gcgacaacgg agcgtggtat aggggccagg ggacccaggt caccgtctcc   360
tca                                                                  363

<210> SEQ ID NO 212
<211> LENGTH: 381
<212> TYPE: DNA
<213> ORGANISM: Camelus bactrianus

<400> SEQUENCE: 212
caggtgcagc tgcaggagtc tggaggaggc tcggtgcagg ctgggggggtc tctgagactc    60
```

```
tcctgtgcag cctctacatc aatatacagt aacaactaca tggcctggtt ccgccagact    120
ccaggaaagg ggcgcgaggg ggtcgcagct gtttatattg atgatgggcg accatactat    180
gccgactccg tgaagggccg attcaccatc tccctagaca gcgccaagaa cacggtgtat    240
ttgcaaatga acagcctgaa acctgaggac actgccatgt actactgtgc ggcagctcca    300
ggccccttaa gtcatgatta ctggtacacg tccgccaact atgactactg gggcccgggg    360
acccaggtca ccgtctcctc a                                              381

<210> SEQ ID NO 213
<211> LENGTH: 381
<212> TYPE: DNA
<213> ORGANISM: Camelus bactrianus

<400> SEQUENCE: 213
caggtgcagc tgcaggagtc tgggggaggc tcggtgcaga ccggagggtc tctgagactc     60
tcctgtgcag cctctacatc aatatacagt aacaactaca tggcctggtt cagccaggct    120
ccaggaaagg ggcgcgaggg ggtcgcagct gtttatattg atgatggtcg cccatactat    180
gccgactccg tgaagggccg attcaccatc tccctagaca gcgccaagaa cacggtgtat    240
ctgcaaatga accgcctgaa acctgaggac actgccatgt actactgtgc ggcagctcca    300
ggccccttaa gtcataatta ctggtacacg tccgccaact atgactactg gggccagggg    360
acccaggtca ccgtctcctc a                                              381

<210> SEQ ID NO 214
<211> LENGTH: 381
<212> TYPE: DNA
<213> ORGANISM: Camelus bactrianus

<400> SEQUENCE: 214
caggtgcagc tgcaggagtc tgggggaggc tcggtgcaga ccggagggtc tctgagactc     60
tcctgtgcag cctctacatc aatatacagt aacaactaca tggcctggtt cagccaggct    120
ccaggaaagg ggcgcgaggg ggtcgcagct gtttatattg atgatggtcg cccatactat    180
gccgactccg tgaagggccg attcaccatc tccctagaca gcgccaagaa cacggtgtat    240
ctgcaaatga acagcctgaa acctgaggac actgccatgt actactgtgc ggcaacacca    300
ggccccttaa gtcagcatta ctggtacacg tccgccaact atgactactg gggccagggg    360
acccaggtca ccgtctcctc a                                              381

<210> SEQ ID NO 215
<211> LENGTH: 363
<212> TYPE: DNA
<213> ORGANISM: Camelus bactrianus

<400> SEQUENCE: 215
caggtgcagc tgcaggagtc tgggggaggc ttggtgcagc ctgggggtc tctgagactc      60 tcctgtgcag cctctggatt caccttcagt atccttgcca tgagctgggt ccgccaggct    120
ccagggaagg gactcgaatg gatctcaact attaataata gtggtggcac cacattctat    180
gctgactccg tgaagggccg cttcaccatc tccagagaca cgccaagaa cacgctgtat     240 ctgcaattga atagcctgag aactgaggac acggccatgt attactgccg acggtgcacg    300
gatatttact gttcactttc cggcggatgg acgggccagg ggacccaggt caccgtctcc    360
tca                                                                  363
```

<210> SEQ ID NO 216
<211> LENGTH: 381
<212> TYPE: DNA
<213> ORGANISM: Camelus bactrianus

<400> SEQUENCE: 216

| | | | | | | |
|---|---|---|---|---|---|---|
| caggtgcagc | tgcaggagtc | tggaggaggc | tcggtgcaga | ccggagggtc | tctgagactc | 60 |
| tcctgtgcag | cctctacatc | aatatacaat | aacaactaca | tggcctggtt | cagccaggct | 120 |
| ccaggaaagg | ggcgcgaggg | ggtcgcggct | gtttatgttg | gtgatggtcg | cacatactat | 180 |
| gccgactccg | tgaagggccg | attcaccatc | tccctagaca | gcgccaagaa | cacggtgtat | 240 |
| ctgcaaatga | acagcctgaa | acctgaggac | actgccatgt | actactgtgc | ggcagctcca | 300 |
| ggccccttaa | gtcataatta | ctggtacacg | tccgccaact | atgactactg | gggccagggg | 360 |
| acccaggtca | ccgtctcctc | a | | | | 381 |

<210> SEQ ID NO 217
<211> LENGTH: 381
<212> TYPE: DNA
<213> ORGANISM: Camelus bactrianus

<400> SEQUENCE: 217

| | | | | | | |
|---|---|---|---|---|---|---|
| caggtgcagc | tgcaggagtc | tgggggaggc | tcggtgcaga | ccggagggtc | tctgagactc | 60 |
| tcctgtacag | cctctacatc | aatatacagt | aacaactaca | tggcctggtt | cagccaggct | 120 |
| ccaggaaagg | ggcgcgaggg | ggtcgcagct | gtttatattg | acgatggtcg | cccatactat | 180 |
| gccgactccg | tgaagggccg | attcaccatc | tccctagaca | gcgccaagaa | cacggtgtat | 240 |
| ctgcaaatga | acagcctgaa | acctgaggac | actgccatgt | actactgtgc | ggcagctcca | 300 |
| ggccccttaa | gtcgtaatta | ctggtacacg | tccgccaact | atgactactg | gggccagggg | 360 |
| acccaggtca | ccgtctcctc | a | | | | 381 |

<210> SEQ ID NO 218
<211> LENGTH: 381
<212> TYPE: DNA
<213> ORGANISM: Camelus bactrianus

<400> SEQUENCE: 218

| | | | | | | |
|---|---|---|---|---|---|---|
| caggtgcagc | tgcaggagtc | tggaggaggc | tcggtgcaga | ccggagggtc | tctgagactc | 60 |
| tcctgtacat | gctctacatc | aatatacagt | aacaactaca | tggcctggtt | cagccaggct | 120 |
| ccaggaaagg | ggcgcgaggg | ggtcgcagct | gtttatattg | gtgatggtcg | cccatactat | 180 |
| gccgactccg | tgaagggccg | attcaccatc | tccctagaca | gcgccaagaa | cacggtgtat | 240 |
| ctgcaaatga | acagcctgaa | acctgaggac | actgccatgt | actactgtgc | ggcagctcca | 300 |
| ggccccttaa | gtcataatta | ctggtacacg | tccgccaact | atgactactg | gggccagggg | 360 |
| acccaggtca | ccgtctcctc | a | | | | 381 |

<210> SEQ ID NO 219
<211> LENGTH: 381
<212> TYPE: DNA
<213> ORGANISM: Camelus bactrianus

<400> SEQUENCE: 219

| | | | | | | |
|---|---|---|---|---|---|---|
| caggtgcagc | tgcaggagtc | tggaggaggc | tcggtgcaga | ccggagggtc | tctgagactc | 60 |
| tcctgtgcag | cctctacatc | aatatacagt | aacaactaca | tggcctggtt | cagccaggct | 120 |
| ccaggaaagg | ggcgcgaggg | ggtcgcagct | gtttatattg | gtgatggtcg | cccatactat | 180 |

```
gccgactccg tgaagggccg attcaccatc tccctagaca gcgccaagaa cacggtgtat    240
ctgcaaatga acagcctgaa acctgaggac actgccatgt actactgtgc ggcagctcca    300
ggccccttaa gtcataatta ctggtacacg tccgccaact atgactactg gggccagggg    360
acccaggtca ccgtctcctc a                                              381
```

<210> SEQ ID NO 220
<211> LENGTH: 363
<212> TYPE: DNA
<213> ORGANISM: Camelus bactrianus

<400> SEQUENCE: 220

```
caggtgcagc tgcaggagtc tggaggaggc ttggtgcagc ctgggggtc tctgagactc      60 tcctgtgcag cctctggatt caccttcagt attcgtgcca tgagctgggt ccgccaggct    120
ccagggaagg gactcgagtg ggtctcaact attaatagtg gtggtgatag ccgatactat    180
gcagactccg tgaagggccg attcaccatc tccagagaca cgccaagaa cacaatgtat     240 ctgcaattga acagcctgaa aactgaggac acggccatgt attactgtgt aagatgtagt    300
gatatttact gctacaacgg agcgtcgtat aggggccagg ggacccaggt caccgtctcc    360
tca                                                                  363
```

<210> SEQ ID NO 221
<211> LENGTH: 366
<212> TYPE: DNA
<213> ORGANISM: Camelus bactrianus

<400> SEQUENCE: 221

```
caggtgcagc tgcaggagtc tggaggaggc ttggtgcagc ctgggggtc tctgagactc      60 tcctgtgcag cctctggatt cacattcagt agctacgaca tgagctgggt ccgccaggct    120
ccagggaagg ggatcgagtg ggtctcagtt attaatagtg gtggtagtaa cacagactat    180
gcagactccg tgaagggccg attcaccatc tccagagaca cgccaagaa cacgctgtat     240 ctgcaaatga acagcctgaa aactgaggac actgccgtgt attactgcgc cacagcctgg    300
atgggctata gcgactatct cgatggaatc gcccggggcc aggggaccca ggtcaccgtc    360
tcctca                                                               366
```

<210> SEQ ID NO 222
<211> LENGTH: 363
<212> TYPE: DNA
<213> ORGANISM: Camelus bactrianus

<400> SEQUENCE: 222

```
caggtgcagc tgcaggagtc tgggggaggc ttggtgcagc ctgggggtc tctgagactc      60 tcctgtgaag cctctggact ccccttcagc atcattgcca tgagctgggt ccgccaggct    120
ccagggaagg gactcgagtg ggtctcaact attaatagtg atggtggcac cacacactat    180
gcagactccg tgaagggccg cttcaccatc tccagagaca cgccaagaa cacgctgtat     240 ctgcaattga atagcctgag gactgaggac acggccatgt attactgccg acggtgcacg    300
gatatttact gttcaggttc cggcggatgg acgggccagg gacccaggt caccgtctcc     360 tca                                                                  363
```

<210> SEQ ID NO 223
<211> LENGTH: 363
<212> TYPE: DNA

<213> ORGANISM: Camelus bactrianus

<400> SEQUENCE: 223

| caggtgcagc | tgcaggagtc | tggaggaggc | ttggtgcagc | ctggggggtc | tctgagactc | 60 |
| tcctgtgaag | cctctggact | ccccttcagc | atcattgcca | tgagctgggt | ccgccaggct | 120 |
| ccagggaagg | gactcgagtg | ggtctcaact | attaatagtg | atggtggcac | cacacactat | 180 |
| gcagactccg | tgaagggccg | cttcaccatc | tccagagaca | acgccaagaa | cacgctgtat | 240 |
| ctgcaattga | atagcctgag | gactgaggac | acggccatgt | attactgccg | acggtgcacg | 300 |
| gatatttact | gttcaggttt | cggcggatgg | acgggccagg | ggacccaggt | caccgtctcc | 360 |
| tca | | | | | | 363 |

<210> SEQ ID NO 224
<211> LENGTH: 363
<212> TYPE: DNA
<213> ORGANISM: Camelus bactrianus

<400> SEQUENCE: 224

| caggtgcagc | tgcaggagtc | tgggggaggc | tcggtgcagg | ctggagggtc | tctgagactc | 60 |
| tcctgtgcag | cctctggatt | caccggcagt | atttatgcca | tgagctgggt | ccgccaggct | 120 |
| ccagggaagg | gactcgagtg | ggtctcaact | attagtagta | gtggtggtag | cgattctat | 180 |
| gcagactccg | tgaagggccg | attcaccatc | tccagagaca | acgccaagaa | cacgctgtat | 240 |
| ctgcaattga | acagccttaa | aactgaggac | acggccatgt | attactgtgc | aagatgtagt | 300 |
| gatatttact | gcgacaacgg | agcgtcgtat | aggggccagg | ggacccaggt | caccgtctcc | 360 |
| tca | | | | | | 363 |

<210> SEQ ID NO 225
<211> LENGTH: 381
<212> TYPE: DNA
<213> ORGANISM: Camelus bactrianus

<400> SEQUENCE: 225

| caggtgcagc | tgcaggagtc | tgggggaggc | tcggtgcaga | ccggagggtc | tctgagactc | 60 |
| tcctgtgcag | cctctacatc | aatatacagt | aacaactaca | tggcctggtt | ccgccaggct | 120 |
| ccaggaaagg | ggcgcgaggg | ggtcgcagct | gtttatattg | gtgatggtcg | cccatactat | 180 |
| gccgactccg | cgaagggccg | attcaccatc | tccctagaca | gcgccaagaa | cacggtgtat | 240 |
| ctgcacatga | acagcctgaa | acctgaggac | actgccatgt | actactgtgc | ggcagctcca | 300 |
| ggcccccttaa | gtcgtcatta | ctggtacacg | tccgccaact | atgactactg | gggcccgggg | 360 |
| acccaggtca | ccgtctcctc | a | | | | 381 |

<210> SEQ ID NO 226
<211> LENGTH: 381
<212> TYPE: DNA
<213> ORGANISM: Camelus bactrianus

<400> SEQUENCE: 226

| caggtgcagc | tgcaggagtc | tgggggaggc | tcggtgcaga | ccggagggtc | tctgagactc | 60 |
| tcctgtgcag | cctctacatc | aatatacagt | aacaactaca | tggcctggtt | ccgccaggtt | 120 |
| ccaggaaagg | ggcgcgaggg | ggtcgcagct | gtttatattg | atgatggtcg | cacatactat | 180 |
| gccgactccg | tgaagggccg | attcaccatc | tccctagaca | gcgccaagaa | cacggtgtat | 240 |
| ctgcaaatga | acagcctgaa | acctgaggac | actgccatgt | actactgtgc | ggcagctcca | 300 |

```
ggcccottaa gtcgtcatta ctggtacacg tccgccaact atgactactg gggcccgggg    360
acccaggtca ccgtctcctc a                                              381
```

<210> SEQ ID NO 227
<211> LENGTH: 381
<212> TYPE: DNA
<213> ORGANISM: Camelus bactrianus

<400> SEQUENCE: 227

```
caggtgcagc tgcaggagtc tgggggaggc tcggtgcaga ccggagggtc tctgagactc     60
tcctgtacag cctctacatc aatatacagt aacaactaca tggcctggtt cagccaggct    120
ccaggaaagg ggcgcgaggg ggtcgcagct gtttatattg atgatggtcg ccccctactat   180 gccgactccg tgaagggccg attcaccatc tccctagaca cgccaagaa cacggtgtat    240 ctgcaaatga acagcctgaa acctgaggac actgccatgt actactgtgc ggcagctcca   300 ggcccottaa gtcgtaatta ctggtacacg tccgccaact atgactactg gggccagggg   360
acccaggtca ccgtctcctc a                                              381
```

<210> SEQ ID NO 228
<211> LENGTH: 381
<212> TYPE: DNA
<213> ORGANISM: Camelus bactrianus

<400> SEQUENCE: 228

```
caggtgcagc tgcaggagtc tgggggaggc tcggtgcaga ccggagggtc tctgagactc     60
tcctgtgcag cctctacatc actatacagt tacaactaca tggcctggtt cagccaggct    120
ccaggaaagg ggcgcgaggg ggtcgcagct gtttatgttg gtgatggtcg cccatactat   180
gccgactccg tgaagggccg attcaccatc tccctagaca cgccaagaa cacggtgtat    240 ctgcaaatga acagcctgaa acctgaggac actgccatgt actactgtgc ggcagctcca   300 ggcccottaa gtcataatta ctggtacacg tccgccaact atgactactg gggccagggg   360
acccaggtca ccgtctcctc a                                              381
```

<210> SEQ ID NO 229
<211> LENGTH: 363
<212> TYPE: DNA
<213> ORGANISM: Camelus bactrianus

<400> SEQUENCE: 229

```
caggtgcagc tgcaggagtc tgggggaggc ttggtgcagc ctgggggtc tctgagactc     60 tcctgtgcag cctctggatt gcccttcagt atcattgcca tgagctgggt ccgccaggct    120
ccagggaagg gaatcgagtg ggtctcaact attaatagtg gtggtggcac cacacactat   180
gcagactccg tgaagggccg cttcaccatc tccagagaca cgccaagaa cacgctgtat    240 ctgcaattga atagcctgag aactgaggac acggccgtgt attactgccg acggtgcgcg   300
gatatttact gttcaggttc cggcggatgg acgggcctgg ggacccaggt caccgtctcc   360
tca                                                                  363
```

<210> SEQ ID NO 230
<211> LENGTH: 381
<212> TYPE: DNA
<213> ORGANISM: Camelus bactrianus

<400> SEQUENCE: 230

```
caggtgcagc tgcaggagtc tggaggaggc tcggtgcaga ccggagggtc tctgagactc    60
tcctgtgtag cctctacatc aatatacagt aacaactaca tggcctggtt cagccaggct   120
ccaggaaagg ggcgcgaggg ggtcgcagct gtttatattg atgatggtcg cccatactat   180
gccgactccg tgaagggccg attcaccatc tccctagaca cgccaagaa cacggtgtat    240 ctgcaaatga acagcctgaa acctgaggac actgccatgt actactgtgc ggcagctcca   300
ggccccttaa gtcgtagtta ctggtacacg tccgccaact atgactactg gggccagggg   360
acccaggtca ccgtctcctc a                                             381

<210> SEQ ID NO 231
<211> LENGTH: 381
<212> TYPE: DNA
<213> ORGANISM: Camelus bactrianus

<400> SEQUENCE: 231
caggtgcagc tgcaggagtc tggaggaggc tcggtgcaga ccggagggtc tctgagactc    60
tcctgtgcag cctctacatc aatatacagt aacaactaca tggcctggtt cagccaggct   120
ccaggaaagg ggcgcgaggg ggtcgcagct gtttatattg atgatggtcg cacatactat   180
gccgactccg tgaagggccg attcaccatc tccctagaca cgccaagaa cacggtgtat    240 ctgcaaatga acagcctgaa acctgaggac actgccatgt actactgtgc ggcagctcca   300
ggccccttaa gtcgtaatta ctggtacacg tccgccaact atgactactg gggccagggg   360
acccaggtca ccgtctcctc a                                             381

<210> SEQ ID NO 232
<211> LENGTH: 381
<212> TYPE: DNA
<213> ORGANISM: Camelus bactrianus

<400> SEQUENCE: 232
caggtgcagc tgcaggagtc tggggaggc tcggtgcaga ccggagggtc tctgagactc     60
tcctgtacag cctctacatc aatatacagt aacaactaca tggcctggtt cagccaggct   120
ccaggaaagg ggcgcgaggg ggtcgcagct gtttatattg acgatggtcg cccatactat   180
gccgactccg tgaagggccg attcaccatc tccctagaca cgccaagaa cacggtgtat    240 ctgcaaatga acagcctgaa acctgaggac actgccatgt actactgtgc ggcagctcca   300
ggccccttaa gtcgtaatta ctggtacacg tccgccaact atgactactg gggccagggg   360
acccaggtca ccgtctcctc a                                             381

<210> SEQ ID NO 233
<211> LENGTH: 381
<212> TYPE: DNA
<213> ORGANISM: Camelus bactrianus

<400> SEQUENCE: 233
caggtgcagc tgcaggagtc tggggaggc ttggtgcaga ccggagggtc tctgagactc     60
tcctgtgcag cctctacatc aatatacagt aacaactacc tggcctggtt cagccaggct   120
ccaggaaagg ggcgcgaggg ggtcgcagct gtttatattg gtgatggtcg cccatactat   180
gccgactccg tgaagggccg attccccatc tccctaaaca gcgccagaa caaggtgtat    240 ctgcaaatga acagcctgaa acctgaggac actgccatgt actactgtgc ggcagctcca   300
ggccccttaa gtcgtaatta ctggtacacg tccgccaact atgactactg gggccagggg   360
acccaggtca ccgtctcctc a                                             381
```

<210> SEQ ID NO 234
<211> LENGTH: 381
<212> TYPE: DNA
<213> ORGANISM: Camelus bactrianus

<400> SEQUENCE: 234

```
caggtgcagc tgcaggagtc tggaggaggc tcggtgcaga ccggagggtc tctgagactc      60
tcctgtgcag cctctacatc aatcgacagt aacaactaca tggcctggtt ccgccaggct     120
ccaggaaagg ggcgcgaggg ggtcgcagct gtttatattg atgatggtcg cccatactat     180
gccgactccg tgaagggccg attcaccatc tccctagaca gcgccaagaa cacggtgtat     240
ctgcaaatga acagcctgaa acctgaggac actgccatgt actactgtgc ggcagctcca     300
ggccccttaa gtcgtcatta ctggtacacg tccgccaact atgactactg ggcccggggg     360
acccaggtca ccgtctcctc a                                                381
```

<210> SEQ ID NO 235
<211> LENGTH: 381
<212> TYPE: DNA
<213> ORGANISM: Camelus bactrianus

<400> SEQUENCE: 235

```
caggtgcagc tgcaggagtc tggaggaggc tcggtgcaga ccggagggtc tctgagactc      60
tcctgtgcag cctctacatc aatatacagt aacaactaca tggcctggtt cagccaggct     120
ccaggaaagg ggcgcgaggg ggtcgcagct gtttatattg ctgatgaccg cccatactat     180
gccgactccg tgaagggccg attcaccatc tccctagaca gcgccaagaa cacggtgtat     240
ctgcaaatga acagcctgaa acctgaggac actgccatgt actactgtgc ggcagctcca     300
ggccccttaa gtcgtaatta ctggtacacg tccgccaact atgactactg ggccagggg      360
acccaggtca ccgtctcctc a                                                381
```

<210> SEQ ID NO 236
<211> LENGTH: 381
<212> TYPE: DNA
<213> ORGANISM: Camelus bactrianus

<400> SEQUENCE: 236

```
caggtgcagc tgcaggattc tggggggaggc tcggtgcaga ccggagggtc tctgcgactc     60
tcctgtgcag cctctacatc aatatacagt atcaactaca tggcctggtt cagccaggct    120
ccaggaaagg ggcgcgaggg ggtcgcagct gtttatactg gtgatggtcg cccatactat    180
gccgactccg tgaagggccg attcaccatc tccctagaca gcgccaagaa cacggtgtat    240
ctgcaaatga acagcctgaa acctgaggac actgccatgt actactgtgc ggcagctcca    300
ggccccttaa gtcgtaatta ctggtacacg tccgccaact atgactactg ggccagggg     360
acccaggtca ccgtctcctc a                                               381
```

<210> SEQ ID NO 237
<211> LENGTH: 381
<212> TYPE: DNA
<213> ORGANISM: Camelus bactrianus

<400> SEQUENCE: 237

```
caggtgcagc tgcaggagtc tggaggaggc tcggtgcagg ctggagggtc tctgagactc      60
tcctgtgcag cctctggata caccgcagt agctactgca tgggctggtt ccgccaggct     120
```

| | |
|---|---|
| ccagggaagg agcgcgagag ggtcgcatat atttattctg gtagtggaag cacacactat | 180 |
| gccgactccg tgaagggccg attcaccatc tcccaagaca acggcaagaa cacgctatat | 240 |
| ctgcaaatga acaatctgaa acctgaggac actgccatgt actactgtgc ggcagggaca | 300 |
| agtggtactt cgtgccccac cggtgcgttc atgtatgagt actggtactg gggccagggg | 360 |
| acccaggtca ccgtctcctc a | 381 |

<210> SEQ ID NO 238
<211> LENGTH: 381
<212> TYPE: DNA
<213> ORGANISM: Camelus bactrianus

<400> SEQUENCE: 238

| | |
|---|---|
| caggtgcagc tgcaggagtc tgggggaggc tcggtgcagg ctggagggtc tctgagactc | 60 |
| tcctgtgcag cctctacatc aatatacagt aacaactaca tggcctggtt ccgccaggct | 120 |
| ccaggaaagg ggcgcgaggg ggtcgcagct gtttatgttg gtgatggtcg cccatactat | 180 |
| gccgactccg tgaagggccg attcaccatc tccctagaca gcgccaagaa cacggtgtat | 240 |
| ctgcaaatga acagcctgaa acctgaggac actgccatgt actactgtgc ggcagctcca | 300 |
| ggccccttaa gtcataatta ctggtacacg tccgccaact atgactactg gggccagggg | 360 |
| acccaggtca ccgtctcctc a | 381 |

<210> SEQ ID NO 239
<211> LENGTH: 381
<212> TYPE: DNA
<213> ORGANISM: Camelus bactrianus

<400> SEQUENCE: 239

| | |
|---|---|
| caggtgcagc tgcaggagtc tgggggaggc tcggtgcaga ccggagggtc tctgagactc | 60 |
| tcctgtgcag cctctacatc aatatacagt aacaactaca tggcctggtt cagccaggct | 120 |
| ccaggaaagg ggcgcgaggg ggtcgcagct gtttatattg gtgatggtcg cccatactat | 180 |
| gccgactccg tgaagggccg attcaccatc tccctagaca gcgccaggaa cacggtgtat | 240 |
| ctgcaaatga acagcctgaa acctgaggac actgccatgt actactgtgc ggcagctcca | 300 |
| gggcccttaa gtcgtcatta ctggtacacg tccgccaact atgactactg gggccagggg | 360 |
| acccaggtca ccgtctcctc a | 381 |

<210> SEQ ID NO 240
<211> LENGTH: 381
<212> TYPE: DNA
<213> ORGANISM: Camelus bactrianus

<400> SEQUENCE: 240

| | |
|---|---|
| caggtgcagc tgcaggagtc tggaggaggc tcggtgcagg ccggagggtc tctgagactc | 60 |
| tcctgtgcag cctctacatc aatatacagt aacaactaca tggcctggtt cagccaggct | 120 |
| ccaggaaagg ggcgcgaggg ggtcgcagct gtttatattg atgatggtcg ccctactat | 180 |
| gccgactccg tgaagggccg attcaccatc tccctagaca gcgccaagaa cacggtgtat | 240 |
| ctgcaaatga acagcctgaa acctgaggac actgccatgt actactgtgc ggcagctcca | 300 |
| ggccccttaa gtcgtaatta ctggtacacg tccgccaact atgactactg gggccagggg | 360 |
| acccaggtca ccgtctcctc a | 381 |

<210> SEQ ID NO 241
<211> LENGTH: 363

<212> TYPE: DNA
<213> ORGANISM: Camelus bactrianus

<400> SEQUENCE: 241

```
caggtgcagc tgcaggagtc tggaggagac ttggtgcagc ctgggggtc tctgagactc      60
tcctgtgcag cctctgggct ccccttcagt atcattgcca tgagctgggt ccgccaggct    120
ccagggaagg gactcgagtg ggtctcaact attaataacg atggtggcac cacacactat    180
gcagactccg tgaagggccg cttcaccatc tccagagaca cgccaagaa cacgctatat    240
ctgcaattga atagcctgag aactgaggac acggccatgt attactgccg acggtgcacg    300
gatatttact gttcaggttc cggcggatgg acgggccagg ggacccaggt caccgtctcc    360
tca                                                                   363
```

<210> SEQ ID NO 242
<211> LENGTH: 381
<212> TYPE: DNA
<213> ORGANISM: Camelus bactrianus

<400> SEQUENCE: 242

```
caggtgcagc tgcaggagtc tggaggaggc tcggtgcaga ccggagggtc tctgagactc      60
tcctgtgcag cctctacatc aatatacaat aacaactaca tggcctggtt ccgccaggct    120
ccaggaaagg ggcgcgaggg cgtcgcagct gtttatattg atgatggtcg cccatactat    180
gccgactccg tgaagggccg attcaccatc tccctagaca gcgccaagaa cacggtgtat    240
ctgcaaatga acagcctgaa acctgaggac actgccatgt actactgtgc ggcagctcca    300
ggccccttaa gtcgtcatta ctggtacacg tccgccaact atgactactg gggcccgggg    360
acccaggtca ccgtctcctc a                                               381
```

<210> SEQ ID NO 243
<211> LENGTH: 381
<212> TYPE: DNA
<213> ORGANISM: Camelus bactrianus

<400> SEQUENCE: 243

```
caggtgcagc tgcaggagtc tgggggaggc tcggtgcaga ccggagggtc tctgagactc      60
tcctgtgcag cctctacatc aatatacagt aacaactaca tggcctggtt ccgccaggct    120
ccaggaaagg ggcgcgaggg ggtcgcagct gtttatattg gtgatggtcg cacatactat    180
gccgactccg cgaagggccg attcaccatc tccctagaca gcgccaagaa cacggtgtat    240
ctgcatatga acagcctgaa acctgacgac actgccatgt actactgtgc ggcagctcca    300
ggccccttaa ctcgtcattt ctggtacacg tccgccaact atgactactg gggcccgggg    360
acccaggtca ccgtctcctc a                                               381
```

<210> SEQ ID NO 244
<211> LENGTH: 381
<212> TYPE: DNA
<213> ORGANISM: Camelus bactrianus

<400> SEQUENCE: 244

```
caggtgcagc tgcaggagtc tgggggaggc tcggtgcaga ccggagggtc tctgagactc      60
tcctgtgcag cctctacatc actatacagt tacaactaca tggcctggtt cagccaggct    120
ccaggaaagg ggcgcggggg ggtcgcagct gtttatgttg gtgatggtcg cccatactat    180
gccgactccg tgaagggccg attcaccatc tccctagaca gcgccaagaa cacggtgtat    240
```

```
ctgcaaatga acagcctgaa acctgaggac actgccatgt actactgtgc ggcagctcca    300
ggccccttaa gtcataatta ctggtacacg tccgccaact atgactactg gggccagggg    360
acccaggtca ccgtctcctc a                                              381
```

<210> SEQ ID NO 245
<211> LENGTH: 381
<212> TYPE: DNA
<213> ORGANISM: Camelus bactrianus

<400> SEQUENCE: 245

```
caggtgcagc tgcaggagtc tggaggaggc tcggtgcagg ctggagggtc tctgagactc     60
tcctgtgcag cctctggata caccgtcagt aacaactaca tgggctggtt ccgccaggct    120 cagggaagg ggcgcgaggg ggtcgcagct gtttatattg gtgatggtcg cccatactat    180
gccgactccg tgaagggccg attcaccatc tccctagaca gcgccaagaa cacggtgtat    240
ctgcaaatga acagcctgaa acctgaggac actgccatgt actactgtgc ggcagctcca    300
ggccccttaa gtcagcatta ctggtacacg tccgccaact atgactactg gggccagggg    360
acccaggtca ccgtctcctc a                                              381
```

<210> SEQ ID NO 246
<211> LENGTH: 339
<212> TYPE: DNA
<213> ORGANISM: Camelus bactrianus

<400> SEQUENCE: 246

```
caggtgcagc tgcaggagtc tgggggaggc ttggtgcagc ctgggggtc tctgagactc      60 tcctgtgcag cctttggatt caccttcggt agctattgga tgaagtgggt ccgccaggct    120
ccagggaagg atctcgagtg ggtcccaatt attgataatg gtggtcgtag cacatggtat    180
gcagactccg tgaagggccg attcaccatt tccagagaca atgccaagaa ctcgctgtat    240
ctgcaattga acagcctgaa aattgaggac acggccatgt attactgtgc ggaccggaac    300
gggaacaggg gccaggggac ccaggtcacc gtctcctca                            339
```

<210> SEQ ID NO 247
<211> LENGTH: 381
<212> TYPE: DNA
<213> ORGANISM: Camelus bactrianus

<400> SEQUENCE: 247

```
caggtgcagc tgcaggagtc tgggggaggc tcggtgcaga ccggagggtc tctgagacac     60
tcctgtgcag cctctacatc aatatacagt aacaactaca tggcctggtt cagccaggct    120
ccaggaaagg ggcgcgaggg ggtcgcagct gtttatattg acgatggtcg accatactat    180
gccgactccg tgaagggccg attcaccatc tccctagaca gcgccaagaa cacggtgtat    240
ctgcaaatga acagcctgaa acctgaggac actgccatgt actactgtgc ggcagctcca    300
ggccccttaa gtcataatta ctggtacacg tctgccaact atgactactg gggccagggg    360
acccaggtca ccgtctcctc a                                              381
```

<210> SEQ ID NO 248
<211> LENGTH: 381
<212> TYPE: DNA
<213> ORGANISM: Camelus bactrianus

<400> SEQUENCE: 248

```
caggtgcagc tgcaggagtc tgggggaggc tcggtgcaga ccggagggtc tctgagactc     60
```

```
tcctgtgcag cctctacatc aatatacagt aacaactaca tggcctggtt ccgccaggct    120
ccaggaaagg ggcgcgaggg ggtcgcagct gtttatattg gtgatggtcg cccatactat    180
gccgactccg tgaagggccg attcaccatc tccctagaca gcgccaagaa cacggtgtat    240
ctgcacatga acagcctgaa acctgaggac actgccatgt actactgtgc ggcagctcca    300
ggccccttaa gtcgtcatta ctggtacacg tccgccaact atgactactg ggcccgggg     360 acccaggtca ccgtctcctc a                                              381
```

<210> SEQ ID NO 249
<211> LENGTH: 381
<212> TYPE: DNA
<213> ORGANISM: Camelus bactrianus

<400> SEQUENCE: 249

```
caggtgcagc tgcaggagtc tgggggaggc tcggtaacga ccggagggtc tctgagactc     60
tcctgtgcag cctctacatc aatatacagt aacaactaca tggcctggtt ccgccaggct    120
ccaggaaagg ggcgcgaggg ggtcgcagct gtttatattg gtgatggtcg cccatactat    180
gccgactccg tgaagggccg attcaccatc tccctagaca gcgccaagaa cacggtgtat    240
ctgcaaatga acagcctgaa acctgaggac actgccatgt actactgtgc ggcagctcca    300
ggccccttaa gtcgtcatta ctggtacacg tccgccaact atgactactg ggcccgggg     360 acccaggtca ccgtctcctc a                                              381
```

<210> SEQ ID NO 250
<211> LENGTH: 363
<212> TYPE: DNA
<213> ORGANISM: Camelus bactrianus

<400> SEQUENCE: 250

```
caggtgcagc tgcaggagtc tgggggaggc ttggtgcagc ctggggggtc tctgagactc     60
tcctgtgcag cctctggatt caccttcagt atcatggcca tgagctgggt ccgccaggct    120
ccagggaggg gactcgagtg ggtctcaact attaatagtg atggtggcaa gacatactat    180
gcagactccg tgaagggccg cttcaccgcc tccagagaca cgccaagaa cacgctgtat    240 ctgcaattga atagcctgag aactgaggac acggccatgt attactgccg acggtgcgcg    300
gatatttact gttcaggttc cggcggatgg acgggccagg ggacccaggt caccgtctcc    360
tca                                                                  363
```

<210> SEQ ID NO 251
<211> LENGTH: 378
<212> TYPE: DNA
<213> ORGANISM: Camelus bactrianus

<400> SEQUENCE: 251

```
caggtgcagc tgcaggagtc tgaggaggc tcggtgcaga ctggagggtc tctgagactc      60
tcctgtgcag tctctggatt caccgacacc tacttcgcct gggctggtt ccgccaggct     120 ccagggaagg agcgcgaggg ggtcgcagct attgatagtg atggtagcac aagctacgca    180
gactccgtga agggccgatt caccatctcc aaagacaacg ccaagaacac ggtgtatctg    240
caaatgaaca gcctgaaacc tgaggacact gccatgtact actgtgcggc agctccaggc    300
cccttaagtc gtaactactg gtacacgtcc gccaactatg actactgggg ccaggggacc    360
caggtcaccg tctcctca                                                  378
```

<210> SEQ ID NO 252
<211> LENGTH: 381
<212> TYPE: DNA
<213> ORGANISM: Camelus bactrianus

<400> SEQUENCE: 252

| | | | | | |
|---|---|---|---|---|---|
| caggtgcagc | tgcaggagtc | tgggggaggc | tcggtgcaga | ccggagggtc | tctgagactc | 60 |
| tcctgtgcag | cctctacatc | aatatacagt | aacaactaca | tggcctggtt | ccgccaggct | 120 |
| ccagcaaagg | gacgcgaggg | ggtcgcagct | gtttatattg | gtgatggtcg | cccatactat | 180 |
| gccgactccg | tgaagggccg | attcaccatc | tccctagaca | gcgccaagaa | cacggtgtat | 240 |
| ctgcaaatga | acagcctgaa | acctgaggac | actgccatat | actactgtgc | ggcagctcca | 300 |
| ggccccttaa | gtcgtcatta | ctggtacacg | tccgccaact | atgactactg | ggcccgggg | 360 |
| acccaggtca | ccgtctcctc | a | | | | 381 |

<210> SEQ ID NO 253
<211> LENGTH: 381
<212> TYPE: DNA
<213> ORGANISM: Camelus bactrianus

<400> SEQUENCE: 253

| | | | | | |
|---|---|---|---|---|---|
| caggtgcagc | tgcaggagtc | tggaggaggc | tcggtgcaga | ccggagggtc | tctgagactc | 60 |
| tcctgtgcag | cctctacatc | aatatacaat | aacaactaca | tggcctggtt | cagccaggct | 120 |
| ccaggaaagg | ggcgcgaggg | ggtcgcagct | gtttatattg | aagatggtcg | cccatactat | 180 |
| gccgactccg | tgaagggccg | attcaccatc | tccctagaca | gcgccaagaa | cacggtgtat | 240 |
| ctgcaaatga | acagcctgaa | acctgaggac | actgccatgt | actactgtgc | ggcagctcca | 300 |
| ggccccttaa | gtcgtaacta | ctggtacacg | tccgccaact | atgactactg | gggccagggg | 360 |
| acccaggtca | ccgtctcctc | a | | | | 381 |

<210> SEQ ID NO 254
<211> LENGTH: 381
<212> TYPE: DNA
<213> ORGANISM: Camelus bactrianus

<400> SEQUENCE: 254

| | | | | | |
|---|---|---|---|---|---|
| caggtgcagc | tgcaggagtc | tgggggaggc | tcggtgcaga | ccggagggtc | tctgagactc | 60 |
| tcctgtgcag | cctctacatc | aatatacagt | aacaactaca | tggcctggtt | ccgccaggct | 120 |
| ccaggaaagg | ggcgcgaggg | ggtcgcagct | gtttatattg | atgacggtcg | cacatactat | 180 |
| gccgactccg | tgaagggccg | attcgccatc | tccctagaca | gcgccaagaa | cacggtgtat | 240 |
| ctgcaaatga | acagcctgaa | acctgaggac | actgccatgt | actactgtgc | ggcagctcca | 300 |
| ggccccttaa | gtcgtcatta | ctggtacacg | tccgccaact | atgactactg | ggcccgggg | 360 |
| acccaggtca | ccgtctcctc | a | | | | 381 |

<210> SEQ ID NO 255
<211> LENGTH: 363
<212> TYPE: DNA
<213> ORGANISM: Camelus bactrianus

<400> SEQUENCE: 255

| | | | | | |
|---|---|---|---|---|---|
| caggtgcagc | tgcaggagtc | tgggggaggc | ttggtgcagc | ctgggggtc | tctgagactc | 60 |
| tcctgtgcag | cctctggatt | caccttcagt | agcttggcca | tgagctgggt | ccgccaggct | 120 |
| ccagggaagg | gactcgagtg | ggtctcaact | attaatagtg | ggggtgtcta | cacatactat | 180 |

```
gcagactccg tgaagggccg cttcaccatc tccagagaca acgccaagaa cacgctgtat    240
ctgcaattga ataacctgag aactgaggac acggccatgt attactgccg acggtgcacg    300
gatatttact gttcaggttc cggcggatgg acgggccagg ggacccaggt caccgtctcc    360
tca                                                                   363

<210> SEQ ID NO 256
<211> LENGTH: 363
<212> TYPE: DNA
<213> ORGANISM: Camelus bactrianus

<400> SEQUENCE: 256
caggtgcagc tgcaggagtc tgggggaggc ttggtgcagc ctggggggtc tctgagactc     60
tcctgtgcag tctctggatt caccttcagt atcattgcca tgagctgggt ccgccaggct    120
ccagggaagg gactcgagtg ggtctcaact attaatagtg atggtggcac cacatactat    180
gcagactccg tgaagggccg cttcaccatc tccagagaca acgccaagaa cacgctgtat    240
ctgcaattga atagcctgag aactgaggac acggccatgt attactgccg acggtgcgcg    300
gatatttact gttcaggttc cggcggatgg acgggccagg ggacccaggt caccgtctcc    360
tca                                                                   363

<210> SEQ ID NO 257
<211> LENGTH: 366
<212> TYPE: DNA
<213> ORGANISM: Camelus bactrianus

<400> SEQUENCE: 257
caggtgcagc tgcaggagtc tgggggaggc ttggtgcagc ctggggggtc tctgagactc     60
tcctgtgaag cctctggact cccctttcagt atcattgcca tgagctgggt ccgccaggct   120
ccagggaagg gactcgagtg ggtctcaact attaatagtg atggtggcac cacacactat    180
gcagactccg tgaagggccg cttcaccatc tccagagaca acgccaagaa cacgctgtat    240
ctgcaattga atagcctgag atctgaggac acggccatgt attactgccg acggtgcacg    300
gatatttact gttcaggttc cggcggatcg actaagggcc aggggaccca ggtcaccgtc    360
tcctca                                                                366

<210> SEQ ID NO 258
<211> LENGTH: 381
<212> TYPE: DNA
<213> ORGANISM: Camelus bactrianus

<400> SEQUENCE: 258
caggtgcagc tgcaggagtc tggaggaggc tcggtgcaga ccggagggtc gctgagactc     60
tcctgtgcag cctctacatc aatatacagt aacaactaca tggcctggtt ccgccaggct   120
ccaggaaagg ggcgcgaggg ggtcgcagct gtttatattg gtgatggtcg cccatactat    180
gccgactccg tgaagggccg attcaccatc tccctagaca gcgccaagaa cacggtgtat    240 ctgcaaaatga acagcctgaa acctgaggac actgccatgt actactgtgc ggcagctcca    300 ggcccctttaa gtcgtcatta ctggtacaca ccgccaact atgactactg ggccccgggg    360
acccaggtca ccgtctcctc a                                               381

<210> SEQ ID NO 259
<211> LENGTH: 381
<212> TYPE: DNA
```

<213> ORGANISM: Camelus bactrianus

<400> SEQUENCE: 259

| caggtgcagc tgcaggagtc tggaggaggc tcggtgcagg ctggagggtc tctgagactc | 60 |
| tcctgtgcag cctctggata cacccgcagt agctactgca tgggctggtt ccgccaggct | 120 |
| ccagggaagg agcgcgagag ggtcgcacac atttatactg gtagtggaac gacacactat | 180 |
| gccgactcca tgaagggccg attcaccatc tcccaagaca acggcaagaa cacgctgtat | 240 |
| ctgcaaatga acaatctgaa acctgaggac actgccatgt actactgtgc ggcagggaca | 300 |
| agtggtactt cgtgcgccac cggtccgttc gtgtatgggt actggtactg gggccagggg | 360 |
| acccaggtca ccgtctcctc a | 381 |

<210> SEQ ID NO 260
<211> LENGTH: 387
<212> TYPE: DNA
<213> ORGANISM: Camelus bactrianus

<400> SEQUENCE: 260

| caggtgcagc tgcaggagtc tggaggaggc tcggtgcagg ctggagggtc tctgagactc | 60 |
| tcctgtgcat acacgcccag gcgcttatgc atgggcatgg gctggttccg ccagggtcta | 120 |
| gggaaggagc gcgaggggt cgcaacgatt gatgatgccg aagcacaac ctacgctgac | 180 |
| tccgtgaagg cccgattcac catctcccaa gacaacgcca gaacactct gtatctgcaa | 240 |
| atggacagcc tgaaacccga agacagcgcc atgtattact gcgcggcccg ggctggtgtc | 300 |
| ggttggtatc aggtttcatg cccggaggag agtaggactt ctgcctttgt gtactggggc | 360 |
| cagggaaccc aggtcaccgt ctcctca | 387 |

<210> SEQ ID NO 261
<211> LENGTH: 381
<212> TYPE: DNA
<213> ORGANISM: Camelus bactrianus

<400> SEQUENCE: 261

| caggtgcagc tgcaggagtc tgggggaggc tcggtgcaga ccggagggtc tctgagactc | 60 |
| tcctgtgcag cctctacatc aatatacaat aacaactaca tggcctggtt cagccaggct | 120 |
| ccaggaaagg ggcgcgaggg ggtcgcagct gtttatattg aagatggtcg cccatactat | 180 |
| gccgactccg tgaagggccg attcaccatc tccctagaca gcgccaagaa cacggtgtat | 240 |
| ctgcaaatga acagcctgaa acctgaggac actgccatgt actactgtgc ggcagctcca | 300 |
| ggccccttaa gtcgtaacta ctggtacacg tccgccaact atgactactg gggccagggg | 360 |
| acccaggtca ccgtctcctc a | 381 |

<210> SEQ ID NO 262
<211> LENGTH: 363
<212> TYPE: DNA
<213> ORGANISM: Camelus bactrianus

<400> SEQUENCE: 262

| caggtgcagc tgcaggagtc tgggggaggc ttggtgcagc ctgggggggtc tctgagactc | 60 |
| tcctgtgcag cctctggatt gaccttcagt atcgttgcca tgagctgggt ccgccaggct | 120 |
| ccaggaaagg gactcgagtg ggtctcaact attaatagtg atggtggcag cacatactat | 180 |
| gcagactccg tgaagggccg cttcaccatc tccagagaca cgccaagaa cacgctgtat | 240 |
| ctgcaattga atagcctgag aactgaggac acggccatgt attactgccg acggtgcacg | 300 |

```
gatatttact gttcaggttc cggcggatgg acgggccagg ggacccaggt caccgtctcc    360
tca                                                                 363

<210> SEQ ID NO 263
<211> LENGTH: 381
<212> TYPE: DNA
<213> ORGANISM: Camelus bactrianus

<400> SEQUENCE: 263
caggtgcagc tgcaggagtc tggaggaggc tcggtgcaga ccggagggtc tctgagactc    60
tcctgtgcag cctctacatc aataatcagt ttcaactaca tggcctggtt ccgccgggct   120
ccaggaaagg ggcgcgaggg ggtcgcggct gtttatattg atgatggtcg cccatactat   180
gccgactccg tgaagggccg attcaccatc tccctagact ccgccaagaa cacggtgtat   240
ctgcaaatgg gcagcctgag acctgaggac actgccatgt actactgtgc ggcagctcca   300
ggccccttaa gtcgtaatta ctggcacacg cccgccaact atgactactg gggccagggg   360
acccaggtca ccgtctcctc a                                             381

<210> SEQ ID NO 264
<211> LENGTH: 372
<212> TYPE: DNA
<213> ORGANISM: Camelus bactrianus

<400> SEQUENCE: 264
caggtgcagc tgcaggagtc tggaggaggc tcggtgcaga ccggagggtc tctgagactc    60
tcctgtgcag cctctggata cgccggcagg ctctactcta tgggctggtt ccgccaggtt   120
gcagggaagg agcgcgaggg ggtctcgagt attgaaagtg atggcagtac gttctataca   180
gactccgtga agggccgatt caccacaacc cgagacagcc caagaacac tctatatctc    240 caaatgaaca acctgaaacc tgaggacact gccatgtact actgcgcggc attttgcctg   300
cgagtaggac atggtggtcg ctgcacagag tataaatact ggggccgggg gacccaggtc   360
accgtctcct ca                                                       372

<210> SEQ ID NO 265
<211> LENGTH: 381
<212> TYPE: DNA
<213> ORGANISM: Camelus bactrianus

<400> SEQUENCE: 265
caggtgcagc tgcaggagtc tgggggaggc tcggtgcagg ctggagggtc tctgagactc    60
tcctgtgcag cctctggata cacccgcagt agttactgca tgggctggtt ccgccaggct   120
ccagggaagg agcgcgagag ggtcgcacac atttatactg gtagtggaag cacacactat   180
gccgactccg tgaagggccg attcaccatc tcccaagaca acggcaagaa cacgctgtat   240
ctgcaaatga acaatctgaa acctgaggac actgccatgt actactgtgc ggcagggaca   300
agtggtactt cgtgcgccac cggtccgttc gtgtataaat actggtactg gggccagggg   360
acccaggtca ccgtctcctc a                                             381

<210> SEQ ID NO 266
<211> LENGTH: 369
<212> TYPE: DNA
<213> ORGANISM: Camelus bactrianus

<400> SEQUENCE: 266
```

```
ctggtgcagc tgcaggagtc tgggggaggc ttggtgcagc tgggggggtc tctgagactc      60
tcctgtgcag cctctggatt cgccttcagt acctatgcca tgagctgggt ccgccaggct     120
ccagggaagg gactcgagtg ggtctcaggt attaatggtg gtggtggtaa cacatactat     180
gcagactccg tgaagggccg attcaccatc tccagagaca cgccaagaa cacgctgtat      240 ctgcaattga acagcctgaa aactgaggac acggccatgt attactgtgg acaaggggca     300
tattgggcat attgtaacgg tggttactgc aatcctccgg gccaggggac ccaggtcacc     360
gtctcctca                                                             369
```

<210> SEQ ID NO 267
<211> LENGTH: 381
<212> TYPE: DNA
<213> ORGANISM: Camelus bactrianus

<400> SEQUENCE: 267

```
caggtgcagc tgcaggagtc tgggggaggc tcggtgcaga ccggagggtc tctgagactc      60
tcctgtgcag cctctacatc aatatacagt aacaactaca tggcctggtt cagccaggct     120
ccaggaaagg ggcgcgaggg ggtcgcagct gtttatattg gtgatggtcg cccatactat     180
gccgactccg tgaagggccg attcaccatc tccctagaca gcgccaagga cacggtgtat     240
ctgcaaatga acagcctgaa acctgaggac actgccatgt actactgtgc ggcagctcca     300 ggcccccttaa gtcgtaatta ctggtacacg tccgccaact atgactactg gggccagggg     360
acccaggtca ccgtctcctc a                                               381
```

<210> SEQ ID NO 268
<211> LENGTH: 381
<212> TYPE: DNA
<213> ORGANISM: Camelus bactrianus

<400> SEQUENCE: 268

```
caggtgcagc tgcaggagtc tgggggaggc tcggtgcaga ccggagggtc tctgagactc      60
tcctgtgcag cctctgcatc aatatacagt aacaactaca tggcctggtt cagccaggct     120
ccaggaaagg ggcgcgaggg ggtcgcagct gtttatattg gtgatggtcg cccatactat     180
gacgactccg tgaagggact attcaccatc tccctagaca gcgccaagaa cacggtgtat     240
ctgcaaatga acagcctgaa acctgaggac actgccatgt actactgtgc ggcagctcca     300 ggaccccttaa ttcgtaatta ctggtacacg tccgccaact atgactactg gggccagggg     360
acccaggtca ccgtctcctc a                                               381
```

<210> SEQ ID NO 269
<211> LENGTH: 381
<212> TYPE: DNA
<213> ORGANISM: Camelus bactrianus

<400> SEQUENCE: 269

```
caggtgcagc tgcaggagtc tgggggaggc tcggtgcaga ccggagggtc tctgagactc      60
tcctgtgcag cctctacatc actatacagt tacaactaca tggcctggtt cagccaggct     120
ccaggaaagg ggcgcgaggg ggtcgcagct gtttatgttg gtgatggtcg cccatactat     180
gccgactccg tgaagggccg attcaccatc tccctagaca gcgccaagaa cacggtgtat     240
ctgcaaatga acagcctgaa acctgaggac actgccatgt actactgtgc ggcagctcca     300 ggcccccttaa gtcgtaatta ctggtacacg tccgccaact atgactactg gggccagggg     360
acccaggtca ccgtctcctc a                                               381
```

<210> SEQ ID NO 270
<211> LENGTH: 375
<212> TYPE: DNA
<213> ORGANISM: Camelus bactrianus

<400> SEQUENCE: 270

```
caggtgcagc tgcaggagtc tgggggaggc tcagtgcagg ctggggggtc tctgagactc    60
tcctgcacag cccctggatt cacctccaac acctgcgcca tggcgtggtt ccgccaggct   120
ccagggaaag agcgcgagtt cgtctcatct atgagtactg tcggttccac gaggtttgca   180
gactccgtga agggccgatt caccatctcc aaagacgaag tcaaggacac ggtctatctg   240
caaatgaaca gcctgaaacc tgaggacacg gccatgtatt tttgtaagac ctatgcgtgt   300
agagaatgta ctggtcggta ttgtcgtaca gctccggatg catggggcca ggggacacag   360
gtcaccgtct cctca                                                   375
```

<210> SEQ ID NO 271
<211> LENGTH: 375
<212> TYPE: DNA
<213> ORGANISM: Camelus bactrianus

<400> SEQUENCE: 271

```
caggtgcagc tgcaggagtc tgggggaggc tcagcgcagg ctggggggtc tctgagactc    60
tcctgcacag cccctggatt cacctccaac acctgcgcca tggcgtggta ccgccaggct   120
ccagggaaag agcgcgagtt cgtctcatct cgcagcactg tcggtaccac ggggtatgca   180
gactccgtga agggccgatt caccatctcc aaagacgaag ccaaggacac ggtctatctg   240
caaatgaaca gcctgaaacc tgaggacacg gccatgtatt tttgtaagac ctatgcgtgt   300
agaaattgta ttggtcggca ttgtcgtaca gctccggatg catggggcca ggggacacag   360
gtcaccgtct cctca                                                   375
```

<210> SEQ ID NO 272
<211> LENGTH: 375
<212> TYPE: DNA
<213> ORGANISM: Camelus bactrianus

<400> SEQUENCE: 272

```
caggtgcagc tgcaggagtc tgggggaggc tcagtgcagg ctggggggtc tctgagactc    60
tcctgcacag cccctggatt cacctccaac acctgcgcca tggcgtggtt ccgccaggct   120
ccagggaaag agcgcgagtt tgtctcatcg ctcagcactg tcggtaccac ggggtatgca   180
gactccgtga agggccgatt caccatctcc aaagacgagg ccaaggacac ggtctatctg   240
ctaatgaaca gcctgaaacc cgaggacacg gccatgtatt tttgtaagac atttgcgtgt   300
agagattgtt ctggtcggta ttgtcgtaca gctccggatg catggggcca ggggacacag   360
gtcaccgtct cctca                                                   375
```

<210> SEQ ID NO 273
<211> LENGTH: 375
<212> TYPE: DNA
<213> ORGANISM: Camelus bactrianus

<400> SEQUENCE: 273

```
caggtgcagc tgcaggagtc tgggggaggc tcagtgcagg ctggggggtc tctgagactc    60
tcctgcacag cccctggatt cacctccaac acctgcgcca tggcgtggta ccgccaggct   120
```

```
ccagggaaag agcgcgagtt cgtctcatct cgcagcactg tcggtaccac ggggtatgca    180
gactccgtga agggccgatt caccatctcc aaagacgaag ccaaggacac ggtctatctg    240
caaatgaaca gcctgaaacc tgaggacacg gccatgtatt tttgtaagac ctatgcgtgt    300
agaaattgta ttggtcggca ttgtcgtaca gctccggatg catggggcca ggggacacag    360
gtcaccgtct cctca                                                    375
```

```
<210> SEQ ID NO 274
<211> LENGTH: 387
<212> TYPE: DNA
<213> ORGANISM: Camelus bactrianus

<400> SEQUENCE: 274
caggtgcagc tgcaggagtc tggaggaggc tcggtgcagg ctggaaggtc tctgagactc    60
tcttgtgcag tctcgagata cagcgccagt aacaacgtca tcaagtggat gggctggttc   120
cgccaggctc cagggaagga gcgcgagggg gtcgcggcac tttatactag tggtggtaac   180
acatactatg ccgactccgt gaagggccga ttcaccatct ccagagacta ctccgagaac   240
acggtgtctc tccaaatgaa caacctgaaa ccagaggaca ctggcatgta ctactgtgcg   300
gctactgttg gacggtcct agctggcccg ttatctgcgc gaaaatataa ctactggggc   360
caggggaccc aggtcaccgt ctcctca                                      387
```

```
<210> SEQ ID NO 275
<211> LENGTH: 366
<212> TYPE: DNA
<213> ORGANISM: Camelus bactrianus

<400> SEQUENCE: 275
caggtgcagc tgcaggagtc tgggggaggc ttggtgcagc ctgggggtc tctgagactc     60 tcctgtgcag cctctggatt caccttcagt aactctgaca tggcctggtt cgccaggct   120 ccagggaagg gactcgagtg gtctcagtt attgatagtg gtggtggtta cacatactat   180
gcagactccg tgaagggccg attcaccatc tccagagaca acgccgagaa cacgctgtat   240
ctgcaattga acagcctgaa aactgaggac acggccatgt attactgtgc aaaaaccgat   300
ctaaggtact ctaggattta ccgtacgga aagtggggcc aggggaccca ggtcaccgtc    360
tcctca                                                             366
```

```
<210> SEQ ID NO 276
<211> LENGTH: 387
<212> TYPE: DNA
<213> ORGANISM: Camelus bactrianus

<400> SEQUENCE: 276
caggtgcagc tgcaggagtc tgggggaggc tcggtgcagg ctggaaggtc tctgagactc     60
ccttgtgcag tctcgagata cagcgccagt aacaacgtca tcaagtggat gggctggttc   120
cgccaggctc cagggaagga gcgcgagggg gtcgcggcac tttatactag tggtggtaac   180
acatactatg ccgactccgt gaagggccga ttcaccatct ccagagacta ctccgagaac   240
acggtgtctc tccaaatgaa caacctgaaa ccagaggaca ctggcatgta ctactgtgcg   300
gctactgttg gacggtcct agctggcccg ttatctgcgc gaaaatataa ctactggggc   360
caggggaccc aggtcaccgt ctcctca                                      387
```

```
<210> SEQ ID NO 277
<211> LENGTH: 375
```

```
<212> TYPE: DNA
<213> ORGANISM: Camelus bactrianus

<400> SEQUENCE: 277
caggtgcagc tgcaggagtc tggggggaggc ttggtgcagg caggggggtc tctgacactc    60
tcctgtagag gctctggatt cacctccaac acctgcgcca tggcgtggtt ccgccaggct   120
ccagggaaag agcgcgagtt cgtctcatct atgagtactg tcggttccac gaggtttgca   180
gactccgtga agggccgatt caccatctcc aagacgaag ccaaggacac ggtctatctg    240
caaatgaaca gcctgaaacc tgaggacacg gccatgtatt tttgtaagac ctatgcgtgt   300
agagaatgta ctggtcggta ttgtcgtaca gctccggatg catggggcca ggggacacag   360
gtcaccgtct cctca                                                    375

<210> SEQ ID NO 278
<211> LENGTH: 375
<212> TYPE: DNA
<213> ORGANISM: Camelus bactrianus

<400> SEQUENCE: 278
caggtgcagc tgcaggagtc tggggggaggc tcagtgcagg ctggggggtc tctgagactc    60
tcctgcacag cccctggatt cacctccaac acctgcgcca tggcgtggtt ccgccaggct   120
ccagggaaag agcgcgagtt cgtctcatct atgagcactg gcggtaccac gggatatgga   180
gactccgtga agggccgatt caccagctcc aaagacgcag ccaaggacac ggtctatctg   240
caaatgaaca gcctgaaacc tgaggacacg gccatatatt tttgtaagac ctatgcgtgt   300
agagattgta ttggtcggta ttgtcgtaca gctccggatg catggggcca ggggacacag   360
gtcaccgtct cctca                                                    375

<210> SEQ ID NO 279
<211> LENGTH: 375
<212> TYPE: DNA
<213> ORGANISM: Camelus bactrianus

<400> SEQUENCE: 279
caggtgcagc tgcaggagtc tggggggaggc tcagtgcagg ctggggggtc tctgagactc    60
tcctgcacag cccctggatt cacctccaac acctgcgcca tggcgtggta ccgccaggct   120
ccagggaaag agcgcgagtt cgtctcatct cgcagcactg tcggtaccac ggggtatgca   180
gactccgtga agggccgatt caccctctcc aaggacgaag ccaaggacac ggtctatctg   240
caaatgaaca gcctgaaacc tgaggacacg gccatgtatt tttgtaagac ctatgcgtgt   300
agaaattgta ttggtcggca ttgtcgtaca gctccggatg catggggcca ggggacacag   360
gtcaccgtct cctca                                                    375

<210> SEQ ID NO 280
<211> LENGTH: 378
<212> TYPE: DNA
<213> ORGANISM: Camelus bactrianus

<400> SEQUENCE: 280
caggtgcagc tgcaggagtc tggaggaggg tcggtgcagg ctggagagac tctgagactc    60
tcctgtacag tctctggaga cactttttgaa gcctctggcg tgggctggtt ccgccaggtt   120
tcagggaatg aatgcgactt ggtctcaagt attaatcgtg atggtaccac atactataca   180
ccctccgtgg cgggccgatt tacgatgtcc caaaacaacg ccaagaacac ggtatatctg   240
```

```
caaatgaaca gcctgaaacc tgacgacaca gccgtgtatt actgtgcgac agaccccgcc    300
gtggggattg tagtgaggag cacttgtaga ggcccctttg gttactgggg ccaggggacc    360
caggtcaccg tctcctca                                                  378
```

<210> SEQ ID NO 281
<211> LENGTH: 378
<212> TYPE: DNA
<213> ORGANISM: Camelus bactrianus

<400> SEQUENCE: 281

```
caggtgcagc tgcaggagtc tggaggaggt tcggtgcagg ctggagggtc tctgagactc     60
tcctgtacag tctctggaaa caccgacagt atgaatctca tgggctggtt ccgccaggct    120
ccagggaagg agcgcgaggg ggtcgcaagt atttatactg gaagtaggac cataacctac    180
cccgactccg tgaagggccg attcaccatc tcccaagaca cgccaagaa cacggtgtat    240 ctgcaaatga acagcctgaa acctgaggac actgccatgt actactgtgc ggcagattac    300
cgagctcgat acggtgcctc acttcggaca agtgcctata cctactgggg ccaggggacc    360
caggtcaccg tctcctca                                                  378
```

<210> SEQ ID NO 282
<211> LENGTH: 375
<212> TYPE: DNA
<213> ORGANISM: Camelus bactrianus

<400> SEQUENCE: 282

```
caggtgcagc tgcaggagtc tgggggaggc tcagtgcagg ctgggggtc tctgagactc      60 tcctgcacag cccctggatt cacctccaac acctgcgcca tggcgtggta tcgccaggct    120
ccagggaaag agcgcgagtt cgtctcatct cgcagcactg tcggtaccac ggggtatgca    180
gactccgtga agggccgatt caccatctcc aaagacgaag ccaaggacac ggtctatctg    240
caaatgaaca gcctgaaacc tgaggacacg gccaagtatt tttgtaagac ctatgcgtgt    300
agagattgta tcggtcggta ttgtcgtaca gctccggatg catgggccca ggggacacag    360
gtcaccgtct cctca                                                     375
```

<210> SEQ ID NO 283
<211> LENGTH: 372
<212> TYPE: DNA
<213> ORGANISM: Camelus bactrianus

<400> SEQUENCE: 283

```
caggtgcagc tgcaggagtc tgggggaggc tcggtgcagg ctggagggtc tctgaaactc      60
tcctgcgtag tctctggata cacctggtgt aggtacgaca tgagctggta ccgccaggct    120
ccagggaagg agcgcgagtt cgtctcagtt attgatgata atggtagtac gaactacgca    180
gactccgtga agggccgatt caccatttcc aaagacaacg caacacggt gactctgcaa    240 atgaccagcc tgaaacctgc ggacacggcc atgtattact gtcagacagg aagataccga    300
tcaaggctcg gttatggacg gtgtcccagc ggtgactact ggggcctggg gacccaggtc    360
accgtctcct ca                                                        372
```

<210> SEQ ID NO 284
<211> LENGTH: 372
<212> TYPE: DNA
<213> ORGANISM: Camelus bactrianus

<400> SEQUENCE: 284

```
caggtgcagc tgcaggagtc tgggggaggc tcggtgcagg ctggagggtc tctgagactc    60
tcctgtgcag tctctggata cagcatcagt aattactgca tggggtggtt ccgccagcct   120
ccagggaagg aacgcgaggg ggtcgcaaat attgatacgt ggggtgtgac aagctacaca   180
gactccgtga agggccgctt caccatctcc aaagacaacg ccaagaatac tctgtacctg   240
caaatgaaca gcctgaaacc tgaggacact gccctgtact actgcgcgcg cagacaattt   300
gtcaactgtg cactctggcc gccagtgaat tacgtgaact ggggccaggg gacccaggtc   360
accgtctcct ca                                                       372
```

<210> SEQ ID NO 285
<211> LENGTH: 363
<212> TYPE: DNA
<213> ORGANISM: Camelus bactrianus

<400> SEQUENCE: 285

```
caggtgcagc tgcaggagtc tgggggaggt tcggtgcagg ctgggggtc tctgagactc     60 tcctgtacag cctctggatt caccttcagt acgttagcca tgagctgggt ccgccaggct   120
ccaggaaagg gactcgagtg gtctcaact attagtagta ctggtggcgc cacatactat    180
gcagactccg tgaagggccg attcaccatc tccagagaca cgccaaaaa cacgctgtat    240 ctgcaattga acagcctgaa acctgaggac acggccatgt attactgtcg aaggtgcacg   300
gatatttact gttcaaattc cgcacgatgg acgggccagg ggacccaggt caccgtctcc   360
tca                                                                 363
```

<210> SEQ ID NO 286
<211> LENGTH: 363
<212> TYPE: DNA
<213> ORGANISM: Camelus bactrianus

<400> SEQUENCE: 286

```
caggtgcagc tgcaggagtc tggaggaggc ttggtgcagc ctgggggtc tctgagactc     60 tcctgtacag cctctggatt caccttcagt acgttagcca tgagctgggt ccgccaggct   120
ccaggaaagg gactcgagtg gtctcaact attagtagta ctggtggcgc cacatactat    180
gcagactccg tgaagggccg attcaccatc tccagagaca cgccaaaaa cacgctgtat    240 ctgcaattga acagcctgaa acctgaggac acggccatgt attactgtcg aaggtgcacg   300
gatatttact gttcaaattc cgcacgatgg acgggccagg ggacccaggt caccgtctcc   360
tca                                                                 363
```

<210> SEQ ID NO 287
<211> LENGTH: 360
<212> TYPE: DNA
<213> ORGANISM: Camelus bactrianus

<400> SEQUENCE: 287

```
caggtgcagc tgcaggagtc tggaggaggc ttggtgcagc ctggggggtc tctgagactc    60
tcctgtgtag cctctggatt cagcttcagt agctctggca tgagctgggt ccgccaggct   120
ccagggaagg gactcgagtg gtgtcaact attagttata atggtggtag cacattctat    180
acagactccg tgaagggccg attcaccatc tccagagaca cgccaagaa cacgctgtat    240 ctgcaattga acagcctgaa aactgaggac acggccatgt attactgtgc aaaaagtggg   300
acaccagtgt tggcgcctaa ttcggtccgg ggccagggga cccaggtcac cgtctcctca   360
```

<210> SEQ ID NO 288
<211> LENGTH: 381
<212> TYPE: DNA
<213> ORGANISM: Camelus bactrianus

<400> SEQUENCE: 288

```
caggtgcagc tgcaggagtc tggaggaggc tcggtgcagg ctggagggtc tctgagactc      60
tcctgtgtgt cctctggata cgcctacaat aggtactaca tggcctggtt cagccaggct     120
ccaggaaagg ggcgcgaggg ggtcgcagct gtttatattg gtgatggtcg cccatactat     180
gccgactccg tgaagggccg attcaccatc tccctagaca cgccaagaa cacggtgtat      240
ctgcaaatga acagcctgaa acctgaggac actgccatgt actactgtgc ggcagctcca     300
ggccccttaa gtcgtaatta ctggtacacg tccgccaact atgactactg gggccagggg    360
acccaggtca ccgtctcctc a                                                381
```

<210> SEQ ID NO 289
<211> LENGTH: 366
<212> TYPE: DNA
<213> ORGANISM: Camelus bactrianus

<400> SEQUENCE: 289

```
caggtgcagc tgcaggagtc tgggggaggc tcggtgcagg ctggagggtc tctgagactc     60
tcctgtgtag cctcaggata caccaactgt aggtacgaca tgagctggta ccgccaggct    120
ccagggaagg agcgcgagtt cgtctcatct atcgatagtg aaggtgtggc aaggcacgca    180
gactccgtga aggccgatt cggcatctcc aagacaacg ccaagagcac gctgtatctc      240
caaatgaaca gcctgaaacc tgaggacacg gccgtgtatt actgtaaaac ggattatata    300
acatgtagat ttggtagctg gtccgattcg acctggggcc aggggaccca ggtcaccgtc    360
tcctca                                                                366
```

<210> SEQ ID NO 290
<211> LENGTH: 366
<212> TYPE: DNA
<213> ORGANISM: Camelus bactrianus

<400> SEQUENCE: 290

```
caggtgcagc tgcaggagtc tgggggaggc tcggtgcagg ctggagggtc tctgagactc     60
tcctgtgtag cctctggata caccaactgt aggtacgaca tgagctggta ccgccaggct    120
ccggggaagg agcgcgagtt cgtctcatct atcgatagtg aaggtgtggc aaggcacgca    180
gactccgtga aggccgatt cggcatctcc aagacaacg ccaagagcac gctgtatctc      240
caaatgaaca gcctgaaacc tgaggacacg gccatgtatt actgtaaaat ggattatata    300
agatgtagat ttggtagctg gtccgagtcg acctggggcc aggggaccca ggtcaccgtc    360
tcctca                                                                366
```

<210> SEQ ID NO 291
<211> LENGTH: 375
<212> TYPE: DNA
<213> ORGANISM: Camelus bactrianus

<400> SEQUENCE: 291

```
caggtgcagc tgcaggagtc tgggggaggc tcagtgcagg ctgggggtc tctgagactc      60
tcctgcacag cccctggatt cacctccaac acctgcgcca tggcgtggtt ccgccaggct    120
ccagggaaag agcgcgagtt cgtctcatct atgagtactg tcggttccac gaggtttgca    180
```

```
gactccgtga agggccgatt caccatctcc aaagacgaag ccaaggacac ggtctatctg    240
caaatgaaca gcctgaaacc tgaggacacg gccatgtatt tttgtaagac ctatgcgtgt    300
agagaatgta ctggtcggta ttgtcgtaca gctccggatg catggggcca ggggacacag    360
gtcaccgtct cctca                                                     375

<210> SEQ ID NO 292
<211> LENGTH: 387
<212> TYPE: DNA
<213> ORGANISM: Camelus bactrianus

<400> SEQUENCE: 292
caggtgcagc tgcaggagtc tggaggaggc tcggtgcaga ctggagggtc tctgagactc     60
tcttgtgcag tctcgagata cagcgccagt aacaacgtca tcaagtggat gggctggttc    120
cgccaggctc cagggaagga gcgcgagggg gtcgcggcac tttatactag tggtggtaac    180
acatactatg ccgactccgt gaagggccga ttcaccatct ccagagacta ctccgagaac    240
acggtgtctc tccaaatgaa caacctgaaa ccagaggaca ctggcatgta ctactgtgcg    300
gctactgttg ggacggtcct agctggcccg ttatctgcgc gaaaatataa ctactggggc    360
caggggaccc aggtcaccgt ctcctca                                        387

<210> SEQ ID NO 293
<211> LENGTH: 375
<212> TYPE: DNA
<213> ORGANISM: Camelus bactrianus

<400> SEQUENCE: 293
caggtgcagc tgcaggagtc tgggggaggc tcagtgcagg ctgggggtc tctgagactc      60 tcctgcacag cccctggatt cacctccaac acctgcgcca tggcgtggta ccgccaggct    120
ccagggaaag agcgcgagtt cgtctcatct atcagcactg tccgtaccac ggcatatgca    180
gactccgtga agggccgatt caccatctcc aaagacgaag ccaaggccac ggtctatctg    240
caaatgaaca gcctgaaacc tgaggacacg gccatgtatt tttgtaagag ctatgcgtgt    300
agagattgta ttggtcggta ttgtcgtaca gctccggatg catggggcca ggggacacag    360
gtcaccgtct cctca                                                     375

<210> SEQ ID NO 294
<211> LENGTH: 387
<212> TYPE: DNA
<213> ORGANISM: Camelus bactrianus

<400> SEQUENCE: 294
caggtgcagc tgcaggagtc tgggggaggc tcggtgcagg ctggacagtc tctgagactc     60
tcctgtacag cctctggata taccgacagt cgatactgca tgggctggtt ccgccaggct    120
ccagggaagg agcgcgaacg ggtcacaact atacatactg gtactggtat cacatactat    180
gccgactccg tgaagggccg attctccatc tcccaagaca cgcccagaa cacgatgtat     240 ctgcaaatga acagcctgga acctgaggac actgccatgt actactgtgc gacaaccgat    300
tatgtatatt cagcctcagc ctcttggtgt aatggctacg ggtgtttaa caactggggc     360 caggggaccc aggtcaccgt ctcctca                                        387

<210> SEQ ID NO 295
<211> LENGTH: 387
<212> TYPE: DNA
```

<213> ORGANISM: Camelus bactrianus

<400> SEQUENCE: 295

| caggtgcagc | tgcaggagtc | tgggggagac | tcggtgcagg | ctggaaggtc | tctgagactc | 60 |
| tcttgtgcag | tctcgagata | cagcgccagt | aacaacgtca | tcaagtggat | gggctggttc | 120 |
| cgccaggctc | cagggaagga | gcgcgagggg | gtcgcggcac | tttatactag | tggtggtaac | 180 |
| acatactatg | ccgactccgt | gaagggccga | ttcaccatct | ccagagacta | ctccgagaac | 240 |
| acggtgtctc | tccaaatgaa | caacctgaaa | ccagaggaca | ctggcatgta | ctactgtgcg | 300 |
| gctactgttg | ggacggtcct | agctggcccg | ttatctgcgc | gaaaatataa | ctactggggc | 360 |
| caggggaccc | aggtcaccgt | ctcctca | | | | 387 |

<210> SEQ ID NO 296
<211> LENGTH: 438
<212> TYPE: DNA
<213> ORGANISM: Camelus bactrianus

<400> SEQUENCE: 296

| caggtgcagc | tgcaggagtc | tgggggaggc | tcggtgcagg | ctggagggtc | tctgagactc | 60 |
| tcttgtgcag | tctcgagata | cagcgccagt | aacaacgtca | tcaagtggat | gggctggttc | 120 |
| cgccaggctc | cagggaagga | gcgcgagggg | gtcgcggcac | tttatactag | tggtggtaac | 180 |
| acatactatg | ccgactccgt | gaagggccga | ttcaccatct | ccagagacta | ctccgagaac | 240 |
| acggtgtctc | tccaaatgaa | caacctgaaa | ccagaggaca | ctggcatgta | ctactgtgcg | 300 |
| actactgttg | ggacggtcct | agctggcccg | ttatctgcgc | gaaaatataa | ctactggggc | 360 |
| caggggaccc | aggtcaccgt | ctcctcagag | gagtctcagc | ctcttaatac | tttcatgttt | 420 |
| cagaataata | ggttccga | | | | | 438 |

<210> SEQ ID NO 297
<211> LENGTH: 372
<212> TYPE: DNA
<213> ORGANISM: Camelus bactrianus

<400> SEQUENCE: 297

| caggtgcagc | tgcaggagtc | tgggggaggc | tcggtgcagg | ctggagggtc | tctgagactc | 60 |
| tcctgtgcag | cctctggata | cacctcgagg | ccgaacttca | tggtctggtt | ccgccaggct | 120 |
| ccagggaagg | agcgcgaggc | ggtcgcaggt | atttatactg | ttactggtgg | aacactctat | 180 |
| tccgaccccg | tgaagggccg | attcaccatc | tcccaagaca | aggccaagaa | cacggtgtat | 240 |
| ctgcaaatga | acagcctgaa | tcctgaggac | actgccatgt | actactgtgc | ggttaaatgg | 300 |
| tatggtggta | gctggtcaga | cgccgccact | tttcgtacct | ggggccgggg | gacccaggtc | 360 |
| accgtctcct | ca | | | | | 372 |

<210> SEQ ID NO 298
<211> LENGTH: 375
<212> TYPE: DNA
<213> ORGANISM: Camelus bactrianus

<400> SEQUENCE: 298

| caggtgcagc | tgcaggagtc | tgggggaggc | tcggtgcagg | ctggagggtc | tctgagactc | 60 |
| tcctgtgcag | cctctggata | ctcctataac | atcgattaca | tggcctggtt | ccgccaggct | 120 |
| ccagggaagg | agcgcgaggg | ggtcgcagct | atttatactg | gtagtagacg | cacatactat | 180 |
| tccgactccg | tgaagggccg | attcgccatc | tcccaagaca | acgccgacaa | cacggtgtat | 240 |

```
ctgcaaatga acgccctgaa acctgaggac actgccatgt acttctgtgc ggcccttgtc    300
tcccgaccgg ggcgtagttg ggataaaaat gagtatcggt actggggcca ggggacccag    360
gtcaccgtct cctca                                                     375

<210> SEQ ID NO 299
<211> LENGTH: 375
<212> TYPE: DNA
<213> ORGANISM: Camelus bactrianus

<400> SEQUENCE: 299
caggtgcagc tgcaggagtc tgggggagga ttggtgcagg cagggggtc tctgagactc     60 tcctgtacag cctctggatt cactttgat gattattcca tgggctggtt ccgccaggct    120
ccggggaagg agcgcgaggg gatctcatgt attgattgga gtggtggtcg cacaaactat    180
ggggactccg tgaagggccg attcaccatc tccagagaca acgccaagaa cacgctgtat    240
ctgcaaatga acagcctgaa acctgaagac acggccatgt attactgtgc ggccaacagc    300
gcgtactcga gttgcagcct aagcacgact cattataagt actggggcca ggggacccag    360
gtcaccgtct cctca                                                     375

<210> SEQ ID NO 300
<211> LENGTH: 363
<212> TYPE: DNA
<213> ORGANISM: Camelus bactrianus

<400> SEQUENCE: 300
caggtgcagc tgcaggagtc tgggggaggc ttggtgcagc ctgggggtc tctgagactc     60 tcctgtgcag cctctggatt caccttcagt gcctatggca tgagctgggt ccgccaggct    120
ccagggaagg gattcgagtg ggtctcaact attaatagtg gtggtggcac acatttat     180 gcagactccg tgaagggccg cttcaccatc tccagagaca acgccaagaa cacgctgtat    240
ctgcaattga atagcctgag aactgaggac acggccatgt attactgccg acggtgcgcg    300
gatatttact gttcactttc cggcggatgg acgggccagg ggacccaggt caccgtctcc    360
tca                                                                  363
```